United States Patent [19]
Yamashita

[11] Patent Number: 6,057,362
[45] Date of Patent: May 2, 2000

[54] PROTEASE INHIBITORS

[75] Inventor: Dennis Shinji Yamashita, King of Prussia, Pa.

[73] Assignee: SmithKline Beecham Corporation, Philadelphia, Pa.

[21] Appl. No.: 09/330,287

[22] Filed: Jun. 11, 1999

Related U.S. Application Data

[62] Division of application No. 08/793,915, filed as application No. PCT/US96/18000, Oct. 30, 1996
[60] Provisional application No. 60/008,108, Oct. 30, 1995, provisional application No. 60/007,473, Nov. 22, 1995, provisional application No. 60/008,992, Dec. 21, 1995, provisional application No. 60/013,748, Mar. 20, 1996, provisional application No. 60/013,764, Mar. 20, 1996, provisional application No. 60/013,747, Mar. 20, 1996, provisional application No. 60/017,455, May 17, 1996, provisional application No. 60/017,892, May 17, 1996, provisional application No. 60/022,047, Jul. 22, 1996, and provisional application No. 60/023,494, Aug. 7, 1996.

[51] Int. Cl.[7] ........................ A61K 31/343; C07D 307/91
[52] U.S. Cl. ........................ 514/468; 514/312; 514/337; 514/347; 514/407; 514/445; 514/522; 514/533; 514/529; 546/284.1; 546/293; 546/153; 548/370.1; 549/65; 549/461; 558/389; 560/13
[58] Field of Search ........................ 558/389; 549/65; 549/461; 546/284.1, 293, 153; 548/370.1; 560/13; 514/312, 337, 347, 407, 445, 468, 522, 533, 529

[56] References Cited

U.S. PATENT DOCUMENTS

| | | | |
|---|---|---|---|
| 4,038,247 | 7/1977 | Muller et al. | 260/45.9 |
| 4,447,419 | 5/1984 | Quadro | 424/177 |
| 4,518,528 | 5/1985 | Rasnick | 260/112.5 R |
| 4,638,010 | 1/1987 | Weller, III et al. | 514/423 |
| 4,749,792 | 6/1988 | Natarajan et al. | 546/312 |
| 4,994,471 | 2/1991 | Lalinde et al. | 514/326 |
| 5,057,525 | 10/1991 | Van Daele | 514/318 |
| 5,142,056 | 8/1992 | Kempe et al. | 546/265 |
| 5,206,251 | 4/1993 | Khanna et al. | 514/315 |
| 5,216,168 | 6/1993 | Khanna et al. | 546/242 |
| 5,374,637 | 12/1994 | Van Daele | 514/320 |
| 5,395,824 | 3/1995 | Higuchi et al. | 514/19 |
| 5,422,359 | 6/1995 | Ando et al. | 514/365 |
| 5,424,325 | 6/1995 | Ando et al. | 514/357 |
| 5,501,969 | 3/1996 | Hastings et al. | 435/240.2 |
| 5,523,313 | 6/1996 | Nunami et al. | 514/365 |
| 5,585,387 | 12/1996 | Lu et al. | 514/327 |
| 5,668,128 | 9/1997 | Tsubotani et al. | 514/183 |
| 5,830,850 | 11/1998 | Gelb et al. | 514/2 |

FOREIGN PATENT DOCUMENTS

| | | |
|---|---|---|
| 0 237 082 | 9/1987 | European Pat. Off. . |
| 0 504 938A2 | 3/1992 | European Pat. Off. . |
| 0 525 420 A1 | 2/1993 | European Pat. Off. . |
| 0 543 310 | 5/1993 | European Pat. Off. . |
| 0 603 873 A1 | 6/1994 | European Pat. Off. . |
| 0 611 756 A2 | 8/1994 | European Pat. Off. . |
| 0 623 592 | 11/1994 | European Pat. Off. . |
| WO 92/04371 | 3/1992 | WIPO . |
| WO 94/00095 | 1/1994 | WIPO . |
| WO 94/04172 | 3/1994 | WIPO . |
| WO 94/23033 | 10/1994 | WIPO . |
| WO 95/05192 | 2/1995 | WIPO . |
| WO 94/24182 | 9/1995 | WIPO . |
| WO 96/13523 | 5/1996 | WIPO . |
| WO 96/40737 | 12/1996 | WIPO . |
| WO 97/47642 | 12/1997 | WIPO . |
| WO 97/47643 | 12/1997 | WIPO . |
| WO97/49668 | 12/1997 | WIPO . |
| WO 98/05336 | 2/1998 | WIPO . |
| WO 98/08802 | 3/1998 | WIPO . |

OTHER PUBLICATIONS

Bossard, et al., (1996), J. of Bio. Chem;, vol. 271, No. 21, pp. 12517–12524.
Bromme, et al., (1996), Biochemical Journal, vol. 315, pp. 85–89, especially abstract, Figure 1.
Velasco, et al., (1994), J. of Bio. Chem; vol. 269, No. 43, pp. 27136–27142, especially the abstract.
Magrath, et al., (1992), J. of Med. Chem; vol. 35, No. 23, pp. 4279–4283, especially p. 4281, col. 1, structures 1–4 and 7.
Graybill, et al., (1992), Bioorganic & Medicinal Chemistry Letters; vol. 2, No. 11, pp. 1375–1380, especially p. 1377, Scheme I.
Palmer, et al., (1995), J. of Med. Chem; vol. 38, No. 17, pp. 3193–3196.
Danheiser, (1995), Genetic Engineering News; vol. 15, No. 17, pp. 1–1 and 35–36.
Rasnick, (1996), Perspectives in Drug Discovery & Design; vol. 6, pp. 48–63.
Potempa, et al., "Host and *Porphyromonas gingivalis* proteinases in periodontitis: A biochemical model of infection and tissue destruction", (1994), Perspectives in Drug Discovery and Design, vol. 2, pp. 445–458.
Drake, et al., "Cathepsin K, but Not Cathepsins B, L, or S, Is Abundantly Expressed in Human Osteoclasts", (1996), J. of Biological Chemistry, 271(21), pp. 12511–12516.
Bromme, et al., "Human Cathepsin 02, a Matrix Protein–degrading Cysteine Protease Expressed in Osteoclasts", (1996), J. of Biological Chemistry, 271(4), pp. 2126–2132.
Delaisse, et al., "In Vivo and In Vitro Evidence for the Involvment of Cysteine Proteinases in Bone Resorption", (1984), Biochemical and Biophysical Research Communications, 125(2), pp. 441–447.

(List continued on next page.)

*Primary Examiner*—Laura L. Stockton
*Attorney, Agent, or Firm*—Yuriy P. Stercho; Stephen A. Venetianer; Charles M. Kinzig

[57] ABSTRACT

The present invention provides compounds which inhibit proteases, including cathepsin K, pharmaceutical compositions of such compounds, and methods for treating diseases of excessive bone loss or cartilage or matrix degradation, including osteoporosis; gingival disease including gingivitis and periodontitis; arthritis, more specifically, osteoarthritis and rheumatoid arthritis; Paget's disease-hypercalcemia of malignancy; and metabolic bone disease, comprising inhibiting said bone loss or excessive cartilage or matrix degradation by administering to a patient in need thereof a compound of the present invention.

17 Claims, No Drawings

OTHER PUBLICATIONS

Delaisse, et al., "Inhibition of bone resorption in culture by inhibitors of thiol proteinases", (1980), Biochem. J., 192, pp. 365–368.

Lerner, et al., "Human Cystatin C, a Cysteine Proteinase Inhibitor, Inhibits Bone Resrporption In Vitro Stimulated by Parathyroid Hormone and Parathyroid Hormone–Related Peptide of Malignancy", (1992), J. of Bone and Mineral Research, 7(4), pp. 433–439.

Hill, et al., "Inhibition of Bone Resorption by Selective Inactivators of Cysteine Proteinases", (1994), J. of Cellular Biochemistry, 56, pp. 118–130.

Delaise, et al., "The Effects of Inhibitors of Cysteine–Proteinases and Collagenase on the Resorptive Activity of Isolated Osteoclasts", Bone, 8, pp. 305–313, 1987.

Borg, et al, "Synthesis of 1,2,4–Oxidiazole–, 1,3,4–Oxidiazole–, and 1,2,4–Triazole–Derived Dipeptidomietics", J. Org. Chem., 60, pp. 3112–3120, 1995.

Boden, et al, "Total Synthesis of Lissoclinamide 5, a Cytotoxic Cyclic Peptide from the Tunicate *Lissoclinum patella*", (1994), Tetrahedron. Ltrs., 35(44), pp. 8271–8274.

Everts, et al., "Degradation of Collagen in the Bone–Resorbing Compartment Underlying the Osteoclast Involves Both Cysteine–Proteinases and Matrix Metalloproteinases", (1992), Journal of Cellular Physiology, 150, pp. 221–231.

Shi, et al., "Molecular cloning of human cathepsin O, a novel endoproteinase and homologue of rabbit OC2", (1995), FEBS Ltrs., 357, pp. 129–134.

Inaoka, et al., "Molecular Cloning of Human cDNA for Cathepsin K: Novel Cysteine Proteinase Predominantly Expressed in Bone", (1995), Biochemical and Biophysical Research Communications, 206(1), pp. 89–96.

Elmore, et al., "A New Method for Determining the Absolute Molarity of Solutions of Trypsin and Chymotrypsin . . . ", (1968), Biochem J., 107, pp. 103–107.

Barker, et al., "The Reaction of a α–Aza–Amino Acid Derivative with Chymotrypsin and Its Use as a Ligand . . . ", (1974), Biochem J., 139, 555–563.

Gray, et al., "$N^\alpha$–Ethyloxycarbonyl–α–Azaornithine Phen . . . ", (1977), Tetrahedron, 33, pp. 837–840.

Tezuka, et al., "Molecular Cloning of a Possible Cysteine Proteinase Predominantly Expressed in Osteoclasts", (1994), J. Biolog. Chem., 269(2), pp. 1106–1109.

Gupton, et al., "Reaction of Azapeptides with Chymotrypsin–like Enzymes", (1984), J. Biol. Chem., 259:7, pp. 4279–4287.

Powers, et al., "Reaction of Azapeptides with Human Leukocyte Elastase and Pricine Pancreatic Elastase", (1984), J. Biol. Chem., 259:7, pp. 4288–4294.

McConnell, et al., "New Leupeptin Analogues: Synthesis and Inhibition Data", J. Med. Chem, 33, pp. 86–93, 1990.

Umezawa, "Structures and Activities of Protease Inhibitors of Microbial Origin", Meth. Enzymol., pp. 678–695, 1976.

Barrett, et al., "L–trans–Epoxysuccinyl–leucylamido(4–guanidino)butane (E–64) and its analogues . . . ", (1982), Biochem. J., 201, pp. 189–198.

Han et al., Azatides: "Solution and Liquid Phase Syntheses of a New Peptidomimetic", 1996, J. Amer. Chem. Soc., 118:11, pp. 2539–2544.

Grinde, "Selective Inhibition of Lysomal Protein Degradation By the Thiol Proteinase . . . " (1982), Biochem. J. Biophys. Acta., 701, pp. 328–333.

Baggio, et al., "From Poor Substrates to Good Inhibitors: Design of Inhibitors for Serine and Thiol Proteases", (1996), Biochem., 35:11, pp. 3351–3353.

Calabretta, et al., "Peptidyl and azapeptidyl methylketones as substrate analog inhibitors of papain and cathepsin B", (1995), Eur. J. Med. Chem., 30, pp. 931–941.

McConnell, et al., "Inhibition Studies of Some Serine and Thiol Proteinases by New Leupeptin Analogues", (1993), J. Med. Chem, 36, pp. 1084–1089.

Afridi, et al., "Heterocyclic Rearrangements. Part XIV. Attempts to Activate Ring–opening–Ring–closure Rearrangements with Carbon as the Central Atom", (1976), J.C.S. Perkin Trans I, vol. 3, pp. 315–320.

Kosary, et al., "Synthesis of pyridylthiazoles as antisecretory agents", (1989), Pharmazie, 44:3, pp. 191–193.

Sridevi, et al., "Some reactions and rearrangements of isoxazol–3–carbonyl azides and hydrazides", (1990), Indian J. of Chem., 29B:2, pp. 182–183.

Greenlee, et al., "Azapeptides: A New Class of Angiotensin–Converting Enzyme Inhibitors", (1984), Biochem. & Biophys. Research Communications, 122:2, pp. 791–797.

Auger, et al., "Solid–State 13C NMR Study of a Transglutaminase–Inhibitor Adduct", (1993), Biochemistry, vol. 32, No. 15, pp. 3930–3034.

Castelhano, et al., "Synthesis, Chemistry and Absolute Configuration of Novel Transglutaminase Inhibitors Containing a 3–Halo–4,5–dihydroisoxazole", (1988), Bioorg. Chem., vol. 16, No. 3, pp. 335–340.

Kawada, et al., "Polymer Compositions", (1971), Chemical Abstracts, vol. 83, DN 83: 180329; JP 50058142 (1975).

Thompson, et al., "Design of Potent and Selective Human Cathepsin K Inhibitors that Span the Active Site", (1997), Proc. Natl. Acad. Sci., vol. 94, pp. 14249–14254.

PROTEASE INHIBITORS

This application is a divisional application of Ser. No. 08/793,915, filed on Apr. 30, 1998; which is a 371 of International Application No. PCT/US96/18000 filed Oct. 30, 1996, which claims the benefit of priority of Provisional Application Nos. 60/008,108, filed Oct. 30, 1995, 60/007,473, filed Nov. 22, 1995, 60/008,992, filed Dec. 21, 1995, 60/013,748, filed Mar. 20, 1996, 60/013,764, filed Mar. 20, 1996, 60/013,747, filed Mar. 20, 1996, 60/017,455, filed May 17, 1996, 60/017,892, filed May 17, 1996, 60/022,047, filed Jul. 22, 1996 and 60/023,494, filed Aug. 7, 1996.

FIELD OF THE INVENTION

This invention relates in general to hydrazidyl, bis-hydrazidyl and bis-aminomethyl carbonyl protease inhibitors, particularly such inhibitors of cysteine and serine proteases, more particularly compounds which inhibit cysteine proteases, even more particularly compounds which inhibit cysteine proteases of the papain superfamily, yet more particularly compounds which inhibit cysteine proteases of the cathepsin family, most particularly compounds which inhibit cathepsin K. Such compounds are particularly useful for treating diseases in which cysteine proteases are implicated, especially diseases of excessive bone or cartilage loss, e.g., osteoporosis, periodontitis, and arthritis.

BACKGROUND OF THE INVENTION

Cathepsins are a family of enzymes which are part of the papain superfamily of cysteine proteases. Cathepsins B, H, L, N and S have been described in the literature. Recently, cathepsin K polypeptide and the cDNA encoding such polypeptide were disclosed in U.S. Pat. No. 5,501,969 (called cathepsin O therein). Cathepsin K has been recently expressed, purified, and characterized. Bossard, M. J., et al., (1996) *J. Biol. Chem* 271, 12517–12524; Drake, F. H., et al., (1996) *J. Biol. Chem* 271, 12511–12516; Bromme, D., et al., (1996) *J. Biol. Chem.* 271, 2126–2132.

Cathepsin K has been variously denoted as cathepsin O or cathepsin O2 in the literature. The designation cathepsin K is considered to be the more appropriate one.

Cathepsins function in the normal physiological process of protein degradation in animals, including humans, e.g., in the degradation of connective tissue. However, elevated levels of these enzymes in the body can result in pathological conditions leading to disease. Thus, cathepsins have been implicated as causative agents in various disease states, including but not limited to, infections by pneumocystis carinii, trypsanoma cruzi, trypsanoma brucei brucei, and *Crithidia fusiculata;* as well as in schistosomiasis, malaria, tumor metastasis, metachromatic leukodystrophy, muscular dystrophy, amytrophy, and the like. See International Publication Number WO 94/04172, published on Mar. 3, 1994, and references cited therein. See also European Patent Application EP 0 603 873 A1, and references cited therein. Two bacterial cysteine proteases from *P. gingivallis,* called gingipains, have been implicated in the pathogenesis of gingivitis. Potempa, J., et al. (1994) *Perspectives in Drug Discovery and Design,* 2, 445–458.

Cathepsin K is believed to play a causative role in diseases of excessive bone or cartilage loss. Bone is composed of a protein matrix in which spindle- or plate-shaped crystals of hydroxyapatite are incorporated. Type I collagen represents the major structural protein of bone comprising approximately 90% of the protein matrix. The remaining 10% of matrix is composed of a number of non-collagenous proteins, including osteocalcin, proteoglycans, osteopontin, osteonectin, thrombospondin, fibronectin, and bone sialoprotein. Skeletal bone undergoes remodelling at discrete foci throughout life. These foci, or remodelling units, undergo a cycle consisting of a bone resorption phase followed by a phase of bone replacement.

Bone resorption is carried out by osteoclasts, which are multinuclear cells of hematopoietic lineage. The osteoclasts adhere to the bone surface and form a tight sealing zone, followed by extensive membrane ruffling on their apical (i.e., resorbing) surface. This creates an enclosed extracellular compartment on the bone surface that is acidified by proton pumps in the ruffled membrane, and into which the osteoclast secretes proteolytic enzymes. The low pH of the compartment dissolves hydroxyapatite crystals at the bone surface, while the proteolytic enzymes digest the protein matrix. In this way, a resorption lacuna, or pit, is formed. At the end of this phase of the cycle, osteoblasts lay down a new protein matrix that is subsequently mineralized. In several disease states, such as osteoporosis and Paget's disease, the normal balance between bone resorption and formation is disrupted, and there is a net loss of bone at each cycle. Ultimately, this leads to weakening of the bone and may result in increased fracture risk with minimal trauma.

Several published studies have demonstrated that inhibitors of cysteine proteases are effective at inhibiting osteoclast-mediated bone resorption, and indicate an essential role for a cysteine proteases in bone resorption. For example, Delaisse, et al., *Biochem. J.,* 1980, 192, 365, disclose a series of protease inhibitors in a mouse bone organ culture system and suggest that inhibitors of cysteine proteases (e.g., leupeptin, Z-Phe-Ala-CHN$_2$) prevent bone resorption, while serine protease inhibitors were ineffective. Delaisse, et al., *Biochem Biophys. Res. Commun.,* 1984, 125, 441, disclose that E-64 and leupeptin are also effective at preventing bone resorption in vivo, as measured by acute changes in serum calcium in rats on calcium deficient diets. Lerner, et al., *J. Bone Min. Res.,* 1992, 7, 433, disclose that cystatin, an endogenous cysteine protease inhibitor, inhibits PTH stimulated bone resorption in mouse calvariae. Other studies, such as by Delaisse, et al., *Bone,* 1987, 8, 305, Hill, et al., *J Cell. Biochem,* 1994, 56, 118, and Everts, et al., *J. Cell. Physiol.,* 1992, 150, 221, also report a correlation between inhibition of cysteine protease activity and bone resorption. Tezuka, et al., *J. Biol. Chem.,* 1994, 269, 1106, Inaoka, et al., *Biochem Biophys. Res. Commun.,* 1995, 206, 89 and Shi, et al, *FEBS Lett.,* 1995, 357, 129 disclose that under normal conditions cathepsin K, a cysteine protease, is abundantly expressed in osteoclasts and may be the major cysteine protease present in these cells.

The abundant selective expression of cathepsin K in osteoclasts strongly suggests that this enzyme is essential for bone resorption. Thus, selective inhibition of cathepsin K may provide an effective treatment for diseases of excessive bone loss, including, but not limited to, osteoporosis, gingival diseases such as gingivitis and periodontitis, Paget's disease, hypercalcemia of malignancy, and metabolic bone disease. Cathepsin K levels have also been demonstrated to be elevated in chondroclasts of osteoarthritic synovium. Thus, selective inhibition of cathepsin K may also be useful for treating diseases of excessive cartilage or matrix degradation, including, but not limited to, osteoarthritis and rheumatoid arthritis. Metastatic neoplastic cells also typically express high levels of proteolytic enzymes that degrade the surrounding matrix. Thus, selective inhibition of cathepsin K may also be useful for treating certain neoplastic diseases.

Several cysteine protease inhibitors are known. Palmer, (1995) *J. Med. Chem.,* 38, 3193, disclose certain vinyl sulfones which irreversibly inhibit cysteine proteases, such as the cathepsins B, L, S, O2 and cruzain. Other classes of compounds, such as aldehydes, nitriles, α-ketocarbonyl compounds, halomethyl ketones, diazomethyl ketones, (acyloxy)methyl ketones, ketomethylsulfonium salts and epoxy succinyl compounds have also been reported to inhibit cysteine proteases. See Palmer, id, and references cited therein.

U.S. Pat. No. 4,518,528 discloses peptidyl fluoromethyl ketones as irreversible inhibitors of cysteine protease. Published International Patent Application No. WO 94/04172, and European Patent Application Nos. EP 0 525 420 A1, EP 0 603 873 A1, and EP 0 611 756 A2 describe alkoxymethyl and mercaptomethyl ketones which inhibit the cysteine proteases cathepsins B, H and L. International Patent Application No. PCT/US94/08868 and and European Patent Application No. EP 0 623 592 A1 describe alkoxymethyl and mercaptomethyl ketones which inhibit the cysteine protease IL-1β convertase. Alkoxymethyl and mercaptomethyl ketones have also been described as inhibitors of the serine protease kininogenase (International Patent Application No. PCT/GB91/01479).

Azapeptides which are designed to deliver the azaamino acid to the active site of serine proteases, and which possess a good leaving group, are disclosed by Elmore et al., *Biochem. J.,* 1968, 107, 103, Garker et al., *Biochem. J.,* 1974, 139, 555, Gray et al., *Tetrahedron,* 1977, 33, 837, Gupton et al.,*J. Biol. Chem.,* 1984, 259, 4279, Powers et al., *J. Biol. Chem.,* 1984, 259, 4288, and are known to inhibit serine proteases. In addition,*J. Med Chem.,* 1992, 35, 4279, discloses certain azapeptide esters as cysteine protease inhibitors.

Antipain and leupeptin are described as reversible inhibitors of cysteine protease in McConnell et al.,*J. Med. Chem.,* 33, 86; and also have been disclosed as inhibitors of serine protease in Umezawa et al., 45 *Meth. Enzymol.* 678. E64 and its synthetic analogs are also well-known cysteine protease inhibitors (Barrett, *Biochem. J.,* 201, 189, and Grinde, *Biochem Biophys. Acta,* 701, 328).

U.S. Pat. No. 5,142,056 describes 1,3-diamidopropanones which inhibit HIV protease. 1,3-diamidopropanones have also been described as analgesic agents (U.S. Pat. Nos. 4,749,792 and 4,638,010).

Certain heterocyclic derivatives of amino acids have been disclosed in the art. For instance, Hamada, et al., PEPTIDE CHEMISTRY, 1983. Proceedings of the 21st Symposium on Peptide Chemistry (1984), and Boden, et al., *Tet. Lett.,* 1994, 35, 8271 (1994) disclose thiazole derivatives; and Borg, et al., 1995, 60, 3112, disclose oxadiazole and triazole derivatives.

The synthesis of azatides (polyacylhydrazides) as peptide mimetics has recently been disclosed by Han and Janda, *J. Am. Chem. Soc.* 1996, 118, 2539.

Thus, a structurally diverse variety of cysteine protease inhibitors have been identified. However, these known inhibitors are not considered suitable for use as therapeutic agents in animals, especially humans, because they suffer from various shortcomings. These shortcomings include lack of selectivity, cytotoxicity, poor solubility, and overly rapid plasma clearance. A need therefore exists for methods of treating diseases caused by pathological levels of cysteine proteases, including cathepsins, especially cathepsin K, and for novel inhibitor compounds useful in such methods.

We have now discovered a novel class of hydrazidyl, bis-hydrazidyl and bis-aminomethyl carbonyl compounds which are protease inhibitors, most particularly of cathepsin K.

SUMMARY OF THE INVENTION

An object of the present invention is to provide hydrazidyl, bis-hydrazidyl and bis-aminomethyl carbonyl protease inhibitors, particularly such inhibitors of cysteine and serine proteases, more particularly such compounds which inhibit cysteine proteases, even more particularly such compounds which inhibit cysteine proteases of the papain superfamily, yet more particularly such compounds which inhibit cysteine proteases of the cathepsin family, most particularly such compounds which inhibit cathepsin K, and which are useful for treating diseases which may be therapeutically modified by altering the activity of such proteases.

Accordingly, in the first aspect, this invention provides a compound according to Formula I.

In another aspect, this invention provides a pharmaceutical composition comprising a compound according to Formula I and a pharmaceutically acceptable carrier, diluent or excipient.

In yet another aspect, this invention provides a method of treating diseases in which the disease pathology may be therapeutically modified by inhibiting proteases, particularly cysteine and serine proteases, more particularly cysteine proteases, even more particularly cysteine proteases of the papain superfamnily, yet more particularly cysteine proteases of the cathepsin family, most particularly cathepsin K.

In a particular aspect, the compounds of this invention are especially useful for treating diseases characterized by bone loss, such as osteoporosis and gingival diseases, such as gingivitis and periodontitis, or by excessive cartilage or matrix degradation, such as osteoarthritis and rheumatoid arthritis.

DETAILED DESCRIPTION

The present invention provides compounds of Formula I:

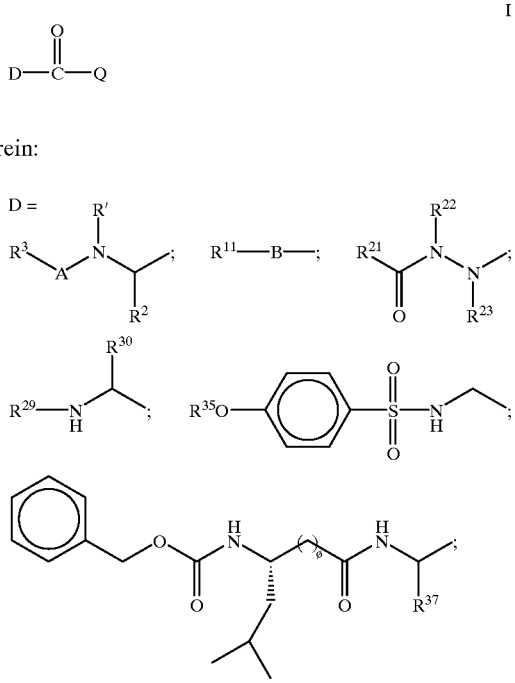

wherein:

-continued

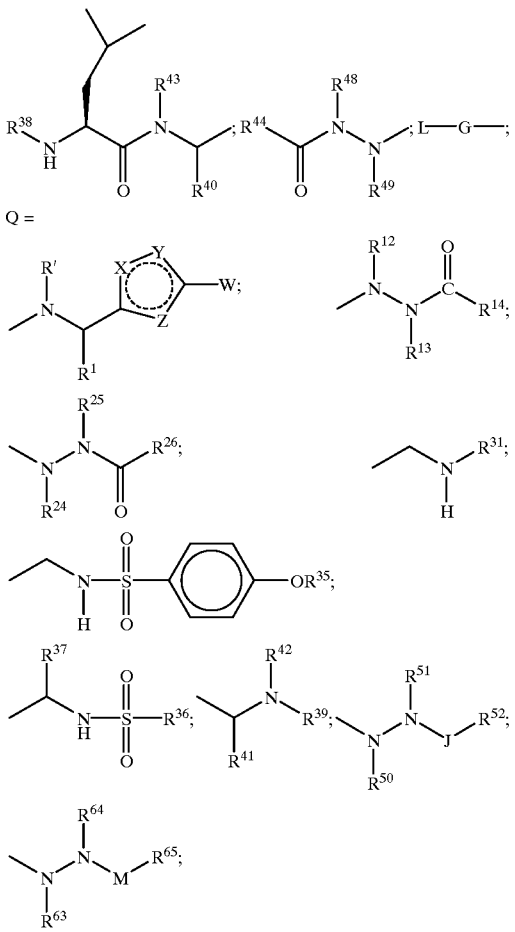

Q = where:

A = absent, 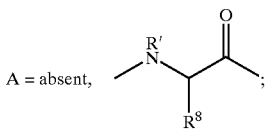

B = 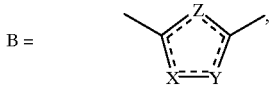

L=$C_{2-6}$alkyl, Ar-$C_{0-6}$alkyl, Het-$C_{0-6}$alkyl, CH($R^{66}$)N$R^{60}R^{68}$, CH($R^{66}$)Ar, CH($R^{66}$)OAr', N$R^{66}R^{67}$;
M=C(O), $SO_2$;

G = 

J=C(O), $SO_2$;
T=Ar, Het;
V=$C_{3-7}$cycloalkyl;
W=H, —CN, —$CF_3$, —$NO_2$, —$COR^7$, —$CO_2R^6$, —CONH$R^6$, —$SO_2$NH$R^6$, —NHS$O_2R^6$, —NHCO$R^7$, —O—CO$R^6$, —S$R^6$, NR'$R^6$, NR'(C=NH)NH$R^5$, Cl, Br, I, F;

X=Y=Z=N, O, S or $CR^4$,
provided that at least two of X, Y and Z are heteroatoms and at least one of X, Y and Z is N, or one of X, Y and Z is C=N, C=C or N=N and the other two are $CR^4$ or N, provided that X, Y and Z together comprise at least two N;

═ indicates a single or double bond in the five-membered heterocycle;
m=0, 1, 2;
n=1 to 6;
φ=0, 1, 2;
Ar=phenyl, naphthyl, optionally substituted by one or more of Ph-$C_{0-6}$alkyl, Het-$C_{0-6}$alkyl, $C_{1-6}$alkoxy, Ph-$C_{0-6}$alkoxy, Het-$C_{0-6}$alkoxy, OH, $(CH_2)_{1-6}NR^{58}R^{59}$, $O(CH_2)_{1-6}NR^{58}R^{59}$;
Ar'=phenyl or naphthyl, optionally substituted by one or more of Ph-$C_{0-6}$alkyl, Het-$C_{0-6}$alkyl, $C_{1-6}$alkoxy, Ph-$C_{0-6}$alkoxy, Het-$C_{0-6}$alkoxy, OH, $(CH_2)_{1-6}NR^{58}R^{59}$, $O(CH_2)_{1-6}NR^{58}R^{59}$, or halogen;
R'=H, $C_{1-6}$alkyl, Ar-$C_{0-6}$alkyl, Het-$C_{0-6}$alkyl;
$R^1$=H, $C_{1-6}$alkyl;
$R^2$=$C_{4-6}$alkyl, $C_{0-6}$alkenyl, benzyl;
$R^3$=$C_{1-6}$alkyl, Ar-$C_{0-6}$alkyl, Het-$C_{0-6}$alkyl, $R^5$CO—, $R^5SO_2$—, $R^5$OC(O)—, $R^5$NHCO—;
$R^4$=H, $C_{1-6}$alkyl, Ar-$C_{0-6}$alkyl, Het-$C_{0-6}$alkyl;
$R^5$=Ar$_{0-6}$alkyl, Het-$C_{0-6}$alkyl;
$R^6$=H, $C_{1-6}$alkyl, $CH_2CF_3$, Ar-$C_{0-6}$alkyl, Het-$C_{0-6}$alkyl;
$R^7$=$C_{1-6}$alkyl, Ar-$C_{0-6}$alkyl, Het-$C_{0-6}$alkyl;
$R^8$=H; $C_{2-6}$ alkenyl; $C_{2-6}$alkynyl; Het; Ar; $C_{1-6}$alkyl, optionally substituted by OR', SR', NR'$_2$, $CO_2$R', $CO_2$NR'$_2$, N(C=NH)$NH_2$, Het or Ar;
$R^9$=H, $C_{1-6}$alkyl, Ar-$C_{0-6}$alkyl, Het-$C_{0-6}$alkyl;
$R^{10}$=$C_{1-6}$alkyl, Ar-$C_{0-6}$alkyl, Het-$C_{0-6}$alkyl;
$R^{11}$=H, $C_{1-6}$alkyl, Ar-$C_{1-6}$alkyl, Het-$C_{0-6}$alkyl, or

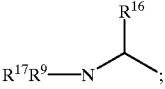

$R^{12}$=H, $C_{1-6}$alkyl, Ar-$C_{0-6}$alkyl, Het-$C_{0-6}$alkyl;
$R^{13}$=H, $C_{1-6}$alkyl, Ar-$C_{0-6}$alkyl, Het-$C_{0-6}$alkyl;

$R^{14}$ = 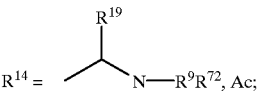

$R^{15}$=H, $C_{1-6}$alkyl, $C_{2-6}$alkenyl, $C_{2-6}$alkenyl, Ar, Het, or $C_{1-6}$alkyl optionally substituted by $OR^9$, $NR^9_2$, $CO_2R^9$, $CONR^9_2$, N(C=NH)NH—, Het or Ar;
$R^{16}$=$C_{2-6}$alkenyl, $C_{2-6}$alkynyl, $C_{2-6}$alkyl, Ar, Het, or $C_{2-6}$alkyl optionally substituted by $OR^9$, $SR^9$, $NR^9_2$, $CO_2R^9$, $CONR^9_2$, N(C=NH)NH—, Het or Ar;
$R^{19}$=H, $C_{1-6}$alkyl, $C_{2-6}$alkenyl, $C_{2-6}$alkynyl, Ar, Het, or $C_{1-6}$alkyl optionally substituted by $OR^9$, $SR^9$, $NR^9_2$, $CO_2R^9$, $CONR^9_2$, N(C=NH)NH—, Het or Ar;
$R^{17}$=$R^{72}$=H, $C_{1-6}$alkyl, $R^{10}$, $R^{10}$C(O)—, $R^{10}$C(S)—, $R^{10}$OC(O)—;
$R^{21}$=$R^{26}$=$C_{5-6}$alkyl; $C_{2-6}$alkenyl; $C_{3-11}$cycloalkyl; T-$C_{3-6}$alkyl; V-$C_{1-6}$alkyl; T-$C_{2-6}$ alkenyl; T-$(CH_2)_n$CH(T)$(CH_2)_n$; optionally substituted by one or two halogens, $SR^{20}$, $OR^{20}$, $NR^{20}R^{27}$ or $C_{1-4}$ alkyl;

$R^{27}=R^{28}CO, R^{28}OCO$;

$R^{28}=C_{1-6}$alkyl; $C_{3-11}$cycloalkyl; Ar; Het; T-$C_{1-6}$alkyl; T-$(CH_2)_nCH(T)(CH_2)_n$; optionally substituted by one or two halogens, $SR^{20}$, $OR^{20}$, $NR^{20}R^{73}$ or $C_{1-6}$alkyl;

$R^{20}=R^{22}=R^{23}=R^{24}=R^{25}=R^{73}=$H, $C_{1-4}$alkyl, Ar-$C_{0-6}$alkyl, Het-$C_{0-6}$alkyl;

$R^{29}=$

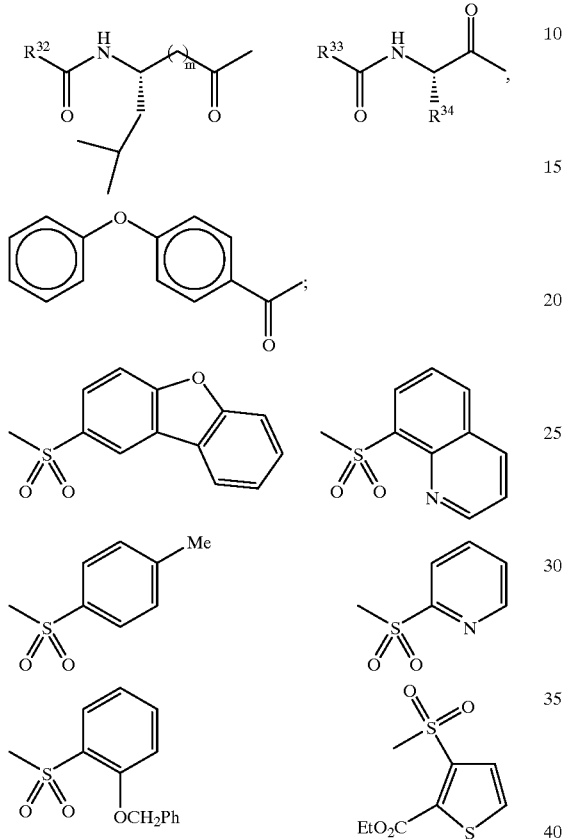

Cbz-leucinyl-; 2-, 3-, or 4-pyridyl methyloxycarbonyl-leucinyl-; 4-imidazole acetyl-leucinyl-, phenyl acetyl-leucinyl, N,N-dimethyl-glycinyl leucinyl, 4-pyridyl acetyl-leucinyl, 2-pyridyl sulfonyl-leucinyl, 4-pyridyl carbonyl-leucinyl, acetyl-leucinyl, benzoyl-leucinyl, 4-phenoxy-benzoyl-, 2- or 3-benzyloxybenzoyl-, biphenyl acetyl, alpha-isobutyl-biphenyl acetyl, Cbz-phenyalaninyl, Cbz-norleucinyl-, Cbz-norvalinyl-, Cbz-glutamyl-, Cbz-epsilon-(t-butyl ester)-glutamyl; acetyl-leucinyl-, 6- or 8-quinoline carbonyl, biphenyl acetyl, alpha-isobutyl-biphenyl acetyl, acetyl, benzoyl, 2- or 3-benzyloxy benzoyl, 4-phenoxy benzoyl-, Cbz-amino acid-; 2-, 3-, or 4-pyridylmethyloxycarbonyl-aminoacid-; aryl $C_0$–$C_6$alkyloxy carbonyl-amino acid-, heteroaryl $C_0$–$C_6$alkyloxy carbonyl-amino acid-, aryl $C_0$–$C_6$alkyloxy carbonyl-amino acid-, heteroaryl $C_0$–$C_6$alkyloxy carbonyl-amino acid-, $C_1$–$C_6$alkyloxy carbonyl-amino acid-; $C_1$–$C_6$alkyl carbonyl, aryl $C_0$–$C_6$alkyl carbonyl, heteroaryl $C_0$–$C_6$alkyl carbonyl, aryl $C_0$–$C_6$alkyl carbonyl, heteroaryl $C_0$–$C_6$alkyl carbonyl, $C_1$–$C_6$alkyl sulfonyl, aryl $C_0$–$C_6$alkyl sulfonyl, heteroaryl $C_0$–$C_6$alkyl sulfonyl, aryl $C_0$–$C_6$alkyl sulfonyl, heteroaryl $C_0$–$C_6$alkyl sulfonyl;

$R^{30}=$—H, $C_{1-6}$ alkyl;

$R^{31}=$

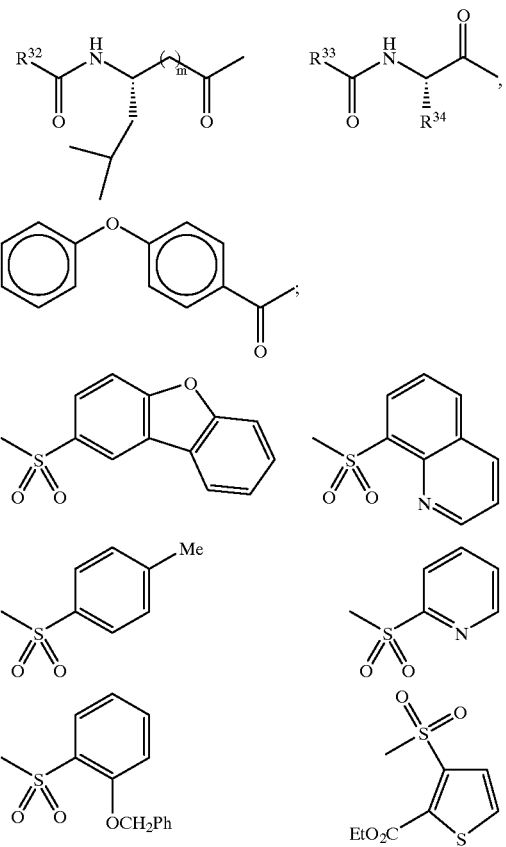

Cbz-leucinyl-; 2-, 3-, or 4-pyridyl methyloxycarbonyl-leucinyl-; 4-imidazole acetyl-leucinyl-, phenyl acetyl-leucinyl, N,N-dimethyl-glycinyl leucinyl, 4-pyridyl acetyl-leucinyl, 2-pyridyl sulfonyl-leucinyl, 4-pyridyl carbonyl-leucinyl, acetyl-leucinyl, benzoyl-leucinyl, 4-phenoxybenzoyl-, 2- or 3-benzyloxybenzoyl-, biphenyl acetyl, alpha-isobutyl-biphenyl acetyl, Cbz-phenylalaninyl, Cbz-norleucinyl-, Cbz-norvalinyl-, Cbz-glutamyl-, Cbz-epsilon-(t-butyl ester)-glutamyl; acetyl-leucinyl-, 6- or 8-quinoline carbonyl, biphenyl acetyl, alpha-isobutyl-biphenyl acetyl, acetyl, benzoyl, 2- or 3-benzyloxy benzoyl, 4-phenoxy benzoyl-, Cbz-amino acid-; 2-, 3-, or 4-pyridylmethyloxycarbonyl-aminoacid-; aryl $C_0$–$C_6$alkyloxy carbonyl-amino acid-, heteroaryl $C_0$–$C_6$alkyloxy carbonyl-amino acid-, aryl $C_0$–$C_6$alkyloxy carbonyl-amino acid-, heteroaryl $C_0$–$C_6$alkyloxy carbonyl-amino acid-, $C_1$–$C_6$alkyloxy carbonyl-amino acid-; $C_1$–$C_6$alkyl carbonyl, aryl $C_0$–$C_6$alkyl carbonyl, heteroaryl $C_0$–$C_6$alkyl carbonyl, aryl $C_0$–$C_6$alkyl carbonyl, heteroaryl $C_0$–$C_6$alkyl carbonyl, $C_1$–$C_6$alkyl sulfonyl, aryl $C_0$–$C_6$alkyl sulfonyl, heteroaryl $C_0$–$C_6$alkyl sulfonyl, aryl $C_0$–$C_6$alkyl sulfonyl, heteroaryl $C_0$–$C_6$alkyl sulfonyl;

$R^{32}=$OCH$_2$Ar, OCH2$C_{1-6}$alkyl, aryl substituted $C_{0-6}$alkyl, heteroaryl substituted $C_{0-6}$alkyl, 4-imidazole methylene; 2-, 3-, or 4-pyridylmethylneneoxy; 4-pyridyl methylene, 2-pyridyl sulfonyl, 4-pyridyl, aryl substituted $C_{0-6}$alkyloxy, heteroaryl substituted $C_{0-6}$alkyloxy;

$R^{33}$=$C_{1-6}$alkyl, —$CH_2Ph$, —$CH_2CH_2CO_2R^{34}$;
$R^{34}$=—H, $C_{1-6}$alkyl;
$R^{35}$=Ar, HetAr;
$R^{36}$=Aryl, heteroaryl, pyridyl, isoquinolinyl;
$R^{37}$=$C_{1-6}$alkyl, —$CH_2Ph$, —$CH_2CH_2CO_2R^{34}$;
$R^{38}$=Cbz; $C_{1-6}$alkyl or aryl substituted Cbz; $C_{1-6}$alkyl —CO; benzoyl; $C_{1-6}$alkyl or aryl substituted benzoyl;

$R^{39}$ =

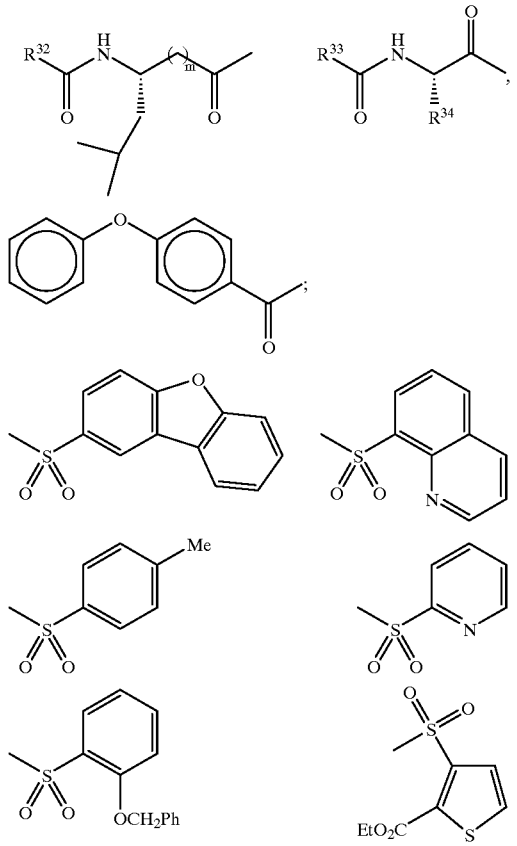

Cbz-leucinyl-; 2-, 3-, or 4-pyridyl methyloxycarbonyl-leucinyl-; 4-imidazole acetyl-leucinyl-, phenyl acetyl-leucinyl, N,N-dimethyl-glycinyl leucinyl, 4-pyridyl acetyl-leucinyl, 2-pyridyl sulfonyl-leucinyl, 4-pyridyl carbonyl-leucinyl, acetyl-leucinyl, benzoyl-leucinyl, 4-phenoxy-benzoyl-, 2- or 3-benzyloxybenzoyl-, biphenyl acetyl, alpha-isobutyl-biphenyl acetyl, Cbz-phenylalaninyl, Cbz-norleucinyl-, Cbz-norvalinyl-, Cbz-glutamyl-, Cbz-epsilon-(t-butyl ester)-glutamyl; acetyl-leucinyl-, 6- or 8-quinoline carbonyl, biphenyl acetyl, alpha-isobutyl-biphenyl acetyl, acetyl, benzoyl, 2- or 3-benzyloxy benzoyl, 4-phenoxy benzoyl-,
Cbz-amino acid-; 2-, 3-, or 4-pyridylmethyloxycarbonyl-amino acid-; aryl $C_0$–$C_6$alkyloxy carbonyl-amino acid-, heteroaryl $C_0$–$C_6$alkyloxy carbonyl-amino acid-, aryl $C_0$–$C_6$alkyloxy carbonyl-amino acid-, heteroaryl $C_0$–$C_6$alkyloxy carbonyl-amino acid-, $C_1$–$C_6$alkyloxy carbonyl-amino acid-; $C_1$–$C_6$alkyl carbonyl, aryl $C_0$–$C_6$alkyl carbonyl, heteroaryl $C_0$–$C_6$alkyl carbonyl, aryl $C_0$–$C_6$alkyl carbonyl, heteroaryl $C_0$–$C_6$alkyl carbonyl, $C_1$–$C_6$alkyl sulfonyl, aryl $C_0$–$C_6$alkyl sulfonyl, heteroaryl $C_0$–$C_6$alkyl sulfonyl, aryl $C_0$–$C_6$alkyl sulfonyl, heteroaryl $C_0$–$C_6$alkyl sulfonyl;

$R^{40}$=H and $C_{1-6}$alkyl;

$R^{41}$=H and $C_{1-6}$alkyl;

$R^{42}$=$C_{1-6}$alkyl, aryl substituted $C_{1-6}$alkyl and hetero aryl substituted $C_{1-6}$alkyl; H when $R^{43}$ is $C_{1-6}$alkyl, aryl substituted $C_{1-6}$alkyl; and heteroaryl substituted $C_{1-6}$alkyl;

$R^{43}$=$C_{1-6}$alkyl, aryl substituted $C_{1-6}$alkyl and hetero aryl substituted $C_{1-6}$alkyl; H when $R^{42}$ is $C_{1-6}$alkyl, aryl substituted $C_{1-6}$alkyl; and heteroaryl substituted $C_{1-6}$alkyl;

$R_{44}$=$CH(R^{53})NR^{45}R^{54}$, $CH(R^{55})Ar$, $C_{5-6}$alkyl;

$R^{45}$=$R^{46}$=$R^{47}$=$R^{48}$=$R^{49}$=$R^{50}$=$R^{51}$=H, $C_{1-6}$alkyl, Ar-$C_{0-6}$alkyl, Het-$C_{0-6}$alkyl;

$R^{52}$=Ar, Het, $CH(R^{56})Ar$, $CH(R^{56})OAr$, $N(R^{56})Ar$, $C_{1-6}$alkyl, $CH(R^{56})NR^{46}R^{57}$;

$R^{53}$=$C_{2-6}$alkyl, Ar-$C_{0-6}$alkyl, Het-$C_{0-6}$alkyl, $R^{53}$ and $R^{45}$ may be connected to form a pyrrolidine or piperidine ring;

$R^{54}$=$R^{57}$=$R^{47}$, $R^{47}C(O)$, $R^{47}C(S)$, $R^{47}OC(O)$;

$R^{55}$=$R^{56}$=$R^{58}$=$R^{59}$=H, $C_{1-6}$alkyl, Ar-$C_{0-6}$alkyl, Het-$C_{0-6}$alkyl;

$R^{60}$=$R^{61}$=$R^{62}$=$R^{63}$=$R^{64}$=H, $C_{1-6}$alkyl, Ar-$C_{0-6}$alkyl, or Het-$C_{0-6}$alkyl;

$R^{65}$=$C_{1-6}$alkyl, Ar, Het, $CH(R^{69})Ar$, $CH(R^{69})OAr$, $N(R^{69})Ar$, $CH(R^{69})NR^{61}R^{70}$;

$R^{66}$=$R^{69}$=$R^{71}$=H, $C_{1-6}$alkyl, $(CH_2)_{0-6}$-$C_{3-6}$cycloalkyl, Ar-$C_{0-6}$alkyl, Het-$C_{0-6}$alkyl;

$R^{67}$=$C_{1-6}$alkyl, $(CH_2)_{0-6}$-$C_{3-6}$cycloalkyl, Ar-$C_{0-6}$alkyl, Het-$C_{0-6}$alkyl; $R^{66}$ and $R^{67}$ may be combined to form a 3–7 membered monocyclic or 7–10-membered bicyclic carbocyclic or heterocyclic ring, optionally substituted with 1–4 of $C_{1-6}$alkyl, Ph-$C_{0-6}$alkyl, Het-$C_{0-6}$alkyl, $C_{1-6}$alkoxy, Ph-$C_{0-6}$alkoxy, Het-$C_{0-6}$alkoxy, OH, $(CH_2)_{1-6}NR^{58}R^{59}$, $O(CH_2)_{1-6}NR^{58}R^{59}$;

$R^{68}$=$R^{70}$=$R^{62}$, $R^{62}C(O)$, $R^{62}C(S)$, $R^{62}OC(O)$, $R^{62}OC(O)NR^{59}CH(R^{71})(CO)$;

and pharmaceutically acceptable salts thereof.

The compounds of Formula I are hydrazidyl, bis-hydrazidyl and bis-aminomethyl carbonyl compounds having in common key structural features required of protease substrates, most particularly cathepsin K substrates. These structural features endow the present compounds with the appropriate molecular shape necessary to fit into the enzymatic active site, to bind to such active site, and to react with a sulfhydryl group on the active site, thereby blocking the site and inhibiting enzymatic biological activity. Referring to Formula I, such structural features include the central electrophilic carbonyl, a peptidyl or peptidomimetic molecular backbone on either side of the central carbonyl, a terminal carbobenzyloxy moiety (e.g., Cbz-leucinyl), or a mimic thereof, on the backbone on one or both sides of the carbonyl, and optionally, an isobutyl side chain extending from the backbone on one or both sides of the carbonyl.

Compounds of Formula I wherein

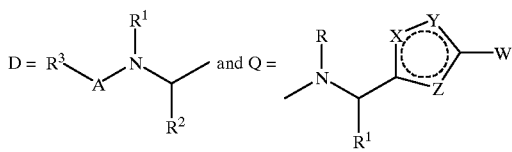

are preferred embodiments of the present invention. For the sake of convenience, such compounds are referred to herein after as compounds of Formula II.

More preferred embodiments of the present invention include compounds of Formula II wherein:
X=S, Y=CH, and Z=N;
X=CH, Y=S, and Z=N;
X=N, Y=N, and Z=S;
X=N, Y=N, and Z=O; and
X=N, Y=N, and Z=N.

Preferably $R^1$ is H, methyl or isobutyl. Preferably $R^1$ is isobutyl.

Preferably $R^2$ is isobutyl or benzyl.

Preferably $R^3$ is $R^5OC(O)$—, particularly benzyloxycarbonyl.

Preferably A is a D- or L- amino acid or is absent, preferably A is absent

Preferably W is CN, $NHR^6$, $SR^6$, $CONHR^6$ or $CO_2R^6$. Suitably $R^6$ is H, $C_{1-4}$alkyl, phenyl or benzyl. Typically, W is $CO_2H$, $CO_2$-$C_{1-4}$alkyl, $CO_2$-Ph, $CO_2$-$CH_2$Ph, $CONH_2$, $NH_2$ or SH.

The following compounds of Formula II are particularly preferred:

(2S,1'S)-2-(benzyloxycarbonyl)amino-N-[1'-(2-carboxythiazol-4-yl)-3'-methylbutyl]4-methylpentanamide;
(2S,1'S)-2-(benzyloxycarbonyl)amino-N-[1'-(2-carboxamidothiazol-4-yl)-3'-methylbutyl]-4-methylpentanamide;
(2S,1'S)-2-(benzyloxycarbonyl)amino-N-[1'-(2-carboethoxythiazol-4-yl)-3'-methylbutyl]-4-methylpentanamide;
(2S,1'S)-2-(benzyloxycarbonyl)amino-N-[1'-(2-cyanothiazol-4-yl)-3'-methylbutyl]-4-methylpentanamide;
(2S,1'S)-2-(benzyloxycarbonyl)amino-N-[1'-[2-(N'-benzylcarboxamido)thiazol-4-yl]-3'-methylbutyl]-4-methylpentanamide;
(2S,1'S)-2-(benzyloxycarbonyl)amino-N-[1'-[2-[N'-3-methylpropyl)carboxamido]thiazol-4-yl)]-3'-methylbutyl]-4-methylpentanamide;
(2S,1'S)-2-(benzyloxycarbonyl)amino-N-[1'-[2-[N'-2-phenylethyl) carboxamido]thiazol-4-yl)]-3'-methylbutyl]-4-methylpentanamide;
(2S,1'S)-2-(benzyloxycarbonyl)amino-N-[1'-(4-carboethoxythiazol-2-yl)-3'-methylbutyl]-4-methylpentanamide;
(2S,1'S)-2-(benzyloxycarbonyl)amino-N-[1'-(4-carboxythiazol-2-yl)-3'-methylbutyl]-4-methylpentanamide;
(2S,1'S)-2-(benzyloxycarbonyl)amino-N-[1'-(4-carboethoxythiadiazol-2-yl)-3'-methylbutyl]-4-methylpentanamide;
(2S,1'S)-2-(benzyloxycarbonyl)amino-N-[1'-(2-carbo-2,2,2-trifluoroethoxythiazol-4-yl)-3'-methylbutyl]-4-methylpentanamide;
(2S,1'S)-2-(benzyloxycarbonyl)amino-N-[1'-(4-carboethoxyoxadiazol-2-yl)-3'-methylbutyl]4-methylpentanamide;
(2S,1'S)-2-(benzyloxycarbonyl-L-leucinyl)amino-N-[1'-(4-carboethoxythiazol-2-yl)-3'-methylbutyl]-4-methylpentanamide;
(2S,1'S)-2-(benzyloxycarbonyl)amino-N-[1'-(4-carboxamidooxadiazol-2-yl)-3'-methylbutyl]-4-methylpentanamide;
(2S,1'S)-2-(benzyloxycarbonyl)amino-N-[1'-(2-carboethoxythiazol-4-yl)-3'-methylbutyl]-3-phenylpropanamide;
(2S,1'S)-2-(benzyloxycarbonyl-L-leucinyl)amino-N-[1'-(2-carboethoxythiazol-4-yl)-3'-methylbutyl]-4-methylpentanamide;
(2S,1'S)-2-(benzyloxycarbonyl)amino-N-[1'-(5-mercapto-1,2,4-oxadiazol-3-yl)-3'-methylbutyl]-4-methylpentanamide;
(2S,1'S)-2-(benzyloxycarbonyl)amino-N-[1'-(2-mercaptothiazol-4-yl)-3'-methylbutyl]-4-methylpentanamide;
(2S)-2-(benzyloxycarbonyl)amino-N-(4-carboethoxythiazol-2-yl)methyl-4-methylpentanamide;
(2S,1'S)-2-(benzyloxycarbonyl)amino-N-[1'-(2-benzyloxycarbonylthiazol-4-yl)-3'-methylbutyl]-4-methylpentanamide;
(2S,1'S)-2-(benzyloxycarbonyl)amino-4-methyl-N-[3'-methyl-1'-(2-phenoxycarbonylthiazol-4-yl)butyl]pentanamide;
(2S,1'S)-2-(benzyloxycarbonyl)amino-4-methyl-N-[3'-methyl-1'-[2-(2-methylpropyloxycarbonyl)thiazol-4-yl]butyl]pentanamide;
(2R,1'S)-2-(benzyloxycarbonyl)amino-N-[1'-(carboethoxythiazol-2-yl)ethyl]-4-methylpentanamide;
(2R,1'R)-2-(benzyloxycarbonyl)amino-N-[1'-(4-carbethoxythiazol-2-yl)ethyl]-4-methylpentanamide; and
(2S,1'S)-N-[1'-(2-aminothiazol-4-yl)-3'-methylbutyl]-2-(benzyloxycarbonyl)amino-4-methylpentanamide.

Most particularly preferred compounds of Formula II are:

(2S,1'S)-2-(benzyloxycarbonyl)amino-N-[1'-(2-carboethoxythiazol-4-yl)-3'-methylbutyl]-4-methylpentanamide;
(2S,1'S)-2-(benzyloxycarbonyl)amino-N-[1'-(4-carboethoxythiazol-2-yl)-3'-methylbutyl]-4-methylpentanamide; and
2S,1'S)-2-(benzyloxycarbonyl-L-leucinyl)amino-N-[1'-(4-carboethoxythiazol-2-yl)-3'-methylbutyl]-4-methylpentanamide.

Compounds of Formula I wherein

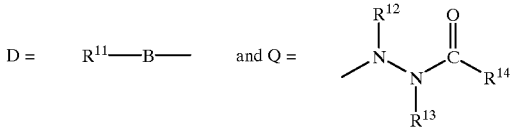

are preferred embodiments of the present invention. For the sake of convenience, such compounds are referred to herein after as compounds of Formula III.

With respect to compounds of Formula III:
Preferably B is

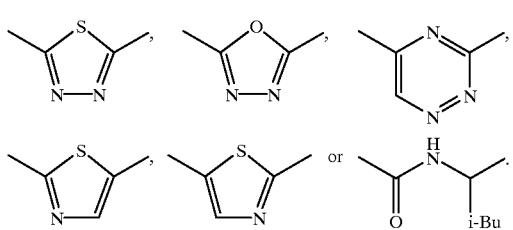

More preferably B is

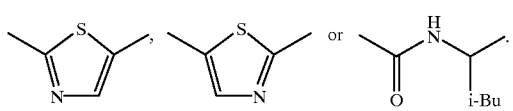

Preferably $R^{11}$ is

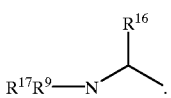

Preferably $R^{12}$ and $R^{13}$ are H.
Preferably $R^{14}$ is

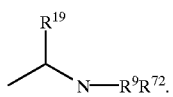

Preferably $R^{15}$, $R^{16}$, $R^{18}$ and $R^{19}$ are $C_{1-6}$alkyl.
More preferably $R^{15}$ and $R^{18}$ are $C_{4-6}$alkyl.
Preferably Ar is phenyl optionally substituted by one or two groups chosen from halogen, $CF_3$, $NO_2$, $SR^9$, $OR^9$, $NR_9$ or $C_{1-4}$alkyl.
Preferably $R^{17}$ and $R^{72}$ are $R^{10}OC(O)$—; and more preferably $R^{10}$ is Ar-$C_{1-4}$alkyl.
Preferably, $R^{16}$ and $R^{19}$ are $C_{4-6}$alkyl; more preferably, $R^{16}$ and $R^{19}$ are i-Bu.
Preferably $R^{17}$ and $R^{72}$ are Cbz.
One particular embodiment of the invention of Formula III is a compound of Formula F:

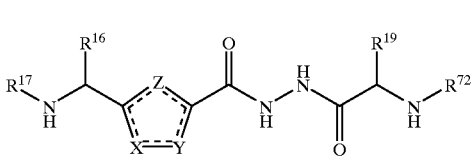

wherein X, Y, Z, $R^{16}$, $R^{17}$, $R^{19}$ and $R^{72}$ are as described in Formula III.
Most particularly preferred compounds of Formula III are:

(1S)-N-[4-[(1-benzyloxycarbonylamino)-3-methylbutyl] thiazol-2-ylcarbonyl]-N'-(N-benzyloxycarbonyl-L-leucinyl)hydrazide;
N-benzyloxycarbonyl-L-leucinyl-N'-benzyloxycarbonyl-L-leucinyl-L-leucinylhydrazide; and
(1S)-N-[2-[(1-benzyloxycarbonylamino)-3-methylbutyl] thiazol-4-ylcarbonyl]-N'-(N-benzyloxycarbonyl-L-leucinyl)hydrazide.

Compounds of Formula I wherein

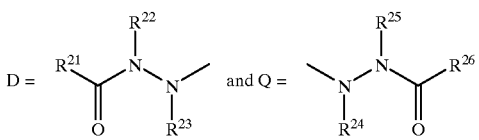

are preferred embodiments of the present invention. For the sake of convenience, such compounds are referred to herein after as compounds of Formula IV.

A more preferred embodiment of the present invention is a compound of Formula IV wherein $R^{21}$ and $R^{26}$ are selected from the group consisting of:

N-Cbz-leucinyl, N-Cbz-glycinyl, N-acetyl-leucinyl, N-Cbz-alanyl.

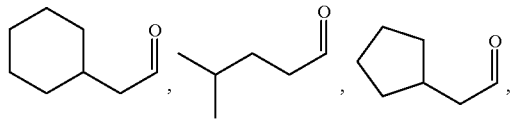

and $R^{22}$, $R^{23}$, $R^{24}$ and $R^{25}$ are H.
Particularly preferred embodiments of Formula IV are:

2,2'-(N,N'-bis-benzyloxycarbonyl-L-leucinyl) carbohydrazide;
2,2'-(N,N'-bis-cyclohexylacetyl)carbohydrazide;
2,2'-(N,N'-bis-4-methylpentanoyl)carbohydrazide;
2,2'-(N,N'-bis-cyclopentylacetyl)carbohydrazide;
2,2'-(N,N'-bis-benzyloxycarbonylglycinyl)carbohydrazide;
2,2'-(N,N'-bis-acetyl-L-leucinyl)carbohydrazide;
2,2'-(N,N'-bis-benzyloxycarbonyl-L-alanyl)carbohydrazide; and
2-(N-benzyloxycarbonyl-L-leucinyl)-2'-[N'-(4-methylpentanoyl)]carbohydrazide.
2,2'-(N,N'-bis-benzyloxycarbonyl-L-leucinyl) carbohydrazide is a most preferred embodiment of Formula IV.

Compounds of Formula I wherein

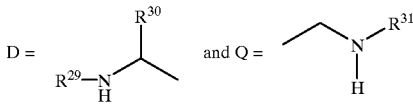

are preferred embodiments of the present invention. For the sake of convenience, such compounds are referred to herein after as compounds of Formula V.

In more preferred compounds of Formula V, when $R^{30}$= $C_1$–$C_6$ allyl, $R^{30}$ is preferably Me or —$CH_2CH_2Me_2$. When $R^{33}$=$C_1$—$C_6$ alkyl, $R^{33}$ is preferably —Pr, —Bu, or —$CH_2CH_2Me_2$. When $R^{34}$=$C_1$–$C_6$ alkyl, $R^{34}$ is preferably -t-Bu.
Even more preferred embodiments of Formula V include:

bis-(Cbz-leucinyl)-1,3-diamino-propan-2-one;
bis-1,3-(4-phenoxy-benzoyl)-diamino-propan-2-one;
1-(Cbz-leucinyl)-amino-3-(acetyl-leucinyl)-amino-propan-2-one;
1-(Cbz-leucinyl)-amino-3-(Cbz-glutamyl-t-butyl ester)-amino-propan-2-one;
1-(Cbz-leucinyl)-amino-3-(Cbz-glutamyl)-amino-propan-2-one;

bis-1,3-(Cbz-leucinyl)-diamino-(S)-butanone-2-one;
1-(Cbz-leucinyl)-amino-3-(Cbz-phenylalanyl)-amino-propan-2-one;
1-(Cbz-leucinyl)-amino-3-(Cbz-norleucinyl)-amino-propan-2-one;
1-(Cbz-leucinyl)-amino-3-(Cbz-norvalinyl)-amino-propan-2-one;
bis-1,3-(Cbz-leucinyl)-diamino-5-methyl-(S)-hexan-2-one;
1-(acetyl-leucinyl)-amino-3-(4-phenoxy-benzoyl)-amino-propan-2-one;
1-(Cbz-homo-leucinyl)-amino-(Cbz-leucinyl)-3-amino-propan-2-one;

1-(Cbz-leucinyl)-amino-3-(acetyl-leucinyl)-amino-propan-2-one is a most particularly preferred embodiment of the present invention of Formula V.

Compounds of Formula I wherein

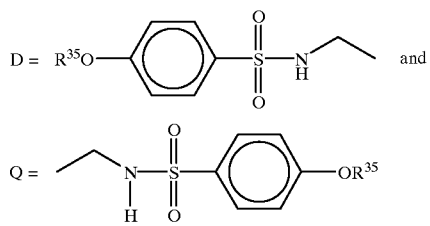

are preferred embodiments of the present invention. For the sake of convenience, such compounds are referred to herein after as compounds of Formula VI.

More preferably, $R^{35}$=Ph,

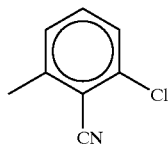

or pyridine, even more preferably,

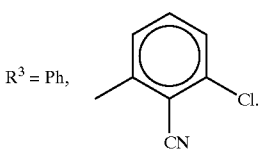

Ph may be optionally substituted with $C_{1-6}$alkyl, $C_{1-6}$alkoxy, halogens and cyano groups. When $R^{35}$=pyridine, R may be 2-pyridyl, 3-pyridyl, or 4-pyridyl.

Most particularly preferred embodiments of Formula VI include:

bis-1,3-(4-(3-chloro-2-cyano-phenoxy)-phenyl sulfonamido)-propan-2-one;
bis-1,3-(4-phenoxy-phenyl sulfonamido)-propan-2-one.

Compounds of Formula I wherein

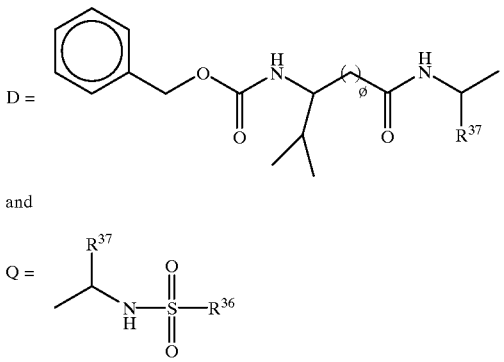

are preferred embodiments of the present invention. For the sake of convenience, such compounds are referred to herein after as compounds of Formula VII.

More preferably, $R^{36}$ is selected from the group consisting of:

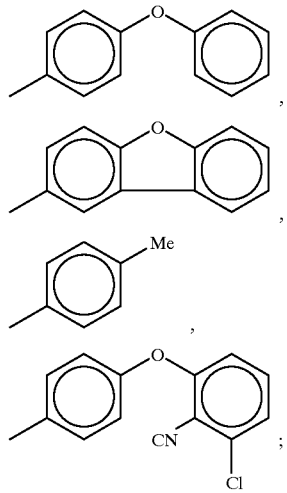

and $R^{37}$=Me in the more preferred compounds of Formula VII.

Particularly preferred embodiments of Formula VII are:

1-(Cbz-leucinyl)-amino-3-(4-(3-chloro-2-cyano-phenoxy)-phenyl sulfonamido)-propan-2-one;
1-(Cbz-leucinyl)-amino-3-(tosyl-amino)-propan-2-one;
1-(Cbz-leucinyl)-amino-3-((4-phenoxy-phenyl)-sulfonamido)-propan-2-one;
1-(Cbz-leucinyl)-amino-3-(2-dibenzofuransulfonamido)-propan-2-one;
1-(Cbz-homo-leucinyl)-amino-3-(2-dibenzofuransulfonamido)-propan-2-one; and
1-(Cbz-leucinyl)-amino-3-(2-dibenzofuransulfonamido)-(S)-butan-2-one.

1-(Cbz-leucinyl)-amino-3-((4-phenoxy-phenyl)-sulfonamido)-propan-2-one, 1-(Cbz-leucinyl)-amino-3-(2-dibenzofuransulfonamido)-propan-2-one, and 1-(Cbz-leucinyl)-amino-3-(2-dibenzofuransulfonamido)-(S)-butan-2one are most particularly preferred embodiments of Formula VII.

Compounds of Formula I wherein

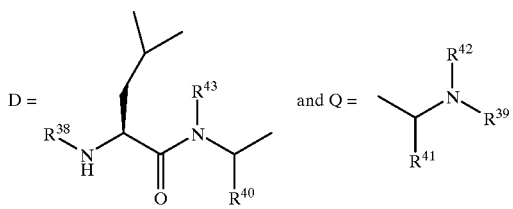

are preferred embodiments of the present invention. For the sake of convenience, such compounds are referred to herein after as compounds of Formula VIII.

A more preferred embodiment of Formula VIII is when $R^{43}$ is 2-dibenzofuranylsulfonyl.

Particularly preferred embodiments of Formula VIII are:

(S)-Phenylmethyl [1-[[[3-[benzyloxycarbonyl-leucinyl-amino]-2-oxopropyl]-1-(benzyl)amino]carbonyl]-3-methylbutyl]carbamate.

(S)-Phenylmethyl [1-[[[3-[(2-dibenzofuranylsulfonyl)amino]-2-oxopropyl]-3-(benzyl)amino]carbonyl]-3-methylbutyl]carbamate (S)-Phenylmethyl [1-[[[3-[(2-dibenzofuranylsulfonyl)amino]-2-oxopropyl]-3-(4-pyridinylmethyl)amino]carbonyl]-3-methylbutyl]carbamate 1-[[[3-[(2-dibenzofuranylsulfonyl)amino]-2-oxopropyl]-3-(4-pyridinylmethyl) benzamide (S)-Phenylmethyl [1-[[[3-[(2-dibenzofuranylsulfonyl)amino]-2-oxopropyl]-1-(4-pyridinylmethyl)amino]carbonyl]-3-methylbutyl]carbamate.

(S)-Phenylmethyl [1-[[[3-[(2-dibenzofuranylsulfonyl)amino]-2-oxopropyl]-1-(4-pyridinylmethyl)amino]carbonyl]-3-methylbutyl]carbamate is a most particularly preferred embodiment of Formula VIII.

Compounds of Formula I wherein

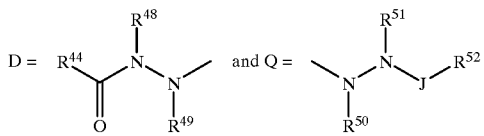

are preferred embodiments of the present invention. For the sake of convenience, such compounds are referred to herein after as compounds of Formula IX.

Compounds of Formula IX wherein:
$R^{44}CH(R^{53})NHR^{54}$;
$R^{45}, R^{46}, R^{48}, R^{49}, R^{50}$ and $R^{51}$ are H;
$R^{47}$ is independently $CH_3$, benzyl, 2-pyridinylmethoxy, 4-dimethylaminobenzyl;
J=C(O);
$R^{52}$=Ar, $CH(R^{10})Ar$, $CH(R^{10})OAr$, $N(R^{10})Ar$, $CH(R^{10})NR''R^{11}$;
$R^{53}$=ethyl, i-Bu;
$R^{54}=R^{47}$, $R^{47}C(O)$, $R^{47}OC(O)$;
$R^{56}$=H, $CH_3$, i-Bu;
$R^{57}=R^{47}$, $R^{47}OC(O)$;
Ar=phenyl or naphthyl, optionally substituted by one or more of Ph-$C_{0-6}$alkyl, Het-$C_{0-6}$alkyl, $C_{1-6}$alkoxy, Ph-$C_{0-6}$alkoxy, Het-$C_{0-6}$alkoxy, OH, $(CH_2)_{1-6}NR^{58}R^{59}$, $O(CH_2)_{1-6}NR^{58}R^{59}$;

$R^{58}, R^{59}$=H, $C_{1-6}$alkyl, Ar-$C_{0-6}$alkyl; Het-$C_{0-6}$alkyl,
are more preferred embodiments of the present invention.

The following compounds of Formula IX are particularly preferred:

2-[N-(N-benzyloxycarbonyl-L-leucinyl)]-2'-[N'-(4-phenoxyphenylsulfonyl)]carbohydrazide;

2-[N-(N-benzyloxycarbonyl-L-alanyl)]-2'-[N-(N-benzyloxycarbonyl-L-leucinyl)]carbohydrazide;

2-[N-(N-benzyloxycarbonyl-L-leucinyl)]-2'-[N'-(4-phenylbenzoyl)]carbohydrazide;

2-[N-(N-benzyloxycarbonyl-L-leucinyl)]-2'-[N'-4-methoxybenzoyl)]carbohydrazide;

2-[N-(N-benzyloxycarbonyl-L-leucinyl)]-2'-[N'-(4-phenoxybenzoyl)]carbohydrazide;

2-(N-acetyl)-2'-[N'-(N-benzyloxycarbonyl-L-leucinyl)]carbohydrazide;

2-[N-(N-acetyl-L-leucinyl)]-2'-[N'-(N-benzyloxycarbonyl-L-alanyl)]carbohydrazide;

2-[N-(N-acetyl-L-alanyl)]-2'-[N'-(N-benzyloxycarbonyl-L-leucinyl)]carbohydrazide;

2-[N-(N-benzyloxycarbonyl-L-leucinyl)]-2'-[N'-[4-(N,N-dimethylaminomethyl)benzoyl)]]carbohydrazide;

2-[N-(N-benzyloxycarbonyl-L-leucinyl)]-2'-[N'-[4-hydroxy-[3-(4-morpholinomethyl)]]benzoyl]carbohydrazide;

2-[N-(N-benzyloxycarbonyl-L-leucinyl)]-2'-[N'-[4-[(N,N-dimethylaminomethyl)benzyloxy]carbonyl-L-leucinyl]carbohydrazide;

2-(N-benzoyl)-2'-[N'-(N-benzyloxycarbonyl-L-leucinyl)]carbohydrazide;

2-[N-(N-benzyloxycarbonyl-L-leucinyl)]-2'-[N'-[3-(4-morpholinomethyl)benzoyl]]carbohydrazide;

2-[N-(3-benzyloxybenzoyl)]-2'-[N'-(N-benzyloxycarbonyl-L-leucinyl)]carbohydrazide;

2-[N-(N-benzyloxycarbonyl-L-leucinyl)]-2'-[N'-[4-[3-N-N-dimethylamino)-1-propyloxy]benzoyl]]carbohydrazide;

2-[N-(2-benzyloxybenzoyl)]-2'-[N'-(N-benzyloxycarbonyl-L-leucinyl)]carbohydrazide;

2-[N-(N-benzyloxycarbonyl-L-leucinyl)]-2'-[N'-[3-(4-pyridylmethoxy)benzoyl]]carbohydrazide;

2-[N-(4-benzyloxybenzoyl)]-2'-[N'-(N-benzyloxycarbonyl-L-leucinyl)]carbohydrazide;

2-[N-(N-benzyloxycarbonyl-L-leucinyl)]-2'-[N'-(3-benzyloxy-5-methoxy)benzoyl]carbohydrazide;

2-[N-(N-benzyloxycarbonyl-L-leucinyl)]-2'-[N'-(3-benzyloxy-4,5-dimethoxy)benzoyl]carbohydrazide;

2-[N-(N-benzyloxycarbonyl-L-leucinyl)]-2'-[N'-(3-benzyloxy-5-ethoxy)benzoyl]carbohydrazide;

2-[N-(N-benzyloxycarbonylglycinyl)]-2'-[N'-(N-benzyloxycarbonyl-L-leucinyl)]carbohydrazide;

2-[N-(3-benzyloxybenzoyl)]-2'-[N'-(N-benzyloxycarbonyl-L-prolinyl)]carbohydrazide;

2-[N-(N-benzyloxycarbonyl-L-leucinyl)]-2'-[N'-(4-phenylphenylacetyl)]carbohydrazide;

(2'S)-2-[N-(3-benzyloxybenzoyl)]-2'-[N'-(N-benzyloxycarbonyl-2-aminobutyryl)]carbohydrazide;

2,2'-[N,N'-[bis-4-phenylphenylacetyl)]]carbohydrazide;

(2'RS)-2-[N-(N-benzyloxycarbonyl-L-leucinyl)]-2'-[2-(4-phenylphenoxy)propionyl]carbohydrazide;

2-[N-(3-benzyloxybenzoyl)]-2'-[N'-(4-methylpentanoyl)]carbohydrazide;

(2RS,2'RS)-2,2'-[N,N'-[bis-[2-(4-phenylphenyl)-4-methylpentanoyl)]]]carbohydrazide;

(2'RS)-2-[N-(N-benzyloxycarbonyl-L-leucinyl)]-2'-[N'-[2-(4-phenylphenyl)-4-methylpentanoyl)]]carbohydrazide;

(2'RS)-2-[N-(3-benzyloxybenzoyl)]-2'-[N-[2-(4-phenylphenyl)-4-methylpentanoyl)]]carbohydrazide;

2-[N-(3-benzyloxybenzoyl)]-2'-[N'-(N-benzyloxycarbonyl-N-methyl-L-leucinyl)]carbohydrazide;
2-[N-(3-benzyloxybenzoyl)]-2'-[N'-[N-(2-pyridinylmethoxycarbonyl)-L-leucinyl]]carbohydrazide;
2-[N-[3-(4-pyridylmethoxy)benzoyl]]-2'-[N'-[N-(2-pyridinylmethoxycarbonyl)-L-leucinyl]]carbohydrazide;
(2RS)-2-[N-[2-(4-phenylphenyl)-4-methylpentanoyl)]]-2'-[N'-[N-(2-pyridinylmethoxycarbonyl)-L-leucinyl]]carbohydrazide;
2-[N-(N-benzyloxycarbonyl-L-leucinyl)]-2'-[N'-[2-4-phenylphenyl)-4-methylpentanoyl)]]carbohydrazide;
2-[N-(N-benzyloxycarbonyl-L-leucinyl)]-2'-[N'-[2-(4-phenylphenyl)-4-methylpentanoyl)]]carbohydrazide;
2-[N-(N-benzyloxycarbonyl-L-leucinyl)]-2'-[N'-[N-(4-phenylphenyl)-N-(2-methylpropyl)carbamoyl]]carbohydrazide;
2-[N-(3-benzyloxybenzoyl)]-2'-[N'-(N-methyl-L-leucinyl)]carbohydrazide;
2-[N-(N-benzyloxycarbonyl-L-leucinyl)]-2'-[N'-(N-methyl-L-leucinyl)]carbohydrazide.

Compounds of Formula I wherein

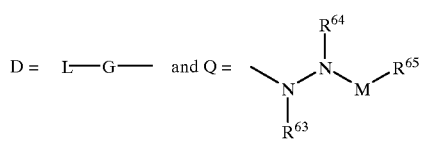

are preferred embodiments of the present invention. For the sake of convenience, such compounds are referred to herein after as compounds of Formula X.

With respect to Formula X:

More preferably G is

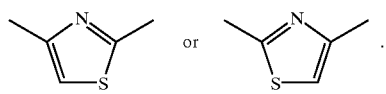

More preferably $R^{63}$ and $R^{64}$ are H and $R^{66}$ and $R^{69}$ are i-butyl.

More preferably $R^{65}$ is $CH(R^{69})NR^{61}R^{70}$, in which $R^{69}$ is i-butyl and $R^{61}$ is H. More preferably $R^{70}$ is $R^{62}OC(O)$, in which $R^{62}$ is

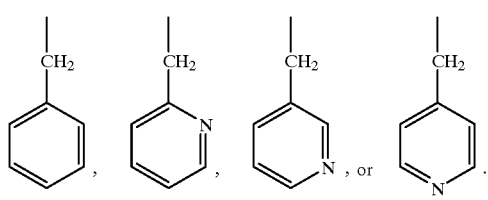

Alternately, $R^{65}$ is Ar or $CH(R^{69})$Ar, in which Ar in said $R^{65}$ group is

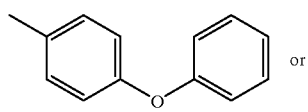

or

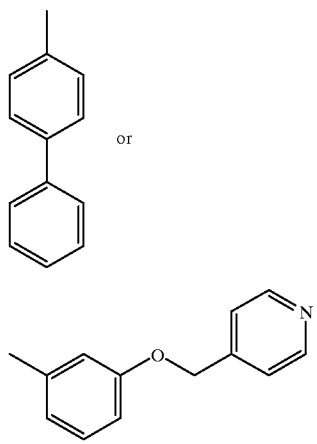

More preferably, L is $CH(R^{66})NR^{60}R^{68}$, $CH(R^{66})Ar$, $NR^{66}R^{67}$, $CH(R^{66})OAr'$, Ar, or Het, in which $R^{66}$ is i-butyl and Ar in said L group is

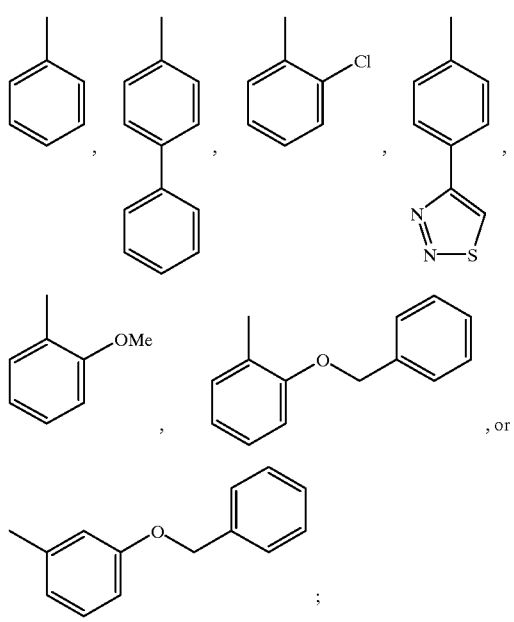

or Het in said L group is

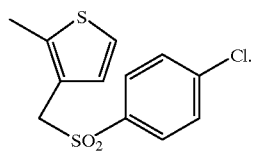

More preferably L is $NR^{66}R^{67}$ or $CH(R^{66})R^{60}R^{68}$.

One particularly preferred embodiment is a compound of Formula G:

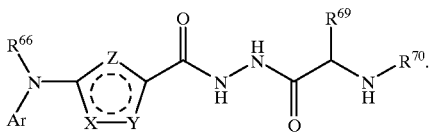

Another particularly preferred embodiment is a compound of Formula H:

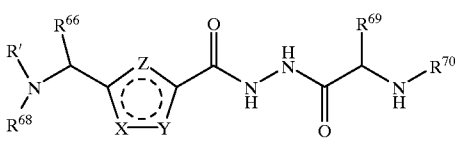

The following compounds of Formula X are most particularly preferred:

(1S)-N-[2-[(1-benzyloxycarbonylamino)-3-methylbutyl]thiazol-4-ylcarbonyl]-N'-(4-phenoxyphenylsulfonyl)hydrazide;

(1S)-N-[4-[1-(N-benzyloxycarbonyl-L-leucinylamino)-3-methylbutyl]thiazol-2-ylcarbonyl]-N'-(N-benzyloxycarbonyl-L-leucinyl)hydrazide;

(1S)-N-[2-[(1-benzyloxycarbonylamino)-3-methylbutyl]thiazol-4-ylcarbonyl]-N'-(4-phenylphenylacetyl)hydrazide;

(1S)-N-[2-[(1-benzyloxycarbonylamino)-3-methylbutyl]thiazol-4-ylcarbonyl]-N'-[3-(4-pryidinylmethoxy)benzoyl]hydrazide;

N-[2-(2-chlorophenoxymethyl)thiazol-4-ylcarbonyl]-N'-[N-(4-pyridinylmethoxycarbonyl)-L-leucinyl]hydrazide;

N-[N-(4-pyridinylmethoxycarbonyl)-L-leucinyl]-N'-[2-[4-(1,2,3-thiadiazol-4-yl)phenyl]thiazol-4-yl carbonyl]hydrazide;

N-[2-[3-(4-chlorophenylsulfonylmethyl)thien-2-yl]thiazol-4-ylcarbonyl]-N'-[N-(4-pyridinylmethoxycarbonyl)-L-leucinyl]hydrazide;

(1S,2'RS)-N-[2-[(1-benzyloxycarbonylamino)-3-methylbutyl]thiazol-4-ylcarbonyl]-N'-[2'-(4-phenylphenylacetyl)-4-methylpentanoyl-]hydrazide;

N-[2-(3-benzyloxyphenyl)thiazol-4-ylcarbonyl]-N'-[N-(2-pyridinylmethoxycarbonyl)-L-leucinyl]hydrazide;

(1RS)-N-[2-[1-(4-phenylphenyl)-3-methylbutyl]thiazol-4-ylcarbonyl]-N'-[N-(4-pyridinylmethoxycarbonyl)-L-leucinyl]hydrazide;

N-[2-(2-benzyloxyphenyl)thiazol-4-ylcarbonyl]-N'-[N-(4-pyridinylmethoxycarbonyl)-L-leucinyl]hydrazide;

N-[2-[N-methyl-N-(4-phenylphenyl)amino]thiazol-4-ylcarbonyl]-N'-[N-(4-pyridinylmethoxycarbonyl)-L-leucinyl]hydrazide;

N-(N-benzyloxycarbonyl-L-leucinyl)-N'-[2-(4-phenylbenzyl)thiazol-4-ylcarbonyl]hydrazide;

N-[2-(4-phenylphenylbenzyl)thiazol-4-ylcarbonyl]-N'-[N-(4-pyridinylmethoxycarbonyl)-L-leucinyl]hydrazide;

N-(N-benzyloxycarbonyl-L-leucinyl)-N'-[2-[N-(2-methylpropyl)-N-phenylamino]thiazol-4-ylcarbonyl]hydrazide;

N-[2-[N-(2-methylpropyl)-N-phenylamino]thiazol-4-ylcarbonyl]-N'-[N-(4-pyridinylmethoxycarbonyl)-L-leucinyl]hydrazide;

N-[2-(2-benzyloxyphenyl)thiazol-4-ylcarbonyl]-N'-[N-(3-pyridinylmethoxycarbonyl)-L-leucinyl]hydrazide;

N-[2-(2-benzyloxyphenyl)thiazol-4-ylcarbonyl]-N'-[N-(2-pyridinylmethoxycarbonyl)-L-leucinyl]hydrazide;

N-(N-benzyloxycarbonyl-N-methyl-L-leucinyl)-N'-[2-(2-benzyloxyphenyl)thiazol-4-ylcarbonyl]hydrazide;

N-[2-[N-(2-methylpropyl)-N-phenylamino]thiazol-4-ylcarbonyl]-N'-[N-(2-pyridinylmethoxycarbonyl)-L-leucinyl]hydrazide;

N-[2-[N-(2-methylpropyl)-N-phenylamino]thiazol-4-ylcarbonyl]-N'-[N-(3-pyridinylmethoxycarbonyl)-L-leucinyl]hydrazide; and N-[2-(2-methoxyphenyl)thiazol-4-ylcarbonyl]-N'-[N-(4-pyridinylmethoxycarbonyl)-L-leucinyl]hydrazide.

Definitions

The present invention includes all hydrates, solvates, complexes and prodrugs of the compounds of this invention. Prodrugs are any covalently bonded compounds which release the active parent drug according to Formula I in vivo. If a chiral center or another form of an isomeric center is present in a compound of the present invention, all forms of such isomer or isomers, including enantiomers and diastereomers, are intended to be covered herein. Inventive compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention. In cases wherein compounds may exist in tautomeric forms, such as keto-onol tautomers, each tautomeric form is contemplated as being included within this invention whether existing in equilibrium or predominantly in one form.

The meaning of any substituent at any one occurrence in Formula I or any subformula thereof is independent of its meaning, or any other substituent's meaning, at any other occurrence, unless specified otherwise.

Abbreviations and symbols commonly used in the peptide and chemical arts are used herein to describe the compounds of the present invention. In general, the amino acid abbreviations follow the IUPAC-IUB Joint Commission on Biochemical Nomenclature as described in *Eur. J. Biochem.*, 158, 9 (1984). The term "amino acid" as used herein refers to the D- or L- isomers of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

"$C_{1-6}$alkyl" as applied herein is meant to include substituted and unsubstituted methyl, ethyl, n-propyl, isopropyl, n-butyl, isobutyl and t-butyl, pentyl, n-pentyl, isopentyl, neopentyl and hexyl and the simple aliphatic isomers thereof. Any $C_{1-6}$alkyl group may be optionally substituted independently by one or two halogens, SR', OR', N(R')$_2$, C(O)N(R')$_2$, carbamyl or $C_{1-4}$alkyl, where R' is $C_{1-6}$alkyl. $C_0$alkyl means that no alkyl group is present in the moiety. Thus, Ar-$C_0$alkyl is equivalent to Ar.

"$C_{3-11}$cycloalkyl" as applied herein is meant to include substituted and unsubstituted cyclopropane, cyclobutane, cyclopentane, cyclohexane, cycloheptane, cyclooctane, cyclononane, cyclodecane, cycloundecane.

"$C_{2-6}$ alkenyl" as applied herein means an alkyl group of 2 to 6 carbons wherein a carbon-carbon single bond is replaced by a carbon-carbon double bond. $C_{2-6}$alkenyl includes ethylene, 1-propene, 2-propene, 1-butene, 2-butene, isobutene and the several isomeric pentenes and hexenes. Both cis and trans isomers are included.

"$C_{2-6}$alkynyl" means an alkyl group of 2 to 6 carbons wherein one carbon-carbon single bond is replaced by a carbon-carbon triple bond. $C_{2-6}$ alkynyl includes acetylene, 1-propyne, 2-propyne, 1-butyne, 2-butyne, 3-butyne and the simple isomers of pentyne and hexyne.

"Halogen" means F, Cl, Br, and I.

"Ar" or "aryl" means=phenyl or naphthyl, optionally substituted by one or more of Ph-$C_{0-6}$alkyl, Het-$C_{0-6}$alkyl, $C_{1-6}$alkoxy, Ph-$C_{0-6}$alkoxy, Het-$C_{0-6}$alkoxy, OH, $(CH_2)_{1-6}NR^{58}R^{59}$, $O(CH_2)_{1-6}NR^{58}R^{59}$; where $R^{58}$, $R^{59}$=H, $C_{1-6}$ alkyl; Het-$C_{0-6}$alkyl, from $C_{1-4}$alkyl, OR', N(R')$_2$, SR', CF$_3$, NO$_2$, CN, CO$_2$R', CON(R'), F, Cl, Br and I.

As used herein "Het" or "heterocyclic" represents a stable 5- to 7-membered monocyclic or a stable 7- to 10-membered bicyclic heterocyclic ring, which is either saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure, and may optionally be substituted with one or two moieties selected from $C_{1-4}$alkyl, OR', N(R')$_2$, SR', CF$_3$, NO$_2$, CN, CO$_2$R', CON(R'), F, Cl, Br and I, where R' is $C_{1-6}$alkyl. Examples of such heterocycles include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, pyridyl, pyrazinyl, oxazolidinyl, oxazolinyl, oxazolyl, isoxazolyl, morpholinyl, thiazolidinyl, thiazolinyl, thiazolyl, quinuclidinyl, indolyl, quinolinyl, isoquinolinyl, benzimidazolyl, benzopyranyl, benzoxazolyl, furyl, pyranyl, tetrahydrofuryl, tetrahydropyranyl, thienyl, benzoxazolyl, thiamorpholinyl sulfoxide, thiamorpholinyl sulfone, and oxadiazolyl.

"HetAr" or "heteroaryl" means any heterocyclic moiety encompassed by the above definition of Het which is aromatic in character, e.g., pyridine.

It will be appreciated that the heterocyclic ring described when

includes thiazoles, oxazoles, triazoles, thiadiazoles, oxadiazoles, isoxazoles, isothiazols, imidazoles, pyrazines, pyridazines, pyrimidines, triazines and tetrazines which are available by routine chemical synthesis and are stable. The single and double bonds (i.e., =) in such heterocycles are arranged based upon the heteroatoms present so that the heterocycle is aromatic (e.g., it is a heteroaryl group). The term heteroatom as applied herein refers to oxygen, nitrogen and sulfur. When the heteroaryl group comprises a five membered ring, W is preferably an electron withdrawing group, such as halogen, —CN, —CF$_3$, —NO$_2$, —COR$^7$, —CO$_2$R$^6$, —CONHR$^6$, —SO$_2$NHR$^6$, —NHSO$_2$R$^6$, —NHCOR$^7$, —O—COR$^6$, —SR$^6$ or NR'R$^6$, or a similar electron withdrawing substituent as known in the art.

Certain radical groups are abbreviated herein. t-Bu refers to the tertiary butyl radical, Boc refers to the t-butyloxycarbonyl radical, Fmoc refers to the fluorenylmethoxycarbonyl radical, Ph refers to the phenyl radical, Cbz refers to the benzyloxycarbonyl radical.

Certain reagents are abbreviated herein. DCC refers to dicyclohexylcarbodiimide, DMAP is 2,6-dimethylaminopyridine, EDC refers to N-ethyl-N' (dimethylaminopropyl)-carbodiimide. HOBT refers to 1-hydroxybenzotriazole, DMF refers to dimethyl formamide, BOP refers to benzotriazol-1-yloxy-tris (dimethylamino)phosphonium hexafluorophosphate, DMAP is dimethylaminopyridine, Lawesson's reagent is 2,4-bis(4-methoxyphenyl)-1,3-dithia-2,4-diphosphetane-2,4-disulfide, NMM is N-methylmorpholine, TFA refers to trifluoroacetic acid, TFAA refers to trifluoroacetic anhydride and THF refers to tetrahydrofuran. Jones reagent is a solution of chromium trioxide, water, and sulfuric acid well-known in the art.

Methods of Preparation

Compounds of Formula II wherein X=CH, Y=S and Z=N, and W=CO$_2$R$^7$CN, or CONR'R$^7$ may be conveniently prepared by methods analogous to those described in Scheme 1.

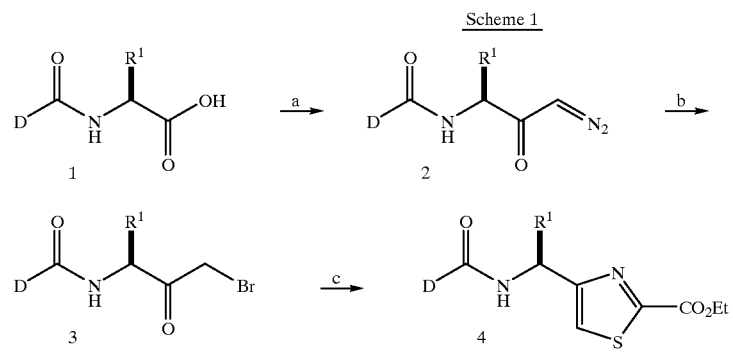

-continued

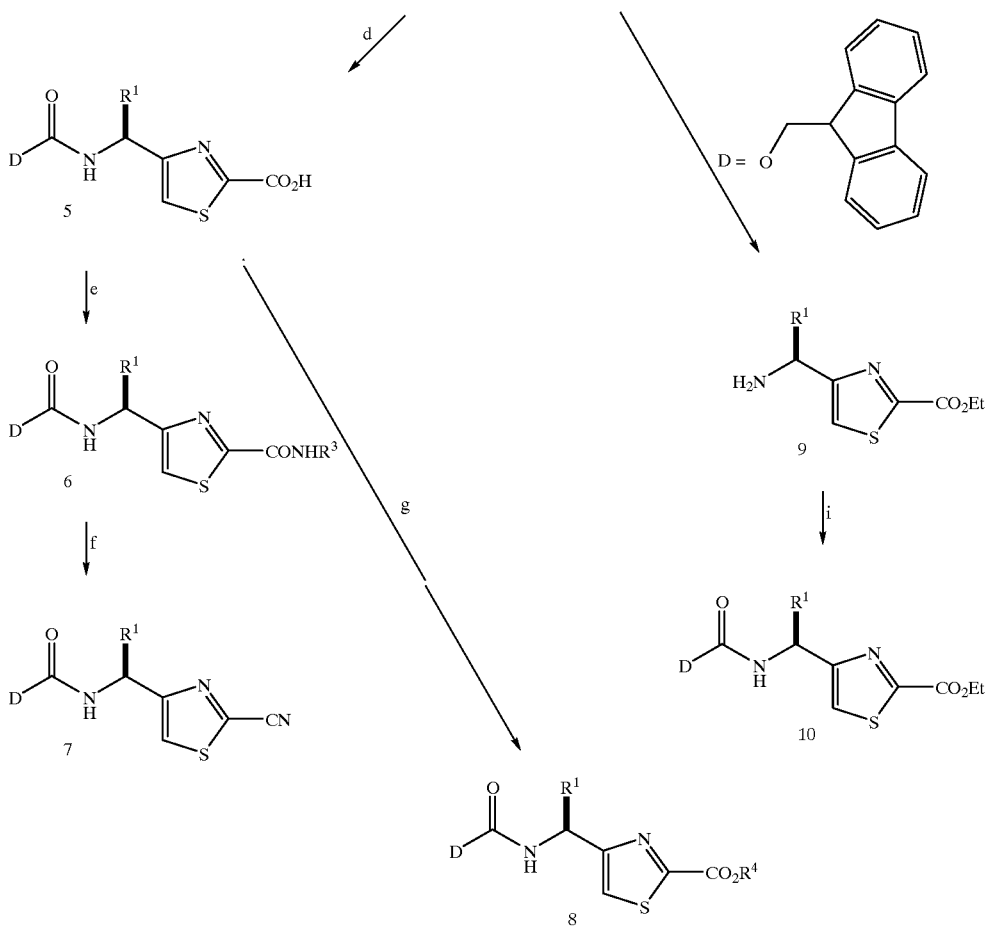

a) i-BuOCOCl, NMM, CH$_2$N$_2$, EtOAc, Et$_2$O;
b) HBr, AcOH, EtOAc, Et$_2$O;
c) H$_2$NCSCO$_2$Et, EtOH;
d) NaOH, H$_2$O, THF;
e) i-BuOCOCl, NMM, NH$_2$, THF or BOP, Et$_3$N, RNH$_2$, CH$_2$Cl$_2$;
f) TFAA, pyridine, CH$_2$Cl$_2$;
g) R$^4$OH, Boc$_2$O, Pyridine or R$^4$OH, EDCl, CH$_2$Cl$_2$;
h) piperidine, DMF;
i) BOP, Et$_3$N, D-CO$_2$H, CH$_2$Cl$_2$ 1-Scheme 1 is treated with isobutyl chloroformate and N-methylmorpholine in ethyl acetate to give a mixed anhydride which is treated with diazomethane in ether to provide 2-Scheme 1. The diazoketone is halogenated using 30% HBr in acetic acid in ethyl acetate/ether solution to provide 3-Scheme 1. This material is treated with ethyl thiooxamate in refluxing ethanol to give 4-Scheme 1. The thiazole carboxylic ester is saponified by treatment with a hydroxide base (such as potassium hydroxide, sodium hydroxide or lithium hydroxide) to yield carboxylic acid 5-Scheme 1. The carboxylic acid is treated with isobutyl chloroformate and N-methylmorpholine, followed by gaseous ammonia to provide primary amide 6-Scheme 1 (R$^3$=H). The primary amide is treated with TFAA and pyridine in dichloromethane to provide 7-Scheme 1. Alternatively, 5-Scheme 1 can be converted to substituted amides, 6-Scheme 1, by treatment with alkyl amines (such as benzylamine, 2-phenylethylamine or isobutylamine) and a peptide coupling reagent (such as BOP, EDC●HCl/1-HOBT or N-methylmorpholine/isobutyl chloroformate) in an aprotic solvent (such as dichloromethane or DMF). The carboxylic acid 5-Scheme 1 can be converted to carboxylic esters 8-Scheme 1 by treatment with a primary or secondary alcohol (such as 2,2,2-trifluoroethanol, isobutyl alcohol, benzyl alcohol or phenol) and a dehydrating reagent (such as DCC/DMAP, EDCI or Boc$_2$O/pyridine) in an aprotic solvent (such as dichloromethane or ether). When R$^2$=9-fluorenylmethoxy, treatment of 4-Scheme 1 with piperidine in DMF gives 9-Scheme 1. Treatment of 9-Scheme 1 with a carboxylic acid (such as N-Cbz-L-phenylalanine or N-Cbz-L-leucinyl-L-leucine) and a peptide coupling reagent (such as BOP) in an aprotic solvent (such as dichloromethane) provides 10-Scheme 1A.

Scheme 1A

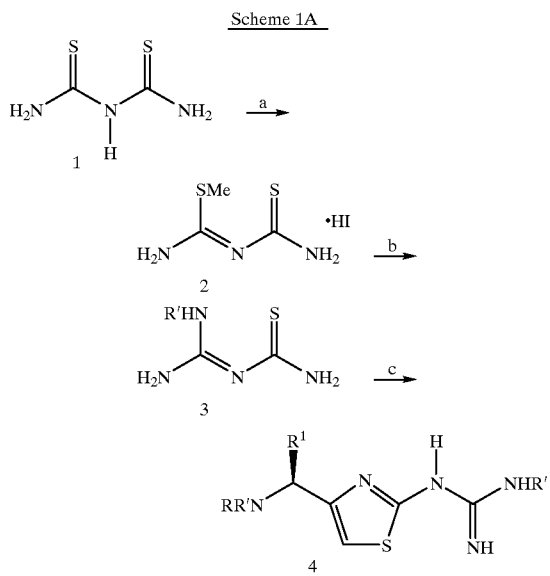

a) MeI, THF;
b) R'NH₂, i-PrOH;
c) Bromomethyl ketone, EtOH

Compounds of Formula II wherein X=CH, Y=S and Z=N are prepared by methods analogous to those described in Scheme 1A. 1-Scheme 1A is treated with iodomethane in an aprotic solvent (such as THF) to afford 2-Scheme 1A, which is treated with a primary amine in a protic solvent (such as isopropanol) to give 3-Scheme 1A. this material is then treated with a bromomethyl ketone in a protic solvent (such as ethanol) to provide 4-Scheme 1A.

Scheme 2

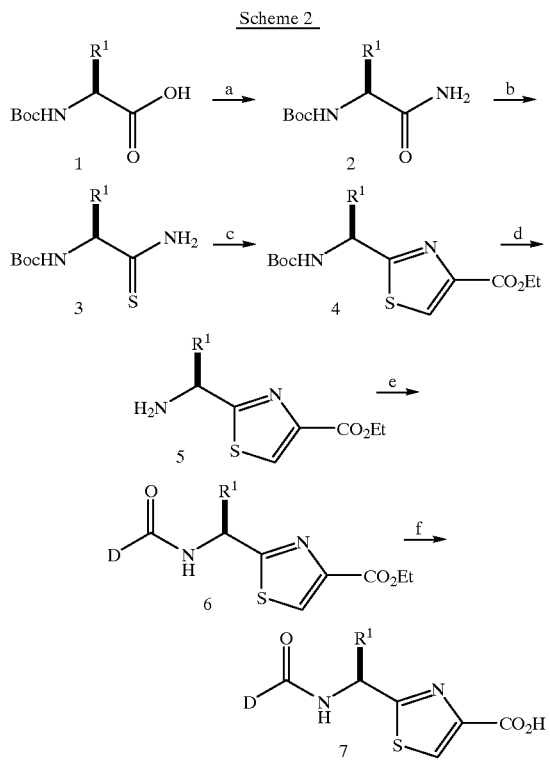

Compounds of Formula II wherein X=S, Y=CH and Z=N may be conveniently prepared by methods analogous to those described in Scheme 2. 1-Scheme 2 is treated with isobutyl chloroformate, N-methylmorpholine and ammonia in THF to provide 2-Scheme 2. This material is converted to the thioamide, 3-Scheme 2, by treatment with Lawesson's reagent in an aprotic solvent (such as THF or toluene). 3-Scheme 2 is converted to the thiazole by condensation with a α-ketoester bearing a suitable leaving group for displacement by a sulfur nucleophile (Cl, Br, I, OMs, O-p-Tos) in dichloromethane. 4-Scheme 2 is treated with TFA to provide 5-Scheme 2. This material is treated with a carboxylic acid (such as N-Cbz-L-leucine, N-Cbz-D-leucine or N-Cbz-L-leucinyl-L-leucine) and a peptide coupling reagent (such as BOP, EDC●HCl/1-HOBT or N-methylmorpholine/isobutyl chloroformate) in an aprotic solvent (such as dichloromethane, DMF or THF) to yield 6-Scheme 2. This material is saponified by treatment with a hydroxide base (such as potassium hydroxide, sodium hydroxide or lithium hydroxide) to yield carboxylic acid 7-Scheme 2.

Scheme 2A

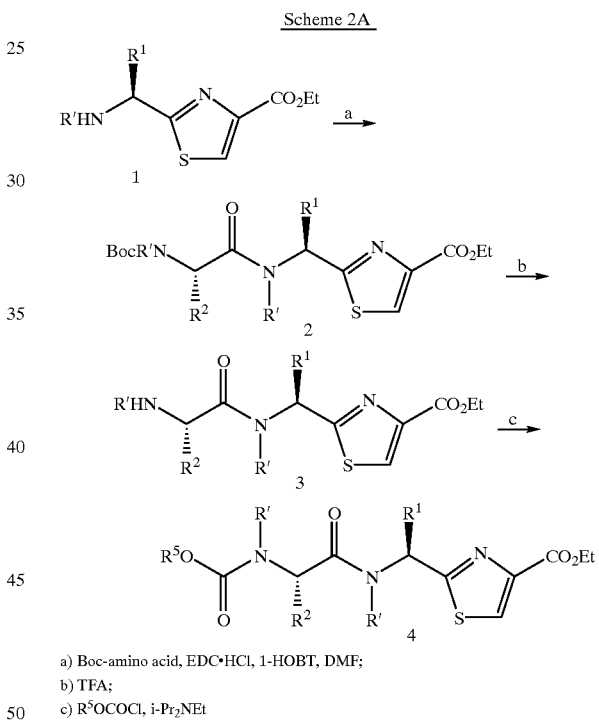

a) Boc-amino acid, EDC•HCl, 1-HOBT, DMF;
b) TFA;
c) R⁵OCOCl, i-Pr₂NEt

Compounds of Formula II wherein X=S, Y=CH and Z=N may also be prepared by methods analogous to those described in Scheme 2A. 1-Scheme2A is treated with a tert-butoxycarbonyl-protected amino acid (such as N-tert-butoxycarbonyl-L-leucine) and a peptide coupling reagent (such as BOP, EDC●HCl/1-HOBT or N-methylmorpholine/ isobutyl chloroformate) in an aprotic solvent (such as dichloromethane, DMF or THF) to yield 2-Scheme 2A, which is treated with trifluoroacetic acid to provide 3-Scheme 2A. This material is treated with a chloroformate (such as 2-biphenylmethyl chloroformate, 2-benzylbenzyl chloroformate, 2-naphthylmethyl chloroformate or 2-phenoxybenzyl chloroformate) and a tertiary amine base (such as diisopropylethylamine) in an aprotic solvent (such as methylene chloride) to provide 4-Scheme 2A.

Scheme 3

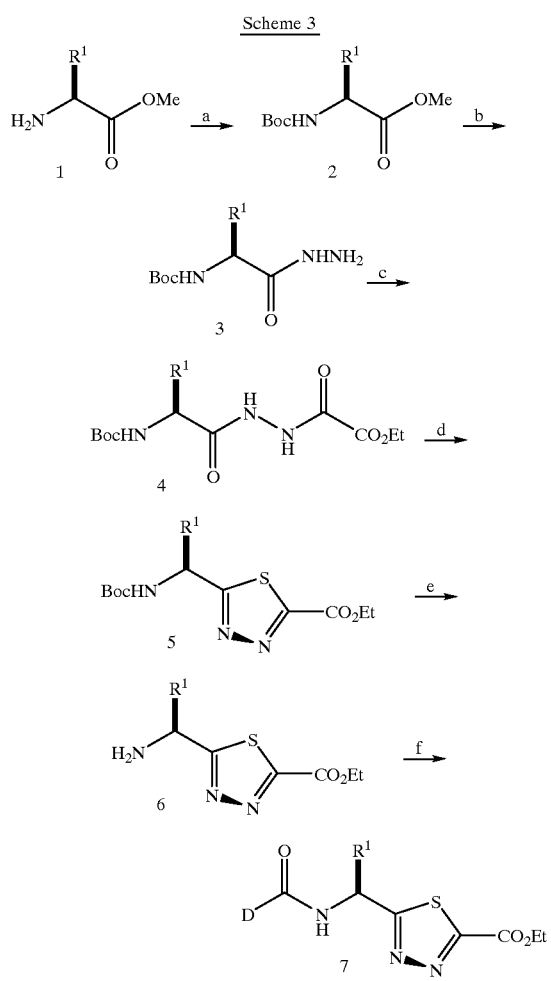

a) Boc₂O, Et₃N, THF;
b) hydrazine hydrate, MeOH;
c) EtO₂CCOCl, Pyridine, CH₂Cl₂;
d) Lawesson's reagent, toluene;
e) TFA, CH₂Cl₂;
f) DCO₂H, EDC·HCl/HOBT, Et₃N, DMF Compounds of Formula II wherein X and Y=N, and Z=S may be conveniently prepared by methods analogous to those described in Scheme 3. 1-Scheme 3 is treated with di-tert-butyl dicarbonate and triethylamine in THF to provide 2-Scheme 3. This material is treated with hydrazine hydrate in methanol to provide 3-Scheme 3. The hydrazide is acylated by treatment with ethyl oxalyl chloride and pyridine in dichloromethane to provide 4-Scheme 3. This material is converted to the thiadiazole, 5-Scheme 3, by treatment with Lawesson's reagent in an aprotic solvent (such as THF or toluene). 5-Scheme 3 is treated with TFA to provide 6-Scheme 3. This material is treated with a carboxylic acid (such as N-Cbz-L-leucine) and a peptide coupling reagent (such as BOP, EDC·HCl/1-HOBT or N-methylmorpholine/isobutyl chloroformate) in an aprotic solvent (such as dichloromethane, DMF or THF) to yield 7-Scheme 3.

Scheme 4

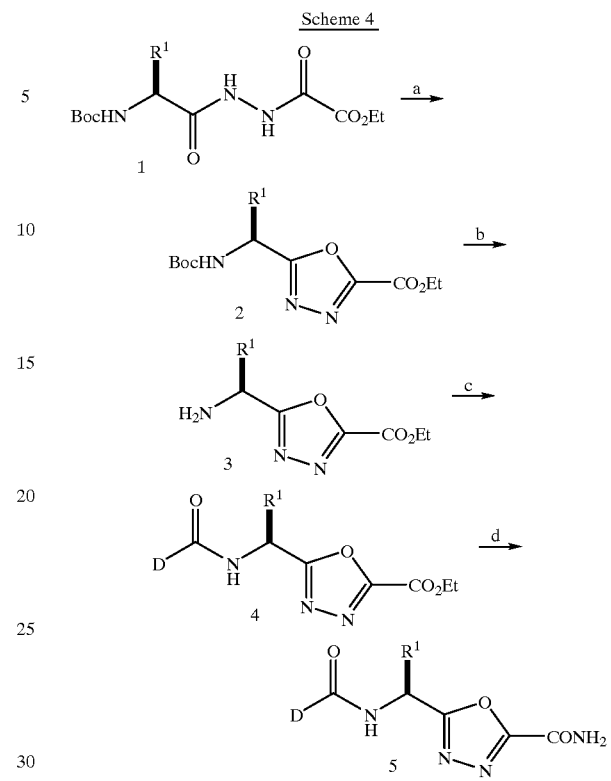

a) SOCl₂, pyridine, Et₂O, toluene;
b) TFA, CH₂Cl₂;
c) DCO₂H, EDC·HCl/HOBT, Et₃N, DMF;
d) NH₃, EtOH Compounds of Formula II wherein X and Y=N, and Z=O, and W=CO₂Et or CONH₂ may be conveniently prepared by methods analogous to those described in Scheme 4. 1-Scheme 4 is treated with thionyl chloride and pyridine in ether, followed by refluxing in toluene to provide 2-Scheme 4. The resultant oxadiazole is treated with TFA to provide 3-Scheme4. This material is treated with a carboxylic acid (such as N-Cbz-L-leucine) and a peptide coupling reagent (such as BOP, EDC·HCl/1-HOBT or N-methylmorpholine/isobutyl chloroformate) in an aprotic solvent (such as dichloromethane, DMF or THF) to yield 4-Scheme 4. The carboxylic ester is treated with ammonia in methanol to yield 5-Scheme 4.

Scheme 5

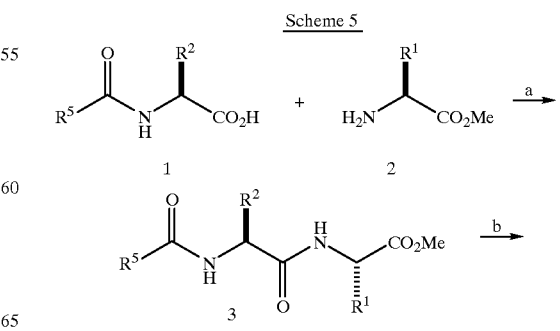

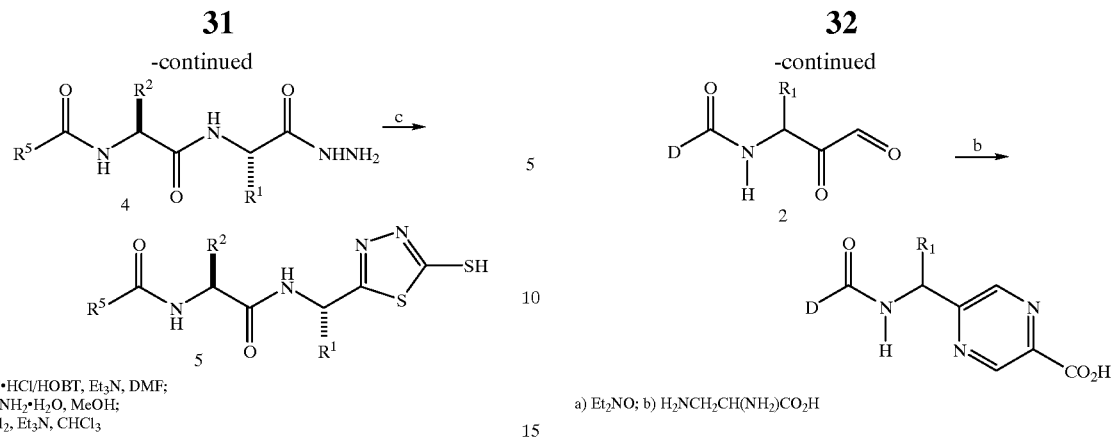

a) EDC•HCl/HOBT, Et₃N, DMF;
b) H₂NNH₂•H₂O, MeOH;
c) CSCl₂, Et₃N, CHCl₃

Compounds of Formula II wherein X and Y=N, and Z=O, and W=SH may be conveniently prepared by methods analogous to those described in Scheme 5. 1-Scheme 5 and 2-Scheme 5 are treated with a peptide coupling reagent (such as BOP, EDC•HCl/1-HOBT or N-methylmorpholine/isobutyl chloroformate) in an aprotic solvent (such as dichloromethane, DMF or THF) to yield 3-Scheme 5. This material is treated with hydrazine hydrate in methanol to provide 4-Scheme 5. Treatment of 4-Scheme 5 with thiophosgene and triethylamine in chloroform provides 5-Scheme 5.

a) Et₂NO; b) H₂NCH₂CH(NH₂)CO₂H

Compounds of Formula II wherein X=CH, Y=N and Z=N and W=C may be prepared by methods analogous to those described in Scheme 7. Treatment of 1-Scheme 7 with diethylamine N-oxide should provide 2-Scheme 7. Condensation of 2-Scheme 7 with a 2,3-diaminocarboxylic acid should then provide 3-Scheme 7, which may be converted to a variety of carboxylic acid derivatives using procedures previously described in other schemes.

Compounds of Formula III may be generally prepared by methods common in the art of organic chemistry for coupling carboxylic acid derivatives to hydrazine. Schemes 8, 9 and 10 are illustrative of a method to prepare compounds Scheme 6

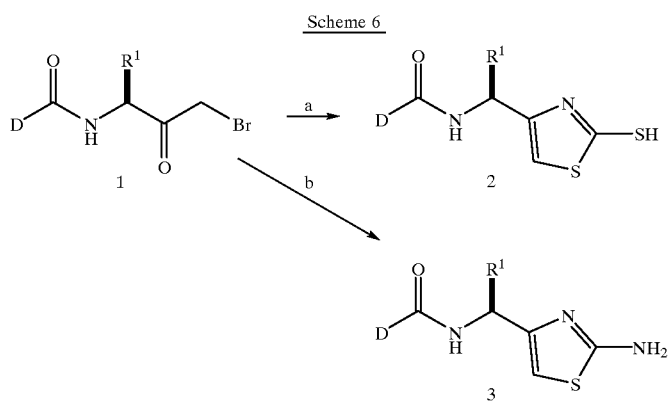

a) H₂NCS₂NH₄+, EtOH; b) H₂NCSNH₂, EtOH

Compounds of Formula II wherein X=CH, Y=S and Z=N, and W=SH or NH₂ may be conveniently prepared by methods analogous to those described in Scheme 6. Condensation of 1-Scheme 6 with ammonium dithiocarbamate in ethanol yielded 2-Scheme 6. Alternatively, 1-Scheme 6 can be condensed with thiourea in ethanol to give 3-Scheme 6.

wherein B or E is a heterocycle. Compounds of Formula X may be conveniently prepared by methods analogous to those described in Schemes 8, 9 and 19–23.

Scheme 7

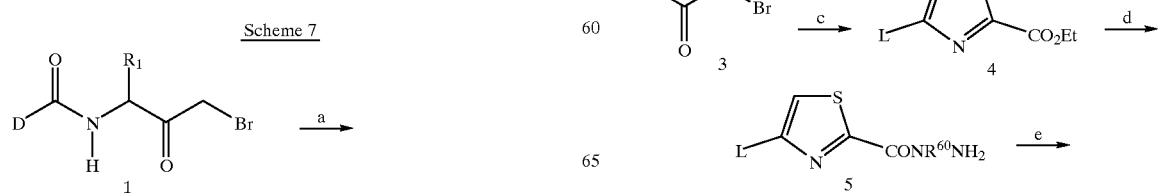

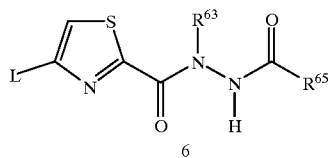

a) i. *i*-BuOCOCl, NMM, THF; ii. CH₂N₂, Et₂O; b) HBr, AcOH, Et₂O;
c) H₂NCSCO₂Et, EtOH; d) R⁶³NHNH₂, EtOH; e) R⁶⁵CO₂H, EDC·HCl, 1-HOBT, DMF.

Compounds wherein X=CH, Y=S and Z=N, are prepared by methods analogous to those described in Scheme 22. 1-Scheme 8 is treated with isobutyl chloroformate and N-methylmorpholine in ether to give a mixed anhydride which is treated with diazomethane in ether to provide 2-Scheme 8. The diazoketone is halogenated using 30% HBr in acetic acid in ether solution to provide 3-Scheme 8. This material is treated with ethyl thiooxamate in refluxing ethanol to give 4-Scheme 8. The thiazole carboxylic ester is treated with a hydrazine (such as hydrazine monohydrate or methyl hydrazine) in ethanol to yield 5-Scheme 8. This material is treated with a carboxylic acid (such as N-Cbz-L-leucine) and a peptide coupling reagent (such as EDC·HCl/1-HOBT) in an aprotic solvent (such as DMF) to provide 6-Scheme 8.

Compounds wherein X=S, Y=CH and Z=N, are prepared by methods analogous to those described in Scheme 9.

Scheme 9

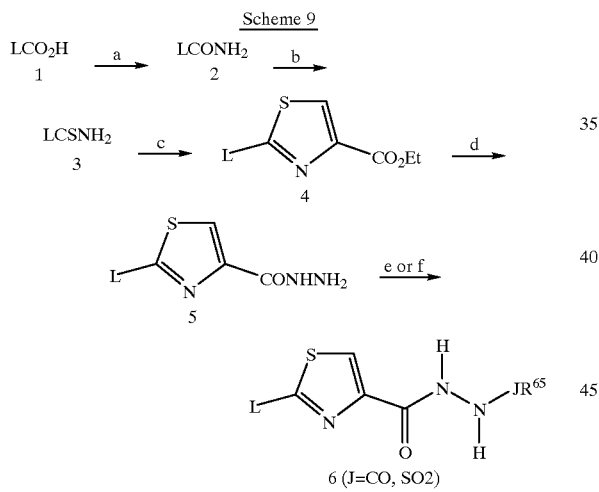

6 (J=CO, SO2)

a) *i*-BuOCOCl, NMM, NH₃, THF; b) Lawesson's reagent, THF; c) i. EtO₂CCOCH₂Br; ii. TFAA, Py, CH₂Cl₂; d) H₂NNH₂·H₂O, EtOH; e) R⁶⁵SO₂Cl, Py, CH₂Cl₂; f) R⁶⁵CO₂H, EDC·HCl, 1-HOBT, DMF.

1-Scheme 9 is converted to 2-Scheme 9 by treatment with isobutyl chloroformate, N-methylmorpholine and ammonia in THF. 2-Scheme 9 is treated with Lawesson's reagent in THF to provide the thioamide 3-Scheme 9. This material is converted to the thiazole by condensation with an α-ketoester followed by treatment with trifluoroacetic anhydride and pyridine in methylene chloride to afford 4-Scheme 21 which is converted to 5-Scheme 9 by treatment with hydrazine monohydrate. This material is treated with a sulfonyl chloride (such as 4-phenoxybenzenesulfonyl chloride) and pyridine in an aprotic solvent (such as dichloromethane) to provide 6-Scheme 9. Alternatively, 6-Scheme 9 may be prepared by treatment with a carboxylic acid (such as N-benzyloxycarbonyl-L-leucine, N-benzyloxycarbonyl-N-methyl-L-leucine, N-(2-pyridinylmethoxycarbonyl)-L-leucine, N-(3-pyridinylmethoxycarbonyl)-L-leucine, N-(4-pyridinylmethoxycarbonyl)-L-leucine, 4-biphenylacetic acid, 3-(4-pyridinylmethoxy)benzioc acid, or 4-methyl-2-(4-phenylphenyl)pentanoic acid) and a peptide coupling reagent (such as EDC·HCl/1-HOBT) in an aprotic solvent (such as DMF).

Compounds wherein

B= 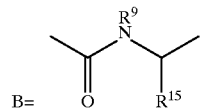

are prepared by routine methods of peptide synthesis as illustrated for instance by Scheme 10.

Scheme 10

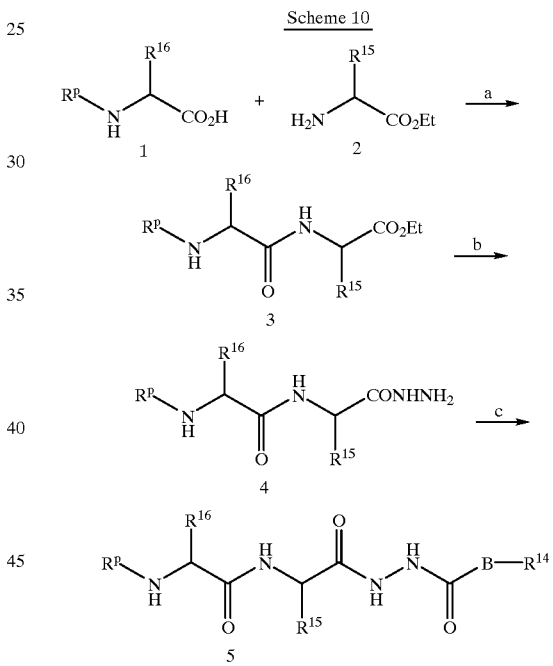

a) EDC·HCl, HOBT, DMF; b) H₂NNH₂·H₂O, EtOH; c) R¹⁴—B—CO₂H, EDC·HCL, HOBT, DMF

Treatment of a mixture of 1-Scheme 10 and 2-Scheme 10 with a peptide coupling reagent (such as BOP or EDC·HCl/1-HOBT) in an aprotic solvent (such as DMF or dichloromethane) provides 3-Scheme 10. This material is treated with hydrazine hydrate in ethanol to yield 4-Scheme10, which is treated with a carboxylic acid (such as N-Cbz-L-leucine) and a peptide coupling reagent (such as BOP or EDC·HCl/1-HOBT) in an aprotic solvent (such as DMF or dichloromethane) to provide 5-Scheme 10.

Compounds of Formula IV wherein R²², R²³, R²⁴ are H, and R²¹=R²⁶ are prepared by methods analogous to those described in Scheme 11.

Scheme 11

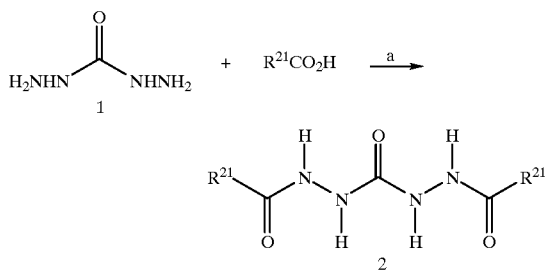

a) EDC•HCl, 1-HOBT, DMF

Symmetric compounds of the Formula IX having RCO as the terminal substituent on both sides are prepared by methods analogous to those described in Scheme 11. Treatment of 1-Scheme 11 with a carboxylic acid (such as 4-biphenylacetic acid or 4-methyl-2-(4-phenylphenyl) pentanoic acid) and a peptide coupling reagent (such as EDC●HCl/1-HOBT) in an aprotic solvent (such as DMF) provides 2-Scheme 11.

Nonsymmetric compounds of the Formula IX, and compounds of Formula IV wherein $R^{22}$, $R^{23}$, $R^{24}$ and $R^{25}$ are H, and $R^{21} \ne R26$, are prepared by methods analogous to those described in Scheme 12.

Scheme 12

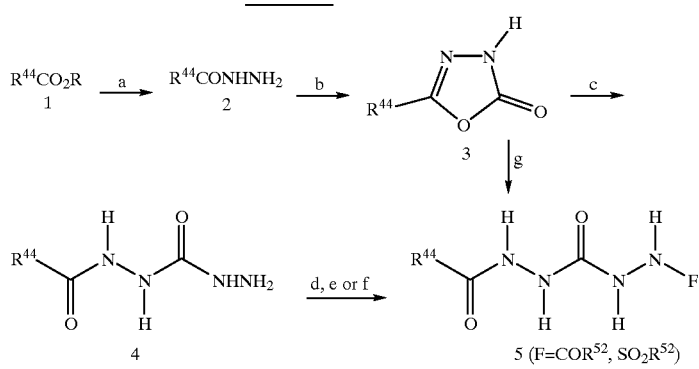

a) H$_2$NNH$_2$•H$_2$O, MeOH; b) Cl$_2$CO, PhMe; c) H$_2$NNH$_2$•H$_2$O, MeOH; d) R$^{49}$CO$_2$H, EDC•HCl, 1-HOBT, DMF; e) R$^{52}$SO$_2$Cl or R$^{52}$COCl, pyridine, DMF; f) R$^{52}$CO$_2$COR$^{52}$; g) R$^{52}$CONR$^{51}$NH$_2$ Treatment of 1-Scheme 12 with hydrazine hydrate in a protic solvent (such as methanol or ethanol) provides 2-Scheme 12, which is treated phosgene in toluene to afford 3-Scheme 12. This material is treated with hydrazine hydrate in a protic solvent (such as methanol or ethanol) to provide 4-Scheme 12. Treatment of 4-Scheme 12 with a sulfonyl chloride (such as 4-phenoxyphenylsulfonyl chloride), an acid chloride (such as benzoyl chloride), or a carbamoyl chloride (such as N-(2-methylpropyl)-N-(4-phenylphenyl) carbamoyl chloride) and pyridine in DMF affords 5-Scheme-12. Alternatively, 5-Scheme-12 may be prepared by treatment of 4-Scheme 12 with a carboxylic acid (such as N-benzyloxycarbonyl-L-alanine, N-benzyloxycarbonyl-L-proline, N-benzyloxycarbonylglycine, (S)-N-benzyloxycarbonyl-2-aminobutyric acid, N-benzyloxycarbonyl-N-methyl-L-leucine, N-tert-butoxycarbonyl-N-methyl-L-leucine, N-acetyl-L-leucine, N-acetyl-L-alanine, N-(2-pyridinylmethoxycarbonyl)-L-leucine, N-[4-(N,N-dimethylaminomethyl) benzyloxycarbonyl]-L-leucine, 4-phenylbenzoic acid, 4-methoxybenzioc acid, 4-phenoxybenzoic acid, 4-(N,N-dimethylaminomethyl)benzoic acid, 4-hydroxy-3-[N-(morpholinomethyl)]benzoic acid, 3-[N-(4-morpholinomethyl)]benzoic acid, 2-benzyloxybenzoic acid, 3-benzyloxybenzoic acid, 4-benzyloxybenzoic acid, 4-(3-dimethylaminomethylpropoxy)benzoic acid, 3-benzyloxy-5-methoxybenzoic acid, 3-benzyloxy-4,5-dimethoxybenzoic acid, 3-benzyloxy-5-ethoxybenzoic acid, 3-(4-pyridinylmethoxy)benzoic acid, 4biphenylacetic acid, 2-(4-phenylphenoxy)propionic acid or 4-methyl-2-(4-phenylphenyl)pentanoic acid) and a peptide coupling reagent (such as BOP, EDC●HCl/1-HOBT or N-methylmorpholine/isobutyl chloroformate) in an aprotic solvent (such as dichloromethane, DMF or THF). 5-Scheme-12 may also be prepared by treatment of 4-Scheme 12 with an anhydride (such as acetic anhydride).

Alternatively, 3-Scheme 12 may be converted directly to 5-Scheme-1 by treatment with a hydrazide (such as 4-methylpentanoyl hydrazide or N-methyl-N-benzyloxycarbonyl-L-leucinyl hydrazide).

Scheme 12A

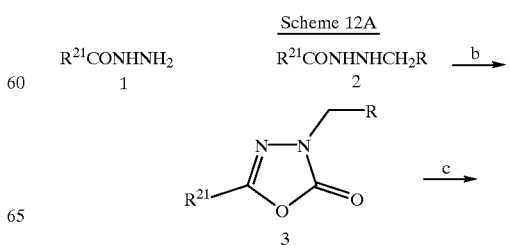

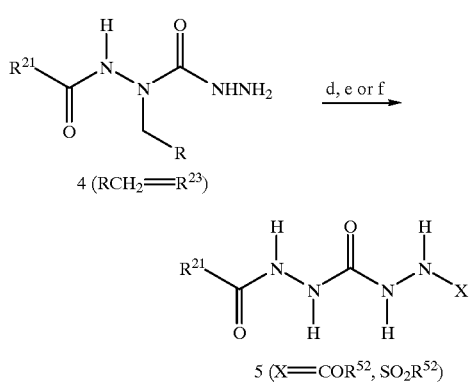

a) i. PhCHO, EtOH; ii. BH3•THF; b) Cl₂CO, PhMe; c) H₂NNH₂•H₂O, MeOH; d) R⁵²CO₂H, EDC•HCl, 1-HOBT, DMF; e) R⁵²SO₂Cl or R⁵²COCl, pyridine, DMF; f) R⁵²CO₂COR⁵²

Nonsymmetric compounds of Formula IV, wherein $R^{23} \neq H$ are prepared by methods analogous to those described in Scheme 12A. 1-Scheme 12A is treated with an aldehyde (such as benzaldehyde) in a protic solvent (such as ethanol) and the resulting imine is treated with borane-THF complex to afford 2-Scheme 12A which is subsequently treated with phosgene in toluene to afford 3-Scheme 12A. This material is treated with hydrazine hydrate in a protic solvent (such as methanol or ethanol) to provide 4-Scheme 12A. Treatment of 4-Scheme 12A with a carboxylic acid (such as N-benzyloxycarbonyl-L-leucine) and a peptide coupling reagent (such as BOP, EDC●HCl/1-HOBT or N-methylmorpholine/isobutyl chloroformate) in an aprotic solvent (such as dichloromethane, DMF or THF) to yield 5-Scheme-12A.

Compounds of Formulae V–VII may be conveniently prepared by methods analogous to those described in Schemes 13–16.

Scheme 13

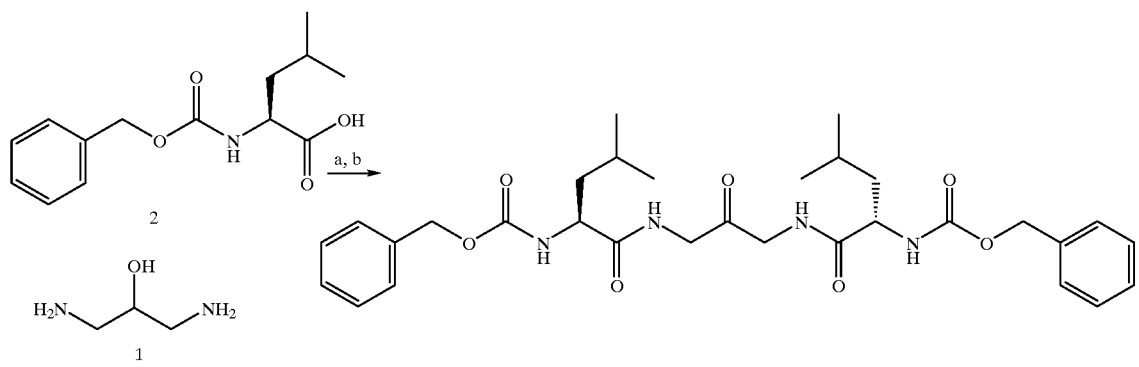

a) HBTU, NMM, DMF; b) Jones, acetone 1,3-Bis-amido propan-2-ones may be prepared by acylation of 1,3-diamino-propan-2-ol 1-Scheme 13 with a carboxylic acid 2-Scheme 13 or a mixture of 2 different carboxylic acids (2 and 3) in equimolar amounts and a coupling reagent such as a dialkyl carbodimide such as DCC or EDCI or HBTU/N-methyl morpholine, followed by oxidation of the carbinol to a ketone with an oxidant such as Jones reagent.

Scheme 14

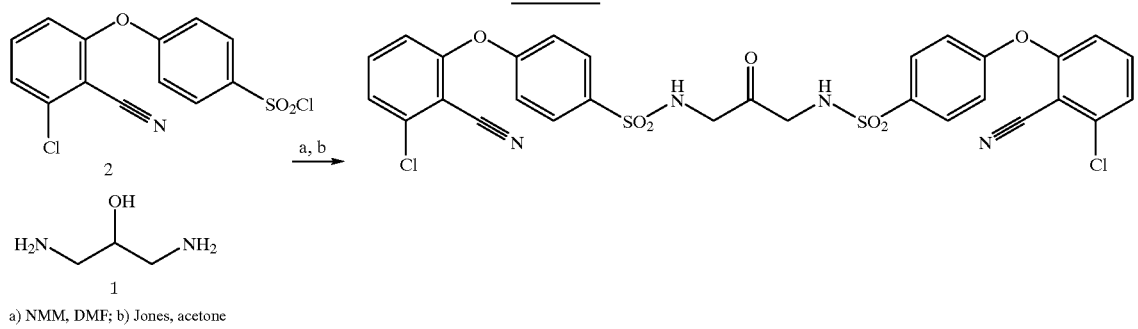

a) NMM, DMF; b) Jones, acetone 1,3-Bis-sulfonamido propanones may be prepared by sulfonylation of 1,3-diamino-propan-2-ol 1-Scheme 14 with a sulfonyl chloride 2-Scheme 14 and a base such as N-methyl morpholine, followed by oxidation of the carbinol to a ketone with an oxidant such as Jones reagent.

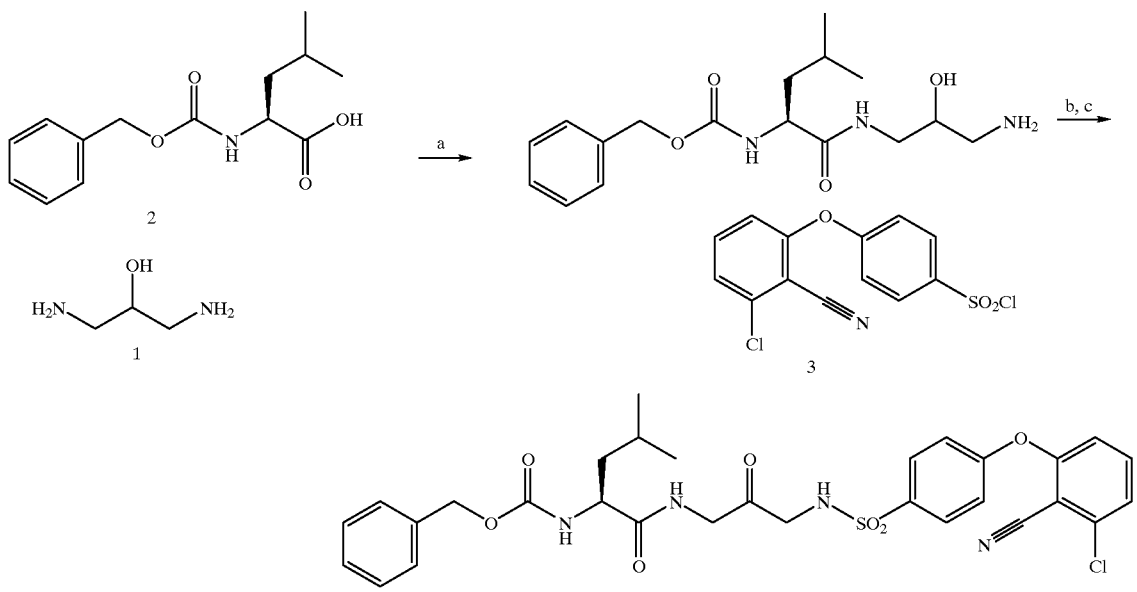

a) EDCI, HOBT, DMF; b) NMM, DMF, 3) Jones, acetone

1-Amido-3-sulfonamido propanones may be prepared by acylation of 1,3-diamino-propan-2-ol 1-Scheme 15 with a carboxylic acid 2-Scheme 15 and a coupling reagent such as a carbodiimide or HBTU/N-methyl morpholine, followed by treatment with an appropriate sulfonyl chloride 3-Scheme 15 and a base such as N-methyl morpholine, followed by oxidation of the carbinol to a ketone with an oxidant such as Jones reagent.

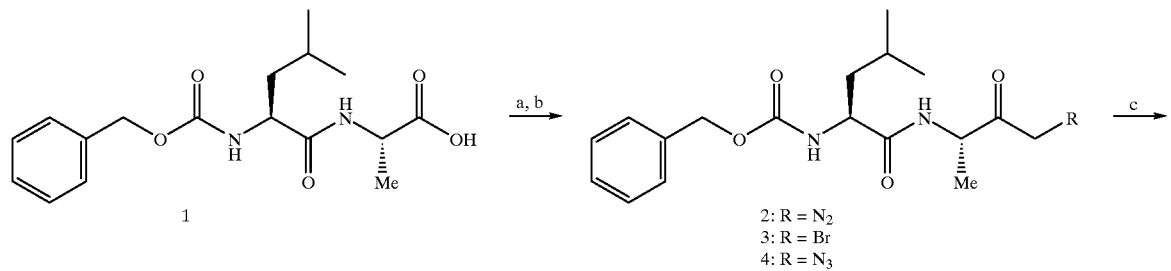

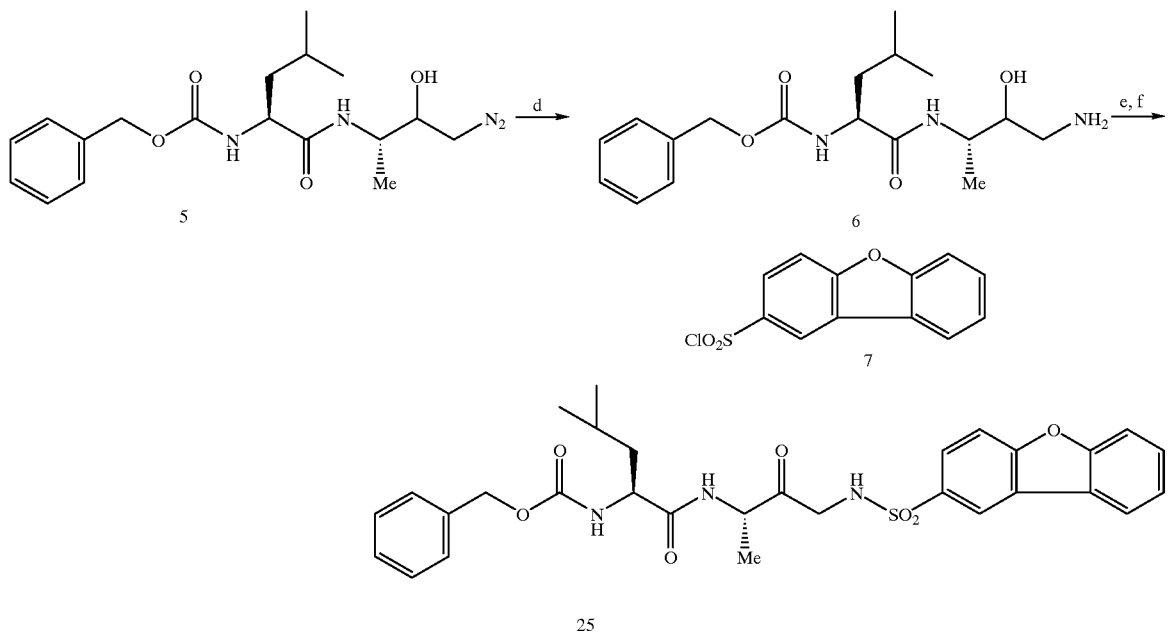

1-Amido-3-sulfonamido alkan-2-ones that are larger than propan-2-one, such as butan-2-one or 5-methyl-hexan-2-one, can be prepared by converting an N-protected peptide such as Cbz-leu-leu-OH 1-Scheme 16 to its bromo methyl ketone 3-Scheme 16 via a diazo methyl ketone 2-Scheme 16. Then, the bromide 3-Scheme 16 is displaced with sodium azide to give the corresponding azide 4-Scheme 16. Reduction of the carbonyl with a reducing agent such as sodium borohydride gives alcohol 5-Scheme 16. Subsequent reduction of the azide with a reducing agent such as 1,3-propandithiol gives the free amine 6-Scheme 16. Acylation or sulfonylation of the amine gives amide or sulfonamide 7-Scheme 16. Finally, oxidation of the carbinol with an oxidant such as Jones gives the desired compounds.

Compounds of Formula VIII may be conveniently made using methods analogous to those in Schemes 17 and 18.

Scheme 17

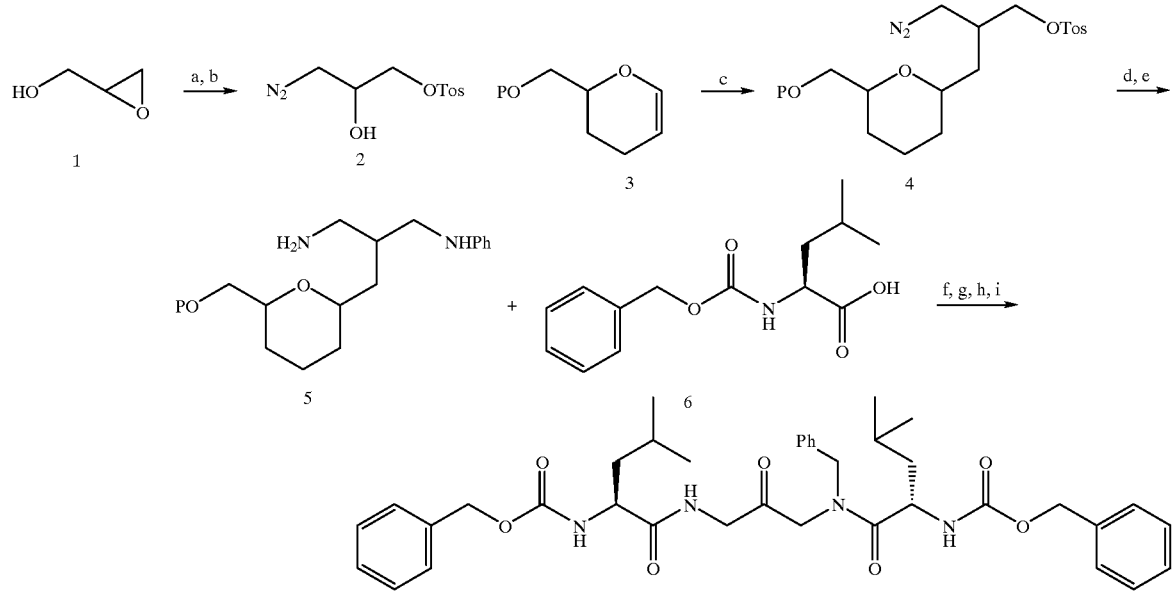

a) NaN₃, MeOH, H₂O; b) Tosyl chloride, triethylamine, CH₂Cl₂; c) Ellman dihydropyran resin (3), PPTS, Cl(CH₂)₂Cl; d) PhCH₂NH₂, toluene, 80 degrees C; e) HATU, N-methyl morpholine, NMP; f) HS(CH₂)₃SH, MeOH, Et₃N; g) Cbz-leucine (6), HBTU, N-methyl morpholine, NMP; h) TFA, CH₂Cl₂, Me₂S; i) Jones reagent, acetone Azide opening of glycidol 1-Scheme 17, followed by tosylation of the primary alcohol gave tosylate 2-Scheme 17. which was coupled to Ellman polymer 3-Scheme 17 as described by described in *J. Med. Chem.* 1995, 38, 1427–1430 to produce polymer 4-Scheme 17, which was reacted with benzyl amine in toluene, then washed extensively with various solvents. Then, the azide was reduced with 1,3-propanedithiol in MeOH, triethylamine, then was washed extensively with various solvents. Coupling of Cbz-leucine 6-Scheme 17 with the diamine 5-Scheme 17 with equimolar amounts and a coupling reagent such as a dialkyl carbodiimide such as DCC or EDCI or HBTU/N-methyl morpholine. Cleavage of the ether line to an alcohol was accomplished with trifluoroacetic acid with various scavengers. Finally, oxidation of the carbinol to a ketone 7-Scheme 17 with an oxidant such as Jones reagent provided the desired final product.

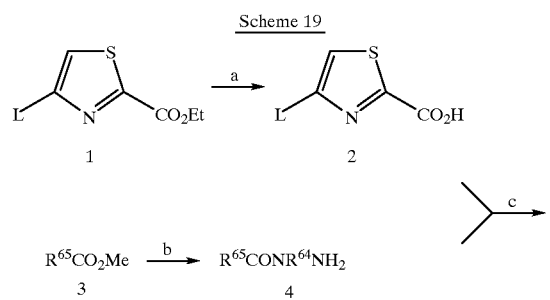

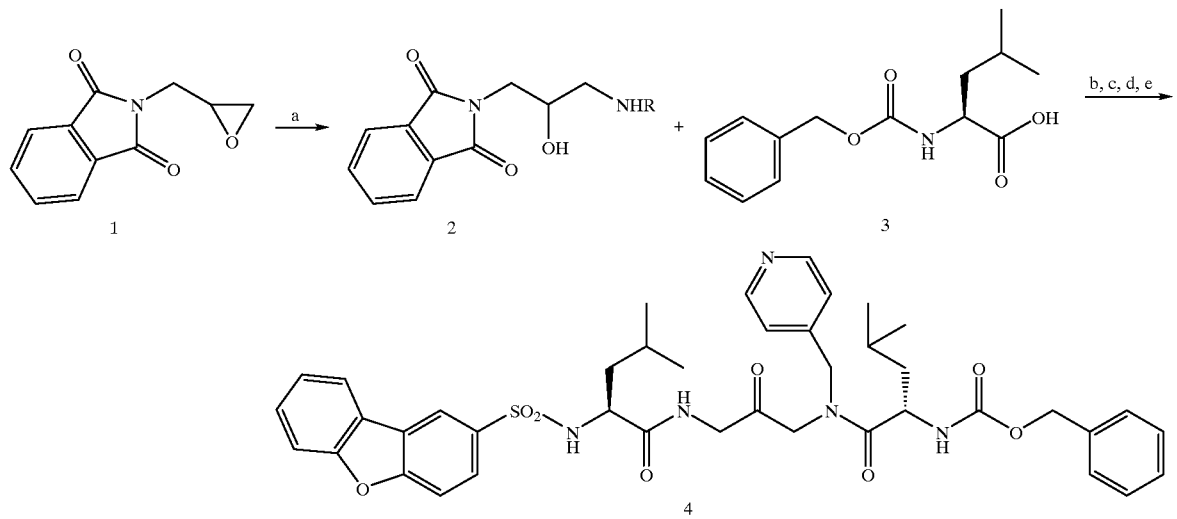

a) 4-pyridyl methyl amine, isopropanol, reflux; b) Cbz-leucine, HBTU, N-methyl morpholine, DMF; c) hydrazine, MeOH, reflux; d) 2-dibenzofuransulfonyl chloride, N-methyl morpholine, DMF; e) Jones reagent, acetone N-(2,3-Epoxypropyl)phthalimide 1-Scheme 18 (Aldrich) was reluxed with an amine such as 4-pyridiyl methyl amine in isopropanol. The secondary amine 2-Scheme 18 was then acylated with an acylating agent such as Cbz leucine or a sulfonylating reagent such as 2-dibenzofuransulfonyl chloride and base such as N-methyl morpholine in DMF. The phthalimide was then removed with hydrazine in MeOH and the resulting free amine was acylated with an acylating agent such as Cbz leucine or a sulfonylating reagent such as 2-dibenzofuransulfonyl chloride and base such as N-methyl morpholine in DMF.

Compounds of Formula IX may conveniently be made using methods analogous to those in Schemes 19 and 20.

Compounds of Formula X may be conveniently made using methods analogous to those described in Schemes 21–27.

-continued

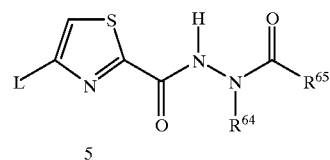

a) KOH, MeOH/H2O; b) R$^{66}$NHNH$_2$, EtOH; c) EDC•HCl, 1-HOBT, DMF

Compounds wherein X=CH, Y=S, Z=N and R$^4$≠H, are prepared by methods analogous to those described in Scheme 19. Carboxylic ester 1-Scheme 19 is treated with a hydroxide base (such as lithoum hydroxide, sodium hydroxide or potassium hydroxide) in methanol/water to provide 2-Scheme 19. 3-Scheme 19 is treated with a hydrazine (such as methylhydrazine) in a protic solvent (such as ethanol) to give 4-Scheme 19. 2-Scheme 19 and 4-Scheme 19 are coupled by treatment with a peptide coupling reagent (such as EDC•HCl/1-HOBT) in an aprotic solvent (such as DMF) to provide 5-Scheme 19.

Scheme 20

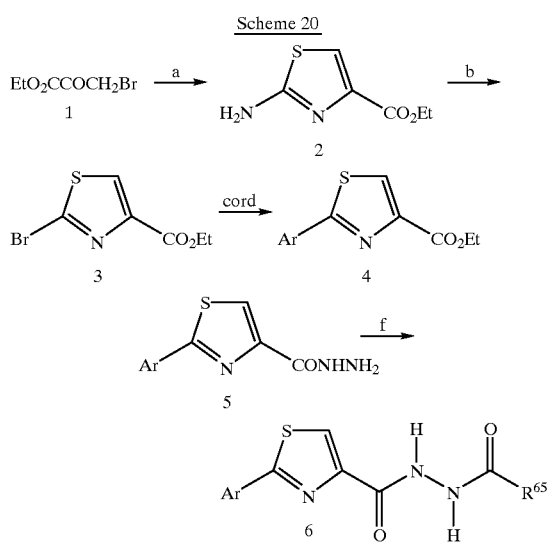

Compounds wherein X=S, Y=CH, Z=N and V=2-methoxyphenyl or 2-benzyloxyphenyl, are prepared by methods analogous to those described in Scheme 20. Ethyl bromopyruvate (1-Scheme 20) is treated with thiourea in refluxing ethanol to provide 2-Scheme 20. which is sled successively with sodium nitrite and copper (I) bromide in 16% aqueous HBr, and the product was heated in ethanol with a catalytic amount of HBr to give 3-Scheme 20. Treatment of this material with an arylboronic acid (such as 2-benzyloxyphenylboronic acid), tetrakis(triphenylphosphine)palladium(0) and cesium fluoride in refluxing DME provides 4-Scheme 20. Alternatively, 4-Scheme 20, may be prepared by treatment of 3-Scheme 20 with an arylstannane (such as 2-trimethylstannylanisole) and tetrakis(triphenylphosphine)palladium(0) in refluxing toluene. Treatment of 4-Scheme 20 with hydrazine hydrate in ethanol provides 5-Scheme 20, which is treated with a carboxylic acid (such as N-benzyloxycarbonyl-N-methyl-L-leucine, N-(2-pyridinylmethoxycarbonyl)-L-leucine, N-(3-pyridinylmethoxycarbonyl)-L-leucine or N-(4-pyridinylmethoxycarbonyl)-L-leucine) and a peptide coupling reagent (such as EDC•HCl/1-HOBT) in an aprotic solvent (such as DMF) to provide 6-Scheme 20.

Scheme 21

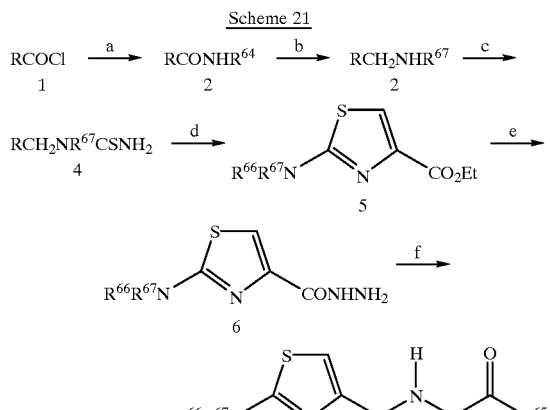

Compounds wherein X=S, Y=CH, Z=N and V=NR$^{66}$R$^{67}$, are prepared by methods analogous to those described in Scheme 21. An acid chloride (1-Scheme 21) is treated with a primary amine (such as 4-aminobiphenyl or aniline) and pyridine in an aprotic solvent (such as methylene chloride) to provide 2-Scheme 21, which is treated with lithium aluminum hydride in THF to afford 3-Scheme 25. Treatment of 3-Scheme 21 with thiophosgene and pyridine in methylene chloride, followed by treatment with ammonia in methanol provides 4-Scheme 21. Alternatively, 4-Scheme 21 may be prepared by treatment of 3-Scheme 21 with benzoyl isothiocyanate, followed by treatment of the intermediate benzoyl thiourea with potassium carbonate in methanol/water. 4-Scheme 21 is treated with hydrazine hydrate in ethanol to give 5-Scheme 21. Treatment of 5-Scheme 21 with a carboxylic acid (such as N-(2-pyridinylmethoxycarbonyl)-L-leucine, N-(3-pyridinylmethoxycarbonyl)-L-leucine or N-(4-pyridinylmethoxycarbonyl)-L-leucine) and a peptide coupling reagent (such as EDC•HCl/1-HOBT) in an aprotic solvent (such as DMF) affords 6-Scheme 21.

Scheme 22

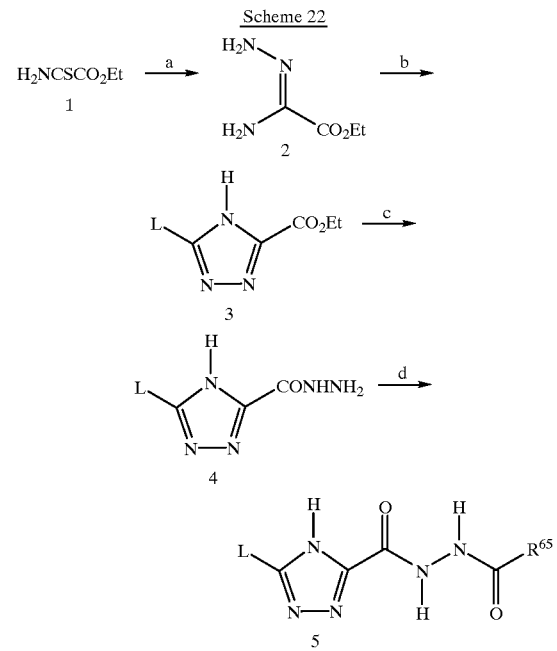

Compounds wherein X and Y=N, and Z=NH, are prepared by methods analogous to those described in Scheme 26. 1-Scheme 22 is ed with hydrazine hydrate in ethanol to give 2-Scheme 22 which is heated with a mixed anhydride to provide triazole 3-Scheme 22. This material is treated with hydrazine hydrate to provide 4-Scheme 22 , which is treated with a carboxylic acid (such as N-benzyloxycarbonyl-L-leucine) and a peptide coupling reagent (such as EDC•HCl/1-HOBT) in an aprotic solvent (such as DMF) to provide 5-Scheme 22.

Scheme 23

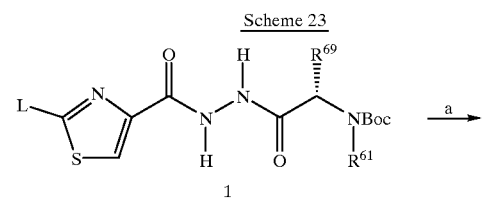

47

-continued

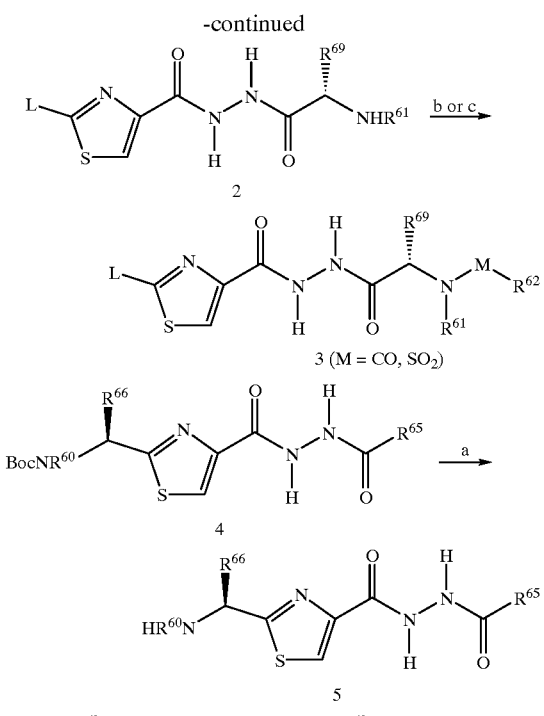

a) TFA; b) R⁶²CO₂H, EDC·HCl, 1-HOBT, DMF; c) R⁶²SO₂Cl, i-Pr₂NEt

Compounds wherein X=S, Y=CH, Z=N, L=CH(R⁶⁶)NR⁶⁰R⁶⁸ where R⁶⁸≠Boc or Cbz, or R⁶⁵=CH(R⁶⁹)NR⁶¹R⁷⁰ where R⁷⁰≠Boc or Cbz are prepared by methods analogous to those described in Scheme 27. 1-Scheme 23 is treated with trifluoroacetic acid to provide 2-Scheme 23. This material is treated with a carboxylic acid (such as pryazinecarboxylic acid, isonicotinic acid, 4-imidazolylacetic acid or pipecolic acid) and a peptide coupling reagent (such as EDC●HCl/1-HOBT) in an aprotic solvent (such as DMF) to provide 3-Scheme 23. 3-Scheme 23 may also be prepared by treatment of 2-Scheme 23 with a sulfonyl chloride (such as 2-pyridinesulfonyl chloride) and a tertieary amine base (such as diisopropylethylamine) in an aprotic solvent (such as methylene chloride). Alternatively, treatment of 4-Scheme 23 with trifluoroacetic acid provides 5-Scheme 23.

Scheme 24

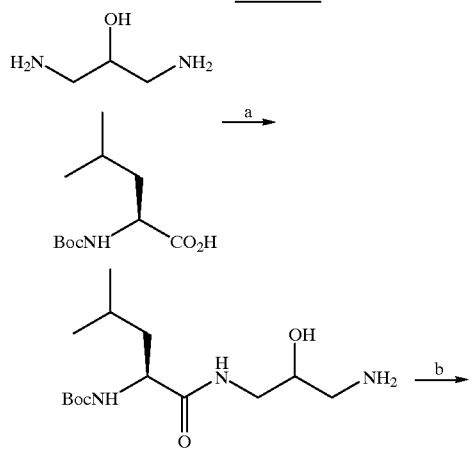

48

-continued

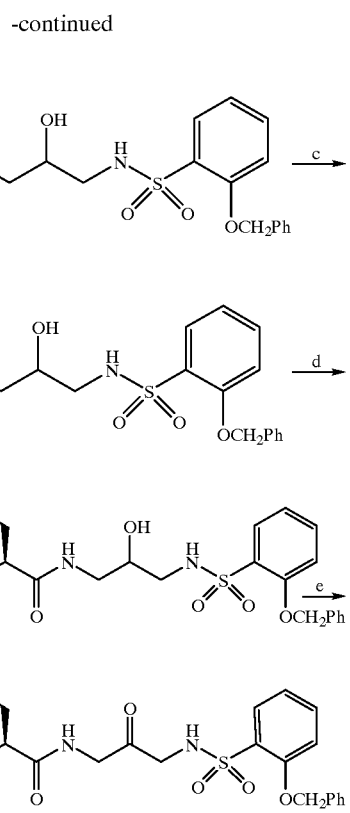

a) EDCI, DMF; b) 2-PhCH₂OPhSO₂Cl, NMM, DMF;
c) TFA, DCM; d) 4-pyridyl acetic acid, HBTU, NMM, DMF; e) Jones 1,3-Diamino-propan-2-ol (or an N-alkyl substituted diamino-propanol) is coupled to a protected leucine analog (either Cbz- or Boc-) and another carboxylic acid or sulfonyl chloride. Removal of the protective group, followed by acylation or sulfonylation, and oxidation of the alcohol provides the desired compounds.

Scheme 25

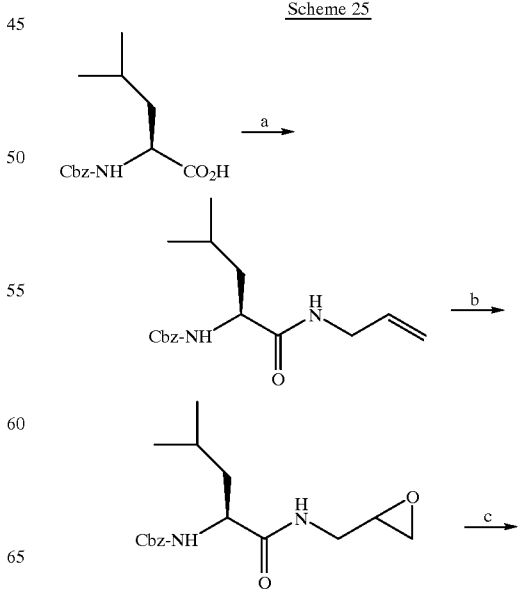

-continued

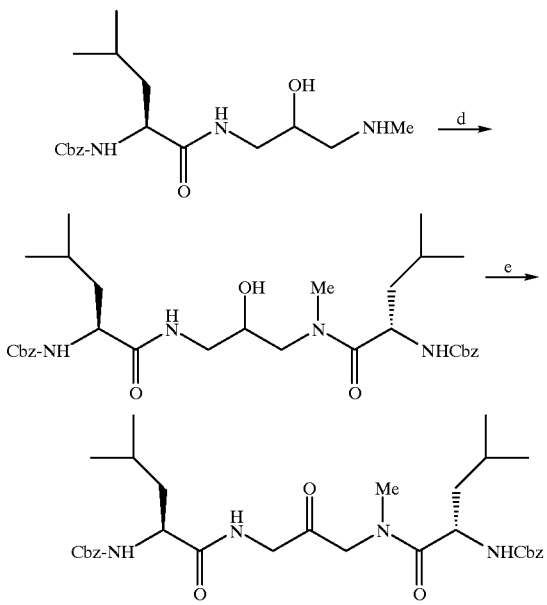

a) HBTU, NMM, DMF, allyl amine; b) mCPBA, DCM; c) MeNH₂, isopropanol, 70 C.; d) Cbz-leucine, EDCI, DMF; e) Jones, acetone N-Allyl amine (or a N-alkyl-N-allyl amine) is coupled to a Cbz-amino acid (or sulfonylated with an aryl sulfonyl chloride), then the alkene is epoxidized with a peracid (or dimethyl diooxirane). The epoxide is opened with a substituted amine, then the amine is acylated or sulfonylated. Final oxidation gives the desired ketones.

The starting materials used herein are commercially available amino acids or are prepared by routine methods well known to those of ordinary skill in the art and can be found in standard reference books, such as the COMPENDIUM OF ORGANIC SYNTHETIC METHODS, Vol. I–VI (published by Wiley-Interscience).

Coupling methods to form amide bonds herein are generally well known to the art. The methods of peptide synthesis generally set forth by Bodansky et al., THE PRACTICE OF PEPTIDE SYNTHESIS, Springer-Verlag, Berlin, 1984; E. Gross and J. Meienhofer, THE PEPTIDES, Vol. 1, 1–284 (1979); and I. M. Stewart and J. D. Young, SOLID PHASE PEPTIDE SYNTHESIS, 2d Ed., Pierce Chemical Co., Rockford, Ill., 1984. are generally illustrative of the technique and are incorporated herein by reference.

Synthetic methods to prepare the compounds of this invention frequently employ protective groups to mask a reactive functionality or minimize unwanted side reactions. Such protective groups are described generally in Green, T. W, PROTECTIVE GROUPS IN ORGANIC SYNTHESIS, John Wiley & Sons, New York (1981). The term "amino protecting groups" generally refers to the Boc, acetyl, benzoyl, Fmoc and Cbz groups and derivatives thereof as known to the art. Methods for protection and deprotection, and replacement of an amino protecting group with another moiety are well known.

Acid addition salts of the compounds of Formula I are prepared in a standard manner in a suitable solvent from the parent compound and an excess of an acid, such as hydrochloric, hydrobromic, hydrofluoric, sulfuric, phosphoric, acetic, trifluoracetic, maleic, succinic or methanesulfonic. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as $Li^+$, $N^+$, $K^+$, $Ca^{++}$, $Mg^{++}$ and $NH_4^+$ are specific examples of cations present in pharmaceutically acceptable salts. Halides, sulfate, phosphtate, alkcanoates (such as acetate and trifluoroacetate), benzoates, and sulfonates (such as mesylate) are examples of anions present in pharmaceutically acceptable salts.

This invention also provides a pharmaceutical composition which comprises a compound according to Formula I and a pharmaceutically acceptable carrier, diluent or excipient. Accordingly, the compounds of Formula I may be used in the manufacture of a medicament. Pharmaceutical compositions of the compounds of Formula I prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these compounds may be encapsulated, tableted or prepared in an emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients such as cocoa butter, glycerin, gelatin or polyethylene glycols and molded into a suppository.

Utility of the Present Invention

The compounds of Formula I are useful as protease inhibitors, particularly as inhibitors of cysteine and serine proteases, more particularly as inhibitors of cysteine proteases, even more particularly as inhibitors of cysteine proteases of the papain superfamily, yet more particularly as inhibitors of cysteine proteases of the cathepsin family, most particularly as inhibitors of cathepsin K. The present invention also provides useful compositions and formulations of said compounds, including pharmaceutical compositions and formulations of said compounds.

The present compounds are useful for treating diseases in which cysteine proteases are implicated, including infections by pneumocystis carinii, trypsanoma cruzi, trypsanoma brucei, and *Crithidia fusiculata*; as well as in schistosomiasis, malaria, tumor metastasis, metachromatic leukodystrophy, muscular dystrophy, amytrophy; and especially diseases in which cathepsin K is implicated, most particularly diseases of excessive bone or cartilage loss, including osteoporosis, gingival disease including gingivitis and periodontitis, arthritis, more specifically, osteoarhritis and rheumatoid arthritis, Paget's disease; hypercalcemia of malignancy, and metabolic bone disease.

Metastatic neoplastic cells also typically express high levels of proteolytic enzymes that degrade the surrounding matrix, and certain tumors and metastatic neoplasias may be effectively treated with the compounds of this invention.

The present invention also provides methods of treatment of diseases caused by pathological levels of proteases, particularly cysteine and serine proteases, more particularly cysteine proteases, even more particularly as inhibitors of cysteine proteases of the papain superfamily, yet more particularly cysteine proteases of the cathepsin family, which methods comprise administering to an animal, particularly a mammal, most particularly a human in need thereof a compound of the present invention. The present invention especially provides methods of treatment of diseases caused by pathological levels of cathepsin K, which methods comprise administering to an animal, particularly a mammal, most particularly a human in need thereof an inhibitor of cathepsin K, including a compound of the present invention. The present invention particularly provides methods for treating diseases in which cysteine proteases are implicated, including infections by pneumocystis carinii, trypsanoma cruzi, trypsanoma brucei, and *Crithidia fusiculata*; as well as in schistosomiasis, malaria, tumor metastasis, metachromatic leukodystrophy, muscular dystrophy, amytrophy, and especially diseases in which cathepsin K is implicated, most particularly diseases of excessive bone or cartilage loss, including osteoporosis, gingival disease including gingivitis and periodontitis, arthritis, more specifically, osteoarthritis and rheumatoid arthritis, Paget's disease, hypercalcemia of malignancy, and metabolic bone disease.

This invention further provides a method for treating osteoporosis or inhibiting bone loss which comprises internal administration to a patient of an effective amount of a compound of Formula I, alone or in combination with other inhibitors of bone resorption, such as bisphosphonates (i.e., allendronate), hormone replacement therapy, anti-estrogens, or calcitonin. In addition, treatment with a compound of this invention and an anabolic agent, such as bone morphogenic protein, iproflavone, may be used to prevent bone loss or to increase bone mass.

For acute therapy, parenteral administration of a compound of Formula I is preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at a concentration effective to inhibit cathepsin K. The compounds are administered one to four times daily at a level to achieve a total daily dose of about 0.4 to about 400 mg/kg/day. The precise amount of an inventive compound which is therapeutically effective, and the route by which such compound is best administered, is readily determined by one of ordinary skill in the art by comparing the blood level of the agent to the concentration required to have a therapeutic effect.

The compounds of this invention may also be administered orally to the patient, in a manner such that the concentration of drug is sufficient to inhibit bone resorption or to achieve any other therapeutic indication as disclosed herein. Typically, a pharmaceutical composition containing the compound is administered at an oral dose of between about 0.1 to about 50 mg/kg in a manner consistent with the condition of the patient. Preferably the oral dose would be about 0.5 to about 20 mg/kg.

No unacceptable toxicological effects are expected when compounds of the present invention are administered in accordance with the present invention.

Biological Assays

The compounds of this invention may be tested in one of several biological assays to determine the concentration of compound which is required to have a given pharmacological effect.

Determination of Cathepsin K Proteolytic Catalytic Activity

All assays for cathepsin K were carried out with human recombinant enzyme. Standard assay conditions for the determination of kinetic constants used a fluorogenic peptide substrate, typically Cbz-Phe-Arg-AMC, and were determined in 100 mM Na acetate at pH 5.5 containing 20 mM cysteine and 5 mM EDTA. Stock substrate solutions were prepared at concentrations of 10 or 20 mM in DMSO with 20 uM final substrate concentration in the assays. All assays contained 10% DMSO. Independent experiments found that this level of DMSO had no effect on enzyme activity or kinetic constants. All assays were conducted at ambient temperature. Product fluorescence (excitation at 360 nM; emission at 460 nM) was monitored with a Perceptive Biosystems Cytofluor II fluorescent plate reader. Product progress curves were generated over 20 to 30 minutes following formation of AMC product.

Inhibition Studies

Potential inhibitors were evaluated using the progress curve method. Assays were carried out in the presence of variable concentrations of test compound. Reactions were initiated by addition of enzyme to buffered solutions of inhibitor and substrate. Data analysis was conducted according to one of two procedures depending on the appearance of the progress curves in the presence of inhibitors. For those compounds whose progress curves were linear, apparent inhibition constants ($K_{i,app}$) were calculated according to equation 1 (Brandt et al., *Biochemistry*, 1989, 28, 140):

$$v = V_m A / [K_a(1 + I/K_{i,app}) + A] \tag{1}$$

where v is the velocity of the reaction with maximal velocity $V_m$, A is the concentration of substrate with Michaelis constant of $K_a$, and I is the concentration of inhibitor.

For those compounds whose progress curves showed downward curvature characteristic of time-dependent inhibition, the data from individual sets was analyzed to give $k_{obs}$ according to equation 2:

$$[AMC] = v_{ss}t + (v_0 - v_{ss})[1 - \exp(-k_{obs}t)]/k_{obs} \tag{2}$$

where [AMC] is the concentration of product formed over time t, $v_0$ is the initial reaction velocity and $v_{ss}$ is the final steady state rate. Values for $k_{obs}$ were then analyzed as a linear function of inhibitor concentration to generate an apparent second order rate constant ($k_{obs}$/inhibitor concentration or $k_{obs}$/[I]) describing the time-dependent inhibition. A complete discussion of this kinetic treatment has been fully described (Morrison et al., *Adv. Enzymol. Relat. Areas Mol. Biol.*, 1988, 61, 201).

Human Osteoclast Resorption Assay

Aliquots of osteoclastoma-derived cell suspensions were removed from liquid nitrogen storage, warmed rapidly at 37° C. and washed x1 in RPMI-1640 medium by centrifugation (1000 rpm, 5 min at 4° C.). The medium was aspirated and replaced with murine anti-HLA-DR antibody, diluted 1:3 in RPMI-1640 medium, and incubated for 30 min on ice The cell suspension was mixed frequently.

The cells were washed x2 with cold RPMI-1640 by centrifugation (1000 rpm, 5 min at 4° C.) and then transferred to a sterile 15 mL centrifuge tube. The number of mononuclear cells were enumerated in an improved Neubauer counting chamber.

Sufficient magnetic beads (5/mononuclear cell), coated with goat anti-mouse IgG, were removed from their stock bottle and placed into 5 mL of fresh medium (this washes away the toxic azide preservative). The medium was removed by immobilizing the beads on a magnet and is replaced with fresh medium.

The beads were mixed with the cells and the suspension was incubated for 30 min on ice. The suspension was mixed frequently. The bead-coated cells were immobilized on a magnet and the remaining cells (osteoclast-rich fraction) were decanted into a sterile 50 mL centrifuge tube. Fresh medium was added to the bead-coated cells to dislodge any trapped osteoclasts. This wash process was repeated x10. The bead-coated cells were discarded.

The osteoclasts were enumerated in a counting chamber, using a large-bore disposable plastic pasteur pipette to charge the chamber with the sample. The cells were pelleted by centrifugation and the density of osteoclasts adjusted to $1.5 \times 10^4$/mL in EMEM medium, supplemented with 10% fetal calf serum and 1.7 g/liter of sodium bicarbonate. 3 mL aliquots of the cell suspension (per treatment) were decanted into 15 mL centrifuge tubes. These cells were pelleted by centrifugation. To each tube 3 mL of the appropriate treatment was added (diluted to 50 uM in the EMEM medium). Also included were appropriate vehicle controls, a positive control (87MEM1 diluted to 100 ug/mL) and an isotype control (IgG2a diluted to 100 ug/mL). The tubes were incubate at 37° C. for 30 min.

0.5 mL aliquots of the cells were seeded onto sterile dentine slices in a 48-well plate and incubated at 37° C. for 2 h. Each treatment was screened in quadruplicate. The slices were washed in six changes of warm PBS (10 mL/well in a 6-well plate) and then placed into fresh treatment or control and incubated at 37° C. for 48 h. The slices were then washed in phosphate buffered saline and fixed in 2% glutaraldehyde (in 0.2M sodium cacodylate) for 5 min., following which they were washed in water and incubated in buffer for 5 min at 37° C. The slices were then washed in cold water and incubated in cold acetate buffer/fast red garnet for 5 min at 4° C. Excess buffer was aspirated, and the slices were air dried following a wash in water.

The TRAP positive osteoclasts were enumerated by bright-field microscopy and were then removed from the surface of the dentine by sonication. Pit volumes were determined using the Nikon/Lasertec ILM21W confocal microscope.

General

Nuclear magnetic resonance spectra were recorded at either 250 or 400 MH using, respectively, a Bruker AM 250 or Bruker AC 400 spectrometer. $CDCl_3$ is deuteriochloroform, $DMSO-d_6$ is hexadeuteriodimethylsulfoxide, and $CD_3OD$ is tetradeuteriomethanol. Chemical shifts are reported in parts per million (d) downfield from the internal standard tetramethylsilane. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Continuous wave infrared (IR) spectra were recorded on a Perkin-Elmer 683 infrared spectrometer, and Fourier transform infrared (FTIR) spectra were recorded on a Nicolet Impact 400 D infrared spectrometer. IR and FTIR spectra were recorded in transmission mode, and band positions are reported in inverse wavenumbers ($cm^{-1}$). Mass spectra were taken on either VG 70 FE, PE Syx API III, or VG ZAB HF instruments, using fast atom bombardment (FAB) or electrospray (ES) ionization techniques. Elemental analyses were obtained using a Perkin-Elmer 240C elemental analyzer. Melting points were taken on a Thomas-Hoover melting point apparatus and are uncorrected. All temperatures are reported in degrees Celsius.

Analtech Silica Gel GF and E. Merck Silica Gel 60 F-254 thin layer plates were used for thin layer chromatography. Both flash and gravity chromatography were carried out on E. Merck Kieselgel 60 (230–400 mesh) silica gel.

Where indicated, certain of the materials were purchased from the Aldrich Chemical Co., Milwaukee, Wis., Chemical Dynamics Corp., South Plainfield, N.J., and Advanced Chemtech, Louisville, Ky.

EXAMPLES

In the following synthetic examples, temperature is in degrees Centigrade (°C.). Unless otherwise indicated, all of the starting materials were obtained from commercial sources. Without further elaboration, it is believed that one skilled in the art can, using the preceding description, utilize the present invention to its fullest extent. These Examples are given to illustrate the invention, not to limit its scope. Reference is made to the claims for what is reserved to the inventors hereunder.

Example 1

Preparation of (2S,1'S)-2-(benzloxycarbonyl)amino-N-[1'-(2carboethoxythiazol-4-yl)-3'-methylbutyl]-4-methylpentanamide a) N-benzyloxycarbonyl-L-leucinyl-L-leucinyl bromomethylketone 1-Methyl-3-nitro-1-nitrosoguanidine (5.9 g, 40.11 mmol) in ether (200 mL) is cooled to 0° C. 40% potassium hydroxide is added slowly and the diazomethane is allowed to collect in the ether solution for 30 minutes at 0° C.

N-Cbz-L-Leucinyl-L-Leucine (Bachem) (4.0 g, 10.58 mmol) is stirred in tetrahydrofuran at −40° C. N-methylmorpholine (1.07 g, 10.58 mmol, 1.16 mL) and isobutyl chloroformate (1.45 g, 10.58 mmol, 1.38 mL) are added. The mixture is stirred at −40° C. for 15 minutes and then filtered into a cold flask to remove precipitated salts. To the filtered solution is added an excess of the previously prepared diazomethane solution and the mixture is allowed to stand at 0° C. for 16 h. An excess of 30% HBr in acetic acid is added at 0° C. and the solution is then washed successively with 1.0N citric acid, saturated aqueous sodium bicarbonate (carefully), and brine. The solution is dried over sodium sulfate, filtered, and evaporated to give the title compound as a white solid (4.10 g). $^1$H NMR (400 MHZ, CDCl$_3$) δ7.34 (m, 5H), 6.51 (d, 1H), 5.15 (d, 1H), 5.10 (s, 2H), 4.78 (m, 1H), 4.20 (m, 1H), 4.04 (dd, 2H), 1.63 (m, 6H), 0.93 (m, 12H).

b) (2S,1'S)-2-(benzyloxycarbonyl)amino-N-[1'-(2-carboethoxythiazol-4-yl)-3'-methylbutyl]-4-methylpentanamide The compound of Example 1(a) (2.0 g, 4.4 mmol) and ethyl thiooxamate (0.59 g, 4.4 mmol) were refluxed in ethanol for 4 h. The solvent was evaporated and the residue chromatographed (silica gel, 2.5% methanol/dichloromethane) to give the title compound as a white solid (1.46 g). $^1$H NMR (400 MHz; CDCl$_3$) δ7.32 (s, 1H), 7.21 (m, 5H), 6.40 (d, 1H), 5.13 (dd, 1H), 5.02 (s, 2H), 4.41 (q, 2H), 4.06 (m, 1H), 1.71 (m, 2H), 1.47 (m, 4H), 1.33 (t, 3H), 0.73 (m, 12H).

Example 2

Preparation of (2S,1'S)-2-benzylcarbonyl)amino-N-[1'-(2-carboxythiazol-4-yl)-3'-methylbutyl]-4-methylpentanamide The compound of Example 1(c) (0.92 g, 1.88 mmol) was stirred in tetrahydrofuran at 0° C. with 1.0N sodium hydroxide. After stirring for 1 h, the solution was quenched with 1.0N citric acid and extracted three times with dichloromethane. The combined organic extracts were evaporated in vacuo to give the title compound as a white solid (0.844 g). $^1$H NMR (400 MHz, CDCl$_3$) δ7.40 (s, 1H), 7.23 (m, 5H), 6.89 (d, 1H), 5.22 (d, 1H), 5.14 (dd, 1H), 5.02 (s, 2H), 4.15 (m, 1H), 1.67 (m, 2H), 1.44 (m, 4H), 0.81 (m, 12H).

Example 3

Preparation of (2S,1'S)-2-(benzyloxycarbonyl) amino-N-[1'-(2-carboxamidothiazol-4-yl)-3'-methylbutyl]-4-methylpentanamide The compound of Example 2 (0.408 g, 0.88 mmol) in tetrahydrofuran was cooled to −40° C. and treated with N-methylmorpholine (0.185 g, 1.85 mmol, 0.2 mL) and isobutyl chloroformate (0.12 g, 0.88 mmol, 0.11 mL). The mixture was stirred at −40° C. for 15 minutes and then ammonia was bubbled through the solution for several minutes. The mixture was allowed to warm to room temperature and was then diluted with ethyl acetate and washed successively with 1.0N citric acid, 5% aqueous sodium bicarbonate, and brine. The organic solution was dried over magnesium sulfate, filtered, and evaporated to a residue which was chromatographed (silica gel, 3% methanol/dichloromethane) to give the title compound as a white solid (0.245 g). $^1$H NMR (400 MHz, CDCl$_3$) δ7.22 (m, 5H), 7.04 (s, 1H), 6.40 (br s, 1H), 5.51 (br s, 1H), 5.09 (m, 1H), 5.02 (dd, 2H), 4.07 (m, 1H), 1.66–1.42 (m, 6H), 0.82 (m, 12H).

Example 4

Preparation of (2S,1'S)-2-(benzyloxycarbonyl) amino-N-[1'-(2-cyanothiazol-4-yl)-3'-methylbutyl]-4-methylpentanamide The compound of Example 3 (0.185 g, 0.4 mmol) was dissolved in dichloromethane, cooled to 0° C. and treated with TFAA (0.093 g, 0.44 mmol, 0.06 mL) and pyridine (0.07 g, 0.88 mmol, 0.07 mL). After 3 h, the mixture was poured into a solution of saturated aqueous sodium bicarbonate and extracted with dichloromethane. The organic extracts were washed with 5% hydrochloric acid and brine, dried over magnesium sulfate, filtered, and evaporated to an oil which was chromatographed (silica gel, 40% ethyl acetate/hexane) to give the title compound as a white solid (0.095 g). $^1$H NMR (400 MHz, CDCl$_3$) δ7.44 (s, 1H), 7.29 (s, 5H), 6.51 (br d, 1H), 5.14 (m, 1H), 5.07 (s, 2H), 4.11 (m, 1H), 1.78–1.41 (m, 6H), 0.83 (m, 12H).

Example 5

Preparation of (2S,1'S)-2-(benzyloxycarbonyl) amino-N-[1'-[2-(N-benzylcarboxamido)thiazol-4-yl]-3'-methylbutyl]-4-methylpentamide To a solution of the compound of Example 2 (0.12 g, 0.26 mmol) in dichloromethane under argon at room temperature is added benzylamine (0.03 g, 0.29 mmol, 0.03 mL), BOP reagent (0.115 g, 0.26 mmol), and triethyl amine (0.026 g, 0.26 mmol, 0.04 mL) which is allowed to stir for 16 h. The solution is washed with water, then brine and the organic layer is dried over magnesium sulfate, filtered, and evaporated to give a residue which was chromatographed (silica gel, 40% ethyl acetate/hexane) to give the title compound as a white solid (0.065 g). $^1$H NMR (400 MHz, CDCl$_3$) δ7.56 (br s, 1H), 7.33 (m, 10H), 6.48 (br d, 1H), 5.15 (dd, 1H), 5.03 (s, 2H), 4.63 (d, 2H), 4.12 (m, 1H), 1.72–1.40 (m, 6H), 0.85 (m, 12H).

Example 6

Preparation of (2S,1'S)-2-benzyloxycarbonyl)amino-N-[1'-[2-[N'-(3-methylpropyl)carboxamido]thiazol-4-yl]-3'-methylbutyl]-4-methylpentanamide Following the procedure of Example 5, except substituting isobutylamine for benzylamine, the title compound was prepared (0.074 g). $^1$H NMR (400 MHz, CDCl$_3$) δ7.27 (s, 5H), 7.19 (s, 1H), 6.38 (br d, 1H), 5.09 (m, 1H), 5.01 (s, 2H), 4.07 (m, 1H), 3.20 (dd, 2H), 1.83 (m, 1H), 1.69–1.40 (m, 6H), 0.90 (d, 6H), 0.81 (m, 12H).

Example 7

Preparation of (2S,1'S)-2-(benzyloxycarbonyl) amino-N-[1'-[2-[N'-(2-phenylethyl)carboxamido] thiazol-4-yl]-3'-methylbutyl]-4-methylpentanamide Following the procedure of Example 5, except substituting 2-phenylethylamine for benzylamine, the title compound was prepared (0.070 g). $^1$H NMR (400 MHz, CDCl$_3$) δ7.30–7.11 (m, 11H), 6.35 (br d, 1H), 5.09 (m, 1H), 5.01 (s, 2H), 4.05 (m, 1H), 3.64 (m, 2H), 2.87 (t, 2H), 1.69–1.40 (m, 6H), 0.80 (m, 12H).

Example 8

Preparation of (2S,1'S)-2-benzyloxycarbonyl)amino-N-[1'-(4-carboethoxythiazol-2-yl)-3'-methylbutyl]-4-methylpentanamide a) N-tert-butoxycarbonyl-(L)-leucinamide To a solution of N-tert-butoxycarbonyl-(L)-leucine (Advanced Chemtech) (5.0 g, 20.0 mmol) in dry THF (100 mL) at −40° C. was added isobutyl chloroformate (2.7 g, 20.0 mmol) and N-methylmorphiline (4.2 g, 42 mmol). After 15 minutes of stirring, ammonia was bubbled through the mixture for an additional 15 minutes, then warmed to room temperature and allowed to stir for 2 hours. Mixture filtered and filtrate concentrated in vacuo to yield title compound as a white solid (4.9 g, 19.7 mmol). $^1$H NMR (400 MHz, CDCl$_3$) δ6.38 (br s, 1H), 5.79 (br s, 1H), 5.04 (br d, 1H), 4.13 (m, 1H), 1.71–1.49 (m, 3H), 1.39 (s, 9H), 0.92 (dd, 6H).

b) N-tert-butoxycarbonyl-L-leucinethioamide

To a stirring solution of the compound of Example 8(a) (2.38 g, 10.35 mmol) in dry THF was added Lawessons reagent (2.51 g, 6.21 mmol) and the mixture was stirred at room temperature under argon overnight. The solvent was evaporated and the residue chromatographed (silica gel, 2.5% methanol/dichloromethane) to give the title compound as a white solid (2.3 g). $^1$H NMR (400 MHz, CDCl$_3$) δ8.54 (br s, 1H), 7.97 (br s, 1H), 5.28 (br d, 1H), 4.52 (m, 1H), 1.72–1.58 (m, 3H), 1.40 (s, 9H), 0.92 (d, 6H).

c) (1S)-1-(tert-butoxycarbonyl)amino-1-(4-carboethoxythiazol-2-yl)-3-methylbutane The compound of Example 8(b) (2.40 g, 9.76 mmol) was stirred in dry acetone (20 mL) under argon at –10° C. Ethylbromopyruvate (2.12 g, 10.73 mmol, 1.35 mL) was added and stirred for 1 h at –10° C. The solution was poured into a well stirred mixture of chloroform and water and then saturated with sodium bicarbonate. The organic phase was separated and the aqueous layer extracted with chloroform. The combined organic extracts were dried over MgSO$_4$, filtered, and evaporated to an oil. The oily residue was treated with TFAA (2.19 g, 10.73 mmol, 1.5 mL) and pyridine (1.70 g, 21.47 mmol, 1.75 mL) in dichloromethane for 1 h at –20° C. Excess solvent was removed in vacuo and the residue was dissolved in dichloromethane. The solution was washed with saturated aqueous sodium bicarbonate and 1.0N KHSO$_4$ until pH 7. The solution was dried over sodium sulfate, filtered, and evaporated to an oil which was chromatographed (4% methanol/dichloromethane) to give the title compound as a tan solid (1.2 g). $^1$H NMR (400 MHz, CDCl$_3$) δ7.98 (s, 1H), 5.04 (br d, 1H), 4.95 (m, 1H), 4.31 (q, 2H), 1.88 (m, 1H), 1.63 (m, 2H), 1.40 (s, 9H), 1.32 (t, 3H), 0.85 (dd, 6H).

d) (2S,1'S)-2-(benzyloxycarbonyl)amino-N-[1-4-carboethoxythiazol-2-yl)-3'-methylbutyl]-4-methylpentanamide The compound of Example 8(c) (1.0 g, 2.92 mmol) was dissolved in neat TFA (1.0 mL) and stirred for 15 minutes. The solution was diluted with methanol and evaporated in vacuo. A portion of the residue obtained (0.36 g, 1.49 mmol) was dissolved in dichloromethane with N-Cbz-L-leucine (0.394 g, 1.49 mmol), BOP reagent (0.66 g, 1.49 mmol), and triethylamine (0.73 g, 7.2 mmol, 1.0 mL) and stirred at room temperature for 16 h. The solution was washed with water, then brine and dried over magnesium sulfate, filtered, and evaporated to a residue which was chromatographed (silica gel, 40% ethyl acetate/hexane) to give the title compound as a white solid (0.396 g). $^1$H NMR (400 MHz, CDCl$_3$) δ7.96 (s, 1H), 7.25 (s, 5H), 6.61 (br d, 1H), 5.30 (m, 1H), 5.09 (br d, 1H), 5.01 (s, 2H), 4.33 (q, 2H), 4.10 (m, 1H), 1.90–1.58 (m, 6H), 1.29 (t, 3H), 0.81 (dd, 12H).

Example 9

Preparation of (2S,1'S)-2-(benzyloxycarbonyl)amino-N-[1'-(4-carboxythiazol-2-yl)-3-'methylbutyl]-4-methylpentanamide Following the procedure of Example 2, except substituting (2S,1'S)-2-(benzyloxycarbonyl)amino-N-1'-(4-carboethoxythiazol-2-yl)-3'-methylbutyl]-4-methylpentanamide for (2S,1'S)-2-(benzyloxycarbonyl)amino-N-[1'-(2-carboxythiazol-4-yl)-3'-methylbutyl]-4-methylpentanamide, the title compound was prepared (0.301 g). $^1$H NMR (400 MHz, CDCl$_3$) δ8.06 (s, 1H), 7.24 (m, 5H), 7.11 (d, 1H), 5.30 (m, 2H), 5.04 (s, 2H), 4.16 (m, 1H), 1.88–1.40 (m, 6H), 0.71 (dd, 12H).

Example 10

Preparation of (2S,1'S)-2-(benzyloxycarbonyl)amino-N-[1'-(4-carboethoxythiadiazol-2-yl)-3'-methylbutyl]-4-methylpentanamide a) N-tert-butoxycarbonyl-L-leucine methyl ester To a stirring suspension of L-leucine methyl ester hydrochloride (Aldrich) (6.00 g, 33.0 mmol) and di-tert-butyl dicarbonate (7.21 g, 33.0 mmol) in THF (35 mL) was added triethylamine (3.34 g, 33.0 mmol, 4.60 mL). The mixture was allowed to stir at room temperature for 3 d. The mixture was diluted with ethyl acetate and washed with 1N HCl (2 times), water, and saturated brine, then dried over magnesium sulfate, filtered and concentrated to give the title compound as a colorless oil (8.02 g, 99%). $^1$H NMR (400 MHz, CDCl$_3$) δ4.88 (d, 1H), 4.33–4.31 (m, 1H), 7.73 (s, 3H), 1.75–1.48 (m, 3H), 1.44 (s, 9H), 0.96 (d, 3H), 0.93 (d, 3H).

b) N-tert-butoxycarbonyl-L-leucine hydrazide

To a string solution of the compound of Example 10(a) (8.02 g, 32.7 mmol) in methanol (250 mL) was added hydrazine hydrate (16.38 g, 327 mmol, 15.9 mL). After stirring for 22 h at room temperature, the solution was concentrated and the residue was azeotroped with toluene to provide the title compound as a white foam (8.02 g, 100%). $^1$H NMR (400 MHz, CDCl$_3$) δ7.71 (br s, 1H), 4.99 (d, 2H), 4.12–4.10 (m, 1H), 3.94 (br s, 2H), 1.68–1.49 (m, 3H), 1.44 (s, 9H), 0.95 (d, 3H), 0.92 (d, 3H).

c) (2S)-N-[2-(benzyloxycarbonyl)amino-4-methylpentanoyl]-N'-carboethoxycarbonylhydrazide To a stirring solution of the compound of Example 10(b) (8.02 g, 32.7 mmol) and pyridine (2.85 g, 36.0 mmol, 2.91 mL) in dichloromethane (200 mL) was added ethyl oxalyl chloride (4.91 g, 36.0 mmol, 4.02 mL). After stirring at room temperature for 2 h, thye solution was washed with 1 N HCl, water, stirred aqueous sodium bicarbonate and saturated brine, then dried over magnesium sulfate, filtered, and concentrated to afford the title compound as a white foam (9.84 g, 87%). $^1$H NMR (400 MHz, CDCl$_3$) δ9.32 (br s, 2H), 5.04 (d, 2H), 4.38 (q, 2H), 4.28 (m, 1H), 1.77–1.56 (m, 3H), 1.44 (s, 9H), 1.39 (t, 3H), 0.96 (d, 3H), 0.94 (d, 3H).

d) (1S)-1-(tert-butoxycabonyl)amino-1-(4-carboethoxythiadiazol-2-yl)-3-methylbutane To a stirring solution of the compound of Example 10(c) (2.50 g, 7.24 mmol) in toluene (70 mL) was added Lawesson's reagent (1.46 g, 3.62 mmol). The mixture was heated at reflux for 3 h. The solution was diluted with ether, washed with saturated aqueous sodium bicarbonate and sa brine, then dried over magnesium sulfate, filtered and concentrated to leave a pale yellow oil. The crude material was purified by flash chromatography on 75 g of 230 mesh silica gel, eluting with 1:4 ethyl acetate/hexanes, to provide the title compound as a pale yellow solid (1.75 g, 70%). $^1$H NMR (400 MHz, CDCl$_3$) δ5.19 (m, 1H), 5.13 (d, 1H), 4.51 (q, 2H), 1.95 (m, 1H), 1.83–1.73 (m, 2H), 1.44 (s, 9H), 1.00 (d, 3H), 0.98 (d, 3H).

e) (1S)-1-amino-1-(4-carboethoxythiadiazol-2-yl)3-methylbutane bis-trifluoroacetate salt To a stirring solution of the compound of Example 10(d) (1.75 g, 5.1 mmol) in dichloromethane (40 mL) was added TFA (10 mL). After sing for 5 min at room temperature, the solution was concentrated to give the title compound as an oily pale yellow solid (2.40 g, 100%). $^1$H NMR (400 MHz, CDCl$_3$) δ9.83 (br s, 4H), 5.20 (m, 1H), 4.51 (q, 2H), 2.07 (m, 2H), 1.70 (m, 1H), 1.44 (t, 3H), 1.00 (t, 3H).

f) (2S,1'S)-2-benzyloxycarbonyl)amino-N-[1'-(4-carboethoxythiadiazol-2-yl)-3'-methylbutyl]-4-methylpentanamide To a stirring solution of the compound of Example 10(e) (566.1 mg, 1.20 mmol), N-Cbz-L-leucine (250.5 mg, 1.32 mmol), 1-(3-dimethylaminopropyl)-3-ethylcarbodiimide hydrochloride (253.3 mg, 1.32 mmol) and 1-hydroxybenzotriazole (32.5 mg, 0.24 mmol) in 2.5 mL of DMF was added triethylamine (243.1 mg, 2.40 mmol, 0.335 mL). After stirring at room temperature for 3 d, the mixture was diluted with ethyl acetate and washed with water, saturated aqueous sodium bicarbonate and saturated brine, then dried over magnesium sulfate, filtered and concentrated to give a yellow oil. The cride material was purified by flash chromatography on 20 g of 230–400 mesh silica gel, eluting with 1:2 ethyl acetate/hexanes, to provide the title compound as a white solid (271 mg, 46%). $^1$H NMR (400 MH, CDCl$_3$) δ7.35 (s, 5H), 6.77 (d, 1H), 5.49 (m, 1H), 5.12 (dd, 2H), 4.51 (q, 2H), 4.20 (m, 1H), 1.97 (m, 1H), 1.88 (m, 1H), 1.66 (m, 3H), 1.52 (m, 1H), 1.45 (t, 3H), 0.97–0.92 (m, 12H).

Example 11

Preparation of (2S,1'S)-2-(benzyloxycarbonyl) amino-N-[1'-(2-carbo-2,2,2-trifluoroethoxythiazol-4-yl)-3'-methylbutyl]-4-methylpentanamide The compound of Example 2 (0.200 g, 0.433 mmol), 1,1,1 trifluoroethanol (0.052 g, 0.52 mmol, 0.04 mL), pyridine (0.1 mL), and di-t-butyl dicarbonate (0.104 g, 0.477 mmol) were stirred in ethyl acetate at room temperature for 16 h. The solution was diluted with ethyl acetate and washed successively with 5% hydrochloric acid, 10% aqueous sodium bicarbonate, and brine. The organic layer was dried over magnesium sulfate, filtered, and evaporated to give a residue which was chromatographed (silica gel, 20% ethyl acetate/hexane) to give the title compound as a white solid (0.098 g). $^1$H NMR (400 MHz, CDCl$_3$) δ7.50 (s, 1H), 7.36 (s, 5H), 6.64 (d, 1H), 5.22 (m, 2H), 5.09 (s, 2H), 4.73 (m, 2H), 4.16 (m, 1H), 1.66–1.41 (m, 6H), 0.87 (m, 12H).

Example 12

Preparation of (2S,1'S)-2-(benzyloxycarbonyl) amino-N-[1'-(4-carboethoxyoxadiazol-2-yl)-3'-methylbutyl]-4-methylpentanamide a) (1S)-1-(tert-butoxycarbonyl)amino-1-(4-carboethoxyoxadiazol-2-yl)-3-methylbutane To a stirring solution of the compound of Example 10(c) (2.50 g, 7.24 mmol) and pyridine (1.49 g, 18.8 mmol, 1.52 mL) in ether (15 m) was added thionyl chloride (1.12 g, 9.41 mmol, 0.69 mL). After stirring at room temperature for 2 h, the solid was removed by filtration and the filtrate was concentrated. The residue was dissolved in toluene and heated at reflux. After 12 h, the solution was concentrated to leave a brown oil. The residue was purified by flash chromatography on 175 g of 230–400 mesh silica gel, eluting with 1:4 ethyl acetate/hexanes, to give the title compound as a pale yellow oil (0.84 g, 35%). $^1$H NMR (400 MHz, CDCl$_3$) δ5.14 (m, 1H), 5.03 (br d, 1H), 4.52 (q, 2H), 1.78–1.70 (m, 3H), 1.44 (s, 9H), 0.99 (d, 6H).

b) (1S)-1-amino-1-(4-carboethoxyoxadiazol-2-yl)3-methylbutane

Following the procedure of Example 10(e), except substituting (1S)-1-(tert-butoxycarbonyl)amino-1-(4-carboethoxyoxadiazol-2-yl)-3-methylbutane for (1S)-1-(tert-butoxycarbonyl)amino-1-(4-carboethoxythiadiazol-2-yl)-3-methylbutane, the title compound was prepared (582 mg, 100%). $^1$H NMR (400 MHz, CDCl$_3$) δ4.99 (t, 1H), 4.52 (q, 2H), 2.10–2.02 (m, 2H), 1.77–1.70 (m, 1H), 1.44 (t, 3H), 1.00 (t, 6H).

c) (2S,1'S-2-(benzyloxycarbonyl)amino-N-[1'-(4-carboethoxyoxadiazol-2-yl)-3'-methylbutyl]-4-methylpentanamide Following the procedure of Example 10(f), except substituting (1S)-1-amino-1-(4-carboethoxyoxadiazol-2-yl)-3-methylbutane for (1S)-1-amino-1-(4-carboethoxythiadiazol-2-yl)-3-methylbutane, the title compound was prepared (235 mg, 39%). $^1$H NMR (400 MHz, CDCl$_3$) δ7.26 (s, 5H), 6.64 (s, 1H), 5.45–5.39 (m, 1H), 5.12 (m, 3H), 4.52 (q, 2H), 4.20 (m, 1H), 1.81 (m, 2H), 1.68–1.64 (m, 3H), 1.54–1.50 (m, 1H), 1.46 (t, 3H), 0.97–0.92 (m, 12H).

Example 13

Preparation of (2S,1'S)-2-benzyloxycarbonyl-L-leucinyl)amino-N-[1'-(4-carboethoxythiazol-2-yl)-3'-methylbutyl]-4-methylpentanamide The compound of Example 8(c) (160.7 mg, 0.47 mmol) was dissolved in neat TFA (1.0 mL) and stirred for 15 minutes. The solution was diluted with methanol and evaporated to dryness. The residue was dissolved in DMF (2 mL) and to the resulting solution was added N-Cbz-L-leucinyl-L-leucine (194.0 mg, 0.52 mmol), 1-(3-dimethylaminopropyl)-3-ethylcarbodiimide hydrochloride (99.0 mg, 0.52 mmol) and 1-hydroxybenzotriazole (13.0 mg, 0.094 mmol) and triethylamine (94.7 mg, 0.936 mmol, 0.13 mL). After stirring at room temperature for 24 h, the mixture was diluted with ethyl acetate and washed with water, saturated aqueous sodium bicarbonate and saturated brine, then dried over magnesium sulfate, filtered and concentrated. The residue was purified by flash chromatography on 230–400 mesh silica gel, eluting with ethyl acetate/hexanes, to provide the title compound (0.146 g). $^1$H NMR (400 MHz, CDCl$_3$) δ8.04 (s, 1H), 7.33 (m, 5H), 7.14 (d, 1H), 6.61 (d, 1H), 5.37 (m, 2H), 5.08 (m, 2H), 4.47 (m, 1H), 4.39 (q, 2H), 4.18 (m, 1H), 1.98–1.45 (m, 9H), 1.38 (t, 3H), 0.94–0.86 (m, 18H).

Example 14

Preparation of (2S,1'S)-2-(benzyloxycarbonyl) amino-N-[1'-(4-carboxamidooxadiazol-2-yl)-3'-methylbutyl]-4-methylpentanamide Ammonia was bubbled through a solution of the compound of Example 12 (96.8 mg, 0.2 mmol) in ethanol (2 mL) for 5 inm. After sting an additional 5 min, the solution was concentrated to give the title compound as a white solid (91.2 mg, 98%). $^1$H NMR (400 MHz, CDCl$_3$/CD$_3$OD) δ7.29 (s, 5H), 5.90 (d, 1H), 5.30 (t, 1H), 5.04 (s, 2H), 4.15 (m, 1H), 1.76 (m, 2H), 1.59–1.43 (m, 4H), 0.92–0.85 (m, 12H).

Example 15

Preparation of (2S,1'S)-2-(benzyloxycarbonyl) amino-N-[1'-(2-carboethoxythiazol-4-yl)-3'-methylbutyl]-3-phenylpropanamide a) N-(9-fluorenylmethoxycarbonyl)-L-leucinyl bromomethyl ketone Following the procedure of Example 1(a), except substituting N-(9-fluorenylmethoxycarbonyl)-L-leucine for N-benzyloxycarbonyl-L-leucinyl-L-leucine, the title compound was prepared (5.6 g). $^1$H NMR (400 MHz, CDCl$_3$) δ7.71 (d, 2H), 7.51 (d, 2H), 7.34 (dd, 2H), 7.22 (dd, 2H), 5.08 (d, 1H), 4.53 (m, 1H), 4.36 (dd, 2H), 4.13 (dd, 2H), 3.89 (dd, 2H), 1.62–1.41 (m, 3H), 0.88 (m, 6H).

b) (1S)-1-(2-carboethoxythiazol-4-yl)-1-(9-fluorenylmethoxycarbonyl)amino-3-methylbutane Following the procedure of Example 1(b), except substituting N-(9-fluorenylmethoxycarbonyl)-L-leucinyl bromomethyl ketone for N-Benzyloxycarbonyl-L-leucinyl-L-leucinyl bromomethylketone, the title compound was prepared (4.13 g). $^1$H NMR (400 MHz CDCl$_3$) $\delta$7.72 (d, 2H), 7.49 (d, 2H), 7.32 (dd, 2H), 7.22 (dd, 2H), 7.19 (s, 1H), 5.31 (d, 1H), 4.88 (m, 1H), 4.40 (q, 2H), 4.28 (d, 2H), 4.08 (t, 1H), 1.62–1.41 (m, 3H), 1.36 (t, 3H), 0.88 (m, 6H).

c) (1S)-1-amino-1-(2-carboethoxythiazol-4-yl)-3-methylbutane

The compound of Example 15(b) (0.5 g., 1.1 mmol) was stir in a 5% piperidine/DMF solution for 10 minutes at room temperature. The solvents were evaporated and the solid obtained was dried in vacuo to give the title compound (0.27 g).

d) (2S,1'S)-2-(benzyloxycarbonyl)amino-N-[1'-(2-carboethoxythiazol-4-yl)-3'-methylbutyl]-3-phenylpropanamide Following the procedure of Example 5, except substituting (1S)-1-amino-1-(2-carboethoxythiazol-4-yl)-3-methylbutane for benzylamine, and N-Cbz-L-phenylalanine for (2S,1'S-2-(benzyloxycarbonyl)amino-N-[1'-(2-carboxythiazol-4-yl)-3'-methylbutyl]-4-methylpentanamide, the title compound was prepared (0.162 g). $^1$H NMR (400 MHz, CDCl$_3$) $\delta$7.27 (m, 5H), 7.11 (s, 1H), 7.04 (m, 5H), 6.12 (d, 1H), 5.24 (d, 1H), 5.10 (q, 1H), 5.01 (s, 2H), 4.37 (q, 2H), 4.21 (m, 1H), 2.91 (m, 2H), 1.62 (m, 3H), 1.37 (t, 3H), 0.81 (m, 6H).

Example 16

Preparation of (2S,1'S)-2-(benzyloxycarbonyl-L-leucinyl)amino-N-[1'-(2-carboethoxythiazol-4yl)-3'-methylbutyl]-4-methylpentanamide Following the procedure of Example 5, except substituting (1S)-1-amino-1-(2-carboethoxythiazol-4-yl)-3-methylbutane for benzylamine, and N-Cbz-L-leucinyl-L-leucine for (2S,1'S)-2-(benzyloxycarbonyl)amino-N-[1'-2-carboxythiazol-4-yl)-3'-methylbutyl]4-methylpentanamide, the title compound was prepared (0.098 g.). $^1$H NMR (400 MHz, CDCl$_3$) $\delta$7.39 (s, 1H), 7.25 (m, 5H), 6.87 (d, 1H), 6.49 (d, 1H), 5.30 (d, 1H), 5.16 (q, 1H), 4.99 (s, 2H), 4.36 (q, 2H), 4.31 (m, 1H), 4.09 (m, 1H), 1.74–1.38 (m, 9H), 1.32 (t, 3H), 0.80 (m, 15H).

Example 17

Preparation of (2S,1'S)-2-(benzyloxycarbonyl) amino-N-[1'-(5-mercapto-1,2,4-oxadiazol-3-yl)-3-methylbutyl]-4-methylpentanamide a) N-benzyloxycabonyl-L-leucinyl-L-leucine methyl ester N-Cbz-L-leucine (Chemical Dynamics) (1.32 g, 4.97 mmol), L-leucine methyl ester hydrochloride (Aldrich) (0.99 g, 5.47 mmol), 1-hydroxybenzotriazole (0.14 g, 1.0 mmol) and 1-(3-dimethylaminopropyl)-3-ethylcarbodiimide hydrochloride (1.05 g, 5.47 mmol) were combined, dissolved in 25 mL of DMF and stirred at room temperature for 15 h. The solution was diluted with ethyl acetate (250 mL) and washed successively with water, 0.1 N HCl, saturated aqeous NaHCO$_3$ and saturated brine, then dried (MgSO$_4$), filtered, and concentrated. The residue was purified by flash chromatography on 230–400 mesh silica gel, eluting with 1:3 ethyl acetate hexanes, to give the title compound as a white solid (1.28 g, 66%). $^1$H NMR (400 MHz, CDCl$_3$) $\delta$7.37–7.32 (m, 5H), 6.28 (d, 1H), 5.28 (m, 3H), 4.61–4.58 (m, 1H), 4.20 (m, 1H), 3.74 (s, 3H), 1.69–1.54 (m, 6H), 0.96–0.92 (m, 12H).

b) N-benzyloxycarbonyl-L-leucinyl-L-leucinylhydrazide

To as stirring solution of the compound of Example 17(a) (1.28 g, 3.26 mmol) in 25 mL of methanol was added hydrazine hydrate (1.63 g, 32.6 mmol, 1.58 mL) and the solution was allowed to stir at room temperature for 15 h. The solution was evaporated to dryness to give the title compound as a white solid (1.28 g, 100%). $^1$H NMR (400 MHz, CDCl$_3$) $\delta$8.05 (br s, 1H), 7.35–7.32 (m, 5H), 6.67 (d, 1H), 5.50 (d, 1H), 5.11 (s, 2H), 4.46 (m, 1H), 4.21 (m, 1H), 3.88 (br s, 2H), 1.64–1.51 (m, 6H), 0.92–0.88 (m, 12H).

c) (2S,1'S)-2-(benzyloxycarbonyl)amino-N-[1'-(5-mercapto-1,2,4-oxadiazol-3-yl)-3'-methylbutyl]-4-methylpentanamide To a stirring solution of the compound of Example 17(b) (0.3 g, 0.76 mmol) in 1.5 mL of chloroform was added triethylamine (0.155 g, 1.53 mmol, 0.213 mL) and thiophosgene (0.088 g, 0.76 mmol, 0.058 mL). The solution was heated at reflux for 3 h, then cooled to room temperature. The mixture was diluted with ethyl acetate, washed with water and saturated brine, dried (MgSO$_4$), filtered, and concentrated. The residue was purified by flash chromatography on 230–400 mesh silica gel, eluting with 11% methanol in dichloromethane, to give the title compound as a white solid (0.20 g, 61%). $^1$H NMR (400 MHz, CDCl$_3$) $\delta$7.36 (m, 6H), 6.85 (d, 1H), 5.37 (d, 1H), 5.14 (m, 3H), 4.24 (m, 1H), 1.65 (m, 6H), 0.95–0.87 (m, 12H).

Example 18

Preparation of (2S,1'S)-2-(benzyloxycarbonyl) amino-N-[1'-(2-mercaptothiazol-4-yl)-3'-methylbutyl]-4-methylpentanamide The compound of Example 1(a) (1.0 g, 2.2 mmol) and ammonium dithiocarbamate (0.25 g., 2.2 mmol) were dissolved in ethanol and heated to 55° C. for 13 hours. The solvent was evaporated and the residue chromatographed (silica gel, 20% ethyl acete/hexane) to give the title compound as a white solid (0.58 g). $^1$H NMR (400 MHz, CDCl$_3$) $\delta$7.24 (m, 5H), 7.10 (s, 1H), 6.33 (s, 1H), 6.00 (d, 1H), 5.11 (q, 2H), 4.94 (m, 1H), 4.05 (m, 1H), 1.49 (m, 6H), 0.78 (m, 12H).

Example 19

Preparation of (2S)-2-(benzyloxycarbonyl)amino-N-(4-carboethoxythiazol-2-yl)methyl-4-methylpentanamide a) 1-(tert-butoxycarbonyl)amino-1-(4-carboethoxythiazol-2-yl)methane Following the procedure of Example 8(a)–8(c), except substituting N-tert-butoxycarbonylglycine for N-tert-butoxycarbonyl-(L)-leucine in step (a), the title compound was prepared (1.9 g, 58% overall). $^1$H NMR (400 MHz, CDCl$_3$) $\delta$8.11 (s, 1H), 5.31 (s, 1H), 4.56 (d, 2H), 4.43 (q, 2H), 1.45 (s, 9H), 1.42 (t, 3H).

b) (2S)-2-(benzyloxycarbonyl)amino-N-(4-carboethoxythiazol-2-yl)methyl-4-methylpentanamide Following the procedure of Example 13, except substituting 1-(tert-butoxycarbonyl)amino-1-4-carboethoxythiazol-2-yl)methane for (1S)-1-tert-butoxycarbonyl)amino-1-(4-carboethoxythiazol-2-yl)-3-methylbutane, and N-Cbz-L-leucine for N-Cbz-L-leucinyl-L-leucine, the title compound was prepared (0.120 g, 32%). MS (MH$^+$): 434.2.

Example 20

Preparation of (2S,1'S)-2-(benzloxycarbonyl)amino-N-[1'-(2-benzyloxycarbonylthiazol-4-yl)-3'-methybutyl]-4-methylpentanamide The compound of Example 2 (0.105 g., 0.22 mmol) was dissolved in dichloromethane and treated with 1-(3-dimethylaminopropyl)-3-ethylcarbodiimide methiodide (0.062 g., 0.22 mmol) and benzyl alcohol (0.03 mL, 0.22 mmol). The mixture was allowed to stir at room temperature for 4 hours and the solvents were evaporated and the residue obtained was cheromatographed (silica gel, 30% ethyl acetate/hexane) to give the title compound as a white solid (0.04 g). $^1$H NMR (400 MHz, CDCl$_3$) δ7.37 (s, 1H), 7.26 (m, 10H), 6.50 (d, 1H), 5.33 (s, 2H), 5.11 (q, 2H), 5.09 (m, 1H), 4.99 (s, 2H), 4.04 (m, 1H), 1.49 (m 6H), 0.78 (m, 12H).

Example 21

Preparation of (2S,1'S)-2-(benzyloxycarbonyl)amino-4-methyl-N-[3'-methyl-1'-(2-phenoxycarbonylthiazol-4-yl)butyl]pentanamide Following the procedure of Example 20, except substituting phenol for benzyl alcohol, the title compound was prepared (0.075 g). $^1$H NMR (400 MHz, CDCl$_3$) δ7.41 (s, 1H), 7.26 (m, 10H), 6.49 (d, 1H), 5.20 (m, 1H), 5.04 (m, 1H), 5.00 (s, 2H), 4.08 (m, 1H), 1.49 (m, 6H), 0.82 (m, 12H).

Example 22

Preparation of (2S,1'S)-2-(benzyloxycarbonyl)amino-4-methyl-N-[3'-methyl-1'-[2-(2-methylpropyloxycarbonyl)thiazol-4-yl]butyl]pentanamide Following the procedure of Example 20, except substituting isobutyl alcohol for benzyl alcohol, the title compound was prepared (0.075 g). $^1$H NMR (400 MHz, CDCl$_3$) δ7.25 (m, 6H), 6.50 (d, 1H), 5.11 (q, 2H), 5.09 (m, 1H), 4.99 (s, 2H), 4.11 (d, 2H), 3.91 (m, 1H), 2.02 (m, 1H), 1.70–1.39 (m, 6H), 0.82 (d, 6H), 0.78 (m, 12H).

Example 23

Preparation of (2R,1'S)-2-(benzyloxycarbonyl)amino-N-[1'-(4-carboethoxythiazol-2-yl)ethyl]-4-methylpentanamide Following the procedure of Example 19, except substituting N-tert-butoxycarbonyl-L-alanine for N-tert-butoxycarbonylglycine in step (a), and N-Cbz-D-leucine for N-Cbz-L-leucine in step (b), the title compound was prepared as white solid (0.135 g, 36%). MS (MH$^+$): 448.2.

Example 24

Preparation of (2R,1'R)-2-(benzyloxycarbonyl)amino-N-[1'-(4-carboethoxythiazol-2-yl)ethyl]-4-methylpentanamide Following the procedure of Example 19, except substituting N-tert-butoxycarbonyl-D-alanine for N-tert-butoxycarbonylglycine in step (a), and N-Cbz-D-leucine for N-Cbz-L-leucine in step (b), the title compound was prepared as white solid (0.110 g, 29%). MS (MH$^+$): 448.2.

Example 25

Preparation of (2S,1'S)-N-[1'-(2-aminothiazol-4-yl)-3'-methylbutyl]-2-(benzyloxycarbonyl)amino-4-methylpentanamide To a stirring solution of the compound of Example 1(a) (0.85 g, 1.87 mmol) in 4 mL of ethanol was added thiourea (0.142 g, 1.87 mmol). The solution was allowed to stir at room temperature for 90 min. The solution was concentrated, the residue was dissolved in ethyl acetate and washed with sated aqeous NaHCO$_3$ and saturated brine, then dried (MgSO$_4$), filtered, and concentrated. The residue was purified by flash chromatography on 230–400 mesh silica gel, eluting with 1:1 ethyl acetate/hexanes, to give the title compound as a white solid (0.64 g, 78%). $^1$H NMR (400 MHz, CDCl$_3$) δ7.36 (m, 5H), 6.30 (m, 2H), 5.12 (m, 3H), 4.95–4.91 (m, 3H), 4.16 (m, 1H), 1.63 (m, 4H), 1.49 (m, 2H), 0.93–0.89 (m, 12H).

Example 26

Preparation of (1S)-N-[4-[(1-benzyloxycarbonylamino)-3-methylbutyl]thiazol-2-ylcarbonyl]-N'-(N-benzyloxycarbonyl-L-leucinyl) hydrazide a) N-benzyloxycarbonyl-L-leucinyl bromomethyl ketone 1-methyl-3-nitro-1-nitrosoguanidine (6.65 g, 45.2 mmol) in ether (225 mL) is cooled to 0° C. 40% sodium hydroxide is added slowly and the diazomethane is allowed to collect in the ether solution for 30 minutes at 0° C. The ether solution is then decanted and left at 0° C.

N-Cbz-L-leucine (2.10 g, 7.6 mmol) was dissolved in THF (10 mL), cooled to −40° C., and 4-methylmorpholine (0.77 g, 7.6 mmol, 0.83 mL) was added, followed by dropwise addition of isobutyl chloroformate (1.04 g, 7.6 mmol, 0.98 mL). After 15 min, the solution was filtered into the previously prepared 0° C. solution of ethereal diazomethane. The resulting solution was allowed to stand at 0° C. for 23 h. HBr (30% in acetic acid) (45.2 mmol, 9 mL) was added and the resulting solution was stirred at 0° C. for 5 min, then washed sequentially with 0.1 N HCl, saturated aqueous NaHCO$_3$ and saturated brine, then dried (MgSO$_4$), filtered and concentrated to give the title compound as a colorless oil (2.43 g, 94%).

b) (1S)-1-benzyloxycarbonylamino-1-(2-carboethoxythiazol-4-yl)-3-methylbutane

A solution of the compound of Example 26(a) (1.57 g, 4.58 mmol) and ethyl thiooxamate (0.61 g, 4.58 mmol) in ethanol (10 mL) was heated at reflux for 4 h. The solution was then cooled, concentrated and the residue was purified by flash chromatography on 230–400 mesh silica gel, eluting with 1:4 ethyl acetate/hexanes, to give the title compound as a yellow oil (1.0 g, 58%). $^1$H NMR (400 MHz, CDCl$_3$) δ7.41 (s, 1H), 7.34–7.31 (m, 5H), 5.40 (d, 1H), 5.10 (d, 1H), 5.05 (d, 1H), 4.98 (q, 1H), 4.48 (q, 2H), 1.80–1.76 (m, 2H), 1.57–1.53 (m, 1H), 1.44 (t, 3H), 0.95 (d, 3H), 0.93 (d, 3H).

c) (1S)-1-benzyloxycarbonylamino-1-(2-hydrazinocarbonylthiazol-4-yl)-3-methylbutane A solution of the compound of Example 26(b) (0.30 g, 0.8 mmol) and hydrazine hydrate (0.40 g, 8.0 mmol, 0.39 mL) in ethanol (8 mL) was allowed to stir at room temperature for 2 h. The solution was then concentrated to yield the title compound as a white foam (0.28 g, 98%). $^1$H NMR (400 MHz, CDCl$_3$) δ8.29 (s, 1H), 7.37–7.35 (m, 5H), 5.18 (d, 1H), 5.09 (dd, 2H), 4.95 (q, 1H), 4.07 (d, 2H), 1.71 (t, 2H), 1.55 (m, 1H), 0.96 (d, 3H), 0.94 (d, 3H).

d) (1S)-N-[4-[(1-benzyloxycarbonylamino)-3-methylbutyl]thiazol-2-ylcarbonyl]-N'-(N-benzyloxycarbonyl-L-leucinyl) hydrazide A solution of the compound of Example 26(c) (100 mg, 0.28 mmol), N-Cbz-L-leucine (80.5 mg, 0.30 mmol), 1-(3-dimethylaminopropyl)-3-ethylcarbodiimide hydrochloride (58.2 mg, 0.30 mmol) and 1-hydroxybenzotriazole (7.5 mg, 0.06 mmol) in DMF (0.6 mmol) was allowed to stir at room temperature for 18 h. The solution was diluted with ethyl acetate and washed successively with water, 0.1 N HCl, saturated aqueous NaHCO$_3$ and saturated brine, then dried (MgSO$_4$), filtered and concentrated. The residue was purified by flash chromatography on 230–400 mesh silica gel, eluting with 1:1 ethyl acetate/hexanes, to provide the title compound as a white solid (111.4 mg, 66%). mp 110–112° C.

Example 27

Preparation of N-benzyloxycarbonyl-L-leucinyl-N'-benzloxycarbonyl-L-leucinyl-L-leucinylhydrazide a) N-benzyloxycarbonyl-L-leucinyl-L-leucine methyl ester Following the procedure of Example 26(d), except L-leucine methyl ester hydrochloride for (1S)-1-benzyloxycarbonylamino-1-(2-hydrazinocarbonylthiazol-4-yl)-3-methylbutane, the title compound was prepared as a white solid (1.28 g, 66%). $^1$H NMR (400 MHz, CDCl$_3$) δ7.37–7.32 (m, 5H), 6.28 (d, 1H), 5.28 (m, 3H), 4.61–4.58 (m, 1H), 4.20 (m, 1H), 3.74 (s, 3H), 1.69–1.54 (m, 6H), 0.96–0.92 (m, 12H).

b) N-benzyloxycarbonyl-L-leucinyl-L-leucinylhydrazide

Following the procedure of Example 26(c), except substituting N-benzyloxycarbonyl-L-leucinyl-L-leucine methyl ester for (1S)-1-benzyloxycarbonylamino-1-(2-carboethoxythiazol-4-yl)-3-methylbutane, the title compound was prepared as a white solid (1.28 g, 100%). $^1$H NMR (400 MHz, CDCl$_3$) δ8.05 (br s, 1H), 7.35–7.32 (m, 5H), 6.67 (d, 1H), 5.50 (d, 1H), 5.11 (s, 2H), 4.46 (m, 1H), 4.21 (m, 1H), 3.88 (br s, 2H), 1.64–1.51 (m, 6H), 0.92–0.88 (m, 12H).

c) N-benzyloxycarbonyl-L-leucinyl-N'-benzyloxycarbonyl-L-leucinyl-L-leucinylhydrazide Following the procedure of Example 26(d), except substituting N-benzyloxycarbonyl-L-leucinyl-L-leucinylhydrazide for (1S)-1-benzyloxycarbonylamino-1-(2-hydrazinocarbonylthiazol-4-yl)-3-methylbutane, the title compound was prepared as a white solid (0.059 g). MS (M+Na$^+$): 662.1.

Example 28

Preparation of (1S)-N-[2-[(1-benzyloxycarbonylamino)-3-methylbutyl]thiazol-4-ylcarbonyl]-N'-(N-benzyloxycarbonyl-L-leucinyl) hydrazide a) N-tert-butoxycarbonyl-(L)-leucinamide To a solution of N-tert-butoxycarbonyl-(L)-leucine (7.0 g, 28.1 mmol) in dry THF (100 mL) at –40° C. was added isobutylchloroformate (3.8 g, 28.1 mmol) and N-methylmorphiline (6.0, 59 mmol). After 15 minutes of stirring, ammonia was bubbled through the mixture for an additional 15 minutes, then warmed to room temperature and allowed to stir for 2 hours. Mixture filtered and filtrate concentrated in vacuo to yield title compound as a white solid (6.5, 28.0 mmol). $^1$HNMR (400 MHz, CDCl$_3$) δ6.38 (br s, 1H), 5.79 (br s, 1H), 5.04 (br d, 1H), 4.13 (m, 1H), 1.71–1.49 (m, 3H), 1.39 (s, 9H), 0.92 (dd, 6H).

b) N-tert-butoxycarbonyl-(L)-leucinethioamide

To a stirring solution of the compound of Example 26(a) (6.5, 28.0 mmol) in dry THF was added Lawesson's reagent (6.8 g, 16.9 mmol) and the mixture was stirred at room temperature under argon overnight. The solvent was evaporated and the residue chromatographed (silica gel, 12% ethyl acetate/hexane) to give the title compound as a white solid (5.4 g, 77%). $^1$HNMR (400 MHz, CDCl$_3$) δ8.54 (br s, 1H), 7.97 (br s, 1H), 5.28 (br d, 1H), 4.52 (m, 1H), 1.72–1.58 (m, 3H), 1.40 (s, 9H), 0.92 (m, 6H).

c) (1S)-1-(tert-butoxycarbonyl)amino-1-(4-carboethoxythiazol-2-yl)-3-methylbutane The compound of Example 26(b) (5.4 g, 21.7 mmol) was stirred in dry acetone (100 mL) under argon at –10° C. Ethylbromopyruvate (4.7 g, 23.9 mmol) was added and stirred for 1 h at –10° C. The solution was poured into a well stirred mixture of chloroform and water and then into saturated sodium bicarbonate solution. The organic phase was separated and the aqueous layer extracted with chloroform. The combined organic extracts were dried over MgSO$_4$, filtered and concentrated to an oil. The oily residue was treated with TFAA (5.0 g, 23.9 mmol) and pyridine (3.8 g, 47.8 mmol) in dichloromethane for 1 h at –20° C. Excess solvent was removed in vacuo and the residue was dissolved in dichloromethane. The solution was washed with sacked aqueous sodium bicarbonate and 1.0N KHSO$_4$ until pH 7. The solution was dried over magnesium sulfate, filtered and concentrated to an oil which was chromatographed (silica gel, 7.5% ethyl acetate/hexane) to give the title compound as a tan solid (4.5 g, 61%). $^1$HNMR (400 MHz, CDCl$_3$) δ7.98 (s, 1H), 5.04 (br d, 1H), 4.95 (m, 1H), 4.31 (q, 2H), 1.88 (m, 1H), 1.63 (m, 2H), 1.40 (s, 9H), 1.32 (t, 3H), 0.85 (dd, 6H).

d) (1S)-1-(Benzyloxycarbonyl)amino-1-(carboethoxythiazol-2-yl)-3-methylbutane

The compound of Example 26(c) (0.250 g, 0.731 mmol) was dissolved in TFA (2 mL) and stirred at room temperature for 15 minutes when diluted with methanol and concentrated in vacuo. The residue was dissolved in methylene chloride and treated with triethylamine (0.739 g, 7.31 mmol) followed by benzyl chloroformate (1.2 g, 7.31 mmol). The solution stirred at room temperature for 2 h when partition between ethyl acetate/water. The organic layer was washed with brine, collected, dried (MgSO$_4$) and concentrated to a residue that was chromatographed (silica gel, 15% ethyl acetate/hexane) to give the title compound as an oil (0.198 g, 72%). $^1$HNMR (400 MHz, CDCl$_3$) δ8.01 (s, 1H), 7.32 (m, 5H), 5.51 (br d, 1H), 5.14 (m, 1H), 5.10 (s, 2H), 4.37 (q, 2H), 1.93 (m, 1H), 1.81–1.67 (m, 2H), 1.39 (t, 3H), 0.95 (m, 6H).

e) (1S)-N-[2-[(1-benzyloxycarbonylamino)-3-methylbutyl]thiazol-4-ylcarbonyl]-N'-(N-benzyloxycarbonyl-L-leucinyl) hydrazide Following the procedure of Example 26(c)-1(d), except substituting (1S)-1-(Benzyloxycarbonyl)amino-1-(4-carboethoxythiazol-2-yl)-3-methylbutane for (1S)-1-benzyloxycarbonylamino-1-(2-carboethoxythiazol-4-yl)-3-methylbutane in step (c), the title compound was prepared. MS$^+$: 610.0.

Example 29

Preparation of 2,2'-(N,N'-bis-oxycarbonyl-L-leucinyl)carbohydrazide

To a stirring solution of N-Cbz-L-leucine (Chemical Dynamics Corp.) (2.94 g, 11.1 mmol) in 22 mL of DMF was added carbohydrazide (0.5 g, 5.6 mmol), 1-(3-dimethylaminopropyl)-3-ethylcarbodiimide hydrochloride (2.13 g, 11.1 mmol) and 1-hydroxybenzotriazole (0.3 g, 2.2 mmol). After stirring at room temperature for 22 h, the solution was poured into 500 mL of water. The precipitate was collected by vacuum filtration and washed with water (4×150 mL) and dichloromethane (4×150 mL), then dried under vacuum to provide the title compound as a white solid (1.49 g, 46%). MS(ESI): 607.1 (M+Na)$^+$.

Example 30

Preparation of 2,2'-(N,N'-bis-cyclohexylacetyl) carbohydrazide

Following the procedure of Example 29, except substituting cyclohexylacetic acid for N-Cbz-L-leucine, the title compound was prepared (0.410 g, 73%). MS(ESI): 339.3 (M+H)$^+$.

Example 31

Preparation of 2,2'-(N,N'-bis-4-methylpentanoyl) carbohydrazide

Following the procedure of Example 29, except substituting 4-methylpentanoic acid for N-Cbz-L-leucine, the title compound was prepared as a white solid (0.212 g, 44%). MS(ESI): 287.3 (M+H)$^+$.

Example 32

Preparation of 2,2'-(N,N'-bis-cyclopentylacetyl) carbohydrazide

Following the procedure of Example 29, except substituting cyclopentylacetic acid for N-Cbz-L-leucine, the title compound was prepared as a white solid (0.345 g, 67%). MS(ESI): 311.2 (M+H)$^+$.

Example 33

Preparation of 2,2-(N,N'-bis-benzyloxycarbonylglycinyl)carbohydrazide

Following the procedure of Example 29, except substituting N-Cbz-Glycine for N-Cbz-L-leucine, the title compound was prepared as a white solid (0.719 g, 91%). MS(ESI): 473.1 (M+H)$^+$.

Example 34

Preparation of 2,2'-(N,N'bis-acetyl-L-leucinyl) carbohydrazide

Following the procedure of Example 29, except substituting N-acetyl-L-leucine for N-Cbz-L-leucine, the title compound was prepared as a white solid (0.153 g, 23%). MS(ESI): 401.3 (M+H)$^+$.

Example 35

Preparation of 2,2'-(N,N'-bis-benzloxycarbonyl-L-alanyl)carbohydrazide

Following the procedure of Example 29, except substituting N-Cbz-L-alanine for N-Cbz-L-leucine, the title compound was prepared as a white solid (0.762 g, 91%). MS(ESI): 501.1 (M+H)$^+$.

Example 36

Preparation of 2-(N-benzyloxycarbonyl-L-leucinyl)-2'-[N'-(4-methylpentanoyl]carbohydrazide a) N-benzyloxycarbonyl-L-leucine methyl ester To a solution of leucine methyl ester hydrochloride (5.0 g, 27.5 mmol) in 1,4-dioxane (50 mL) was added sodium carbonate (30.3 mL, 2M in water) followed by benzyl chloroformate (4.69 g, 27.5 mmol). The mixture stirred at room temperature for 24 hours when partitioned between ethyl acetate and water. The organic layer was collected, dried (MgSO$_4$), filtered and concentrated to give the title compound as a colorless oil (7.67 g, 100%). $^1$HNMR (400 MHz, CDCl$_3$) δ7.39 (m, 5H), 5.38 (d, 2H), 5.12 (s, 2H), 4.42 (m, 1H), 3.75 (s, 3H), 1.73–1.50 (m, 3H), 0.94 (m, 6H).

b) N-benzyloxycarbonyl-L-leucinyl hydrazide

To a solution of the compound of Example 36(a) (7.67 g, 27.5 mmol) in methanol (40 mL) was added hydrazine monohydrate (13.5 g, 270 mmol). The solution was stirred at room temperature for 24 hours when partitioned between water and ethyl acetate. The organic layer was collected, dried (MgSO$_4$), filtered and concentrated to give the title compound as an off-white solid (7.67 g, 100%). $^1$HNMR (400MHz, CDCl$_3$) δ8.14 (s, 1H), 7.38 (m, 5H), 5.64 (d, 1H), 5.09 (dd, 2H), 4.20 (m, 1H), 3.81 (s br, 2H), 1.69–1.51 (m, 3H), 0.92 (dd, 6H).

c) 1-benzyloxycarbonylamino-3-methyl-1-(1,3,4-oxadiazol-2-onyl)butane

A solution of the compound of Example 36(b) (1.0 g, 3.58 mmol) in methylene chloride (12 mL) was added dropwise to a solution of 4-nitrophenylchloroformate (0.361 g, 1.79 mmol) in methylene chloride (8 mL) at 0° C. The solution warmed to room temperature and stirred for one hour when partitioned between ethyl acetate and water. The organic layer was washed with aqueous NaHCO$_3$ then collected, dried (MgSO$_4$), filtered and concentrated to a residue which was chromatographed (20% ethyl acetate/hexane) to give the title compound as a pale yellow solid (0.322 g, 59%). $^1$HNMR (400 MHz, CDCl$_3$) δ9.18 (s, 1H), 7.38 (m, 5H), 5.13 (m, 3H), 4.79 (m, 1H), 1.71 (m, 3H), 0.98 (dd, 6H).

d) 4-methylpentanoyl hydrazide

Following the procedure of Example 36(b) except substituting ethyl isocaproate for benzyloxycarbonyl-L-leucinyl methyl ester, the title compound was prepared as a white solid (1.8 g, 100%). $^1$HNMR (400 MHz, CDCl$_3$) δ7.48 (s br, 1H), 3.62 (s br, 2H), 2.13 (t, 2H), 1.51 (m, 3H), 0.85 (d, 6H).

e) 2-benzyloxycarbonyl-L-leucinyl)-2'-[N'-(4-methylpentanoyl)]carbohydrazide

The compounds of Example 36(c) (0.100 g, 0.325 mmol) and Example 36(d) (0.042 g, 0.325 mmol) were combined and dissolved in ethanol (1 mL). The solution was brought to reflux for 24 hours then concentrated to a solid yellow residue which was washed with cool methylene chloride to yield the title compound as a white solid (0.053 g, 37%). MS (MH$^+$): 436.2.

Example 37

Preparation of bis-(Cbz-leucinyl)-1,3-diamino-propan-2-one

Cbz-leucine (500 mg, 1.88 mmol), EDCI (558 mg, 1.88 mmol) was dissolved in DMF (4.0 ml) with 1,3-diamino-propan-2-ol (85 mg, 0.94 mmol) and Hunig's base (0.3 ml, 1.88 mmol) and was stirred at RT overnight. The reaction was diluted with EtOAc (20 ml) and was extracted with water (2×20 ml). The combined organics were dried with magnesium sulfate, filtered, concentrated in vacuo. The intermediate was then dissolved in acetone (4.0 ml) and Jones reagent (2.0 ml, 1.5 M) was added dropwise and the reaction was stirred at RT overnight. The excess Jones reagent was then quenched with isopropanol (1.0 ml), then the reaction was diluted with EtOAc (20 ml) and was extracted with water (2×20 ml) to remove the inorganic salts. The combined organics were dried with magnesium sulfate, filtered, concentrated, and chromatographed (silica gel, 2–5% MeOH/methylene chloride) to give the title compound as a white solid (410 mg, 75%). MS(ES) M+H$^+$=583, M+Na$^+$=605.

Example 38

Preparation of bis-1,3-(4-phenoxy-benzoyl)diamino-propan-2-one

Following the procedure of Example 37, except substituting "4-phenoxybenzoic acid" for "Cbz-leucine", the title compound was prepared: MS(ES) M+H$^+$=481, M+Na$^+$=503.

Example 39

Preparation of 1-(Cbz-leucinyl)-amino-3-(acetyl-leucinyl)-amino-propan-2-one

Following the procedure of Example 37, except substituting "a mixture of N-Ac-leucine and Cbz-leucine" for "Cbz-leucine", the title compound was prepared: MS(ES) M+H$^+$=491, M+Na$^+$=513.

Example 40

Preparation of 1-Cbz-leucinyl)-amino-3-(Cbz-glutamyl-t-butyl ester-aminopropan-2-one Following the procedure of Example 37, except substituting "a mixture of Cbz-glutamic acid gamma t-butyl ester and Cbz-leucine" for "Cbz-leucine", the title compound was prepared: MS(ES) M+H$^+$=655.

Example 41

Preparation of 1-(Cbz-leucinyl)-amino-3-(Cbz-glutamyl)amino-propan-2-one 1-(Cbz-leucinyl)-amino-3-(Cbz-glutamyl)-amino-propan-2-one (5 mg, 0.007 mmol) was dissolved in a solution of trifluoroacetic acid (0.5 ml) and methylene chloride (0.5 ml), then was stirred at RT for 2 h, the reaction was dilutied with toluene (10 ml), then was concentrated in vacuo to provide the title compound: MS(ES) M+H$^+$=599.

Example 42

Preparation of bis-1,3-(Cbz-leucinyl)diamino-(S)-butanone-2-one a) Cbz-leu-ala-bromo methyl ketone Isobutyl chloroformate (1.46 ml, 11.3 mmol) was added dropwise to a solution of Cbz-leu-ala-OH (4.0 g, 11.3 mmol) and N-methyl morpholine (1.24 ml, 11.3 mmol) in THF (40 ml) at –40 degrees C. The reaction was sired 15 min, then was filtered, and was washed with ether. Diazomethane (40.1 mmol from 5.9 g of 1-methyl-3-nitro-nitroso-guanidine and 18 ml of 40% KOH in 150 ml of ether) in ether (200 ml) was added and the reaction was placed in a refrigerator overnight. 30% HBr/AcOH (7 ml) was added dropwise to the crude reaction mixture and was stirred 5 minutes. The solution was washed with aqueous citric acid (50 ml×2), saturated aqueous sodium bicarbonate (3×150 ml), then brine (100 ml). The combined organics were dried with magnesium sulfate, filtered, and concentrated in vacuo to give a solid which was used in the next step without purification, MS(ES) M+H$^+$=413 and 415, M+Na$^+$=435 and 437.

b) Cbz-leu-leu-azido methyl ketone

Cbz-leu-ala-bromo methyl ketone (650 mg, 1.6 mmol) was dissolved in DMF (7 ml), then sodium azide (122 mg, 1.9 mmol) and potassium fluoride (137 mg, 2.36 mmol) was added and the reaction was stirred overnight. The reaction was partitioned between EtOAc and water, then the combined organic extracts were dried with magnesium sulfate, filtered, concentrated in vacuo, then chormatographed (2–5% MeOH, methylene chloride, silica gel) to provide the title compound as a white solid (330 mg, 53%), MS(ES) M+Na$^+$=398.

c) Cbz-leu-2-amino-4azido-propan-3-ol

Cbz-leu-leu-azido methyl ketone (330 mg, 0.9 mmol) was dissolved in EtOH (5 ml) and sodium borohydride (100 mg, 2.65 mmol) was added at RT and the reaction was sired for 15 minutes. The reaction was quenched with water (10 ml) and was extracted with EtOAc (25 ml). The combined organic extracts were dried with magnesium sulfate, filtered, concentrated to give the title compound without further purification, MS(ES) M+H+=378, M+Na$^+$=400.

d) Cbz-leu-2-amino-4-amino-propan-3-ol

Cbz-leu-2-amino-4-azido-propan-3-ol (300 mg, 0.8 mmol) was dissolved in MeOH (4 ml) and triethyl amine (0.33 ml, 2.4 mmol), propan-1,3-dithiol (0.35 ml, 3.82 mmol) was added and the reaction was sired overnight, concentrated in vacuo, then the white solid was washed with hexane providing the title compound which was used in the next reaction without further purification, MS(ES) M+H$^+$=352.

e) bis-1,3-(Cbz-leucinyl)-diamino-(S)-butanone-2-ol

Cbz-leu-2-amino-4amino-propan-3-ol (140 mg, 0.4 mmol) and Cbz-leucine (106 mg, 0.4 mmol) were dissolved in DMF (2 ml) and N-methyl morpholine (0.08 ml, 0.8 mmol) and HBTU (151 mg, 0.4 mmol) and was stirred overnight. The reaction was partitioned between EtOAc and water, the combined organics were dried with magnesium sulfate, filtered, concentrated to give the title compound, MS(ES) M+H$^+$=599, M+Na+=621.

f) bis-1,3-(Cbz-leucinyl)-diamino-(S)-butanone-2-one

Bis-1,3-(Cbz-leucinyl)-diamino-(S)-butanone-2-ol (240 mg, 0.4 mmol) was dissolved in acetone (2 ml). Jones reagent (0.5 ml, 1.5 M) was added dropwise and the reaction was stirred at RT overnight. The excess Jones reagent was then quenched with isopropanol (1.0 ml), then the reaction was diluted with EtOAc (20 ml) and was extracted with water (2×20 ml) to remove the inorganic salts. The combined organics were dried with magnesium sulfate, filtered, concentrated, and chromatographed (silica gel, 2–5% MeOH/methylene chloride) to give the title compound as a white solid (80 mg, 33%). MS(ES) M–H$^+$=595.

Example 43

Preparation of 1-(Cbz-leucinyl)-amino-3-(Cbz-phenylalanyl)-amino-propan-2-one

Following the procedure of Example 37, except substituting "a mixture of Cbz-phenylalanine and Cbz-leucine" for "Cbz-leucine", the title compound was prepared (70%): MS(ES) M+H$^+$=617, M+Na$^+$=639.

Example 44

Preparation of 1-(Cbz-leucinyl)-amino-3-(Cbz-norleucinyl)-amino-propan-2-one

Following the procedure of Example 37, except substituting "a mixture of Cbz-norleucine and Cbz-leucine" for "Cbz-leucine", the title compound was prepared: MS(ES) M+H$^+$=583, M+Na$^+$=605.

Example 45

Preparation of 1-(Cbz-leucinyl)-amino-3-(Cbz-norvalinyl)-amino-propan-2-one

Following the procedure of Example 37, except substituting "a mixture of Cbz-norvaline and Cbz-leucine" for "Cbz-leucine", the title compound was prepared: MS(ES) M+H$^+$=569, M+Na$^+$=591.

Example 46

Preparation of bis-1,3-(Cbz-leucinyl)-diamino-5-methyl-(S)-hexan-2-one a) bis-1,3-(Cbz-leucinyl)-diamino-5-methyl-(S)-hexan-2-one Following the procedure of Example 42(a)–(f), except substituting "Cbz-leu-leu-OH" for "Cbz-leu-ala-OH" the title compound was prepared: MS(ES) M+H$^+$=639.

Example 47

Preparation of 1-(acetyl-leucinyl)-amino-3-(4-phenoxy-benzoyl)-amino-propan-2-one Following the procedure of Example 37, except substituting "a mixture of N-Ac-leucine and 4-phenoxy-benzoic acid" for "Cbz-leucine", the title compound was prepared: MS(ES) M+H$^+$=440.

Example 48

Preparation of 1-(Cbz-homo-leucinylamino-(Cbz-leucinyl)-3-amino-propan-2-one

Following the procedure of Example 37, except substituting "a mixture Cbz-homo-leucine and Cbz-leucine" for "Cbz-leucine", the title compound was prepared: MS(ES) M+H$^+$=597, M+Na$^+$=619.

Example 49

Preparation of bis-1,3-(4-(3-chloro-2-cyano-phenoxy)phenyl sulfonamido)-propan-2-one 4-(3-Chloro-2-cyano-phenoxy)-phenyl sulfonyl chloride (1.3 g, 4 mmol, Maybridge) was added to a solution of 1,3-diamino-propan-2-ol (0.18 g, 2 mmol) in DMF (10 ml)/N-methyl morpholine (0.44 ml, 4 mmol) and was stirred 3 h at RT. The reaction was partitioned between water and EtOAc and the combined organics were dried with magnesium sulfate, then concentrated in vacuo. The crude bis-1,3-(4-(3-chloro-2-cyano-phenoxy)-phenyl sulfonamido)-propan-2-ol (0.28 g, 0.4 mmol) was then dissolved in acetone (1.0 ml) and Jones reagent (0.44 ml, 1.5 M) was added dropwise, and the reaction was stirred overnight at RT. The excess Jones reagent was then quenched with isopropanol (1.0 ml), then the reaction was diluted with EtOAc (20 ml) and was extracted with water (2×20 ml) to remove the inorganic salts. The combined organics were dried with magnesium sulfate, filtered, concentrated, and chromatographed (silica gel, 2–5% MeOH/methylene chloride) to give the title compound as a white solid (90 mg, 34%). MS(ES) M+H$^+$=671, M+Na$^+$=693.

Example 50

Preparation of bis-1,3-(4-phenoxy-phenyl sulfonamido)-propan-2-one

Following the procedure of Example 49, except substituting 4-phenoxyphenyl sulfonyl chloride for 4(3-Chloro-2-cyano-phenoxy)-phenyl sulfonyl chloride, the title compound was prepared: MS(ES) M–H$^+$=551.

Example 51

Preparation of 1-(Cbz-leucinyl)-amino-3-(4-(3-chloro-2-cyano-phenoxy)-phenyl sulfonamido)-propan-2-one Cbz-leucine (660 mg, 2.5 mmol), EDCI (480 mg, 2.5 mmol), HOBT (340 mg, 2.5 mmol) was dissolved in DMF (10 ml) with 1,3-diamino-propan-2-ol (225 mg, 2.5 mmol) and was stirred at RT overnight N-methyl morpholine (0.41 ml, 3.75 mmol) was added followed by 4-(3-Chloro-2-cyano-phenoxy)phenyl sulfonyl chloride (820 mg, 2.5 mmol, Maybridge) was added and the reaction was stirred 3 h at RT. The reaction was partitioned between water and EtOAc and the combined organics were dried with magnesium sulfate, then concentrated in vacuo. The crude 1-(Cbz-leucinyl)-amino-3-(4-(3-chloro-2-cyano-phenoxy)-phenyl sulfonamido)-propan-2-ol was then dissolved in acetone (5.0 ml) and Jones reagent (3.0 ml, 1.5 M) was added dropwise, and the reaction was stirred overnight at RT. The excess Jones reagent was then quenched with isopropanol (1.0 ml), then the reaction was diluted with EtOAc (20 ml) and was extracted with water (2×20 ml) to remove the inorganic salts. The combined organics were dried with magnesium sulfate, filtered, concentrated, and chromatographed (silica gel 2–5% MeOH/methylene chloride), then the product was triturated from methylene chloride to give the title compound as a white solid (26 mg, 2%). MS(ES) M+H$^+$=627.

Example 52

Preparation of 1-(Cbz-leucinyl)-amino-3-(tosyl-amino)-propan-2-one

Following the procedure of Example 51, except substituting tosyl chloride for 4-(3-Chloro-2-cyano-phenoxy)-phenyl sulfonyl chloride, the title compound was prepared: MS(ES) M–H$^+$=488.

Example 53

Preparation of 1-(Cbz-leucinyl)-amino-3-((4-phenoxy-phenyl)-sulfonamido)-propan-2-one Following the procedure of Example 51, except substituting 4-phenoxyphenyl-sulfonyl chloride for 4-(3-Chloro-2-cyano-phenoxy)-phenyl sulfonyl chloride, the title compound was prepared: MS(ES) M+H$^+$=568, M+Na$^+$=590.

Example 54

Preparation of 1-(Cbz-leucinyl)-amino-3-(2-dibenzofuransulfonamido)-propan-2-one Following the procedure of Example 51, except 2-dibenzofuransulfonyl chloride for 4-(3-Chloro-2-cyano-phenoxy)-phenyl sulfonyl chloride, the title compound was prepared: MS(ES) M+H$^+$=566, M+Na$^+$=588.

Example 55

Preparation of 1-(Cbz-homo-leucinyl)-amino-3-(2-dibenzofuransulfonamido)-propan-2-one Following the procedure of Example 51, except 2-dibenzofuransulfonyl chloride for 4-(3-Chloro-2-cyano-phenoxy)-phenyl sulfonyl chloride and Cbz-homo-leucine for Cbz-leucine, the title compound was prepared: MS(ES) M+Na$^+$=602.

Example 56

Preparation of 1-(Cbz-leucinyl)-amino-3-(2-dibenzofuransulfonamido)-(S)-butan-2-one a) 1-(Cbz-leucinyl)-amino-3-(2-dibenzofuransulfonamido)-(S)-butan-2-ol Cbz-leu-2-amino-4-amino-propan-3-ol (150 mg, 0.42 mmol, as described in Example 56(a)–(d)) and 2-dibenzosulfonyl chloride were dissolved in DMF (2 ml) and N-methyl morpholine (0.09 ml, 0.84 mmol) and were stirred overnight. The reaction was partitioned between EtOAc and water, the combined organics were dried with magnesium sulfate, filtered, concentrated to give the title compound, MS(ES) M+H$^+$=582, M+Na$^+$=604.

b) 1-(Cbz-leucinyl)-amino-3-(2-dibenzofuransulfonamido)-(S)-butan-2-one

1-Cbz-leucinyl)amino-3-(2-dibenzofuransulfonamido)-(S)-butan-2-ol (240 mg, 0.4 mmol) was dissolved in acetone (2 ml). Jones reagent (0.5 ml, 1.5 M) was added dropwise and the reaction was stirred at RT overnight. The excess Jones reagent was then quenched with isopropanol (1.0 ml), then the reaction was diluted with EtOAc (20 ml) and was extracted with water (2×20 ml) to remove the inorganic salts. The combined organics were dried with magnesium sulfate, filtered, concentrated, and chromatographed (silica gel, 2–5% MeOH/methylene chloride) to give the title compound as a white solid (70 mg, 29%). MS(ES) M−H$^+$=578.

Example 57

Preparation of (S)-Phenylmethyl [1-[[[3-[Benzyloxycarbonyl-leucinyl-amino]-2-oxopropyl]-1-(benzyl)amino]carbonyl]-3-methylbutyl]carbamate a) 2-hydroxy-3-azido-propanol Sodium azide (1.7 g, 26 mmol) was added to a solution of glycidol (Aldrich, 1.3 g, 17.5 mmol) in MeOH (45 ml) and water (5 ml) and was heated to 65 degrees C. for 4 h. The reaction was diluted with water (25 ml), extracted with EtOAc (2×50 ml); the combined organic layers were extracted with water (2×50 ml), then brine (50 ml), then were dried with magnesium sulfate, filtered concentrated in vacuo, and chromatographed (silica gel, 30% EtOAc/hexanes) to produce a white solid (1.37 g, 67%); MS(ES) M+H+=118.4.

b) 2-hydroxy-3-azido-propan-tosylate

Tosyl chloride (1.3 g, 12 mmol) was added to a solution of 2-hydroxy-3-azido-propanol (1.17 g, 10 mmol) and triethyl amine (3.6 g, 36 mmol) in methylene chloride (50 ml) and was at RT for 4 h. The reaction was diluted with water (20 ml), extracted with EtOAc (2×50 ml); the combined organic layers were extracted with pH 7 buffer (2×50 ml), then were dried with magnesium sulfate, filtered, concentrated in vacuo, and chromatographed (silica gel, 30% EtOAc/hexanes) to produce a white solid (1.2 g, 44%); MS(ES) M+H+=272.2.

c) 2-(Merrifield polymer-6-(oxymethylene-tetrahydropyran-acetal)-3-azido-propan-tosylate c) 2-Hydroxy-3-azido-propan-tosylate (1.2 g, 4.4 mmol) was added to a slurry of Ellman dihydropyran polymer (cf. (3), Scheme 1) (150 mg, 0.3 mmol) in ClCH2CH2Cl (25 ml), then pyridinium p-toluenesulfonate (0.84 g, 4.4 mmol) and was agitated, at 80 degrees C. by gentle bubbling with argon. The polymer was filtered, washed with DMF (2×10 ml), then MeOH (20 ml), then methylene chloride (4×20 ml); IR 2105 cm−1; Magic Angle Spinning 1H NMR: d 8.0, 7.4, 5.0, 3.4.

d) 2-(Merrifield polymer-6-(oxymethylene-tetrahydropyran-acetal)-3-azido propan-N-benzyl-amine Benzl amine (0.32 g, 3 mmol) was added to a slurry of 2-(Merrifield polymer-6-(oxymethylene-tetrahydropyran-acetal)-3-azidopropan-tosylate (500 mg, 1 mmol) in N-methyl pyrolidinone (25 ml) and was and was agitated at 80 degrees C. by gentle bubbling with argon. The polymer was filtered, washed with DMF (2×10 ml), then MeOH (20 ml), then methylene chloride (4×20 ml); IR 2105 cm−1; Magic Angle Spinning 1H NMR: d 7.1, 4.7, 4.0, 3.8.

e) 2-(Merrifield polymer-6-(oxymethylene-tetrahydropyran-acetal)-3-azido-propan-N-benzyl-(Cbz-leucinyl)-amine Cbz-leucine (0.82 g, 3.0 mmol) was added to a slurry of 2-(Merrifield polymer-6-(oxymethylene-tetrahydropyran-acetal)-3-azido-propan-N-benzyl-amine (120 mg, 0.22 mmol) in DMF (10 ml), diisopropyl ethyl amine (1.2 ml, 6 mmol) and HATU (Perspective Biosystems, 2.2 g, 6 mmol) and was shaken at room temperature overnight. The resin was filtered, washed with DMF (3×10 ml). The above procedure was repeated, and the final resin washed with MeOH (2×20 ml), then methylene chloride (5×20 ml); IR 2105, 1735, 1630 cm−1; Magic Angle Spinning 1H NMR: d 7.2, 4.7, 4.1.

f) 2-(Merrifield polymer-6-(oxymethylene-tetrahydropyran-acetal)-3-amino-propan-N-benzyl-(Cbz-leucinyl)-amine Propanedithiol (0.5 ml, xx mmol) was added to a slurry of 2-(Merrifield polymer-6-(oxymethylene-tetrahydropyran-acetal)-3-azido-propan-N-benzyl-(Cbz-leucinyl)-amine (150 mg, 0.27 mmol) in MeOH (5 ml) and triethylamine (0.5 ml) and was gently rocked overnight. The resin was filtered, washed with MeOH (2×20 ml), then with DMF (1×10 ml), then with methylene chloride (5×20 ml), and was dried in a vacuum oven overnight; IR 1735, 1640, cm$^{-1}$.

g) 2-(Merrifield polymer-6-(oxymethylene-tetrahydropyran-acetal)-3-(Cbz-leucinyl)-amino-propan-N-benzyl-(Cbz-leucinyl)-amine Cbz-leucine (0.82 g, 3.0 mmol) was added to a slurry 2-(Merrifield polymer-6-(oxymethylene-tetrahydropyran-acetal)-3-amino-propan-N-benzyl-(Cbz-leucinyl)-amine (150 mg, 0.27 mmol) in N-methyl pyrollidinone (10 ml), diisopropyl ethyl amine (1.2 ml, 6 mmol) and HBTU (2.2 g, 6 mmol) and was shaken at room temperature overnight. The resin was filtered, washed with DMF (3×10 ml). The above procedure was repeated, and the final resin washed with MeOH (2×10 ml), then methylene chloride (5×20 ml); Magic Angle Spinning 1H NMR: d 7.6, 7.4, 5.1, 5.0, 3.4, 0.8.

h) 1-N-benzyl-1-Cbz-leucinyl-amino-3-Cbz-leucinyl-amino-propan-2-ol 2-(Merrifield polymer-6-(oxymethylene-tetrahydropyran-acetal)-3-Cbz-leucinyl)-amino-propan-N-benzyl-(Cbz-leucinyl)-amine (150 mg, 0.27 mmol) was shaken as a slurry with 85:5:10 TFA/water/methylene chloride (5 ml) for 4 h at RT. The solution was filtereed and the filtrate was concentrated in vacuo, then chromatographed (silica gel, 5% MeOH/methlene chloride) to produce a yellow solid (65 mg, 35%); MS(ES) M+H+=675.1.

i) 1-N-benzyl-1-Cbz-leucinyl-amino-3-Cbz-leucinyl-amino-propan-2-one

1-N-benzyl-1-Cbz-leucinyl-amino-3-Cbz-leucinyl-amino-propan-2-ol (65 mg, 0.96 mmol) was dissolved in acetone (5 ml) and Jones reagent (2 ml, excess) was added dropwise at room temperature and the reaction was stirred overnight. The excess Jones reagent was then quenched with isopropanol (5 ml) and the reaction was diluted with water (5 ml) and was extracted with EtOAc (2×20 ml). The combined organic layers were extracted with water (2×15 ml), then brine (10 ml), then were dried with magnesium sulfate, filtered concentrated in vacuo to produce a yellow solid, which was chromatographed (silica gel, 50% EtOAc/Hexanes) to produce a white solid (16.5 mg, 29%); MS(ES) M+H$^+$=673.1.

Example 58

Preparation of (S)-Phenylmethyl [1-[[[3-[(2-dibenzofuranylsulfonyl)amino]-2-oxopropyl]-3-(benzyl)amino]carbonyl]-3-methylbutyl]carbamate a) N-(2-hydroxy-3-N-benzylamino-propyl)phthalimide N-(2,3-Epoxypropyl)phthalimide (Aldrich, 2.03 g, 10 mmol) was reluxed with benzyl amine (1.07 g, 10 mmol) in isopropanol (15 ml) for 3 h. The reaction was cooled to RT, then concentrated in vacuo producing a white gum, which was triturated with MeOH, then filtered producing a white solid (0.48 g, 15%); MS(ES) M+H$^+$=311.

b) N-(2-hydroxy-3-(N-benzyl-2-dibenzofuransulfonamide)-propyl)phthalimide

N-(2-hydroxy-3-N-benzylamino-propyl)phthalimide (0.31 g, 1 mmol) was stirred with 2-dibenzofuransulfonyl chloride (0.27 g, 1 mmol) in N-methyl morpholine (0.8 ml) and DMF (5 ml) overnight. The reaction was diluted with water (10 ml), extracted with EtOAc (2×20 ml), the combined organic layers were extracted with water (3×20 ml), then brine (20 ml), then were dried with magnesium sulfate, filtered, concentrated in vacuo to produce an oil, which was chromatographed (silica gel, 30% EtOAc/hexanes) to produce a white foam (0.37 g, 69%); MS(ES) M+H$^+$=541, MS(ES) M+Na$^+$=563, MS(ES-negative) M+HCO$_2$$^-$=585.

c) 2-hydroxy-(N-benzyl-2-dibenzofuransulfonamide)-propyl-3-amine

N-(2-hydroxy-3-(N-benzyl-2-dibenzofuransulfonamide)-propyl)phthalimide (0.37 g, 0.69 mmol) was refluxed with hydrazine hydrate (0.34 g, 6.85 mmol) in MeOH (7 ml) for 1.5 h. The reaction was cooled to RT, then was concentrated in vacuo. The resulting white solid was triturated with MeOH, then filtered to produce the desired product as a white solid (0.27 g, 96%); MS(ES) M+H$^+$=411.

d) Cbz-leucinyl-(2-hydroxy-(N-benzyl-2-dibenzofuransulfonamide))propyl-3-amine 2-hydroxy-(N-benzyl-2-dibenzofuransulfonamide)-propyl-3-amine (0.2 g, 0.5 mmol) was stirred with Cbz-leucine (0.13 g, 0.5 mmol) in N-methyl morpholine (0.6 ml) and DMF (2 ml), then HBTU (0.19 g, 0.5 mmol) was added and the reaction was stirred overnight at RT. The reaction was diluted with water (10 ml), extracted with EtOAc (2×20 ml). A solid that was insoluble in both layers was filtered off. The combined organic layers were extracted with water (2×20 ml), then brine (20 ml), then were dried with magnesium sulfate, filtered, concentrated in vacuo to produce a white solid, which was used in the next reaction without further purification; MS(ES) M+H$^+$=658, MS(ES) M+Na$^+$=680.

e) (S)-Phenylmethyl [1-[[[3-[(2-dibenzofuranylsulfonyl)amino]-2-oxopropyl]-3-(benzyl)amino]carbonyl]-3-methylbutyl]carbamate Cbz-leucinyl-(2-hydroxy-(N-benzyl-2-dibenzofuransulfonamide))propyl-3-amine (0.16 g, 0.244 mmol) was dissolved in acetone (2 ml). Jones reagent (0.5 ml, 1.5 M) was added added and the reaction was stirred overnight. The excess Jones reagent was then quenched with isopropanol (1 ml) and the reaction was diluted with water (10 ml) and was extracted with EtOAc (2×20 ml). The combined organic layers were extracted with water (2×20 ml), then brine (20 ml), then were dried with magnesium sulfate, filtered, concentrated in vacuo to produce a white solid, which was chromatographed (silica gel, 1:1 EtOAc/hexanes) to produce a white solid (0.14 g, 88%); MS(ES) M–H$^+$=654, MS(ES) M+Cl$^+$=690, MS(ES) M+HCO$_2$$^-$=700.

Example 59

Preparation of (S)-Phenylmethyl [1-[[[3-[(2-dibenzofuranylsulfonyl)amino]-2-oxopropyl]-3-(4-pyridinylmethyl)amino]carbonyl]-3-methylbutyl] carbamate Following the procedure of Example 58(a)–(e), except substituting "4-pyridyl methyl amine" for "benzylamine" and, the title compound was prepared; MS(ES) M+H$^+$=657.

Example 60

Preparation of 1-[[[3-[(2-dibenzofuranylsulfonyl)amino]-2-oxopropyl]-3-(4-pyridinylmethyl) benzamide Following the procedure of Example 58(a)–(e), except substituting "benzoic acid" for "Cbz-leucine", the title compound was prepared; MS(ES) M–H$^+$=511, MS(ES) M+Cl$^-$=547.

Example 61

Preparation of (S)-Phenylmethyl [1-[[[3-[(2-dibenzofuranylsulfonyl)amino]-2-oxopropyl]-1-(4-pyridinylmethyl)amino]carbonyl]-3-methylbutyl] carbamate Following the procedure of Example 58(a)–(e), except substituting "4-pyridyl methyl amine" for "benzylamine" and "Cbz-leucine and HBTU" for "2-dibenzofuransulfonyl chloride " and "2-dibenzofuransulfonyl chloride" for "Cbz-leucine and HBTU", the title compound was prepared; MS(ES) M+H$^+$=657.

Example 62

Preparation of 2-[N-(N-benzyloxycarbonyl-L-leucinyl)]-2'-[N'-(4-phenoxyphenylsulfonyl)] carbohydrazide a) N-benzyloxycarbonyl-L-leucine methyl ester To a stirring solution of L-leucine methyl ester hydrochloride (2.0 g, 11.0 mmol) in 1,4-dioxane (20 mL) was added Na$_2$CO$_3$ (12.1 ml, 2M in water) followed by benzylchloroformate (1.96 g, 11.5 mmol). The mixture was stirred at room temperature for 4 h then partitioned between ethyl acetate and water. The organic layer was washed with brine, dried (MgSO$_4$), filtered and concentrated to yield the title compound as a colorless oil (3.1 g, 100%). $^1$H NMR (400 MHz, CDCl$_3$) δ7.34 (m, 5H), 5.27 (d, 1H), 5.12 (s, 2H), 4.41 (s, 2H), 3.75 (s, 3H), 1.65 (m, 3H), 0.96 (m, 6H).

b) N-benzyloxycarbonyl-L-leucinylhydrazide

To a stirring solution of the compound of Example 62(a) (3.1 g, 11.0 mmol) in 15 mL of methanol was added hydrazide hydrate (5.9 g, 118 mmol). The solution was stirred at room temperature for 16h then concentrated to yield the title compound as an off-white solid (3.1 g, 100%). MS(ESI): 280.2 (M+H)$^+$.

c) (1S)-1-benzyloxycarbonylamino-3-methyl-1-(1,3,4-oxadiazol-2-on-5-yl)butane

To a stirring solution of the compound of Example 62(b) (3.0 g, 10.8 mmol) in toluene (50 mL) was added phosgene (56 mL, 1.93M in toluene). The solution was heated at reflux for 4 h then concentrated to yield the title compound as a pale yellow foam (3.15 g, 96%). MS(ESI): 306.1 (M+H)$^+$.

d) 2-[N-(N-benzyloxycarbonyl-L-leucinyl)]carbohydrazide

To a stirring solution of the compound of Example 62(c) (0.147 g, 0.482 mmol) in 2 mL of methanol was added hydrazine hydrate (0.241 g, 4.82 mmol). The solution was stirred at room temperature for 24 h then concentrated and purified by column chromatography (silica gel, methanol/dichloromethane) to yield the title compound as a white foam (0.097 g, 60%). MS(ESI): 338.2 (M+H)$^+$.

e) 2-[N-(N-benzyloxycarbonyl-L-leucinyl)]-2-[N'-(4-phenoxyphenylsulfonyl)]carbohydrazide To a stirring solution of the compound of Example 62(d) (0.097 g, 0.288 mmol) in 2 mL of DMF was added pyridine (0.046 g, 0.576 mmol) followed by 4-phenoxyphenylsulfonylchloride (0.155 g, 0.576 mmol). The solution was stirred at room temperate for 16 h then partitioned between ethyl acetate and water. The organic layer was washed with brine, dried (MgSO$_4$), filtered and concentrated. The residue was purified by column chromatography (silica gel, ethyl acetate/hexane) to yield the title compound as a white solid (0.052 g, 32%). MS(ESI): 570.1 (M+H)$^+$.

Example 63

Preparation of 2-[N-(N-benzyloxycarbonyl-L-alanyl)]-2'-[N-(N-benzyloxycarbonyl-L-leucinyl)] carbohydrazide To a stirring solution of the compound of Example 62(d) (0.100 g, 0.297 mmol) in 2 mL of DMF was added N-benzyloxycarbonyl-L-alanine (0.070 g, 0.312 mmol), 1-hydroxybenzotriazole (0.008 g, 0.059 mmol), and 1-(3-dimethylaminopropyl)-3-ethylcarbodiimide hydrochloride (0.060 g, 0.312 mmol). After stirring at room temperature for 16 h, the solution was poured into 150 mL of water. The precipitate was filtered and washed with water (150 mL) and dried under high vacuum to yield the title compound as a white solid (0.062 g, 39%). MS(ESI): 543.1 (M+H)$^+$.

Example 64

Preparation of 2-[N-(N-benzyloxycarbonyl-L-leucinyl)]-2'-[N'-(4-phenylbenzoyl)]carbohydrazide Following the procedure of Example 63, except substituting 4-phenylbenzoic acid for N-benzyloxycarbonyl-L-alanine, the title compound was prepared as a white solid (0.121 g, 53%). MS(ESI): 518.1 (M+H)$^+$.

Example 65

Preparation of 2-[N-(N-benzyloxycarbonyl-L-leucinyl)]-2'-[N'-(4-methoxybenzoyl)]carbohydrazide Following the procedure of Example 63, except substituting 4-methoxybenzoic acid for N-benzyloxycarbonyl-L-alanine the title compound was prepared as a white solid (0.057 g, 27%). MS(ESI): 472.1 (M+H)$^+$.

Example 66

Preparation of 2-[N-(N-benzyloxycarbonyl-L-leucinyl)]-2'-[N'-(4-phenoxybenzoyl)]carbohydrazide Following the procedure of Example 63, except substituting 4-phenoxybenzoic acid for N-benzyloxycarbonyl-L-alanine the title compound was prepared as a white solid (0.102 g, 43%). MS(ESI): 534.1 (M+H)$^+$.

Example 67

Preparation of 2-(N-acetyl)-2'-[N'-(N-benzyloxycarbonyl-L-leucinyl)]carbohydrazide To the compound of Example 62(d) (0.100 g, 0.297 mmol) was added acetic anhydride (0.303 g, 2.97 mmol). The solution was stirred at room temperature for 16h then concentrated to an off-white solid which was washed with dichloromethane to yield the title compound as a white solid (0.086 g, 76%). MS(ESI): 380.1 (M+H)$^+$.

Example 68

Preparation of 2-[N-(N-acetyl-L-leucinyl)]-2'-[N'-(N-benzyloxycarbonyl-L-alanyl)]carbohydrazide a) 2-[N-(N-benzyloxycarbonyl-L-alanyl)]carbohydrazide Following the procedure of Example 62(a)–62(d), except substituting L-alanine ethyl ester hydrochloride for L-leucine methyl ester hydrochloride in step (a), the title compound was prepared as a pale yellow foam (1.1 g, 3.8 mmol). MS(ESI): 296.2 (M+H)$^+$.

b) 2-[N-(N-acetyl-L-leucinyl)]-2'-[N'-(N-benzyloxycarbonyl-L-alanyl)]carbohydrazide To a stirring solution of the compound of Example 63(d) (0.150 g, 0.508 mmol) in DMF (2 mL) was added N-acetyl-L-leucine (0.092 g, 0.534 mmol), 1-hydroxybenzotriazole (0.014 g, 0.102 mmol), and 1-(3-dimethylaminopropyl)-3-ethylcarbodiimide hydrochloride (0.102 g, 0.534 mmol). After stirring at room temperature for 16h, the solution was diluted with ethyl acetate, washed successively with water, saturated aqueous sodium bicarbonate, and brine. The organic layer was dried (MgSO$_4$), filtered and concentrated. The residue was purified by column chromatography (silica gel, methanol/dichloromethane) to yield the title compound as a white solid (0.028 g, 12%). MS(ESI): 451.1 (M+H)$^+$.

Example 69

Preparation of 2-[N-(N-acetyl-L-alanyl)]-2'-[N'-(N-benzloxycarbonyl-L-leucinyl)]carbohydrazide Following the procedure of Example 68(b), except substituting N-acetyl-L-alanine for N-acetyl-L-leucine and 2-[N-(N-benzyloxycarbonyl-L-leucinyl)]carbohydrazide for 2-[N-(N-benzyloxycarbonyl-L-alanyl)]carbohydrazide, the title compound was prepared as a white solid (0.050 g, 25%). MS(ESI): 473.1 (M+Na)$^+$.

Example 70

Preparation of 2-[N-(N-benzyloxycarbonyl-L-leucinyl)]-2'-[N'-[4-(N,N-dimethylaminomethyl)benzoyl)]]carbohydrazide a) methyl 4-(N,N-dimethylaminomethyl)benzoate Methyl 4-(bromomethyl)benzoate (2.0 g, 8.73 mmol) was added to a saturated solution of dimethylamine in methanol. After stirring for 25 min, the solution was concentrated and the residue was partitioned between 1N NaOH and ethyl acetate. The organic layer was washed with saturated brine, dired (MgSO$_4$), filtered, and concentrated to provide the title compound as a colorless liquid (1.67 g, 99%). $^1$H NMR (250 MHz, CDCl$_3$) δ8.00 (d, 2H), 7.39 (d, 2H), 3.91 (s, 3H), 3.47 (d, 2H), 2.25 (s, 6H).

b) 4-(N,N-dimethylaminomethyl)benzoic acid lithium salt

The compound of Example 70(a) (1.67 g, 8.6 mmol) was dissolved in THF/H$_2$O (1:1) and LiOH•H$_2$O (0.39 g, 9.3 mmol) was added. The mixture was stirred at room temperature for 0.5h, then taken to reflux for 1.5h. The mixture was concentrated redissolved in 25 mL of water and reconcentrated to yield a white solid (1.6 g, 100%). $^1$H NMR (400 MHz, CD$_3$OD) δ7.94 (d, 2H), 7.36 (d, 2H), 3.64(s, 2H), 2.35 (s, 6H).

c) 2-[N-(N-benzyloxycarbonyl-L-leucinyl)]-2'-[N'-[4-(N,N-dimethylaminomethyl)benzoyl)]]carbohydrazide Following the procedure of Example 68(b), except substituting 4-(N,N-dimethylaminomethyl)benzoic acid lithium salt for N-acetyl-L-leucine and 2-[N-(N-benzyloxycarbonyl-L-leucinyl)]carbohydrazide for 2-[N-(N-benzyloxycarbonyl-L-alanyl)]carbohydrazide, the title compound was prepared as a pale yellow solid (0.050 g, 17%). MS(ESI): 499.1 (M+H)$^+$.

Example 71

Preparation of 2-[N-(N-benzyloxycarbonyl-L-leucinyl)]-2'-[N'-[4-hydroxy-[3-(4-morpholinomethyl)]]benzoyl]carbohydrazide Following the procedure of Example 68(b), except substituting 4-hydroxy-3-(4morpholinomethyl)benzoic acid for N-acetyl-L-leucine and 2-[N-(N-benzyloxycarbonyl-L-leucinyl)]carbohydrazide for 2-[N-(N-benzyloxycarbonyl-L-alanyl)]carbohydrazide, the title compound was prepared as a white solid (0.065 g, 26%). MS(ESI): 557.0 (M+H)$^+$.

Example 72

Preparation of 2-[N-(N-benzyloxycarbonyl-L-leucinyl]-2'-[N'-[4-(N,N-dimethylaminomethyl)benzyloxy]carbonyl-L-leucinyl]carbohydrazide a) α-isocyanato-L-leucine methyl ester L-leucine methyl ester hydrochloride (25 g, 0.14 mol) was dissolved in methylene chloride (450 mL), cooled to 0° C., and pyridine (43.5 g, 0.55 mol, 44.5 mL) was added, then a 1.93 M solution of phosgene in toluene (0.18 mol, 92.7 mL) was added slowly. After stirring at 0° C. for 2 h, the mixture was poured into 1400 mL of 0.5 N Hcl and 900 mL of ice. The organic layer was washed with 1400 mL of 0.5 N Hcl and 900 mL of ice. The aqueous layers were extracted with methylene chloride (450 mL) and the combined organic layers were washed with 1400 mL of saturated brine and 900 mL of ice, then dried ($MgSO_4$), filtered and concentrated. The residue was distilled (56–58° C.; 0.78 mmHg) to provide the title compound as a colorless liquid (20.4 g, 86%). $^1$H NMR (250 MHz, $CDCl_3$) δ4.04 (dd, 1H), 3.82 (s, 3H), 1.92-1.72 (m, 1H), 1.69-1.62 (m, 2H), 0.96 (d, 3H), 0.94 (d, 3H).

b) 4-(N,N-dimethylamino)benzyl alcohol

To a stirring solution of the compound of Example 70(a) (1.63 g, 8.4 mmol) in 25 mL of ether, cooled to 0° C., was added dropwise a 1 M solution of lithium aluminum hydride (8.4 mmol, 8.4 mL). After 5 min, the reaction was quenched by the addition of water (0.33 mL), 15% aqueous NaOH (0.33 mL) and water (1.0 mL). The precipitate was removed by filtration, washed with ether 2 times and the filtrate was concentrated to provide the title compound as a colorless oil (1.36 g, 98%). $^1$H NMR (250 MHz, $CDCl_3$) δ7.32 (d, 2H), 7.28 (d, 2H), 4.68 (s, 2H), 3.41 (s, 2H), 2.22 (s, 6H).

c) N-[4-(N,N-dimethylaminomethyl)benzyloxycarbonyl]-L-leucine methyl ester

A solution of the compound of Example 72(a) (1.0 g, 5.8 mmol) and the compound of Example 72(b) in toluene (6 mL) was heated at reflux for 24 h. The solution was concentrated and the residue was purified by flash chromatography on 60 g of 230–400 mesh silica gel, eluting with 5% methanol in methylene chloride, to provide the title compound as a pale yellow oil (1.71 g, 87%). $^1$H NMR (400 MHz, $CDCl_3$) δ7.31 (s, 4H), 5.13 (d, 1H), 5.10 (s, 2H), 4.41 (m, 1H), 3.74 (s, 3H), 3.43 (s, 2H), 2.24 (s, 6H), 1.70-1.62 (m, 2H), 1.52 (m, 1H), 0.96 (d, 3H), 0.94 (d, 3H).

d) N-[4-(N,N-dimethylaminomethyl)benzyloxycarbonyl]-L-leucine lithium salt

Following the procedure of Example 70(b), except substituting N-[4(N,N-dimethylaminomethyl)benzyloxycarbonyl]-L-leucine methyl ester for methyl 4-(N,N-diethylaminomethyl)benzoate, the title compound was prepared as a white solid (1.57 g, 95%). $^1$H NMR (400 MHz, $CD_3OD$) δ7.35 (d, 2H), 7.30 (d, 2H), 5.06 (dd, 2H), 4.10 (dd, 1H), 3.48 (s, 2H), 2.23 (d, 6H), 1.69-1.51 (m, 3H), 0.94 (d, 3H), 0.93 (d, 3H).

e) 2-[N-(N-benzyloxycarbonyl-L-leucinyl)]-2'-[N'-[4-(N,N-dimethylaminomethyl)benzyloxy]carbonyl-L-leucinyl]carbohydrazide Following the procedure of Example 68(b), except substituting N-[4-(N,N-dimethylaminomethyl)benzyloxycarbonyl]-L-leucine lithium salt for N-acetyl-L-leucine and 2-[N-(N-benzyloxycarbonyl-L-leucinyl)]carbohydrazide for 2-[N-(N-benzyloxycarbonyl-L-alanyl)]carbohydrazide, the title compound was prepared as a white solid (0.069 g, 18%). MS(ESI): 642.1 (M+H)$^+$.

Example 73

Preparation of 2-(N-benzoyl)-2'-[N'-(N-benzyloxycarbonyl-L-leucinyl)]carbohydrazide Following the procedure of Example 62(e) except substituting benzoyl chloride for 4-phenoxyphenylsulfonylchloride, the title compound was prepared as a white solid (61 mg, 31%). MS(ESI): 442.1 (M+H)$^+$.

Example 74

Preparation of 2-[N-(N-benzyloxycarbonyl-L-leucinyl)]-2'-[N'-[3-(4-morpholinomethyl)benzoyl]]carbohydrazide a) methyl 3-(4-morpholinomethyl)benzoate A solution of morpholine (0.836 g, 9.6 mmol) and methyl 3-(bromomethyl)benzoate in THF (5 mL) and DMF (5 mL) was stirred at 50° C. for 3h. The solution was partitioned between ethyl acetate and water. The organic layer was washed successively with water, saturated aqueous $NaHCO_3$, and brine then dried ($MgSO_4$), filtered and concentrated to yield a colorless oil (0.872 g, 3.72 mmol). $^1$H NMR (400 MHz, $CDCl_3$) δ7.99 (s, 1H), 7.91 (d, 1H), 7.55 (d, 1H), 7.47 (t, 1H), 3.94 (s, 3H), 3.72 (m, 4H), 3.53 (s, 2H), 2.46 (m, 4H).

b) 3-(4-morpholinomethyl)benzoic acid

To a solution of the compound of Example 74(a) (0.872 g, 3.72 mmol) in THF (3 mL) and water (3 mL) was added lithium hydroxide monohydrate (0.171 g, 4.08 mmol). After stirring at room temperature for 3h, the solution was concentrated. The residue was redissolved in water (5 mL) and 3N HCl was added and the solution was lyophilized to yield a yellow solid (0.822 g, 3.72 mmol). MS(ESI): 222.0 (M+H)$^+$.

c) 2-[N-(N-benzyloxycarbonyl-L-leucinyl)]-2'-[N'-[3-4-morpholinomethyl)benzoyl]]carbohydrazide Following the procedure of Example 68(b), except substituting 3-(4-morpholinomethyl)benzoic acid for N-acetyl-L-leucine and 2-[N-(N-benzyloxycarbonyl-L-leucinyl)]carbohydrazide for 2-[N-(N-benzyloxycarbonyl-L-alanyl)]carbohydrazide, the title compound was prepared as a white solid (0.056 g, 20%). MS(ESI): 541.0 (M+H)$^+$.

Example 75

Preparation of 2-[N-(3-benzyloxybenzoyl)]-2'-[N'-(N-benzyloxycarbonyl-L-leucinyl)]carbohydrazide a) methyl 3-benzyloxybenzoate To a suspension of NaH (0.395 g, 9.87 mmol, 60% in mineral oil) in DMF (20 mL) was added methyl 3-hydroxybenzoate (1.0 g, 6.58 mmol). After stirring for 15 min at room temperature, benzyl bromide (1.1 g, 6.58 mmol) was added. After stirring at room temperature for 3h, the solution was partitioned between ethyl acetate and water. The organic layer was washed with water (2×75 mL), saturated aqueous sodium bicarbonate, and brine, then dried ($MgSO_4$), filtered and concentrated to yield an off-white solid (1.013 g, 4.2 mmol). $^1$H NMR (400 MHz, $CDCl_3$) δ7.67 (m, 2H), 7.48-7.34 (m, 6H), 7.19 (m, 1H), 5.12 (s, 2H), 3.95 (s, 3H).

b) 3-benzyloxybenzoic acid

To a solution of the compound of Example 75(a) (0.400 g, 1.65 mmol) in THF (2 mL) and water (2 mL) was added lithium hydroxide monohydrate (0.076 g, 1.82 mmol). After stirring at reflux for 5 h, the solution was partitioned between ethyl acetate and 3N HCl. The organic layer was washed with brine, dried ($MgSO_4$), filtered and concentrated to yield a white solid (0.355 g, 1.56 mmol). $^1$H NMR (400 MHz, $CD_3OD$) δ7.58 (m, 2H), 7.36-7.24 (m. 6H), 7.10 (m, 1H), 5.04 (s, 2H).

c) 2-[N-(3-benzyloxybenzoyl)]-2'-[N'-(N-benzyloxycarbonyl-L-leucinyl)]carbohydrazide Following the procedure of Example 68(b), except substituting 3-benzyloxybenzoic acid for N-acetyl-L-leucine and 2-[N-(N-benzyloxycarbonyl-L-leucinyl)]carbohydrazide for 2-[N-(N-benzyloxycarbonyl-L-alanyl)]carbohydrazide, the title compound was prepared as a white solid (0.062 g, 25%). MS(ESI): 548.1 (M+H)$^+$.

Example 76

Preparation of 2-[N-(N-benzyloxycarbonyl-L-leucinyl)]-2'-[N'-[4-[3-(N-N-dimethylamino)-1-propyloxy]benzoyl]]carbohydrazide a) methyl 4-[3-N,N-dimethylamino)-1-propyloxy]benzoate To a solution of methyl 4-hydroxybenzoate (1.0 g, 6.58 mmol), 3-dimethylamino-1-propanol (1.01 g, 9.87 mmol), and triphenylphosphine (2.6 g, 9.87 mmol) at 0° C. in THF (20 mL) was added dropwise diisopropyl azodicarboxylate (1.99 g, 9.87 mmol). After stirring for 16 h at room temperature the solution was concentrated and the residue purified by column chromatography (silica gel, methanol/dichloromethane) to yield the title compound as an oily solid (125 g, 5.2 mmol). MS(ESI): 238.1 (M+H)$^+$.

b) 4-[3-(N,N-dimethylamino)-1-propyloxy]benzoic acid

Following the prodcedure of Example 74(b) except substituting methyl 4-[3-(N,N-dimethylamino)-1-propyloxy]benzoate for methyl 3-(4-morpholinomethyl)benzoate, the title compound was prepared as a tan solid (1.17 g, 5.2 mmol). MS(ESI): 224.1 (M+H)$^+$.

c) 2-[N-(N-benzyloxycarbonyl-L-leucinyl)]-2'-[N'-[4-[3-(N-N-diethylamino)-1-propyloxy]benzoyl]]carbohydrazide Following the procedure of Example 68(b), except substituting 4-[3-(N,N-dimethylamino)-1-propyloxy]benzoic acid for N-acetyl-L-leucine and 2-[N-(N-benzyloxycarbonyl-L-leucinyl)]carbohydrazide for 2-[N-(N-benzyloxycarbonyl-L-alanyl)]carbohydrazide, the title compound was prepared as a white solid (0.060 g, 21%). MS(ESI): 543.1 (M+H)$^+$.

Example 77

Preparation of 2-[N-(2-benzyloxybenzoyl)]-2'-[N'-(N-benzyloxycarbonyl-L-leucinyl)]carbohydrazide Following the procedure of Example 68(b), except substituting 2-benzyloxybenzoic acid for N-acetyl-L-leucine and 2-[N-(N-benzyloxycarbonyl-L-leucinyl)]carbohydrazide for 2-[N-(N-benzyloxycarbonyl-L-alanyl)]carbohydrazide, title compound was prepared as a white solid (0.056 g, 23%). MS(ESI): 548.1 (M+H)$^+$.

Example 78

Preparation of 2-[N-(N-benzyloxycarbonyl-L-leucinyl)]-2'-[N'-[3-(4-pyridylmethoxy)benzoyl]]carbohydrazide a) methyl 4-pyridinylmethoxybenzoate Following the procedure of Example 76(a) except substituting methyl 3-hydroxybenzoate for methyl 4-hydroxybenzoate and 4-pyridylcarbinol for 3-dimethylamino-1-propanol, the title compound was prepared as a yellow solid (0.599 g, 2.5 mmol). MS(ESI): 244.1 (M+H)$^+$.

b) 4-pyridinylmethoxybenzoic acid

Following the procedure of Example 75(b) except substituting methyl 4-pyridylmethoxybenzoate for methyl 3-benzyloxybenzoate the title compound was prepared as a yellow solid (0.386 g, 1.69 mmol). $^1$H NMR (400 MHz, CD$_3$OD) δ8.54 (d, 2H), 7.64 (m, 2H), 7.57 (m, 2H), 7.40 (m, 1H), 7.26 (m, 1H), 5.24 (s, 2H).

c) 2-[N-(N-benzyloxycarbonyl-L-leucinyl)]-2'-[N'-[3-(4-pyridylmethoxy)benzoyl]]carbohydrazide Following the procedure of Example 68(b), except substituting 4-pyridinylmethoxybenzoic acid for N-acetyl-L-leucine and 2-[N-(N-benzyloxycarbonyl-L-leucinyl)]carbohydrazide for 2-[N-(N-benzyloxycarbonyl-L-alanyl)]carbohydrazide, title compound was prepared as a white solid (0.219 g, 67%). MS(ESI): 549.1 (M+H)$^+$.

Example 79

Preparation of 2-[N-(4-benzyloxybenzoyl)]-2'-[N'-(N-benzyloxycarbonyl-L-leucinyl)]carbohydrazide Following the procedure of Example 75(a)–75(c) except substituting methyl 4-hydroxybenzoate for methyl 3-hydroxybenzoate in step (a), the title compound was prepared as a white solid (0.160 g, 49%). MS(ESI): 548.1 (M+H)$^+$.

Example 80

Preparation of 2-[N-(N-benzyloxycarbonyl-L-leucinyl)]-2'-[N'-(3-benzyloxy-5-methoxy)benzoyl]carbohydrazide a) methyl 3-hydroxy-5-methoxybenzoate A suspension of methyl 3,5-dihydroxybenzoate (2.0 g, 11.9 mmol), K$_2$CO$_3$ (1.6 g, 11.9 mmol), and iodomethane (1.7 g, 11.9 mmol) in acetone (100 mL) was stirred at reflux. After stirring for three hours the mixture was partitioned between ethyl acetate and water. The organic layer was washed with brine, dried (MgSO$_4$), filtered and concentrated. The residue was purified by column chromatography to yield the title compound as a white solid (0.813 g, 4.4 mmol). $^1$H NMR (400 MHz, CDCl$_3$) δ7.16 (m, 1H), 7.12 (m, 1H), 6.61 (m, 1H), 5.04 (s, 1H), 3.91 (s, 3H) 3.82 (s, 3H).

b) methyl 3-benzyloxy-5-methoxybenzoate

Following the procedure of Example 80(a) except substituting methyl 3-hydroxy-5-methoxybenzoate for methyl 3,5-dihydroxybenzoate and benzyl bromide for iodomethane, the title compound was prepared as a tan oil (1.2 g, 4.4 mmol). $^1$H NMR (400 MHz, CDCl$_3$) δ7.45-7.31 (m, 6H), 7.24 (s, 1H), 6.76 (m, 1H), 5.09 (s, 2H), 3.95 (s, 3H), 3.84 (s, 3H).

c) 3-benzyloxy-5-methoxybenzoic acid

Following the procedure of Example 75(b) except substituting methyl 3-benzyloxy-5-methoxybenzoate for methyl 3-benzyloxybenzoate, the title compound was prepared as an orange solid (1.14 g, 4.4 mmol). $^1$HNMR (400 MHz, CDCl$_3$) δ7.42-7.20 (m, 7H), 6.71 (m, 1H), 5.05 (s, 2H), 3.80 (s, 3H).

d) 2-[N-(N-benzyloxycarbonyl-L-leucinyl)]-2'-[N'-(3-benzyloxy-5-methoxy)benzoyl]carbohydrazide Following the procedure of Example 68(b), except substituting 3-benzyloxy-5-methoxybenzoic acid for N-acetyl-L-leucine and 2-[N-(N-benzyloxycarbonyl-L-leucinyl)]carbohydrazide for 2-[N-(N-benzyloxycarbonyl-L-alanyl)]carbohydrazide, title compound was prepared as a white solid (0.201 g, 59%). MS(ESI): 578.0 (M+H)$^+$.

Example 81

Preparation of 2-[N-(N-benzyloxycarbonyl-L-leucinyl)]-2'-[N'-(3-benzyloxy-4.5-dimethoxy)benzoyl]carbohydrazide Following the procedure of Example 68(b), except substituting 3-benzyloxy-4,5-dimethoxybenzioc acid for N-acetyl-L-leucine and 2-[N-(N-benzyloxycarbonyl-L-leucinyl)]carbohydrazide for 2-[N-(N-benzyloxycarbonyl-L-alanyl)]carbohydrazide, the title compound was prepared as a white solid (0.155 g, 43%). MS(ESI): 607.9 (M+H)$^+$.

Example 82

Preparation of 2-[N-(N-benzyloxycarbonyl-L-leucinyl)]-2'-[N'-(3-benzyloxy-5-methoxy)benzoyl]carbohydrazide Following the procedure of Example 80(a)–80(d) except substituting iodoethane for iodomethane in step (a), the title compound was prepared as a white solid (0.162 g, 46%). MS(ESI): 592.3 (M+H)$^+$.

Example 83

Preparation of 2-[N-(N-benzyloxycarbonylglycinyl)]-2'-[N'-(N-benzyloxycarbonyl-L-leucinyl)]carbohydrazide Following the procedure of Example 68(b), except substituting N-benzyloxycarbonylglycine for N-acetyl-L-leucine and 2-[N-(N-benzyloxycarbonyl-L-leucinyl)]carbohydrazide for 2-[N-(N-benzyloxycarbonyl-L-alanyl)]carbohydrazide, the title compound was prepared as a white solid (0.204 g, 65%). MS(ESI): 529.2 (M+H)$^+$.

Example 84

Preparation of 2-[N-(3-benzyloxybenzoyl)]-2'-[N'-(N-benzyloxycarbonyl-L-prolinyl)]carbohydrazide a) 2-[N-(3-benzyloxybenzoyl)]carbohydrazide Following the procedure of Example 62(b)–62(d) except substituting methyl 3-benzyloxybenzoate for N-benzyloxycarbonyl-L-leucine methyl ester in step (b), the title compound was prepared as an off white solid (0.421 g, 67%). MS(ESI): 301.1 (M+H)$^+$.

b) 2-[N-(3-benzyloxybenzoyl)]-2'-[N'-(N-benzyloxycarbonyl-L-prolinyl)]carbohydrazide Following the procedure of Example 68(b), except substituting N-benzyloxycarbonyl-L-proline for N-acetyl-L-leucine and 2-[N-(3-benzyloxybenzoyl)]carbohydrazide for 2-[N-(N-benzyloxycarbonyl-L-alanyl)]carbohydrazide, the title compound was prepared as a white solid (0.219 g, 62%). MS(ESI): 532.0 (M+H)$^+$.

Example 85

Preparation of 2-[N-(N-benzloxycarbonyl-L-leucinyl)]-2'-[N'-(4-phenylphenylacetyl)]carbohydrazide Following the procedure of Example 68(b), except substituting 4-biphenylacetic acid for N-acetyl-L-leucine and 2-[N-(N-benzyloxycarbonyl-L-leucinyl)]carbohydrazide for 2-[N-(N-benzyloxycarbonyl-L-alanyl)]cabohydrazide, the title compound was prepared as a white solid (0.224 g, 71%). MS(ESI): 554.2 (M+Na)$^+$.

Example 86

Preparation of (2'S)-2-[N-(3-benzyloxybenzoyl)]-2'-[N'-(N-benzyloxycarbonyl-2-aminobutyryl)]carbohydrazide Following the procedure of Example 68(b), except substituting (S)-N-benzyloxycarbonyl-2-aminobutyric acid for N-acetyl-L-leucine and 2-[N-(3-benzyloxybenzoyl)]carbohydrazide for 2-[N-(N-benzyloxycarbonyl-L-alanyl)]carbohydrazide, the title compound was prepared as a white solid (0.244 g, 70%). MS(ESI): 520.3 (M+H)$^+$.

Example 87

Preparation of 2.2'-[N,N'-[bis-(4-phenylphenylacetyl)]]carbohydrazide

To a stirring solution of carbohydrazide (0.200 g, 2.22 mmol) in DMF (12 mL) was added 4-biphenylacetic acid (1.04 g, 4.89 mmol), 1-hydroxybenzotriazole (0.060 g, 0.444 mmol), and 1-(3-dimethylaminopropyl)-3-ethylcarbodiimide hydrochloride (0.937 g, 4.89 mmol). After stirring at room temperature for 16 h, the solution was poured into 150 mL of water. The precipitate was filtered and washed with water (150 mL) and dried under high vacuum to yield the title compound as a white solid (0.977 g, 92%). MS(ESI): 501.1 (M+Na)$^+$.

Example 88

Preparation of (2'RS)-2-[N-(N-benzyloxycarbonyl-L-leucinyl)]-2'-[2-(4-phenylphenoxy)propionyl]carbohydrazide Following the procedure of Example 68(b), except substituting 2-(4-phenylphenoxy)propionic acid for N-acetyl-L-leucine and 2-[N-(N-benzyloxycarbonyl-L-leucinyl)]carbohydrazide for 2-[N-(N-benzyloxycarbonyl-L-alanyl)]carbohydrazide, the title compound was prepared as a white solid (0.183 g, 73%). MS(ESI): 562.3 (M+H)$^+$.

Example 89

Preparation of 2-[N-(3-benzyloxybenzoyl)]-2'-[N'-(4-methylpentanoyl)]carbohydrazide Following the procedure of Example 68(b), except substituting 4-methylpentanoic acid for N-acetyl-L-leucine and 2-[N-(3-benzyloxybenzoyl)]carbohydrazide for 2-[N-(N-benzyloxycarbonyl-L-alanyl)]carbohydrazide, the title compound was prepared as a white solid (0.079 g, 30%). MS(ESI): 399.3 (M+H)$^+$.

Example 90

Preparation of (2RS, 2'RS)-2,2'-[N,N'-[bis-[2-(4-phenylphenyl)-4-methylpentanoyl)]]]carbohydrazide a) 4-methyl-2-(4-phenylphenyl)pent-4-enoic acid To a stirring solution of diisopropylamine (0.537 g, 5.31 mmol) in THF (5.2 mL) at 0° C. was added n-butyllithium (2.1 mL, 5.22 mmol, 2.5M in hexane) dropwise. After stirring for 15 min at 0° C., the mixture was cooled to −78° C. and a solution of 4-biphenylacetic acid (0.500 g, 2.36 mmol) in THF (2 mL) was added dropwise. After again warming to 0° C. and cooling to −78° C., 3-bromo-2-methylpropene (0.485 g, 3.54 mmol) was added to the mixture in one portion. After stirring at −78° C. for 1h, the reaction was quenched with 2 mL of water then concentrated. The residue was redissolved in water and extracted with ether (100 mL). The aqueous layer was acidified (3N HCl) and extracted with ether (3×100 mL). The organic layers were combined, dried (MgSO$_4$), filtered and concentrated to yield a white solid (0.449 g, 72%). MS(ESI): 265.3 (M+H)$^-$.

b) 4methyl-2-(4-phenylphenyl)pentanoic acid

To a stirring solution of the compound of Example 90(a) (0.449 g, 1.69 mmol) in ethyl acetate (25 mL) was added palladium on carbon (0.225 g). After stirring under a balloon of hydrogen for 16h, the mixture was filtered through Celite. The filtrate was concentrated to yield an off white solid (0.430 g, 95%). MS(ESI): 267.4 (M+H)⁻.

c) 2RS, 2'RS)-2,2'-[N,N'-[bis-[2-(4phenylphenyl)-4-methylpentanoyl)]]]carbohydrazide Following the procedure of Example 87 except substituting 4-methyl-2-(4-phenylphenyl)pentanoic acid for 4-biphenylacetic acid, the title compound was obtained, after purification by column chromatography (silica gel, methanol/dichloromethane), as a white solid (0.143 g, 33%). MS(ESI): 591.3 (M+H)⁺.

Example 91

Preparation of (2'RS)-2-[N-(N-benzyloxycarbonyl-L-leucinyl)]-2'-N'-[2-(4-phenylphenyl)-4-methylpentanoyl)]]carbohydrazide Following the procedure of Example 68(b), except 4-methyl-2-(4-phenylphenyl)pentanoic acid for N-acetyl-L-leucine and 2-[N-(N-benzyloxycarbonyl-L-leucinyl)] carbohydrazide for 2-[N-(N-benzyloxycarbonyl-L-alanyl)] carbohydrazide, the title compound was prepared as a white solid (0.111 g, 42%). MS(ESI): 588.1 (M+H)⁺.

Example 92

Preparation of (2'RS)-2-[N-3-benzyloxybenzoyl)]-2'-[N'-[2-(4-phenylphenyl)-4-methylpentanoyl)]] carbohydrazide Following the procedure of Example 68(b), except substituting 4-methyl-2-(4-phenylphenyl)pentanoic acid for N-acetyl-L-leucine and 2-([N-(3-benzyloxybenzoyl)] carbohydrazide for 2-[N-(N-benzyloxycarbonyl-L-alanyl)] carbohydrazide, the title compound was prepared as a white solid (0.195 g, 53%). MS(ESI): 551.1 (M+H)⁺.

Example 93

Preparation of 2-[N-(3-benzyloxybenzoyl)]-2'-[N'-(N-benzyloxycarbonyl-N-methyl-L-leucinyl)] carhohydrazide Following the procedure of Example 68(b), except substituting N-benzyloxycarbonyl-N-methyl-L-leucine for N-acetyl-L-leucine and 2-[N-(3-benzyloxybenzoyl)] carbohydrazide for 2-[N-(N-benzyloxycarbonyI-L-alanyl)] carbohydrazide, the title compound was prepared as a white solid (0.341 g, 91%). MS(ESI): 562.2 (M+H)⁺.

Example 94

Preparation of 2-[N-(3-benzloxybenzoyl)]-2'-[N'-[N-(2-pyridinylmethoxycarbonyl)-L-leucinyl]] carbohydrazide a) N-(2-pyridinylmethoxycarbonyl)-L-leucinyl methyl ester Following the procedure of Example 72(c), except substituting 2-pryidylcarbinol for 4-(N,N-dimethylamino) benzyl alcohol, the title compound was prepared as a brown oil (8.06 g, 89%). MS(ESI): 281.2 (M+H)⁺.

b) 2-[N-(2-pyridinylylmethoxycarbonyl)-L-leucinyl] carbohydrazide

Following the procedure of Example 62(b)–62(d) except substituting N-(2-pyridinylmethoxycarbonyl)-L-leucine methyl ester for L-leucine methyl ester in step (b), the title compound was prepared as a pale yellow foam (0.598 g, 69%). MS(ESI): 339.3 (M+H)⁺.

c) 2-[N-(3-benzyloxybenzoyl)]-2'-[N'-[N-(2-pyridinylmethoxycarbonyl)-L-leucinyl]]carbohydrazide Following the procedure of Example 68(b), except substituting 3-benzyloxybenzoic acid for N-acetyl-L-leucine and 2-[N-(2-pyridinylylmethoxycarbonyl)-L-leucinyl] carbohydrazide for 2-[N-(N-benzyloxycarbonyl-L-alanyl)] carbohydrazide, the title compound was prepared as a white solid (0.057 g, 33%). MS(ESI): 549.2 (M+H)⁺.

Example 95

Preparation of 2-[N-[3-(4-pyridylmethoxy) benzoyl]]-2'-[N'-[N-(2-pyridinylmethoxycarbonyl)-L-leucinyl]]carbohydrazide Following the procedure of Example 68(b), except substituting 3-(4-pyridinylmethoxy)benzoic acid for N-acetyl-L-leucine and 2-[N-(2-pyridinylylmethoxycarbonyl)-L-leucinyl]carbohydrazide for 2-[N-(N-benzyloxycarbonyl-L-alanyl)]carbohydrazide, the title compound was prepared as a yellow solid (0.088 g, 27%). MS(ESI): 550.2 (M+H)⁺.

Example 96

Preparation of (2RS)-2-[N-[2-(4-phenylphenyl)-4-methylpentanoyl]]-2'-[N'-[N-(2-pyridinylmethoxycarbonyl)-L-leucinyl]] carbohydrazide Following the procedure of Example 68(b), except 4methyl-2-(4-phenylphenyl)pentanoic acid for N-acetyl-L-leucine and 2-[N-(2-pyridinylylmethoxycarbonyl)-L-leucinyl]carbohydrazide for 2-[N-(N-benzyloxycarbonyl-L-alanyl)]carbohydrazide, the title compound was prepared as a yellow solid (0.056 g, 24%). MS(ESI): 589.4 (M+H)⁺.

Example 97

Preparation of 2-[N-(N-benzyloxycarbonyl-L-leucinyl)]-2'-[N'-[2-(4-pbenylphenyl)-4-methylpentanoyl)]]carbohydrazide The title compound was prepared from the compound of Example 91 using HPLC (Sumipax OA-3100, 4.6×150 mm, 80/20 hexane/ethanol, 1.0 mL/min, retention time=5.9 min).

Example 98

Preparation of 2-[N-(N-benzloxycarbonyl-L-leucinyl)]-2'-[N'-[2-(4-phenylphenyl)-4-methylpentanoyl)]]carbohydrazide The title compound was prepared from the compound of Example 91 using HPLC (Sumipax OA-3100, 4.6×150 mm, 80/20 hexane/ethanol, 1.0 mL/min, retention time=8.1 min).

Example 99

Preparation of 2-[N-(N-benzyloxycarbonyl-L-leucinyl)]-2'-[N'-[N-(4-phenylphenyl)-N-(2-methylpropyl)carbamoyl]]carbohydrazide To a stirring solution of phosgene (0.228 mL, 0.244 mmol, 12.5% solution in benzene) was added dropwise a solution of N-(2-methylpropyl)-N-(4-phenylphenyl)amine (0.050 g, 0.222 mmol) and triethylamine (0.025 g, 0.244 mmol) in dichloromethane (1 mL). After stirring at room temperature for 15 min this solution was added dropwise to a solution of the compound of Example 1(d) (0.083 g, 0.244 mmol) and triethylamine (0.025 g, 0.244 mmol) in dichloromethane (1 mL) at room temperature. After stirring at room temperature for 48h, N-methylmorpholine (0.022 g, 0.222 mmol) and DMF (2 mL) were added to the solution and heated at 50° C. for 16h. The solution was then diluted with ethyl acetate (5 mL) and washed successively with water, aqueous saturated NaHCO$_3$, and brine. The organic layer was dried (MgSO$_4$), filtered and concentrated. The residue was purified by column chromatography (silica gel, methanol/dichloromethane) to yield the title compound as a yellow solid (0.023 g, 18%). MS(ESI): 589.4 (M+H)$^+$.

Example 100

Preparation of 2-[N-(3-benzyloxybenzoyl)]-2'-[N'-(N-methyl-L-leucinyl)]carbohydrazide a) 2-[N-(3-benzyloxybenzoyl)]-2'-[N'-(N-tert-butoxycarbonyl-N-methyl-L-leucinyl)]carbohydrazide Following the procedure of Example 68(b), except substituting N-tert-butoxycarbonyl-N-methyl-L-leucine for N-acetyl-L-leucine and 2-[N-(3-benzyloxybenzoyl)] carbohydrazide for 2-[N-(N-benzyloxycarbonyl-L-alanyl)] carbohydrazide, the title compound was prepared as a white solid (0.183 g, 69%). MS(ESI): 550.4 (M+Na)$^+$.

b) 2-[N-(3-benzyloxybenzoyl)]-2'-[N'-(N-methyl-L-leucinyl)]carbohydrazide

To a stirring solution of the compound of Example 100(a) (0.100 g, 0.189 mmol) in dichloromethane (1 mL) was added trifluoroacetic acid (0.296 g, 2.5 mmol). After stirring at room temperature for 15 min, the solution was concentrated and the residue was purified by column chromatography (silica gel, methanol/dichloromethane) to yield the title compound as a white solid (0.055 g, 68%). MS(ESI): 428.4 (M+H)$^+$.

Example 101

Preparation of 2-[N-(N-benzyloxycarbonyl-L-leucinyl)]-2'-[N'-(N-methyl-L-leucinyl)] carbohydrazide Following the procedure of Example 100(a)–100(b), except substituting 2-[N-(N-benzyloxycarbonyl-L-leucinyl)]carbohydrazide for 2-[N-(3-benzyloxybenzoyl)] carbohydrazide in step (a), the title compound was prepared. MS(ESI): 465.5 (M+H)$^+$.

Example 102

Preparation of (1S)-N-[2-[(1-benzyloxycarbonylamino)-3-methylbutyl]thiazol-4-ylcarbonyl]-N'-(4-phenoxyphenylsulfonyl)hydrazide a) N-benzyloxycarbonyl-L-leucinamide To a stirring solution of N-benzyloxycarbonyl-L-leucine (4.6 g, 17.3 mmol) in THF, cooled to −40° C., was added N-methylmorpholine (3.68 g, 36.4 mmol; 4.0 mL) and isobutyl chloroformate (2.37 g, 17.3 mmol; 2.25 mL). After stirring for 15 min, ammonia was bubbled through the solution for 5 min. The solution was warmed to room temperature, evaporated, and the residue was dissolved in ethyl acetate, washed with 0.1 N Hcl, and saturated brine, then dried (MgSO$_4$), filtered and evaporated to dryness to give the title compound as a white solid (4.58 g, 100%).

b) N-benzyloxycarbonyl-L-leucinethioamide

A solution of the compound of Example 102(a) (4.58 g, 17.3 mmol) and Lawesson's reagent (4.21 g, 10.4 mmol) in THF was allowed to stir at room temperature for 16 h. The solution was concentrated and the residue was purified by flash chromatography on 230–400 mesh silica gel, eluting with 1:3 EtOAc/hexanes, to provide the title compound as a pale yellow solid (3.74 g, 77%).

c) (1S)-1-benzyloxycarbonylamino-1-(4-carboethoxythiazol-2-yl)-3-methylbutane

The compound of Example 102(b) (2.20 g, 7.83 mmol) was dissolved in acetone (35 mL), cooled to −10° C., and ethyl bromopyruvate (1.68 g, 8.62 mmol, 1.08 mL) was added. After stirring for 1 h, the solution was poured into methylene chloride/water, then into saturated aqueous NaHCO$_3$. The aqueous layer was extracted with methylene chloride and the combined organic layers were washed with saturated brine, dried (MgSO$_4$), filtered and concentrated. The residue was dissolved in methylene chloride, cooled to −20° C., pyridine (1.36 g, 17.2 mmol, 1.39 mL) and trifluoroacetic anhydride (1.81 g, 8.62 mmol, 122 mL) were added. After stirring for 1 h, the solution was washed with saturated squeous NaHCO$_3$ and saturated brine, then dired (MgSO$_4$), filtered, and concentrated. Tge residue was purified by flash chromatography on 90 g of 230–400 mesh silica gel, eluting with 1:3 ethyl acetate/hexanes, to provide the title compound as a pale yellow oil (2.36 g, 80%). $^1$H NMR (400 MHz, CDCl$_3$) δ8.08 (s, 1H), 7.38 (m, 5H), 5.42 (s, 3H), 5.23-5.07 (m, 3H), 4.42 (q, 2H), 2.01-1.62 (m, 3H), 1.41 (t, 3H), 0.99 (d, 6H).

d) (1S)-1-benzyloxycarbonylamino-1-(4-hydrazinocarbonylthiazol-2-yl)-3-methylbutane The compound of Example 102(c) (2.16 g, 5.73 mmol) was dissolved in ethanol (60 mL) and hydrazine hydrate (2.87 g, 57.3 mmol, 2.8 mL) was added and the solution was heated at 75° C. for 1 h. The solution was cooled and evaporated to dryness to provide the title compound as a pale yellow foam (2.01 g, 97%). $^1$H NMR (400 MHz, CDCl$_3$) δ8.35 (bs, 1H), 8.03 (s, 1H), 7.37 (m, 5H), 5.29 (d, 1H), 5.14-5.09 (m, 3H), 4.07 (bs, 2H), 1.92-1.82 (m, 1H), 1.79-1.66 (m, 2H), 1.00 (d, 6H).

e) (1S)-N-[2-[(1-benzyloxycarbonylamino)-3-methylbutyl]thiazol-4-ylcarbonyl]-N'-(4-phenoxyphenylsulfonyl)hydrazide To a stirring solution of the compound of Example 102(d) (275 mg, 0.76 mmol) in dichloromethane at room temperature is added pyridine (180 mg, 228 mmol, 0.2 mL) and 4-phenoxybenzenesulfonyl chloride (408 mg, 1.52 mmol). The reaction was stirred for 16 hours and the solvents were evaporated to a residue which was chromatographed (silica gel, 40% ethyl acetate in hexane) to give the title compound as a white solid (0.310 g). MS (ESI): 595.6 (M+H$^+$).

Example 103

Preparation of (1S)-N-[4-[1-(N-benzyloxycarbonyl-L-leucinylamino)-3-methylbutyl]thiazol-2-ylcarbonyl]-N'-(N-benzyloxycarbonyl-L-leucinyl) hydrazide a) N-benzyloxycarbonyl-L-leucinyl-L-leucinyl bromomethylketone 1-Methyl-3-nitro-1-nitrosoguanidine (5.9 g, 40.11 mmol) in ether (200 mL) is cooled to 0° C. 40% potassium hydroxide is added slowly and the diazomethane is allowed to collect in the ether solution for 30 minutes at 0° C.

N-benzyloxycarbonyl-L-Leucinyl-L-Leucine (Bachem) (4.0 g, 10.58 mmol) is stirred in tetrahydrofuran at −40° C. N-methylmorpholine (1.07 g, 10.58 mmol, 1.16 mL) and isobutyl chloroformate (1.45 g, 10.58 mmol, 1.38 mL) are added. The mixture is stirred at −40° C. for 15 minutes and then filtered into a cold flask to remove precipitated salts. To the filtered solution is added an excess of the previously prepared diazomethane solution and the mixture is allowed to stand at 0° C. for 16 h. An excess of 30% HBr in acetic acid is added at 0° C. and the solution is then washed successively with 1.0N citric acid, saturated aqueous sodium bicarbonate (carefully), and brine. The solution is dried over sodium sulfate, filtered, and evaporated to give the title compound as a white solid (4.10 g). $^1$H NMR (400 MHz, CDCl$_3$) δ7.34 (m, 5H), 6.51 (d, 1H), 5.15 (d, 1H), 5.10 (s, 2H), 4.78 (m, 1H), 4.20 (m, 1H), 4.04 (dd, 2H), 1.63 (m, 6H), 0.93 (m, 12H).

b) (2S,1'S)-2-(benzyloxycarbonyl)amino-N-[1'-(2-carboethoxythiazol-4-yl)-3'-methylbutyl]-4-methylpentanamide The compound of Example 103(a) (2.0 g, 4.4 mmol) and ethyl thiooxamate (0.59 g, 4.4 mmol) were refluxed in ethanol for 4 h. The solvent was evaporated and the residue chromatographed (silica gel, 2.5% methanol/dichloromethane) to give the title compound as a white solid (1.46 g). $^1$H NMR (400 M CDCl$_3$) δ7.32 (s, 1H), 7.21 (m, 5H), 6.40 (d, 1H), 5.13 (dd, 1H), 5.02 (s, 2H), 4.41 (q, 2H), 4.06 (m, 1H), 1.71 (m, 2H), 1.47 (m, 4H), 1.33 (t, 3H), 0.73 (m, 12H).

c) (2S,1'S)-2-(benzyloxycarbonyl)amino-N-[1'-(2-hydrazinocarbonylthiazol-4-yl)-3'-methylbutyl]-4-methylpentanamide Following the procedure of Example 102(d), except substituting (2S,1'S)-2-(benzyloxycarbonyl)amino-N-[1'-(2-carboethoxythiazol-4-yl)-3'-methylbutyl]-4-methylpentanamide for (1S)-1-benzyloxycarbonylamino-1-(4-carboethoxythiazol-2-yl)-3-methylbutane, the title compound was prepared. MS (ESI): 476.3 (M+H$^+$).

d) (1S)-N-[4-[1-(N-benzyloxycarbonyl-L-leucinylamino)-3-methylbutyl]thiazol-2-ylcarbonyl]-N'-(N-benzyloxycarbonyl-L-leucinyl)hydrazide To a stirring solution of the compound of Example 103(c) (180 mg, 0.38 mmol) in dimethylformamide is added N-benzyloxycarbonyl-L-leucine (111 mg, 0.42 mmol), 1-(3-dimethylaminopropyl-3-ethylcarbodiimide hydrochloride (80 mg, 0.42 mmol), and 1-hydroxybenzotriazole (13 mg, 0.096 mmol). The reaction mixture is stirred for 16 hours at room temperature, filtered, and washed twice with water. The solvent was evaporated to give the title compound as a white solid. (0.207 g). MS (ESI): 723.9 (M+H$^+$).

Example 104

Preparation of (1S)-N-[2-[(1-benzyloxycarbonylamino)-3-methylbutyl]thiazol-4-ylcarbonyl]-N'-(4-phenylphenylacetyl)hydrazide Following the procedure of Example 103(d), except substituting (1S)-1-benzyloxycarbonylamino-1-(4-hydrazinocarbonylthiazol-2-yl)-3-methylbutane for (2S,1'S)-2-(benzyloxycarbonyl)amino-N-[1'-(2-hydrazinocarbonylthiazol-4-yl)-3'-methylbutyl]-4-methylpentanamide, and 4-biphenylacetic acid for N-benzyloxycarbonyl-L-leucine, the title compound was prepared as a white solid. MS (ESI): 557.2 (M+H)$^+$.

Example 105

Preparation of (1S)-N-[2-[(1-benzyloxycarbonylamino)-3-methylbutyl]thiazol-4-ylcarbonyl]-N'-[3-(4-pryidinylmethoxy)benzoyl]hydrazide a) methyl 3-(4-pyridinyllmethoxy)benzoate To a stirring solution of methyl-3-hydroxybenzoate (1.0 g, 6.58 mmol), 4-pyridylcarbinol (1.1 g, 9.87 mmol), and triphenylphosphine (2.6 g, 9.87 mmol) in THF (25 mL) at 0° C. was added diisopropyl azodicarboxylate (2.0 g, 9.87 mmol) dropwise. After stirring at room temperature for 16h, the solution was concentrated and purified by column chromatography (silica gel, ethyl acetate/hexane) to yield the title compound as a white solid (0.599 g, 37%). MS(ESI): 244.1 (M+H)$^+$.

b) 3-(4-pyridinyllmethoxy)benzoic acid

To a stirring solution of the compound of Example 105(a) (0.599 g, 2.47 mmol) in THF/H$_2$O (1:1, 10 mL) was added lithium hydroxide monohydrate (0.113 g, 2.71 mmol). After stirring at reflux for 3.5h, 1.1 eq of 1N HCl was added and the mixture poured into water. The mixture was extracted with ethyl acetate (2×100 mL). The organic layers were combined, washed with brine, dried (MgSO$_4$), filtered and concentrated to yield the title compound as a yellow solid (0.386 g, 68%). $^1$H NMR (400 MHz, CD$_3$OD) δ8.54 (d, 2H), 7.64 (m, 2H), 7.57 (m, 2H), 7.40 (m, 1H), 7.26 (m, 1H), 5.24 (s, 2H).

c) (1S)-N-[2-[(1-benzyloxycarbonylamino)-3-methylbutyl]thiazol-4-ylcarbonyl]-N'-[3-(4-pryidinylmethoxy)benzoyl]hydrazide Following the procedure of Example 103(d), except substituting (1S)-1-benzyloxycarbonylamino-1-(4hydrazinocarbonylthiazol-2-yl)-3-methylbutane for (2S,1'S)-2-(benzyloxycarbonyl)amino-N-[1'-(2-hydrazinocarbonylthiazol-4yl)-3'-methylbutyl]-4-methylpentanamide, and 3-(4-pyridinylmethoxy)benzoic acid for N-benzyloxycarbonyl-L-leucine, the title compound was prepared as a white solid. MS (ESI): 574.2 (M+H)$^+$.

Example 106

Preparation of N-[2-(2-chlorophenoxymethyl)thiazol-4-ylcarbonyl]-N'-[N-(4-pyridinylmethoxycarbonyl)-L-leucinyl]hydrazide a) α-isocyanato-L-leucine methyl ester L-leucine methyl ester hydrochloride (25 g, 0.14 mol) was dissolved in methylene chloride (450 mL), cooled to 0° C., and pyridine (43.5 g, 0.55 mol, 44.5 mL) was added, then a 1.93 M solution of phosgene in toluene (0.18 mol, 92.7 mL) was added slowly. After stirring at 0° C. for 2 h, the mixture was poured into 0.5 N HCl (1400 mL) and ice (900 mL). The organic layer was washed with 0.5 N HCl (1400 mL) and ice (900 mL). The aqueous layers were extracted with methylene chloride (450 mL) and the combined organic layers were washed with saturated brine (1400 mL) and ice (900 mL), then dried (MgSO$_4$), filtered and concentrated. The residue was distilled (56–58° C.; 0.78 mmHg) to provide the title compound as a colorless liquid (20.4 g, 86%). $^1$H NMR (250 MHz, CDCl$_3$) δ4.04 (dd, 1H), 3.82 (s, 3H), 1.92-1.72 (m, 1H), 1.69-1.62 (m, 2H), 0.96 (d, 3H), 0.94 (d, 3H).

b) N-(4-pyridinylmethoxycarbonyl)-L-leucine methyl ester

A solution of the compound of Example 106(a) (5.10 g, 29.8 mmol) and 4-pyridylcarbinol (3.25 g, 29.8 mmol) in toluene (30 mL) was heated at reflux for 24 h. The solution was concentrated and the residue was purified by flash chromatography on 250 g of 230–400 mesh silica gel, eluting with 3:1 ethyl acetate/hexanes, to give the title compound (7.86 g, 94%). $^1$H NMR (250 MHz, CDCl$_3$) δ8.59 (d, 2H), 7.24 (d, 2H), 5.33 (d, 1H), 5.13 (s, 3H), 4.40 (dt, 1H), 3.75 (s, 3H), 1.81-1.51 (m, 3H), 0.96 (d, 3H), 0.95 (d, 3H).

c) N-(4-pyridinylmethoxycarbonyl)-L-leucine

To a stirring solution the compound of Example 106(b) (1.98 g, 7.06 mmol) in THF (7 mL) was added 7 mL of water followed by LiOH•H$_2$O (325 mg, 7.76 mmol). The mixture was stirred for 30 minutes and then concentrated. The residue was redissolved in water (10 mL) and 3 N HCl was added (2.6 mL). The solution was lyophilized to yield a white solid (2.015 g, 6.44 mmol). MS (ESI): 267.2 (M+H)$^+$.

d) N-[2-(2chlorophenoxymethyl)thiazol-4-ylcarbonyl] hydrazide

Following the procedure of Example 102(d), except substituting ethyl 2-(2-chlorophenoxymethyl)thiazole-4-carboxylate for (1S)-1-benzyloxycarbonylamino-1-(4-carboethoxythiazol-2-yl)-3-methylbutane, the title compound was prepared. MS (ESI): 284.1 (M+H)$^+$.

e) N-[2-(2-chlorophenoxymethyl)thiazol-4-ylcarbonyl]-N'-[N-(4-pyridinylmethoxycarbonyl)-L-leucinyl]hydrazide Following the procedure of Example 103(d), except substituting N-[2-(2-chlorophenoxymethyl)thiazol-4-ylcarbonyl]hydrazide for (2S,1'S)-2-(benzyloxycarbonyl)amino-N-[1'-(2-hydrazinocarbonylthiazol-4-yl)-3'-methylbutyl]-4-methylpentanamide, and N-(4-pyridinylmethoxycarbonyl)-L-leucine for N-benzyloxycarbonyl-L-leucine, the title compound was prepared as a white solid. MS (ESI): 532.1 (M+H)$^+$.

Example 107

Preparation of N-[N-(4-pyridinylmethoxycarbonyl)-L-leucinyl]-N'-[2-[4-(1.2.3-thiadiazol-4-yl)phenyl]thiazol-4-ylcarbonyl]hydrazide a) N-[2-[4-(1,2,3-thiadiazol-4-yl)]thiazol-4-ylcarbonyl]hydrazide Following the procedure of Example 102(d), except substituting ethyl 2-[4-(1,2,3-thiadiazol-4-yl)]thiazole-4-carboxylate for (1S)-1-benzyloxycarbonylamino-1-(4-carboethoxythiazol-2-yl)-3-methylbutane, the title compound was prepared as a white solid. MS (ESI): 304.1 (M+H)$^+$.

b) N-[N -(4-pyridinylmethoxycarbonyl)-L-leucinyl]-N'-[2-[4-(1,2,3-thiadiazol-4-yl)phenyl]thiazol-4-ylcarbonyl]hydrazide Following the procedure of Example 103(d), except substituting N-[2-[4-(1,2,3-thiadiazol-4-yl)]thiazol-4-ylcarbonyl]hydrazide for (2S,1'S)-2-(benzyloxycarbonyl)amino-N-[1'-(2-hydrazinocarbonylthiazol-4-yl)-3'-methylbutyl]-4-methylpentanamide, and N-(4-pyridinylmethoxycarbonyl)-L-leucine for N-benzyloxycarbonyl-L-leucine, the title compound was prepared as a white solid. MS (ESI): 552.1 (M+H)$^+$.

Example 108

Preparation of N-[2-[3-(4-chlorophenylsulfonylmethyl)thien-2-yl]thiazol-4-ylcarbonyl]-N'-[N-(4-pyridinylmethoxycarbonyl)-L-leucinyl]hydrazide a) N-[2-[3-(4-chlorophenylsulfonylmethyl)thien-2-yl]thiazol-4-carbonyl]hydrazide Following the procedure of Example 102(d), except substituting 2-[3-(4-chlorophenylsulfonylmethyl)thien-2-yl]thiazole-4-carboxylate for (1S)-1-benzyloxycarbonylamino-1-(4-carboethoxythiazol-2-yl)-3-methylbutane, the title compound was prepared as a white solid. MS (ESI): 414.1 (M+H)$^+$.

b) N-[2-[3-(4-chlorophenylsulfonylmethyl)thien-2-yl]thiazol-4-ylcarbonyl]-N'-[N-(4-pyridinylmethoxycarbonyl)-L-leucinyl]hydrazide Following the procedure of Example 103(d), except substituting N-[2-[3-(4-chlorophenylsulfonylmethyl)thien-2-yl]thiazol-4-carbonyl]hydrazide for (2S,1'S)-2-(benzyloxycarbonyl)amino-N-[1'-(2-hydrazinocarbonylthiazol-4-yl)-3'-methylbutyl]-4-methylpentanamide, and N-(4-pyridinylmethoxycarbonyl)-L-leucine for N-benzyloxycarbonyl-L-leucine, the title compound was prepared as a white. MS (ESI): 664.0 (M+H)$^+$.

Example 109

Preparation of (1S,2'RS)-N-[2-[(1-benzyloxycarbonylamino)-3-methylbutyl]thiazol-4-ylcarbonyl]-N'-[2'-(4-phenylphenylacetyl)-4-methylpentanoyl]hydrazide a) 4-methyl-2-(4-phenylphenyl)pent-4-enoic acid To a stirring solution of diisopropylamine (0.537 g, 5.31 mmol) in THF (5.2 mL) at 0° C. was added n-butyllithium (2.1 mL, 5.22 mmol, 2.5M in hexane) dropwise. After stirring for 15 min at 0° C., the mixture was cooled to −78° C. and a solution of 4-biphenylacetic acid (0.500 g, 2.36 mmol) in THF (2 mL) was added dropwise. After again warming to 0° C. and cooling to −78° C., 3-bromo-2-methylpropene (0.485 g, 3.54 mmol) was added to the mixture in one portion. After stirring at −78° C. for 1h, the reaction was quenched with 2 mL of water then concentrated. The residue was redissolved in water and extracted with ether (100 mL). The aqueous layer was acidified (3N HCl) and extracted with ether (3×100 mL). The organic layers were combined, dried (MgSO$_4$), filtered and concentrated to yield a white solid (0.449 g, 72%). MS(ESI): 265.3 (M+H)$^-$.

b) 4-methyl-2-(4-phenylphenyl)pentanoic acid

To a stirring solution of the compound of Example 109(a) (0.449 g, 1.69 mmol) in ethyl acetate (25 mL) was added palladium on carbon (0.225 g). After stirring under a balloon of hydrogen for 16h, the mixture was filtered through Celite. The filtrate was concentrated to yield an off white solid (0.430 g, 95%). MS(ESI): 267.4 (M+H)$^-$.

c) (1S,2'RS)-N-[2-[(1-benzyloxycarbonylamino)-3-methylbutyl]thiazol-4-ylcarbonyl]-N'-[2'-(4-phenylphenylacetyl)-4-methylpentanoyl]hydrazide Following the procedure of Example 101(d), except substituting (1S)-1-benzyloxycarbonylamino-1-(4-hydrazinocarbonylthiazol-2-yl)-3-methylbutane for (2S, 1'S)-2-(benzyloxycarbonyl)amino-N-[1'-(2-hydrazinocarbonylthiazol-4-yl)-3'-methylbutyl]-4- methylpentanamide, and 4-methyl-2-(4-phenylphenyl) pentanoic acid for N-benzyloxycarbonyl-L-leucine, the title compound was prepared as a white solid. MS (ESI): 613.2 (M+H)$^+$.

Example 110

Preparation of N-[2-(3-benzyloxyphenyl)thiazol-4-ylcarbonyl]-N'-[N-(2-pyridinylmethoxycarbonyl)-L-leucinyl]hydrazide a) methyl 3-benzyloxybenzoate To a suspension of NaH (0.395 g, 9.87 mmol 60% in mineral oil) in DMF (20 mL) was added methyl 3-hydroxybenzoate (1.0 g, 6.58 mmol). After stirring for 15 min at room temperature, benzyl bromide (1.1 g, 6.58 mmol) was added. After stirring at room temperature for 3h, the solution was partitioned between ethyl acetate and water. The organic layer was washed with water (2×75 mL), saturated aqueous sodium bicarbonate, and brine, then dried (MgSO$_4$), filtered and concentrated to yield an off-white solid (1.013 g, 4.2 mmol). $^1$H NMR (400 MHz, CDCl$_3$) δ7.67 (m, 2H), 7.48-7.34 (m, 6H), 7.19 (m, 1H), 5.12 (s, 2H), 3.95 (s, 3H).

b) 3-benzyloxybenzamide

To a suspension of ammonium hydrochloride (1.070 g, 0.02 mmol) in 20 mL of toluene at 5° C., was slowly added a 2M solution (10 mL) of trimethylaluminium in toluene. After the addition was complete, the reaction mixture was allowed to warm at room temperature and was stirred for 2 hours until gas evolution has ceased.

To a stirring solution of the compound of Example 110(a) (605 mg, 2.49 mmol) in toluene was added a 0.67 M solution of MeAlClNH$_2$ (11 mL, 7.49 mmol) in toluene. The reaction mixture was allowed to stir overnight at reflux. The reaction was quenched with 5% HCl, the organic layer was separated and the aqueous layer extracted three times with ethyl acetate. The organic extracts were combined, dried over MgSO$_4$, filtered and concentrated to afford the title compound as a white solid (409 mg, 72%). MS (ESI): 228.1 (M+H)$^+$.

c) N-[2-(3-benzyloxyphenyl)thiazol-4-ylcarbonyl] hydrazide

Following the procedure of Example 102(b)–102(d), except substituting 3-benzyloxybenzamide for N-benzyloxycarbonyl-L-leucinamide in step (b), the title compound was prepared as a white solid. MS (ESI): 326.2 (M+H)$^+$.

d) N-(2-pyridinylmethoxycarbonyl)-L-leucine

Following the procedure of Example 106(a)–106(c), except substituting 2-pyridylcarbinol for 4-pyridylcarbinol in step (b), the title compound was prepared. $^1$H NMR (400 MHz, CD$_3$OD) δ8.50 (d, 1H), 7.86 (dt, 1H), 7.51 (d, 1H), 7.36 (dd, 1H), 5.20 (d, 1H), 5.16 (d, 1H), 4.19 (t, 1H), 1.78-1.72 (m, 1H), 1.62 (t, 2H), 0.97 (d, 3H), 0.94 (d, 3H).

e) N-[2-(3-benzyloxyphenyl)thiazol-4-ylcarbonyl]-N'-[N-(2-pyridinylmethoxycarbonyl)-L-leucinyl]hydrazide Following the procedure of Example 103(d), except substituting N-[2-(3-benzyloxyphenyl)thiazol-4-ylcarbonyl]hydrazide for (2S,1'S)-2-(benzyloxycarbonyl)amino-N-[1'-(2-hydrazinocarbonylthiazol-4-yl)-3'-methylbutyl]-4-methylpentanamide, and N-(2-pyridinylmethoxycarbonyl)-L-leucine for N-benzyloxycarbonyl-L-leucine, the title compound was prepared as a white solid (106 mg, 0.184 mmol). MS (ESI): 574.2 (M+H)$^+$.

Example 111

Preparation of (1RS)-N-[2-[1-(4-phenylphenyl)-3-methylbutyl]thiazol-4-ylcarbonyl]-N'-[N-(4-pyridinylmethoxycarbonyl)-L-leucinyl]hydrazide a) N-[2-[1-(4-phenylphenyl)-3-methylbutyl]thiazol-4-ylcarbonyl]hydrazide Following the procedure of Example 102(a)–102(d), except substituting 4-methyl-2-(4-phenylphenyl)pentanoic acid for N-benzyloxycarbonyl-L-leucine in step (a), the title compound was prepared as a white solid. MS (ESI): 366.3 (M+H)$^+$.

b) (1RS)-N-[2-[1-(4-phenylphenyl)-3-methylbutyl] thiazol-4-ylcarbonyl]-N'-[N-(4-pyridinylmethoxycarbonyl)-L-leucinyl]hydrazide Following the procedure of Example 103(d), except substituting N-[2-[1-(4-phenylphenyl)-3-methylbutyl]thiazol-4-ylcarbonyl]hydrazide for (2S,1'S)-2-(benzyloxycarbonyl) amino-N-[1'-(2-hydrazinocarbonylthiazol-4-yl)-3'-methylbutyl]-4-methylpentanamide, and N-(4-pyridinylmethoxycarbonyl)-L-leucine for N-benzyloxycarbonyl-L-leucine, the title compound was prepared as a white solid. MS (ESI): 614.3 (M+H)$^+$.

Example 112

Preparation of N-[2-(2-benzyloxyphenyl)thiazol-4-ylcarbonyl]-N'-[N-(4-pyridinylmetboxycarbonyl)-L-leucinyl]hydrazide a) ethyl 2-aminothiazole-4-carboxylate hydrobromide To a stirring suspension of thiourea (6.0 g, 78.8 mmol) in ethanol (80 mL) was added ethyl bromopyruvate (15.4 g, 78.8 mmol). The resulting solution was heated at 45° C. for 23 h. The solution was cooled at 0° C. for 24 h, and the crystals were collected by filtration and washed with cold ethanol to provide the title compound (15.8 g, 79%). $^1$H NMR (400 MHz, CD$_3$OD) δ7.70 (s, 1H), 4.41 (q, 2H), 1.38 (t, 3H).

b) ethyl 2-bromothiazole-4-carboxylate

To a stirring suspension of the compound of Example 112(a) (12.15 g, 48 mmol) in 16% aqueous HBr (150 mL), cooled to 0° C., was added dropwis a solution of sodium nitrite (3.44 g, 49.8 mmol) in water (6 mL). After stirring for 35 min, copper (I) bromide (7.83 g, 54.6 mmol) and 16% aqueous HBr (60 mL) were added and the mixture was heated at 70° C. for 1 h. The mixture was filtered and the filtrate was saturated with NaCl then extracted with ethyl acetate (2×170 mL). The combined extracts were dried (MgSO$_4$), filtered and evaporated to dryness. The residue was combined with combined with the solid collected in the first filtration, heated at reflux in ethanol (500 mL) for 5 min, then filtered. To the filtrate was added 1.5 mL of 48% aqueous HBr and the solution was heated at reflux for 16 h, then concentrated. The residue was partitioned between saturated aqueous NaHCO$_3$ and ethyl acetate. The organic layer was washed with saturated brine, dried (MgSO$_4$), decolorized with charcoal, filtered and concentrated to provide the title compound as a pale yellow solid (7.46 g, 75%). MS (ESI): 236.0 (M+H)$^+$.

c) 2-benzyloxybromobenzene

To a stirring solution of 2-bromophenol (10.0 g, 57.8 mmol), and benzyl bromide (9.9 g, 57.8 mmol) in acetone (150 mL) was added K$_2$CO$_3$ (12.0 g, 86.7 mmol). After stirring at reflux for 4h, the mixture was partitioned between ethyl acetate and water. The organic layer was washed with brine, dried (MgSO$_4$), filtered and concentrated. The residue was purified by column chromatography (silica gel, ethyl acetate/hexane) to yield the title compound as a colorless oil (15.2 g, 57.8 mmol). $^1$HNMR (400 MHz, CDCl$_3$) δ7.62 (m, 1H), 7.54 (m, 2H), 7.45 (m, 2H), 7.37 (m, 1H), 7.28 (m, 1H), 6.98 (m, 1H), 6.91 (m, 1H), 5.17 (s, 2H).

d) 2-benzyloxyphenylboronic acid

To a stirring solution of the compound of Example 112(c) (15.2 g, 57.8 mmol) in THF (100 mL) at −78° C. was added dropwise n-BuLi (23.1 mL, 2.5M in hexane, 57.8 mmol). The mixture stirred at −78° C. for 25 min when added via cannulation to a stirring solution of triisopropylborate (54.4 g, 289 mmol) in THF (100 mL) at −78° C. After warming to room temperature and stirring for 3h, the mixture was poured into 3N HCl (100 mL) and extracted with ethyl acetate (3×200 mL). The organic layers were combined, washed successively with water and brine, dried (MgSO$_4$), filtered and concentrated. The residue was purified by column chromatography (silica gel, ethyl acetate/hexane) to yield the title compound as a pale yellow solid (6.9 g, 30.3 mmol). $^1$HNMR (400 MHz, CDCl$_3$) δ7.90 (d, 1H), 7.42 (m, 6H), 7.07 (t, 1H), 7.02 (d, 1H), 6.05 (s, 2H), 5.16 (s, 2H).

e) ethyl 2-(2-benzyloxyphenyl)thiazole-4-carboxylate

To a stirring solution of the compound of Example 112(b) (4.0 g, 16.9 mmol), the compound of Example 72(d) (4.29 g, 18.8 mmol), tetrakis(triphenylphosphinepalladium(0) (0.65 g, 0.57 mmol) in dimethoxyethane (60 mL) was added cesium fluoride (8.58 g, 56.5 mmol) and the mixture was heated at 85° C. for 16 h. Tetrakis(triphenylphosphine) palladium(0) (0.65 g, 057 mmol) was added and heating at 85° C. was continued for 5 h. The mixture was diluted with water (60 mL) and extracted with ethyl acetate (2×120 mL). The combined extracts were washed with saturated aqueous NaHCO$_3$ and saturated brine, dried (MgSO$_4$), filtered and concentrated. The residue was purified by flash chromatography on 180 g of 230–400 mesh silica gel, eluting with 15% ethyl acetate in hexanes, to provide the title compound as a white solid (3.22 g, 56%). MS (ESI): 340.3 (M+H)$^+$.

f) 2-(2-benzyloxyphenyl)thiazol-4-ylcarbonylhydrazide

Following the procedure of Example 102(d), except substituting ethyl 2-(2-benzyloxyphenyl)thiazole-4-carboxylate for (1S)-1-benzyloxycarbonylamino-1-(4-carboethoxythiazol-2-yl)-3-methylbutane, the title compound was prepared as a white solid. MS (ESI): 326.2 (M+H)$^+$.

g) N-[2-(2-benzyloxyphenyl)thiazol-4-ylcarbonyl]-N'-[N-(4-pyridinylmethoxycarbonyl)-L-leucinyl]hydrazide Following the procedure of Example 103(d), except substituting 2-(2-benzyloxyphenyl)thiazole-4-ylcarbonylhydrazide for (2S, 1'S)-2-(benzyloxycarbonyl)amino-N-[1'-(2-hydrazinocarbonylthiazol-4-yl)-3'-methylbutyl]-4-methylpentanamide, and N-(4-pyridinylmethoxycarbonyl)-L-leucine for N-benzyloxycarbonyl-L-leucine, the title compound was prepared as a white solid. MS (ESI): 574.3 (M+H)$^+$.

Example 113

Preparation of N-[2-[N-methyl-N-(4-phenylphenyl) amino]thiazol-4-ylcarbonyl]-N'-[N-(4-pyridinylmethoxycarbonyl)-L-leucinyl]hydrazide a) N-(4-phenylphenyl)-2-methylpropionamide To a stirring solution of 4-aminobiphenyl (9.53 g, 56.3 mmol) and triethylamine (5.70 g, 56.3 mmol, 7.85 mL) in methylene chloride (60 mL), cooled to 0° C., was added slowly isobutyryl chloride (6.0 g, 56.3 mmol, 5.90 mL). After stirring at 0° C. for 1 h, the mixture was diluted with methylene chloride (120 mL) and washed with 1N NaOH and saturated brine, then dreid (MgSO$_4$), filtered and concentrated. The residue was washed with ether and dried to provide the title compound as a pale yellow crystalline solid (9.83 g, 73%). $^1$HNMR (400 MHz, CDCl$_3$/CD$_3$OD) δ7.58 (d, 2H), 7.50 (m, 4H), 7.40-7.25 (m, 3H), 2.55-2.49 (m, 1H), 1.18 (d, 6H).

b) N-(4-phenylphenyl)-N-(2-methyl-1-propyl)amine

To a stirring solution of lithium aluminum hydride (58.6 mmol) in THF (58.6 mmol), cooled to 0° C., was added slowly over 10 min a solution of the compound of Example 73(a) (9.35 g, 39.0 mmol) in THF (170 mL). After the addition was complete, the ice bath was removed and the solution was heated at 55° C. for 30 min. The mixture was cooled to 0° C. and water (2.22 mL) was slowly added, followed by 15% aqueous NaOH (2.22 mL) and water (6.67 mL). The precipitate was removed by filtration and washed with ether 4 times. The filtrate was evaporated to dryness to proveide the title compound as a pale yellow solid (8.34 g, 97%). MS (ESI): 226.2 (M+H)$^+$.

c) N-(4-phenylphenyl)-N-(2-methyl-1-propyl)thiourea

To a stirring solution of thiophosgene (98.9 mg, 2.6 mmol, 198 uL) in methylene chloride (6.5 mL), cooled to 0° C., was added dropwise a solution of the compound of Example 73(b) (540.7 mg, 2.0 mmol) in methylene chloride (1 mL). After stirring for 2 h. ammonia-satruated methanol (20 mL) was added and the solution was stirred at room temperatur for 2 h. The solution was concentrated and the residue was partitioned between ethyl acetate and 1N HCl. The organic layer was washed with 1N HCl twice, then with saturated brine, then dried (MgSO$_4$), filtered and concentrated. The residue was purified by flash chromatography on 10 g of 230–400 mesh silica gel, eluting with 1:3 ethyl acetate/hexanes, to provide the title compound as a pale yellow solid (470 mg, 83%). MS (ESI): 285.3 (M+H)$^+$.

d) ethyl 2-[N-4-phenylphenyl)-N-2-methyl-1-propyl) amino]thiazole-4-carboxylate

A solution of the compound of Example 113(c) (184.6 mg, 0.65 mmol) and ethyl bromopyruvate (126.6 mg, 0.65 mmol, 81.5 uL) in ethanol (2.5 mL) was heated at reflux of 5 mm, then concentrated. The residue was partitioned between ethyl acetate and saturated aqueous NaHCO$_3$. The aqueous layer was extracted with ethyl acetate and the combined organic layers were washed with saturated brine, dried (MgSO$_4$), filtered and concentrated. The residue was passed through a plug of 230–400 mesh silica gel, eluting with 12% ethyl acetate in hexanes, to provide the title compound as a pale yellow oil (230 mg, 93%). MS (ESI): 381.4 (M+H)$^+$.

e) N-[2-[N-(4-phenylphenyl)-N-(2-methyl-1-propyl) amino]thiazol-4-ylcarbonyl]hydrazide Following the procedure of Example 102(d), except substituting ethyl 2-[N-(4-phenylphenyl)-N-(2-methyl-1-propyl)amino]thiazole-4-carboxylate for (1S)-1-benzyloxycarbonylamino-1-(4-carboethoxythiazol-2-yl)-3-methylbutane, the title compound was prepared as a white solid. MS (ESI): 367.3 (M+H)$^+$.

f) N-[2-[N-methyl-N-(4-phenylphenyl)amino]thiazol-4-ylcarbonyl]-N'-[N-(4-pyridinylmethoxycarbonyl)-L-leucinyl]hydrazide Following the procedure of Example 103(d), except substituting N-[2-[N-(4-phenylphenyl)-N-(2-methyl-1-propyl) amino]thiazol-4-ylcarbonyl]hydrazide for (2S, 1'S)-2-

(benzyloxycarbonyl)amino-N-[1'-(2-hydrazinocarbonylthiazol-4-yl)-3'-methylbutyl]-4-methylpentanamide, and N-(4-pyridinylmethoxycarbonyl)-L-leucine for N-benzyloxycarbonyl-L-leucine, the title compound was prepared as a white solid. MS (ESI): 615.3 (M+H)$^+$.

Example 114

Preparation of N-(N-benzyloxycarbonyl-L-leucinyl)-N'-[2-(4-pbenylbenzyl)thiazol-4-ylcarbonyl]hydrazide a) N-[2-(4-phenylbenzyl)thiazol-4-ylcarbonyl]hydrazide Following the procedure of Example 102(a)–102(d), except substituting 4-biphenylacetic acid for N-benzyloxycarbonyl-L-leucine in step (a), the title compound was prepared as a white solid. MS (ESI): 310.3 (M+H)$^+$.

b) N-(N-benzyloxycarbonyl-L-leucinyl)-N'-[2-(4-phenylbenzyl)thiazol-4-ylcarbonyl]hydrazide Following the procedure of Example 103(d), except substituting N-[2-(4-phenylbenzyl)thiazol-4-ylcarbonyl]hydrazide for (2S,1'S)-2-(benzyloxycarbonyl)amino-N-[1'-(2-hydrazinocarbonylthiazol-4-yl)-3'-methylbutyl]-4-methylpentanamide, the title compound was prepared as a white solid (20 mg, 0.035 mmol). MS (ESI): 557.4 (M+H)$^+$.

Example 115

Preparation of N-[2-(4-phenylphenylbenzyl)thiazol-4-ylcarbonyl]-N'-[N-(4-pyridinylmethoxycarbonyl)-L-leucinyl]hydrazide Following the procedure of Example 103(d), except substituting N-[2-(4-phenylbenzyl)thiazol-4-ylcarbonyl]hydrazide for (2S,1'S)-2-(benzyloxycarbonyl)amino-N-[1'-(2-hydrazinocarbonylthiazol-4-yl)-3'-methylbutyl]-4-methylpentanamide, and N-(4-pyridinylmethoxycarbonyl)-L-leucine for N-benzyloxycarbonyl-L-leucine, the title compound was prepared as a yellow solid (30 mg, 0.053 mmol). MS (ESI): 558.2 (M+H)$^+$.

Example 116

Preparation of N-(N-benzyloxycarbonyl-L-leucinyl)-N'-[2-[N-(2-methylpropyl)-N-phenylamino]thiazol-4-ylcarbonyl]hydrazide a) N-[2-[N-phenyl-N-(2-methyl-1-propyl)amino]thiazol-4-ylcarbonyl]hydrazide Following the procedure of Example 113(a)–113(e), except substituting aniline for 4-aminobiphenyl in step (a), the title compound was prepared as an orang-pink solid (276 mg, 0.950 mmol). MS (ESI): 291.3 (M+H)$^+$.

b) N-(N-benzyloxycarbonyl-L-leucinyl)-N'-[2-[N-(2-methylpropyl)-N-phenylamino]thiazol-4-ylcarbonyl]hydrazide Following the procedure of Example 103(d), except substituting) N-[2-[N-phenyl-N-(2-methyl-1-propyl)amino]thiazol-4-ylcarbonyl]hydrazide for (2S,1'S)-2-(benzyloxycarbonyl)amino-N-[1'-(2-hydrazinocarbonylthiazol-4-yl)-3'-methylbutyl]-4-methylpentanamide, the title compound was prepared as a white solid (92 mg, 0.171 mmol). MS (ESI): 560.3 (M+Na)$^+$.

Example 117

Preparation of N-[2-[N-(2-methylpropyl)-N-phenylamino]thiazol-4-ylcarbonyl]-N'-[N-(4-pyridinylmethoxycarbonyl)-L-leucinyl]hydrazide Following the procedure of Example 113(a)–113(f), except substituting aniline for 4-aminobiphenyl in step (a), the title compound was prepared as a yellow solid (50 mg, 0.092 mmol). MS (ESI): 539.4 (M+H)$^+$.

Example 118

Preparation of N-[2-(2-benzyloxyphenyl)thiazol-4-ylcarbonyl]-N'-[N-(3-pydridinylmethoxycarbonyl)-L-leucinyl]hydrazide Following the procedure of Example 112(a)–112(g), except substituting N-(3-pyridinylmethoxycarbonyl)-L-leucine for N-(4-pyridinylmethoxycarbonyl)-L-leucine in step (g), the title compound was prepared as a white solid (93.8 mg, 53%). MS (ESI): 574.3 (M+H)$^+$.

Example 119

Preparation of N-[2-(2-benzyloxyphenyl)thiazol-4-ylcarbonyl]-N'-[N-(2-pyridinylmethoxycarbonyl)-L-leucinyl]hydrazide Following the procedure of Example 112(a)–112(g), except substituting N-(2-pyridinylmethoxycarbonyl)-L-leucine for N-(4-pyridinylmethoxycarbonyl)-L-leucine in step (g), the title compound was prepared as a white solid (149.7 mg, 85%). MS (ESI): 574.4 (M+H)$^+$.

Example 120

Preparation of N-(N-benzyloxycarbonyl-N-methyl-L-leucinyl)-N'-[2-(2-benzyloxyphenyl)thiazol-4-ylcarbonyl]hydrazide Following the procedure of Example 112(a)–112(g), except substituting N-benzyloxycarbonyl-N-methyl-L-leucine for N-(4-pyridinylmethoxycarbonyl)-L-leucine in step (g), the title compound was prepared as a white solid (153.5 mg, 85%). MS (ESI): 609.3 (M+H)$^+$.

Example 121

Preparation of N-[2-[N-(2-methylpropyl)-N-phenylamino]thiazol-4-ylcarbonyl]-N'-[N-(2-pyridinylmethoxycarbonyl)-L-leucinyl]hydrazide Following the procedure of Example 113(a)–113(f), except substituting aniline for 4-aminobiphenyl in step (a) and N-(2-pyridinylmethoxycarbonyl)-L-leucine for N-(4-pyridinylmethoxycarbonyl)-L-leucine in step (f), the title compound was prepared as a white solid (40 mg). MS (ESI): 539.4 (M+H)$^+$.

Example 122

Preparation of N-[2-[N-(2-methylpropyl)-N-phenylamino]thiazol-4-ylcarbonyl]-N'-[N-(3-pyridinylmethoxycarbonyl)-L-leucinyl]hydrazide Following the procedure of Example 113(a)–113(f), except substituting aniline for 4-aminobiphenyl in step (a) and N-(3-pyridinylmethoxycarbonyl)-L-leucine for N-(4-pyridinylmethoxycarbonyl)-L-leucine in step (f), the title compound was prepared as a white solid (42 mg). MS (ESI): 539.4 (M+H)$^+$.

Example 123

Preparation of N-[2-(2-methoxphenyl)thiazol-4-ylcarbonyl]-N'-[N-(4-pyridinylmethoxycarbonyl)-L-leucinyl]hydrazide a) 2-trimethylstannylanisole To a stirring solution of n-BuLi (2.6 mL, 2.5M in hexane, 6.42 mmol) in diethyl ether (2.5 mL) at −78° C. was added 2-bromoanisole (1.0 g, 5.35 mmol) in diethyl ether (2 mL) dropwise. After stirring for 1h at −78° C., trimethyltin chloride (6.4 mL, 1.0M in THF, 6.42 mmol) was added dropwise. The mixture was allowed to stir an additional 2h while slowly warming to room temperature. The mixture was then washed with saturated aqueous $NaHCO_3$. The aqueous layer was extracted with diethyl ether (1×50 mL) and the organic layers were combined, dried ($MgSO_4$), filtered and concentrated. The residue was purified by column chromatography (silica gel, hexane) to yield the title compound as a colorless oil (1.11 g, 76%). $^1HNMR$ (400 MHz, $CDCl_3$) δ7.47 (d, 1H), 7.40 (t, 1H), 7.05 (t, 1H), 6.90 (d, 1H), 3.36 (s, 3H), 0.34 (s, 9H).

b) ethyl 2-(2-methoxyphenyl)thiazole-4-carboxylate

A mixture of the compound of Example 112(b) (0.250 g, 1.06 mmol), the compound of Example 83(a) (0.287 g, 1.06 mmol), and tetrakis(triphenylphosphine)palladium(0) (0.037 g, 0.0318 mmol) in toluene (2 mL) was stirred at reflux for 16h. The mixture was diluted with ethyl acetate and washed with water and brine. The organic layer was dried ($MgSO_4$), filtered and concentrated. The residue was purified by column chromatography (silica gel, ethyl acetate/hexane) to yield the title compound as a white solid (0.081 g, 29%). $^1HNMR$ (400 MHz, $CDCl_3$) δ8.54 (d, 1H), 8.22 (s, 1H), 7.45 (t, 1H), 7.11 (t, 1H), 7.05 (d, 1H), 4.48 (q, 2H), 4.04 (s, 3H), 1.46 (t, 3H).

c) N-[2-(2-methoxyphenyl)thiazol-4-ylcarbonyl]-N'-[N-(4-pyridinylmethoxycarbonyl)-L-leucinyl]hydrazide Following the procedure of Example 112(f)–112(g), except substituting ethyl 2-(2-methoxyphenyl)thiazole-4-carboxylate for ethyl 2-2--benzyloxyphenyl)thiazole-4-carboxylate in step (f), the title compound was prepared as a white solid. MS (ESI): 498.3 $(M+H)^+$.

The above description fully discloses how to make and use the compounds of the present invention. However, the present invention is not limited to the particular embodiments described hereinabove, but includes all modifications thereof within the scope of the following claims. The various references to journals, patents and other publications which are cited herein comprise the state of the art and are incorporated herein by reference as though fully set forth.

Example 124

Preparation of (2S,1'S)-N-[1'-(4-carboethoxythiazol-2-yl)-3'-methylbutyl]-4-methyl-2-(2-phenylbenzyloxycarbonyl)aminopentanamide a) (2S, 1'S)-2tert-butoxycarbonyl)amino-N-[1'-(4-carboethoxythiazol-2-yl)-3'-methylbutyl]-4-methylpentanamide The compound of Example 8(c)(1.2 g, 3.5 mmol) was stirred at room temperature in neat TFA (2.96 g, 26.0 mmol) for 15 min. The solution was the concentrated in vacuo and redissolved in DMF (25 mL). To the stirring solution was added triethylamine (0.779 g, 7.7 mmol), BOC-Leu-OH (0.972 g, 3.9 mmol), 1-hydroxybenzotriazole (0.095 g, 0.7 mmol), and 1-(3-dimethylaminopropyl)-3-ethylcarbodiimide hydrochloride (0.750 g, 3.9 mmol). After stirring at room temperature for 16 hours, the solution was diluted with ethyl actate and washed successively with water (2×100 mL), $NaHCO_3$, and brine. The organic layer was dried ($MgSO_4$), filtered and concentrated. The residue was purified by column chromatography (silica gel, ethyl acetate/hexane) to yield the title compound as a white solid (1.15 g, 72%). MS(ESI): 456.2 $(M+H)^+$.

b) (2S,1'S)-N-[1'-(4-carboethoxythiazol-2-yl)-3'-methylbutyl]-4-methyl-2-(2-phenylbenzyloxycarbonyl)aminopentanamide To a stirring solution of phosgene (1.5 mL, 2.9 mmol, 1.93M in toluene) at 0° C. was added 2-biphenylmethanol (0.486 g, 2.64 mmol) and diisopropylethylamine (0.375 g, 2.9 mmol). The solution was allowed to stir at 0° C. for 30 min. In a separate reaction vessel, after stirring at room temperature for 10 min, the compound of Example 124(a) (0.150 g, 0.330 mmol) dissolved in TFA (2.0 mL) was concentrated and dissolved in DMF (3 mL). This solution was added to the 2-biphenylmethanol solution followed by diisopropylethylamine (0.213 g, 1.65 mmol). After stirring at room temperature for 1h, the solution was diluted with ethyl acetate and washed successively with water and brine. The organic layer was dried ($MgSO_4$), filtered and concentrated. The residue was purified by column chromatography (silica gel, ethyl acetate/hexane) to yield the title compound as a white solid (0.138 g, 74%). MS(ESI): 566.3 $(M+H)^+$.

Example 125

Preparation of (2S, 1'S)-2-[(2-benzyl)benzyloxycarbonyl)]amino-N-[1'-(4-carboethoxythiazol-2-yl)-3'-methylbutyl]-4-methylpentanamide Following the procedure of Example 124(b), except substituting 2-benzylbenzyl alcohol for 2-biphenylmethanol, the title compound was prepared as a white solid (0.123 g, 64%). MS(ESI): 580.0 $(M+H)^+$.

Example 126

Preparation of (2S, 1'S)-N-[1'-(4-carboethoxythiazol-2-yl)-3'-methylbutyl]-4-methyl-2-[(2-naphthylmethoxycarbonyl)]aminopentanamide Following the procedure of Example 124(b), except substituting 2-naphthalenemethanol for 2-biphenylmethanol, the title compound was prepared as a white solid (0.132 g, 74%). MS(ESI): 540.1 $(M+H)^+$.

Example 127

Preparation of (2S, 1'S)-N-[1'-(4-carboethoxythiazol-2-yl)-3'-methylbutyl]-4-methyl-2-[(3-phenoxybenzyloxycarbonyl)]aminopentanamide Following the procedure of Example 124(b), except substituting 3-phenoxybenzyl alcohol for biphenylmethanol, the title compound was prepared as a white solid (0.107 g, 56%). MS(ESI): 581.9 $(M+H)^+$.

Example 128

Preparation of (2S,1'S)-2-(benzyloxycarbonyl)amino-N-[1'-[2-(2-benzylguanidinyl)thiazol-4-yl]-3'-methylbutyl]-4-methylpentanamide a) S-methyl dithiobiuret hydroiodide salt To a stirring solution of dithiobiuret (5.0 g, 37 mmol) in THF (75 mL) was added iodomethane (13.1 g, 92.5 mmol, 5.76 ml). After stirring at room temperature for 22 h, the solution was diluted with 150 mL of toluene and allowed to stand at 0° C. for 3 h. The crystals were collected by filtration and washed with cold 2:1 toluene/THF, then dried in vacuo to give the title compound as a white solid (8.7 g, 85%). MS(ESI): 149.9 (M+H)$^+$.

b) 3-benzylguanidinyl thiourea

The compound of Example 128(b) (4.35 g, 15.7 mmol) was dissolved in isopropanol (80 mL) and benzylamine (1.77 g, 16.5 mmol, 1.8 mL) was added and the mixture was heated at reflux for 16 h. The hot solution was filtered and the filtrate was cooled to 0° C. After 5 h, the solid was collected by filtration and washed twice with cold iospropanol, then dried in vacuo to provide the title compound as a white solid (2.59 g, 61%). MS(ESI): 209.2 (M+H)$^+$.

c) (2S,1'S)-2-(benzyloxycarbonyl)amino-N-[1'-[2-(2-benzylguanidinyl)thiazol-4-yl]-3'-methylbutyl]-4-methylpentanamide Following the procedure of Example (b), except substituting 3-benzylguanidinyl thiourea for ethyl thiooxamate, the title compound was prepared as a white solid (102 mg, 79%). MS(ESI): 565.1 (M+H)$^+$.

Example 129

Preparation of (1S)-N-[4-[1-(N-benzyloxycarbonylamino)-3-methylbutyl]thiazol-2-ylcarbonyl]-N-methyl-N'-(N-benzyloxycarbonyl-L-leucinyl)hydrazide Following the procedure of Example 26(a)–26(d), except substituting methyl hydrazine for hydrazine in step (c), the title compound was prepared as a white solid. MS(ESI): 624.1 (M+H)$^+$.

Example 130

Preparation of (1S)-N-[4-[1-(N-benzyloxycarbonylamino)-3-methylbutyl]thiazol-2-ylcarbonyl]-N'-(N-benzyloxycarbonyl-L-leucinyl)-N'-methylhydrazide a) N-(N-benzyloxycarbonyl-L-leucinyl)-N-methylhydrazide Following the procedure of Example 26(c), except substituting N-benzyloxycarbonyl-L-leucine methyl ester for (1S)-1-benzyloxycarbonylamino-1-(2-carboethoxythiazol-4-yl)-3-methylbutane and methyl hydrazine for hydrazine, the title compound was prepared.

b) (1S)-1-benzyloxycarbonylamino-1-(2-carboxythiazol-4-yl)-3-methylbutane

The compound of Example 26(c)(0.57 g., 1.5 mmol) was dissolved in tetrahydrofuran and treated with an excess of 1.0N sodium hydroxide. The mixture was allowed to stir for 4 hours, and was quenched with 1.0N citric acid. The solvent was evaporated and the aqueous layer extracted three times with dichloromethane. The organic layers were combined and evaporated to give the acid as a white foam (0.55 g, 100%).

c) (1S)-N-[4-[1-(N-benzyloxycarbonylamino)-3-methylbutyl]thiazol-2-ylcarbonyl]-N'-(N-benzyloxycarbonyl-L-leucinyl)-N'-methylhydrazide Following the procedure of Example 28(e), except substituting N-(N-benzyloxycarbonyl-L-leucinyl)-N-methylhydrazide for (1S)-1-(benzyloxycarbonyl)amino-1-(4-carboethoxythiazol-2-yl)-3-methylbutane and (1S)-1-benzyloxycarbonylamino-1-(2-carboxythiazol-4-yl)-3-methylbutane for N-benzyloxycarbonyl-L-leucine, the title compound was prepared as a white solid. MS (ESI): 624.2 (M+H)$^+$.

Example 131

Preparation of N-(N-benzyloxycarbonyl-L-leucinyl)-N'-(N-benzyloxycarbonyI-L-leucinyl-L-alanylhydrazide Following the procedure of Example 27(a)–27(c), except substituting L-alanine methyl ester for L-leucine methyl ester in step (a), the title compound was prepared as a white solid (225 mg, 42%). MS(ESI): 598.1 (M+H)$^+$.

Example 132

Preparation of N-(N-benzyloxycarbony-L-leucinyl)-N'-(N-benzyloxycarbonyl-L-leucinyl)glycinylhydrazide Following the procedure of Example 27(a)–27(c), except substituting glycine methyl ester for L-leucine methyl ester in step (a), the title compound was prepared as a white solid (307 mg, 42%). MS(ESI): 584.1 (M+H)$^+$.

Example 133

Preparation of (1S)-N-[2-[1-(N-benzyloxycarbonylamino)-3-methylbutyl]-1,3,4-triazol-5-ylcarbonyl]-N'-(N-benzyloxycarbonyl-L-leucinyl)hydrazide a) ethyl oxalamidrazonate To a solution of ethyl thiooxamate (3.0 g, 22.6 mmol) in ethanol (50 mL) was added hydrazine hydrate (1.13 g, 22.6 mmol, 1.09 mL). The mixture was allowed to stir for 3 hours at room temperature, while venting through a scrubber of concentrated sodium hydroxide solution. The solution was allowed to stand for 16 hours and the ethanol was evaporated. The residue was boiled in 30% dichloromethane in petroleum ether, filtered, and crystallized to give the desired compound as a tan solid. (0.264 g, 9%).

b) (1S)-1-benzyloxycarbonylamino-1-(2-carboethoxy-1,3,4-triazol-5-yl)-3-methylbutane N-benzyloxycarbonyl-L-leucine (0.535 g, 2.0 mmol) was stirred in THF at −5° C. Ethyl chloroformate (0.23 mL, 2.4 mmol) and triethylamine (0.25 g, 2.4 mmol, 0.34 mL) were added. The compound of Example 10(a) (0.264 g, 2.0 mmol) was then added and the mixture was allowed to stir at room temperature overnight. The solvents were evaporated and the residue was dissolved in xylenes and heated to 200° C. using a Dean-Stark apparatus. The heating was stopped after 4 hours and the solution was evaporated to a residue which was chromatographed (silica gel, 40% ethyl acetate in hexane) to give the title compound as a white solid (0.498 g, 69%). $^1$H NMR (400 MHz, CDCl$_3$) δ7.20 (m, 5H), 5.71 (d, 1H), 5.04 (s, 2H), 4.99 (dd, 1H), 4.36 (q, 2H), 1.8 ( m, 2H), 1.59 ( m, 1H), 1.31 (t, 3H), 0.83(dd, 6H).

c) (1S)-1-benzyloxycarbonylamino-1-(2-hydrazinocarbonyl-1,3,4-triazol-5-yl)-3-methylbutane Following the procedure of Example 26(c)–26(d), except substituting (1S)-1-benzyloxycarbonylamino-1-(2-carboethoxy-1,3,4-triazol-5-yl)-3-methylbutane for (1S)-1-benzyloxycarbonylamino-1-(2-carboethoxythiazol-4-yl)-3-methylbutane in step (c), the title compound was prepared. MS (ESI): 594.5 (M+H)+.

Example 134

Preparation of (1S)-N-(N-acetyl-L-leucinyl)-N'-[2-[1-(N-benzyloxycarbonylamino)-3-methylbutyl]thiazol-4-carbonyl]hydrazide Following the procedure of Example 28(a)–28(e), except substituting N-acetyl-L-leucine for N-benzyloxycarbonyl-L-leucine in step (e), the title compound was prepared as a white solid (95 mg, 67%). MS(ESI): 518.0 (M+H)+.

Example 135

Preparation of (1S)-N-(N-benzyloxycarbonyl-L-alanyl)-N'-[2-[1-(N-benzyloxycarbonylamino)-3-methylbutyl]thiazol-4-ylcarbonyl]hydrazide Following the procedure of Example 28(a)–28(e), except substituting N-benzyloxycarbonyl-L-alanine for N-benzyloxycarbonyl-L-leucine in step (e), the title compound was prepared as a white solid (129 mg, 82%). MS(ESI): 568.1 (M+H)+.

Example 136

Preparation of (1S)-N-(N-acetyl-L-alanyl)-N'-[2-[1-(N-benzyloxycarbonylamino)-3-methylbutyl]thiazol-4-ylcarbonyl]hydrazide Following the procedure of Example 28(a)–28(c), except substituting N-acetyl-L-alanine for N-benzyloxycarbonyl-L-leucine in step (e), the title compound was prepared as a white solid (74 mg, 57%). MS(ES): 498.1 (M+Na)+.

Example 137

Preparation of (1S)-N-(N-acetyl)-N'-[2-[1-(N-benzyloxycarbonylamino)-3-methylbutyl]thiazol-4-ylcarbonyl]hydrazide Following the procedure of Example 28(a)–28(e), except substituting acetic acid for N-benzyloxycarbonyl-L-leucine in step (e), the title compound was prepared as a white solid (87 mg, 78%). MS(ESI): 405.1 (M+H)+.

Example 138

Preparation of (1S)-N-[2-[1-(N-benzyloxycarbonylamino)-3-methylbutyl]thiazol-4-ylcarbonyl]-N'-[N-(4-pyridinylmethoxycarbonyl)-L-leucinyl]hydrazide Following the procedure of Example 28(a)–28(e), except substituting N-(4-pyridinylmethoxycarbonyl)-L-leucine for N-benzyloxycarbonyl-L-leucine in step (e), the title compound was prepared as a white solid (121 mg, 72%). MS(ESI): 611.0 (M+H)+.

Example 139

Preparation of (1S)-N-[2-[1-(N-benzyloxycarbonyamino)-3-methylbutyl]thiazol-4-ylcarbonyl]-N'-[N-(2-pyridinylmethoxycarbonyl)-L-leucinyl]hydrazide Following the procedure of Example 28(a)–28(e), except substituting N-(2-pyridinylmethoxycarbonyl)-L-leucine for N-benzyloxycarbonyl-L-leucine in step (e), the title compound was prepared as a white solid (125 mg, 65%). MS (ESI): 611.2 (M+H)+.

Example 140

Preparation of (1S)-N-[2-[1-(N-benzyloxycarbonylamino)-3-methylbutyl]thiazol-4-ylcarbonyl-N'-(N-benzyloxycarbonyl-N-methyl-L-leucinyl) hydrazide Following the procedure of Example 28(a)–28(e), except substituting N-benzyloxycarbonyl-N-methyl-L-leucine for N-benzyloxycarbonyl-L-leucine in step (e), the title compound was prepared as a white solid (78 mg, 50%). MS (ESI): 624.3 (M+H)+.

Example 141

Preparation of (1S)-N-[2-[1-(N-benzyloxycarbonyl-N-methylamino)-3-methylbutyl]thiazol-4-ylcarbonyl]-N'-[N-(4-pyridinylmethoxycarbonyl)-L-leucinyl]hydrazide Following the procedure of Example 28(a)–28(e), except substituting N-benzyloxycarbonyl-N-methyl-L-leucine for N-tert-butoxycarbonyl-L-leucine in step (a) and N-(2-pyridinylmethoxycarbonyl)-L-leucine for N-benzyloxycarbonyl-L-leucine in step (e), the title compound was prepared as a white solid (120 mg, 72%). MS (ESI): 625.3 (M+H)+.

Example 142

Preparation of (1'S)-N-(-benzyloxycarbonyl-L-leucinyl)-N'-[2-[1-(N-benzloxycarbonyl-N-methylamino)-3-methylbutyl]thiazol-4-ylcarbonyl] hydrazide Following the procedure of Example 28(a)–28(c), except substituting N-benzyloxycarbonyl-N-methyl-L-leucine for N-tert-butoxycarbonyl-L-leucine in step (a), the title compound was prepared as a white solid (95 mg, 74%). MS (ESI): 624.3 (M+H)+.

Example 143

Preparation of (1S)-N-[2-[1-(N-benzyloxycarbonyl-N-methylamino)-3-methylbutyl]thiazol-4-yl]carbonyl-N'-(N-benzyloxycarbonyl-N-methyl-L-leucinyl)hydrazide Following the procedure of Example 28(a)–28(e), except substituting N-benzyloxycarbonyl-N-methyl-L-leucine for N-tert-butoxycarbonyl-L-leucine in step (a) and N-benzyloxycarbonyl-N-methyl-L-leucine for N-benzyloxycarbonyl-L-leucine in step (e), the title compound was prepared as a white solid (129 mg, 59%). MS (ESI): 683.3 (M+H)+.

Example 144

Preparation of (1S)-N-[2-[1-(N-methylamino)-3-methylbutyl]thiazol-4-ylcarbonyl]-N'-[N-(4-pyridinylmethoxycarbonyl)-L-leucinyl]hydrazide a) (1S)-N-[2-[1-(N-tert-butoxycarbonyl-N-methylamino)-3-methylbutyl]thiazol-4-ylcarbonyl]-N'-[N-(4-pyridinylmethoxycarbonyl)-L-leucinyl]hydrazide Following the procedure of Example 28(a)–28(e), except substituting N-tert-butoxycarbonyl-N-methyl-L-leucine for N-tert-butoxycarbonyl-L-leucine in step (a) and N-(4-pyridinylmethoxycarbonyl-L-leucine for N-benzyloxycarbonyl-L-leucine in step (e), the title compound was prepared as a white solid. MS (ESI): 591.4 (M+H)+.

b) (1S)-N-[-2-[1-(N-methylamino)-3-methylbutyl]thiazol-4-ylcarbonyl]-N'-[N-(4-pyridinylmethoxycarbonyl)-L-leucinyl]hydrazide To a solution of the compound of Example 21(a) in methylene chloride (10 mL) was added trifluoroacetic acid (3 mL). After stirring one hour at room remperature the solution was concentrated and the residue was redissolved in methylene chloride, washed with saturated aqueous sodium bicarbonate, dried over MgSO$_4$ and concentrated to afford the title compound as a white solid (259 mg, 68% for two steps). MS (ESI): 491.4 (M+H)+.

Example 145

Preparation of (1S)-N-[2-[1-(N-benzloxycarbonylamino)-3-methylbutyl]thiazol-4-ylcarbonyl]-N'-[N-(tert-butoxycarbonyl)-L-leucinyl]hydrazide Following the procedure of Example 28(a)–28(e), except substituting N-tert-butoxycarbonyl-L-leucine for N-benzyloxycarbonyl-L-leucine in step (e), the title compound was prepared as a white solid (293 mg, 74%). MS (ESI): 576.4 (M+H)+.

Example 146

Preparation of (1S)-N-[2-[1-(N-benzyloxycarbonylamino)-3-methylbutyl]thiazol-4-ylcarbonyl]-N'-[N-(tert-butoxycarbonyl)-N-methyl-L-leucinyl]hydrazide Following the procedure of Example 28(a)–28(e), except substituting N-tert-butoxycarbonyl-N-methyl-L-leucine for N-benzyloxycarbonyl-L-leucine in step (e), the title compound was prepared as a white solid (120 mg, 87%). MS (ESI): 590.3 (M+H)+.

Example 147

Preparation of (1S)-N-[2-[1-N-benzyloxycarbonylamino)-3-methylbutyl]thiazol-4-ylcarbonyl]-N'-(N-methyl-L-leucinyl)hydrazide Following the procedure of Example 144(b), except substituting (1S)-N-[2-[1-(N-benzyloxycarbonylamino)-3-methylbutyl]thiazol-4-ylcarbonyl]-N'-[N-(tert-butoxycarbonyl)-N-methyl-L-leucinyl]hydrazide for (1S)-N-[2-[1-(N-tert-butoxycarbonyl-N-methylamino)-3-methylbutyl]thiazol-4-ylcarbonyl]-N'-[N-(4-pyridinylmethoxycarbonyl)-L-leucinyl]hydrazide, the title compound was prepared as a white solid (40 mg, 80%). MS (ESI): 490.3 (M+H)+.

Example 148

Preparation of (1S)-N-[2-[1-N-benzyloxycarbonylamino)-3-methylbutyl]thiazol-4-ylcarbonyl]-N'-(L-leucinyl)hydrazide Following the procedure of Example 144(b), except substituting (1S)-N-[2-[1-(N-benzyloxycarbonylamino)-3-methylbutyl]thiazol-4-carbonyl]-N'-[N-tert-butoxycarbonyl]-L-leucinyl]hydrazide for (1S)-N-[2-[1-(N-tert-butoxycarbonyl)-L-leucinyl]hydrazide for (1S)-N-[2-[1-(N-tert-butoxycarbonyl-N-methylamino)-3-methylbutyl]thiazol-4-ylcarbonyl]-N'-[N(4-pyridinylmethoxycarbonyl)-L-leucinyl]hydrazide, the title compound was prepared as a white solid (39 mg, 100%). MS (ESI): 476.4 (M+H)+.

Example 149

Preparation of (1S)-N-[2-[1-N-benzyloxycarbonylamino)-3-methylbutyl]thiazol-4-ylcarbonyl]-N'-[N-(4-imidazolylacetyl)-L-leucinyl]hydrazide Following the procedure of Example 28(c), except substituting (1S)-N-[2-[1-(N-benzyloxycarbonylamino)-3-methylbutyl]thiazol-4-ylcarbonyl]-N'-(L-leucinyl)hydrazide for (1S)-1-(benzyloxycarbonyl)amino-1-(4-carboethoxythiazol-2-yl)-3-methylbutane and 4-imidazoleacetic acid for N-benzyloxycarbonyl-L-leucine, the title compound was prepared as a white solid (50 mg, 47%). MS (ESI): 584.4 (M+H)+.

Example 150

Preparation of (1S)-N-[2-[1-(N-benzyloxycarbonyl-N-methylamino)-3-methylbutyl]thiazol-4-ylcarbonyl]-N'[N-(3-pyridinylmethoxycarbonyl)-N-methyl-L-leucinyl]hydrazide a) N-methyl-L-leucine methyl ester N-methyl-L-leucine (1.3 g, 8.95 mmol) was dissolved in 4M HCl, 1,4-dioxane (10 mL) and methanol (10 mL). The solution was stirred overnight at room temperature, then concentrated to afford the title compound as a white solid (100%). MS (ESI): 160.0 (M+H)+.

b) N-methyl-N-(3-pyridinylmethoxycarbonyl)-L-leucine methyl ester

To a stirring solution of phosgene in toluene (5.63 mL, 6.025 mmol) in methylene chloride (10 mL), cooled to 0° C., was added dropwise a solution of N-methyl-L-leucine methyl ester (673 mg, 4.63 mmol) and pyridine (1.10 g, 0.97 mL, 13.89 mmol) in methylene chloride (4 mL). The solution was stirred at 0° C. for 2 hours. A solution of 3-pyridyl carbinol (0.56 g, 5.09 mmol, 0.49 mL) was then added and the reaction mixture was stirred at room temperature for 5 hours. The solution was concentrated, redissolved in ethyl acetate, washed with water, dried (MgSO$_4$), filtered and concentrated. The crude residue was purified by column chromatography on silica gel (6% methanol in methylene chloride) to afford the title compound as a yellow oil (88 mg, 7%). MS (ESI): 295.4 (M+H)+.

c) N-methyl-N-(3-pyridinylmethoxycarbonyl)-L-leucine

Following the procedure of Example 130(b), except substituting N-methyl-N-(3-pyridinylmethoxycarbonyl)-L-leucine methyl ester (1S)-1-benzyloxycarbonylamino-1-(2-hydrazinocarbonylthiazol-4-yl)-3-methylbutane, the title compound was prepared as an orange solid (84 mg, 100%). MS (ESI): 281.3 (M+H)+.

d) (1S)-N-[2-[1-(N-benzyloxycarbonyl-N-methylamino)-3-methylbutyl]thiazol-4-ylcarbonyl]-N'-[N-(3-pyridinylmethoxycarbonyl)-N-methyl-L-leucinyl]hydrazide Following the procedure of Example 28(a)–28(e), except substituting N-benzyloxycarbonyl-N-methyl-L-leucine for N-tert-butoxycarbonyl-L-leucine in step (a) and N-methyl-N-(3-pyridinylmethoxycarbonyl)-L-leucine for N-benzyloxycarbonyl-L-leucine in step (e), the title compound was prepared as a white solid (55 mg, 38%). MS (ESI): 639.4 (M+H)+.

Example 151

Preparation of (1S)-N-[2-[1-(N-benzyloxycarbonyl-N-methylamino)-3-methylbutyl]thiazol-4-ylcarbonyl]-N'-[N-(3-pyridinylmethoxycarbonyl)-L-leucinyl]hydrazide Following the procedure of Example 28(a)–28(e), except substituting N-benzyloxycarbonyl-N-methyl-L-leucine for N-tert-butoxycarbonyl-L-leucine in step (a) and N-(3-pyridinylmethoxycarbonyl)-L-leucine for N-benzyloxycarbonyl-L-leucine in step (e), the title compound was prepared as a white solid (31 mg, 34%). MS (ESI): 625.4 (M+H)$^+$.

Example 152

Preparation of (1S)-N-[2-[1-(N-benzyloxycarbonylamino)-3-methylbutyl]thiazol-4-ylcarbonyl]-N'-[N-(3-pyridinylmethoxycarbonyl)-L-leucinyl]hydrazide Following the procedure of Example 28(a)–28(e), except substituting N-(3-pyridinylmethoxycarbonyl)-L-leucine for N-benzyloxycarbonyl-L-leucine in step (e), the title compound was prepared as a white solid (63 mg, 42%). MS (ESI): 611.5(M+H)$^+$.

Example 153

Preparation of (1'S)-N-(N-benzyloxycarbonyl-L-leucinyl)-N'-(1-benzyloxycarbonyl)-N'-[2-[1-(N-methylamino)-3-methylbutyl]thiazol-4-ylcarbonyl]-N'-methylhydrazide Following the procedure of Example 28(a)–28(e), except substituting N-benzyloxycarbonyl-N-methyl-L-leucine for N-tert-butoxycarbonyl-L-leucine in step (a) and methyl hydrazine for hydrazine in step (e), the title compound was prepared as a white solid (80 mg, 70%). MS (ESI): 660.4 (M+Na)$^+$.

Example 154

Preparation of (1S)-N-[2-[1-(N-benzyloxycarbonylamino)-3-methylbutyl]thiazol-4-ylcarbonyl]-N'-[N-(2-pyridinylmethoxycarbonyl)-N-methyl-L-leucinyl]hydrazide a) N-methyl-N-(2-pyridinylmethoxycarbonyl)-L-leucine methyl ester N-(2-pyridinylmethoxycarbonyl)-L-leucine methyl ester (490 mg, 1.75 mmol) was dissolved in THF (7.0 mL) and methyl iodide (0.435 mL, 6.99 mmol) was added. The reaction mixture was cooled to 0° C. in a flask protected from moisture. Sodium hydride dispersion (236 mg, 2.62 mmol) was added cautiously and the suspension was stirred for 5 hours at room temperature. Ethyl acetate was then added, followed by water, dropwise. The solution was concentrated in vacuo, and the oily residue partitioned between ether and water. The organic layer was washed with saturated aqueous NaHCO$_3$ and the combined aqueous extracts acidified to pH 3 with citric acid. The product was extracted with ethyl acetate, the extract was washed with water, 5% aqueous sodium thiosulfate and water, dried (MgSO$_4$), filtered and concentrated. The crude product was purified by column chromatography on silica gel (ethyl acetate/hexane, 3:1) to give a yellow oil (235 mg, 46%). MS (ESI): 295.4 (M+H)$^+$.

b) N-methyl-N-(2-pyridinylmethoxycarbonyl)-L-leucine

Following the procedure of Example 130(b), except substituting N-methyl-N-(2-pyridinylmethoxycarbonyl)-L-leucine methyl ester (1S)-1-benzyloxycarbonylamino-1-(2-hydrazinocarbonylthiazol-4-yl)-3-methylbutane, the title compound was prepared as a white solid (223 mg, 100%). MS (ESI): 281.3 (M+H)$^+$.

c) (1S)-N-[2-[1-(N-benzyloxycarbonylamino)-3-methylbutyl]thiazol-4-ylcarbonyl]-N'-[N-(2-pyridinylmethoxycarbonyl)-N-methyl-L-leucinyl]hydrazide Following the procedure of Example 28(a)–28(e), except substituting N-benzyloxycarbonyl-N-methyl-L-leucine for N-tert-butoxycarbonyl-L-leucine in step (a) and N-methyl-N-(2-pyridinylmethoxycarbonyl)-L-leucine for N-benzyloxycarbonyl-L-leucine in step (e), the title compound was prepared as a white solid (50 mg, 44%). MS 1ESI): 639.5 (M+H)$^+$.

Example 155

Preparation of (1S)-N-[2-[1-(N-benzyloxycarbonyl-N-methylamino)-3-methylbutyl]thiazol-4-ylcarbonyl]-N'-[N-(4-pyridinylmethoxycarbonyl)-N-methyl-L-leucinyl]hydrazide a) L-leucine tert-butyl ester isocyanate L-leucine tert-butyl ester hydrochloride (10.185 g, 45.5 mmol) was dissolved in methylene chloride (100 mL), cooled to 0° C. and pyridine (12.7 mL, 182.0 mmol) was added, then phosgene in benzene (47 mL, 59.1 mmol). The solution was stirred at 0° C. for 2 hours. The reaction mixture was washed two times with 300 mL of cold 0.5 M aqueous HCl. Each aqueous layer was extracted with 100 mL methylene chloride. The combined organic phases were washed with a mixture of saturated aqueous NaCl solution and crushed ice, dried over MgSO$_4$, filtered and concentrated to afford the isocyanate as a yellow liquid (5.37 g, 55%).

b) N-(4-pyridinylmethoxycarbonyl)-L-leucine tert-butyl ester

The compound of Example 155(a) (3.05 g, 14.32 mmol) and 4-pyridyl carbinol (1.56 g, 14.32 mmol) were dissolved in toluene (80 mL) and heated at reflux overnight. The solution was concentrated in vacuo and the residue was purified by column chromatography on silica gel (ethyl acetate/hexane, 3:1) to afford the title compound as a colorless oil (2.945 g, 64%). MS (ESI): 323.4 (M+H)$^+$.

c) N-methyl-N-(4-pyridinylmethoxycarbonyl)-L-leucine tert-butyl ester

Following the procedure of Example 154(a), except substituting N-(4-pyridinylmethoxycarbonyl)-L-leucine tert-butyl ester for N-(2-pyridinylmethoxycarbonyl)-L-leucine methyl ester, the title compound was prepared as a yellow liquid (2.038 g, 68% yield). MS (ESI): 337.5 (M+H)$^+$.

d) N-methyl-N-(4-pyridinylmethoxycarbonyl)-L-leucine

Following the procedure of Example 144(b), except substituting N-methyl-N-(4-pyridinylmethoxycarbonyl)-L-leucine tert-butyl ester for (1S)-N-[2-[1-(N-tert-butoxycarbonyl-N-methylamino)-3-methylbutyl]thiazol-4-ylcarbonyl]-N'-[N-(4-pyridinylmethoxycarbonyl)-L-leucinyl]hydrazide, the title compound was prepared as a white solid (343 mg, 72% yield). MS (ESI): 281.3 (M+H)$^+$.

e) (1S)-N-[2-[1-(N-benzyloxycarbonyl-N-methylamino)-3-methylbutyl]thiazol-4-ylcarbonyl]-N'-[N-(4-pyridinylmethoxycarbonyl)-N-methyl-L-leucinyl]hydrazide Following the procedure of Example 28(a)–28(e), except substituting N-benzyloxycarbonyl-N-methyl-L-leucine for N-tert-butoxycarbonyl-L-leucine in step (a) and N-methyl-N-(4-pyridinylmethoxycarbonyl)-L-leucine for N-benzyloxycarbonyl-L-leucine in step (e), the title compound was prepared as a white solid (50 mg, 44%). MS (ESI): 639.5 (M+H)+.

Example 156

Preparation of 2.2'-[N,N'-[bis-(N-acetyl-L-luecinyl)]]carbohydrazide

Following the procedure of Example 29, except substituting N-acetyl-L-leucine for N-benzyloxycarbonyl-L-leucine, the title compound was prepared as a pale yellow solid (0.153 g, 23%). MS(ESI): 401.3 (M+H)+.

Example 157

Preparation of 2-[N-(N-benzloxycarbonyl-L-leucinyl)]-2'-[N'-(4-methylpentanoyl)]carbohydrazide a) N- benzyloxycarbonyl-L-leucine methyl ester To a stirring solution of L-leucine methyl ester (2.0 g, 11.0 mmol) in 1,4-dioxane (20 mL) was added aqueous $Na_2CO_3$ solution (12.1 mL, 2M in $H_2O$) followed by benzylchloroformate (1.96 g, 11.5 mmol). The mixture stirred at room temperature for 4h then partitioned between ethyl acetate and water. The organic layer was washed with saturated brine, dried ($MgSO_4$), filtered and concentrated to yield the title compound as a colorless oil (3.1 g, 100%). $^1$HNMR (400 MHz, $CDCl_3$) δ7.34 (m, 5H), 5.27 (d, 1H), 5.12 (s, 2H), 4.41 (s, 2H), 3.75 (s, 3H), 1.65 (m, 3H), 0.96 (m, 6H).

b) N-(N-benzyloxycarbonyl-L-leucinyl)hydrazide

To a stirring solution of the compound of Example 157(a) (3.1 g, 11.0 mmol) in methanol (15 mL) was added hydrazide hydrate (5.9 g, 118 mmol, 5.7 mL). The solution stirred at room temperature for 16 h then concentrated to yield the title compound as an off-white solid (3.1 g, 100%). MS(ESI): 280.2 (M+H)+.

c) 1-benzyloxycarbonylamino-3-methyl-1-(1,3,4-oxadiazol-2-on-5-yl)butane

To a stirring solution of the compound of Example 157(b) (3.0 g, 10.8 mmol) in toluene (50 mL) was added phosgene (56 mL, 1.93M in toluene). The solution was heated at reflux for 4h, then concentrated to yield the title compound as a pale yellow foam (3.15 g, 96%). MS(ESI): 306.1 (M+H)+.

d) N-(4-methylpentanoyl)hydrazide

To a stirring solution of ethyl isocaproate (2.0 g, 13.8 mmol) in ethanol (25 mL) was added hydrazine monohydrate (6.9 g, 138 mmol, 6.7 mL). After stirring at room temperature for 48 h, the solution was concentrated to yield the title compound as a white solid. (1.8 g, 100%). $^1$HNMR (400 MHz, CDCl3) δ7.48 (s br, 1H), 3.62 (s br, 2H), 2.13 (t, 2H), 1.51 (m, 3H), 0.85 (d, 6H).

e) 2-[N-(N-benzyloxycarbonyl-L-leucinyl)]-2'-[N'-(4-methylpentanoyl)]carbohydrazide The compounds of Example 157(c) (0.100 g, 0.325 mmol) and Example 34(d) (0.042 g, 0.325 mmol) were combined and dissolved in ethanol (1 mL). The solution was heated at reflux for 24 hours, then concentrated to a solid yellow residue which was washed with cool methylene chloride to yield the title compound as a white solid (0.053 g, 37%). MS(ESI): 436.2 (M+H)+.

Example 158

Preparation of 2.2'-[N,N'-[bis-(N-benzyloxycarbonyl-N-methyl-L-leucinyl)]]carbohydrazide Following the procedure of Example 29, except substituting N-benzyloxycarbonyl-N-methyl-L-leucine for substituting N-benzyloxycarbonyl-L-leucine, the title compound was prepared with purification by column chromatography (silica gel, methanol/dichloromethane) as a white foam (0.236 g, 23%). MS (MH+): 613.2.

Example 159

Preparation of 2-[N-(N-acetyl-L-leucinyl)]-2'-[N'-(N-benzyloxycarbonyl-L-leucinyl)]carbohydrazide)

a) 2-[N-(N-benzyloxycarbonyl-L-leucinyl)]carbohydrazide

To a stirring solution of the compound of Example 157(c) (3.15 g, 10.3 mmol) in methanol (2 mL) was added hydrazine hydrate (5.0 g, 100 mmol, 4.8 mL). After stirring at room temperature for 24 h, the solution was concentrated to yield the title compound as a pale yellow foam (3.471 g, 100%). MS(ESI): 338.2 (M+H)+.

b) 2-[N-(N-acetyl-L-leucinyl)]-2'-N'-(N-benzyloxycarbonyl-L-leucinyl)]carbohydrazide To a stirring solution of the compound of Example 159(a) (0.100 g, 0.297 mmol), N-acetyl-L-leucine (0.054 g, 0.312 mmol) and 1-hydroxybenzotriazole (0.008 g, 0.0594 mmol) in DMF (2 mL) was added 1-(3-dimethylaminopropyl)-3-ethylcarbodiimide hydrochloride (0.060 g, 0.312 mmol). After stirring at room temperature for 16 h, the solution was poured into water and extracted with ethyl acetate. The organic layer was dried ($MgSO_4$), filtered and concentrated. The residue was purified by column chromatography (silica gel, methanol/dichloromethane) to yield the title compound as a white solid (0.052 g, 36%). MS(ESI): 493.1 (M+H)+.

Example 160

Preparation of 2,2'-[N,N'-[bis-[N-(4-pyridinylmethoxycarbonyl)-L-leucinyl)]]] carbohydrazide Following the procedure of Example 29, except substituting N-(4-pyridinylmethoxycarbonyl)-L-leucine for N-benzyloxycarbonyl-L-leucine, the title compound was prepared as a white solid (199 mg, 64%). MS(ESI): 587.1 (M+H)+.

Example 161

Preparation of 2,2'-[N,N'-[bis-[N-(2-pyridinylmethoxycarbonyl)-L-leucinyl)]]] carbohydrazide Following the procedure of Example 29, except substituting N-(2-pyridinylmethoxycarbonyl)-L-leucine for N-benzyloxycarbonyl-L-leucine, the title compound was prepared as a white solid (263 mg, 81%). MS(ESI): 587.1 (M+H)+.

Example 162

Preparation of 2-[N-(N-benzloxycarbonyl-L-leucinyl)]-2'-[N'-[N-(2-pyridinylmethoxycarbonyl)-L-leucinyl)]]carbohydrazide Following the procedure of Example 159(a)–159(b) except substituting N-(2-pyridinylmethoxycarbonyl)-L-leucine lithium salt for N-acetyl-L-leucine in step (b), the title compound was prepared as a white solid (0.040 g, 15%). MS(ESI): 586.3 (M+H)+.

Example 163

Preparation of 2-[N-(N-benzyloxycarbonyl-L-leucinyl)]-2'-[N'-[N-(4-pyridinylmethoxycarbonyl)-L-leucinyl)]]carbohydrazide Following the procedure of Example 159(a)–159(b) except substituting N-(4-pyridinylmethoxycarbonyl)-L- leucine lithium salt for N-acetyl-L-leucine in step (b), the title compound was prepared as a white solid (0.045 g, 17%). MS(ESI): 586.3 (M+H)$^+$.

Example 164

Preparation of 2-[N-(N-benzyloxycarbonyl-L-leucinyl)]-2'-[N'-[N-(3-pyridinylmethoxycarbonyl)-L-leucinyl)]]carbohydrazide Following the procedure of Example 159(a)–159(b) except substituting N-(3-pyridinylmethoxycarbonyl)-L-leucine lithium salt for N-acetyl-L-leucine in step (b), the title compound was prepared as a white solid (0.084 g, 32%). MS(ESI): 586.3 (M+H)$^+$.

Example 165

Preparation of 2,2'-[N,N'-[bis-(N-benzyloxycarbonyl-L-leucinyl)-L-leucinyl)]]-2-(N-methyl)carbohydrazide a) N-methyl-N-(N-benzyloxycarbonyl-L-leucinyl)hydrazide To a stirring solution of N-benzyloxycarbonyl-L-leucine methyl ester (2.2 g, 8.15 mmol) in methanol (4 mL) was added methylhydrazine (3.7 g, 80 mmol). After stirring at room temperature for 16 h, the solution was concentrated to yield the title compound as a yellow solid (2.14 g, 7.3 mmol). MS(ESI): 294.1 (M+H)$^+$.

b) 2,2'-[N,N'-[bis-(N-benzyloxycarbonyl-L-leucinyl)]]-2-(N-methyl)carbohydrazide The compound of Example 157(c) (0.250 g, 0.819 mmol) and the compound of Example 165(a) (0.240 g, 0.819 mmol) were combined, dissolved in ethanol and heated at reflux for 24 h. The solution was concentrated and the residue purified by column chromatography (silica gel, methanol/dichloromethane) to yield the title compound as a white solid (0.060 g, 12%). MS(ESI): 599.1 (M+H)$^+$.

Example 166

Preparation of 2.2'-[N,N'-[bis-[N-(3-pyridinylmethoxycarbonyl)-L-leucinyl)]]] carbohydrazide Following the procedure of Example 29, except substituting N-(3-pyridinylmethoxycarbonyl)-L-leucine for N-benzyloxycarbonyl-L-leucine, the title compound was prepared as a white solid (157 mg, 48%). MS(ESI): 587.0 (M+H)$^+$.

Example 167

Preparation of 1-(N-benzyl)-2,2'-[N,N'-[bis-(N-benzyloxycarbonyl-L-leucinyl)]]carbohydrazide a) N-benzylidene-N'-(N-benzyloxycarbonyl-L-leucinyl)hydrazide To a solution of the compound of Example 157(b) (1 g, 3.5 mmol) in ethanol (30 mL) was added benzaldehyde (0.33 mL, 3.2 mmol). The resulting mixture was heated at reflux for 4 h. The mixture was concentrated in vacuo then purified by flash chromatography (silica gel, 10–50% EtOAc/hexane) to yield the title compound as a solid (0.31 g, 23%). MS(ESI): 368.0 (M+H)$^+$.

b) N-benzyl-N'-(N-benzyloxycarbonyl-L-leucinyl)hydrazide

To a cooled solution of compound of Example 167(a) (0.24 g, 0.65 mmol) in THF (5 mL) was added borane tetrahydrofuran complex (0.65 mL, 0.65 mmol; 1M solution in THF). The resulting mixture was stirred at room temperature for 4 h then concentrated in vacuo and diluted with ethyl acetate, washed with water, saturated brine, dried (MgSO$_4$), filtered and concentrated in vacuo to give the title compound as a white solid (0.25 g, 89%). MS(ESI): 370.0 (M+H)$^+$.

c) 1-benzyloxycarbonylamino-3-methyl-1-(3-benzyl-1,3,4-oxadiazol-2-on-5-yl)butane Following the procedure of Example 157(c), except substituting N-benzyl-N'-(N-benzyloxycarbonyl-L-leucinyl)hydrazide for N-(N-benzyloxycarbonyl-L-leucinyl)hydrazide, the title compound was prepared as an oil (0.02 g, 83%). MS(ESI): 396.0 (M+H)$^+$.

d) 1-(N-benzyl)-2-[N-(N-benzyloxycarbonyl-L-leucinyl)]carbohydrazide

Following the procedure of Example 159(a), except substituting 1-benzyloxycarbonylamino-3-methyl-1-(3-benzyl-1,3,4-oxadiazol-2-on-5-yl)butane for 1-benzyloxycarbonylamino-3-methyl-1-(1,3,4-oxadiazol-2-on-5-yl)butane in step (a), the title compound was prepared as a solid (0.013 g, 62%). MS(ESI): 428.0 (M+H)$^+$.

d) 1-(N-benzyl)-2,2'-[N,N'-[bis-(N-benzyloxycarbonyl-L-leucinyl)]]carbohydrazide Following the procedure of Example 159(a)–159(b), except substituting 1-benzyloxycarbonylamino-3-methyl-1-(3-benzyl-1,3,4-oxadiazol-2-on-5-yl)butane for 1-benzyloxycarbonylamino-3-methyl-1-(1,3,4-oxadiazol-2-on-5-yl)butane in step (a), the title compound was prepared as white solid (13 mg, 86%). MS(ESI): 675.0 (M+H)$^+$.

Example 168

Preparation of 2-[N-(N-benzyloxycarbonyl-L-leucinyl)]-2'-[N'-(N-benzyloxycarbonyl-N-methyl-L-leucinyl)]carbohydrazide Following the procedure of Example 159(a)–159(b) except substituting N-benzyloxycarbonyl-N-methyl-L-leucine for N-acetyl-L-leucine in step (b), the title compound was prepared as a white solid (0.141 g, 53%). MS(ESI): 599.4 (M+H)$^+$.

Example 169

Preparation of N-[2-(1-naphthyl)thiazol-4-ylcarbonyl]-N'-[N-(4-pyrindinylmethoxycarbonyl)-L-leucinyl]hydrazide Following the procedure of Example 112(a)–112(g), except substituting 1-naphthyl boronic acid for 2-benzyloxyphenyl boronic acid in step (e), the title compound was prepared as a white solid (0.094 g, 58%). MS(ESI): 518.4 (M+H)$^+$.

Example 170

Preparation of N-[2-(2-biphenyl)thiazol-4-ylcarbonyl]-N'-[N-(-4-pyridinylmethoxycarbonyl)-L-leucinyl]hydrazide Following the procedure of Example 112(a)–112(g), except substituting 2-biphenylboronic acid for 2-benzyloxyphenyl boronic acid in step (e), the title compound was prepared as a white solid (0.100 g, 43%). MS(ESI): 544.3 (M+H)$^+$.

Example 171

Preparation of N-(N-benzyloxycarbonyl-N-methyl-L-leucinyl)-N'-[2-[N-(2-methylpropyl)-N-phenylamino]thiazol-4-ylcarbonyl]hydrazide Following the procedure of Example 116(a)–116(b), except substituting N-benzyloxycarbonyl-N-methyl-L- leucine for N-(4-pyridinylmethoxycarbonyl)-L-leucine in step (b), the title compound was prepared as a white solid (40 mg, 25%). MS (ESI): 552.5 (M+H)+.

Example 172

Preparation of N-[N-methyl-N-(2-pyridinylmethoxycarbonyl)-L-leucinyl]-N'-[2-[N-(2-methylpropyl)-N-phenylamino]thiazol-4-ylcarbonyl]hydrazide Following the procedure of Example 116(a)–116(b), except substituting N-methyl-N-(2-pyridinylmethoxycarbonyl)-L-leucine for N-(4-pyridinylmethoxycarbonyl)-L-leucine in step (b), the title compound was prepared as a white solid solid (70 mg, 71%). MS (ESI): 553.4 (M+H)+.

Example 173

Preparation of N-[2-(2-benzyloxyphenyl)thiazol-4-ylcarbonyl]-N'-(N-tert-butoxycarbonyl-L-leucinyl)hydrazide Following the procedure of Example 112(a)–112(g), except substituting N-tert-butoxycarbonyl-L-leucine for N-(4-pyridinylmethoxycarbonyl)-L-leucine in step (g), the title compound was prepared as a white solid (1.015 g, 94%). MS(ESI): 539.1 (M+H)+.

Example 174

Preparation of N-(N-tert-butoxycarbonyl-L-leucinyl)-N'-[2-[N-(2-methylpropyl)-N-phenylamino]thiazol-4-ylcarbonyl]hydrazide Following the procedure of Example 116(a)–116(b), except substituting N-tert-butoxycarbonyl-L-leucine for N-(4-pyridinylmethoxycarbonyl)-L-leucine in step (b), the title compound was prepared as a white solid (740 mg, 85%). MS (ESI): 504.4 (M+H)+.

Example 175

Preparation of N-(N-tert-butoxycarbonyl-N-methyl-L-leucinyl)-N'-[2-[N-(2-methylpropyl)-N-phenylamino]thiazol-4-ylcarbonyl]hydrazide Following the procedure of Example 116(a)–116(b), except substituting N-tert-butoxycarbonyl-N-methyl-L-leucine for N-(4-pyridinylmethoxycarbonyl)-L-leucine in step (b), the title compound was prepared as a white solid (610 mg, 69%). MS (ESI): 518.4 (M+H)+.

Example 176

Preparation of N-[2-(2-benzyloxyphenyl)thiazol-4-ylcarbonyl]-N'-(N-pyrazinecarbonyl-L-leucinyl)hydrazide a) N-[2-(2-benzyloxyphenyl)thiazol-4-ylcarbonyl]-N'-(L-leucinyl)hydrazide Following the procedure of Example 144(b), except substituting N-[2-(2-benzyloxyphenyl)thiazol-4-ylcarbonyl]-N'-(N-tert-butoxycarbonyl-L-leucinyl)hydrazide for (1S)-N-[2-[1-(N-tert-butoxycarbonyl-N-methylamino)-3-methylbutyl]thiazol-4-ylcarbonyl]-N'-[N-(4-pyridinylmethoxycarbonyl)-L-leucinyl]hydrazide, the title compound was prepared as a white powder (0.766 g, 93%). MS(ESI): 439.3 (M+H)+.

b) N-[2-(2-benzyloxyphenyl)thiazol-4-ylcarbonyl]-N'-[N-(2-pyrazinylcarbonyl)-L-leucinyl]hydrazide Following the procedure of Example 116(b), except substituting N-[2-(2-benzyloxyphenyl)thiazol-4-ylcarbonyl]-N'-(L-leucinyl)hydrazide for N-[2-[N-phenyl-N-(2-methyl-1-propyl)amino]thiazol-4-ylcarbonyl]hydrazide and pyrazinecarboxylic acid for N-(4-pyridinylmethoxycarbonyl)-L-leucine, the title compound was prepared as a white solid (0.146 g, 94%). MS(ESI): 545.4 (M+H)+.

Example 177

Preparation of N-[2-(2-benzyloxyphenyl)thiazol-4-ylcarbonyl]-N'-(N-isonicotinoyl-L-leucinyl)hydrazide Following the procedure of Example 176(a)–176(b), except substituting isonicotinic acid for pyrazinecarboxylic acid in step (b), the title compound was prepared as a white solid (0.135 g, 87%). MS(ESI): 544.3 (M+H)+.

Example 178

Preparation of N-[2-(2-dibenzofuranyl)thiazol-4-ylcarbonyl]-N'-[N-(4-pyridinylmetboxycarbonyl)-L-leucinyl]hydrazide Following the procedure of Example 112(a)–112(g), except substituting 2-bromodibenzofuran for 2-benzyloxybromobenzene in step (d), the title compound was prepared as a white solid (0.079 g, 49%). MS(ESI): 558.3 (M+H)+.

Example 179

Preparation of N-[2-[N-(2-methylpropyl)-N-phenylamino]thiazol-4-ylcarbonyl]-N'-(N-pyrazinecarbonyl-L-leucinyl)hydrazide Following the procedure of Example 176(a)–176(b), except substituting N-(N-tert-butoxycarbonyl-L-leucinyl)-N'-[2-[N-(2-methylpropyl)-N-phenylamino]thiazol-4-ylcarbonyl]hydrazide for N-[2-(2-benzyloxyphenyl)thiazol-4-ylcarbonyl]-N'-(N-tert-butoxycarbonyl-L-leucinyl)hydrazide in step (a), the title compound was prepared as a white solid (36 mg, 27%). MS (ESI): 510.4 (M+H)+.

Example 180

Preparation of N-[2-[N-(2-methylpropyl)-N-phenylamino]thiazol-4-ylcarbonyl]-N'-(N-methyl-N-pyrazinecarbonyl-L-leucinyl)hydrazide Following the procedure of Example 176(a)–176(b), except substituting N-(N-tert-butoxycarbonyl-N-methyl-L-leucinyl)-N'-[2-[N-(2-methylpropyl)-N-phenylamino]thiazol-4-ylcarbonyl]hydrazide for N-[2-(2-benzyloxyphenyl)thiazol-4-ylcarbonyl]-N'-(N-tert-butoxycarbonyl-L-leucinyl)hydrazide in step (a), the title compound was prepared as a white solid (70 mg, 72%). MS (ESI): 524.4 (M+H)+.

Example 181

Preparation of N-(N-isonicotinoyl-L-leucinyl)-N'-[2-[N-(2-methylpropyl)-N-phenylamino]thiazol-4-ylcarbonyl]hydrazide Following the procedure of Example 176(a)–176(b), except substituting N-(N-tert-butoxycarbonyl-N-methyl-L- leucinyl)-N'-[2-[N-(2-methylpropyl)-N-phenylamino]
thiazol-4-ylcarbonyl]hydrazide for N-[2-(2-benzyloxyphenyl)thiazol-4-ylcarbonyl]-N'-(N-tert-butoxycarbonyl-L-leucinyl)hydrazide in step (a) and isonicotinic acid for pyrazinecarboxylic aicd in step (b), the title compound was prepared as a white solid (28 mg, 22%). MS (ESI): 509.4 (M+H)+.

Example 182

Preparation of N-(N-isonicotinoyl-N-methyl-L-leucinyl)-N'-[2-[N-(2-methylpropyl)-N-phenylamino]thiazol-4-ylcarbonyl]hydrazide Following the procedure of Example 176(a)–176(b), except substituting N-(N-methyl-N-tert-butoxycarbonyl-N-methyl-L-leucinyl)-N'-[2-[N-(2-methylpropyl)-N-phenylamino]thiazol-4-ylcarbonyl]hydrazide for N-[2-(2-benzyloxyphenyl)thiazol-4-ylcarbonyl]-N'-(N-tert-butoxycarbonyl-L-leucinyl)hydrazide in step (a) and isonicotinic acid for pyrazinecarboxylic aicd in step (b), the title compound was prepared as a white solid (117 mg, 93%). MS (ESI): 523.4 (M+H)+.

Example 183

Preparation of N-[N-(4-imidazolylacetyl)-L-leucinyl]-N'-[2-[N-(2-methylpropyl)-N-phenylamino]thiazol-4-yIcarbonyl]hydrazide Following the procedure of Example 176(a)–176(b), except substituting N-(N-tert-butoxycarbonyl-N-methyl-L-leucinyl)-N'-[2-[N-(2-methylpropyl)-N-phenylamino]thiazol-4-ylcarbonyl]hydrazide for N-[2-(2-benzyloxyphenyl)thiazol-4-ylcarbonyl]-N'-(N-tert-butoxycarbonyl-L-leucinyl)hydrazide in step (a) and 4-imidazolylacetic acid for pyrazinecarboxylic aicd in step (b), the title compound was prepared as a white solid (60 mg, 53%). $^1$HNMR (400 MHz, CDCl$_3$) δ7.62-7.23 (m, 8H), 6.81 (s, 1H), 4.72-4.66 (m, 1H), 3.75 (d, 1H), 3.55 (d, 2H), 1.96-1.93 (m, 2H), 1.76-1.54 (m, 3H), 0.96-0.84 (m, 12H).

Example 184

Preparation of N-[2-[N-(2-methylpropyl)-N-phenylamino]thiazol-4-yIcarbonyl]-N'-(N-picolinoyl-L-leucinyl)hydrazide Following the procedure of Example 176(a)–176(b), except substituting N-(N-tert-butoxycarbonyl-N-methyl-L-leucinyl)-N'-[2-[N-(2-methylpropyl)-N-phenylamino]thiazol-4-ylcarbonyl]hydrazide for N-[2-(2-benzyloxyphenyl)thiazol-4-ylcarbonyl]-N'-(N-tert-butoxycarbonyl-L-leucinyl)hydrazide in step (a) and picolinic acid for pyrazinecarboxylic acid in step (b), the title compound was prepared as a white solid (50 mg, 44%). MS (ESI): 509.5 (M+H)+.

EXAMPLE 185

Preparation of N-[2-(2-benzyloxyphenyl)thiazol-4-ylcarbonyl]methyl [N-(4-pyridinylmethoxycarbonyl)-L-leucinamide a) 2-(2-benzyloxyphenyl)thiazole-4-carboxylic acid Following the procedure of Example 105(b), except substituting ethyl 2-(2-benzyloxyphenyl)thiazole-4-carboxylate for methyl 3-(4-pyridinyllmethoxy)benzoate, the title compound was prepared as a white solid (0.361 g, 90%). MS(ESI): 312.2 (M+H)+.

b) 2-(2-benzyloxyphenyl)thiazol-4-yl bromomethyl ketone

Following the procedure of Example 103(a), except substituting 2-(2-benzyloxyphenylthiazole-4-carboxylic acid for N-benzyloxycarbonyl-L-Leucinyl-L-Leucine, the title compound was prepared as a white solid (0.327 g, 73%). MS(ESI): 388.2 (M+H)+.

c) 2-(2-benzyloxyphenyl)thiazol-4-yl azidomethyl ketone

A solution of the compound of Example 185(b), (0.319 g, 0.822 mmol), sodium azide (0.064 g. 0.987 mmol), and potassium fluoride (0.072 g, 1.23 mmol) in DMF (6 mL) was stirred at room temperature for 16 h. The solution was then diluted with ethyl acetate and washed successively with water, saturated aqueous sodium hydrogen carbonate, and brine. The organic layer was dried (MgSO$_4$), filtered and concentrated. The residue was purified by column chromatography (silica gel, ethyl acetate/hexane) to yield the title compound as a white solid (0.087 g, 30%). MS(ESI): 373.3 (M+Na)+.

d) 2-azido-1-[2-(2-benzyloxyphenyl)thiazol-4-yl]-1-hydroxyethane

To a stirring solution of the compound of Example 185(c) (0.087 g, 0.249 mmol) in THF (1 mL) at 0° C., was added sodium borohydride (0.031 g, 0.820 mmol) slowly. After 20 min the mixture was diluted with ethyl acetate and washed with water then brine. The organic layer was dried (MgSO$_4$), filtered and concentrated to yield the title compound as a white solid (0.084 g, 96%). $^1$HNMR (400 MHz, CDCl$_3$) δ8.41 (m, 1H), 7.50 (m, 2H), 7.38 (m, 4H), 7.11 (m, 3H), 5.31 (s, 2H), 5.08 (t, 1H), 3.69 (m, 2H), 3.58 (s b, 1H).

e) 2-amino-1-[2-(2-benzyloxyphenyl)thiazol-4-yl]-1-hydroxyethane

To a stirring solution of the compound of Example 185(d) (0.084 g, 0.239 mmol) in methanol (2 mL) was added stannous chloride dihydrate (0.108 g, 0.478 mmol). After stirring at room temperature for 16 h, the mixture was diluted with ethyl acetate and washed successively with water, saturated aqueous NaHCO$_3$, and brine. The organic layer was dried (MgSO$_4$), filtered and concentrated. The residue was purified by column chromatography (silica gel, methanol/dichloromethane) to yield the title compound as a white solid (0.07 5 g, 96%). MS(ESI): 327.3 (M+H)+.

f) 1-[2-(2-benzyloxyphenyl)thiazol-4yl]- 1-hydroxy-2-(4-pyridinylmethoxycarbonyl-L-leucinylamino)ethane Following the procedure of Example 116(b), except substituting 2-amino-1-[2-(2-benzyloxyphenyl)thiazol-4-yl]-1-hydroxyethane for N-[2-[N-phenyl-N-(2-methyl-1-propyl)amino]thiazol-4-ylcarbonyl]hydrazide, the title compound was prepared as a white solid (0.075 g, 57%). MS(ESI): 575.4 (M+H)+.

g) N-[2-(2-benzyloxyphenyl)thiazol-4-ylcarbonyl]methyl [N-4-pyridinylmethoxycarbonyl)-L-leucinamide To a stirring solution of the compound of Example 185(f) (0.075 g, 0.131 mmol) in dichloromethane (1 mL) was added MnO$_2$ (0.300 g, 3.45 mmol). After stirring at room temperature for 24 h, the mixture was filtered and the filtrate was concentrated. The residue was purified by column chromatography (silica gel, methanol/dichloromethane) to yield the title compound as a pale yellow solid (0.017 g, 23%). MS(ESI): 573.4 (M+H)+.

Example 186

Preparation of N-[2-[N-methyl-N-(2-methylpropyl) amino]thiazol-4-ylcarbonyl]-N'-[N-(4-pyridinylmethoxycarbonyl)-L-leucinyl]hydrazide a) N-benzoyl-N'-methyl-N'-(2-methylpropyl)thiourea To a stirring solution of N-methylisobutylamine (3.21 g, 36.8 mmol, 4.45 mL) in 40 mL of $CHCl_3$ was added benzoyl isothiocyanate (6.0 g, 36.8 mmol, 4.95 mL). After stirring for 45 min, the solution was concentrated to yield the title compound as a pale yellow solid (9.22 g, 100%). $^1$HNMR (400 MHz, $CDCl_3$; 2:1 mixture of rotamers) δ7.86 (d, 2H), 7.60 (t, 1H), 7.50 (t, 2H), 3.90 (d, 2H), 3.44 (s, 3H), 3.41 (d, 2H), 3.27 (s, 3H), 2.35-2.32 (m, 1H), 2.13 (m, 1H), 1.06 (d, 6H), 0.90 (d, 6H).

b) N-methyl-N-(2-methylpropyl)thiourea

The compound of Example 186(a) (9.22 g, 36.8 mmol) was suspended in 80 mL of 1:1 methanol/water and solid potassium carbonate (15.27 g, 110 mmol) was added. The mixture was heated at reflux for 48 h, then cooled and partitioned between ethyl acetate and water. The aqueous layer was extracted with ethyl acetate (2×). The combined organic layers were washed with saturated brine, dried ($MgSO_4$), filtered and concentrated to provide the title compound as a pale yellow crystalline solid (4.82 g, 89%). MS(ESI): 147.0 $(M+H)^+$.

c) N-[2-[N-methyl-N-(2-methylpropyl)amino]thiazol-4-ylcarhonyl]-N'-[N-(4-pyridinylmethoxycarbonyl)-L-leucinyl]hydrazide Following the procedure of Example 113(d)–113(f), except substituting N-methyl-N-(2-methylpropyl)thiourea for N-(4-phenylphenyl)-N-(2-methyl-1-propyl)thiourea in step (d), the title compound was prepared as a white solid (202 mg, 97%). MS(ESI): 477.4 $(M+H)^+$.

Example 187

Preparation of N-(N-methyl-N-picolinoyl-L-leucinyl)-N'-[2-[N-(2-methylpropyl)-N-phenylamino]thiazol-4-ylcarbonyl]hydrazide Following the procedure of Example 176(a)–176(b), except substituting N-(N-methyl-N-tert-butoxycarbonyl-N-methyl-L-leucinyl)-N'-[2-[N-(2-methylpropyl)-N-phenylamino]thiazol-4-ylcarbonyl]hydrazide for N-[2-(2-benzyloxyphenyl)thiazol-4-ylcarbonyl]-N'-(N-tert-butoxycarbonyl-L-leucinyl)hydrazide in step (a) and picolinic acid for pyrazinecarboxylic acid in step (b), the title compound was prepared as a white solid (30 mg, 41%). MS (ESI): 523.5 $(M+H)^+$.

Example 188

Preparation of N-[2-(2-benzyloxyphenyl)thiazol-4-ylcarbonyl]-N'-[N-(2-pyridinesulfonyl)-L-leucinyl]hydrazide a) 2-pyridinesulfonylchloride Through a stirring solution of 2-mercaptopyridine (2.235 g, 20 mmol) in water (7.5 mL) and concentrated HCl (26 mL) at 0° C. was bubbled $Cl_2$. After 30 min, 75 mL of ice water was added and extracted with cold ether (2×75 mL). The organic layers were combined and washed successively with cold 10% aqueous $NaHCO_3$, and cold brine. The organic layer was dried ($MgSO_4$), filtered and concentrated to yield the title compound as a clear oil. (3.1 g, 87%).

b) N-[2-(2-benzyloxyphenyl)thiazol-4-ylcarbonyl]-N'-[N-(2-pyridinesulfonyl)-L-leucinyl]hydrazide To a stirring solution of the compound of Example 176(a) (0.125 g, 0.285 mmol), and the compound of Example 188(a) (0.101 g, 0.571 mmol) in dichloromethane (2 mL) was added N-methylmorpholine (0.057 g, 0.571 mmol). After stirring at room temperature for 10 min the solution was diluted with ethyl acetate and washed successively with water and brine. The organic layer was dried ($MgSO_4$), filtered and concentrated. The residue was purified by column chromatography (silica gel, ethyl acetate/hexane) to yield the title compound as a pale yellow solid (0.100 g, 61%). MS(ESI): 580.2 $(M+H)^+$.

Example 189

Preparation of N-[2-N -(2-methylpropyl)-N-phenylamino]thiazol-4-ylcarbonyl]-N'-[N-(2-pyridinesulfonyl)-L-leucinyl]hydrazide Following the procedure of Example 188(b), except substituting N-(L-leucinyl)-N'-[2-[N-(2-methylpropyl)-N-phenylamino]thiazol-4-ylcarbonyl]hydrazide for N-[2-(2-benzyloxyphenyl)thiazol-4-ylcarbonyl]-N'-(L-leucinyl) hydrazide, the title compound was prepared as an orange solid (56 mg, 48%). MS (ESI): 545.3 $(M+H)^+$.

Example 190

Preparation of N-[2-[N-(2-methylpropyl)-N-phenylamino]thiazol-4-ylcarbonyl]-N'-[N-methyl-N-(2-pyridinesulfonyl)-L-leucinyl]hydrazide Following the procedure of Example 188(b), except substituting N-(N-methyl-L-leucinyl)-N'-[2-[N-(2-methylpropyl)-N-phenylamino]thiazol-4-ylcarbonyl]hydrazide for N-[2-(2-benzyloxyphenyl)thiazol-4-ylcarbonyl]-N'-(L-leucinyl)hydrazide, the title compound was prepared as an orange solid (53 mg, 40%). MS (ESI): 559.3 $(M+H)^+$.

Example 191

Preparation of N-[2-[N-methyl-N-(2-methylpropyl) amino]thiazol-4-ylcarbonyl]-N'-[N-(3-pyrindinylmethoxycarbonyl)-L-leucinyl]hydrazide Following the procedure of Example 186(a)–186(c), except substituting N-(3-pyridinylmethoxycarbonyl)-L-leucine for N-(4-pyridinylmetboxycarbonyl)-L-leucine in step (c), the title compound was prepared as a white solid (138 mg, 66%). MS (ESI): 477.4 $(M+H)^+$.

Example 192

Preparation of N-[2-[N-(2-methylpropyl)-N-phenylamino]thiazol-4-ylcarbonyl]-N'-[N-methyl-N-(4-pyridinylmethoxycarbonyl)-L-leucinyl]hydrazide Following the procedure of Example 116(a)–116(b), except substituting N-methyl-N-(4-pyridinylmethoxycarbonyl)-L-leucine for N-(4-pyridinylmethoxycarbonyl)-L-leucine in step (b), the title compound was prepared as a white solid solid (74 mg, 41%). MS (ESI): 553.4 $(M+H)^+$.

Example 193

Preparation of N-[2-[N-(2-methylpropyl)-N-phenylamino]thiazol-4-ylcarbonyl-N'-[N-methyl-N-(3-pyrindinylmethoxycarbonyl)-L-leucinyl] hydrazide Following the procedure of Example 116(a)–116(b), except substituting N-methyl-N-(3- pyridinylmethoxycarbonyl)-L-leucine for N-(4-pyridinylmethoxycarbonyl)-L-leucine in step (b), the title compound was prepared as a white solid solid (50 mg, 38%). MS (ESI): 553.4 (M+H)$^+$.

Example 194

Preparation of N-[2-(2-benzyloxyphenyl)thiazol-4-ylcarbonyl]-N'-[N-methyl-N-(3-pyridinylmethoxycarbonyl)-L-leucinyl]hydrazide Following the procedure of Example 112(a)–112(g), except substituting N-methyl-N-(4-pyridinylmethoxycarbonyl)-L-leucine for N-(4-pyridinylmethoxycarbonyl)-L-leucine in step (g), the title compound was prepared as a white solid (0.028 g, 15%). MS(ESI): 588.4 (M+H)$^+$.

Example 195

Preparation of N-[N-methyl-N-(4-pyridinylmethoxycarbonyl)-L-leucinyl]-N'-[2-(1-naphthyl)thiazol-4-ylcarbonyl]hydrazide Following the procedure of Example 112(a)–112(g), except substituting 1-naphthyl boronic acid for 2-benzyloxyphenyl boronic acid in step (e) and N-methyl-N-(4-pyridinylmethoxycarbonyl)-L-leucine for N-(4-pyridinylmethoxycarbonyl)-L-leucine in step (g), the title compound was prepared as a white solid (0.072 g, 36%). MS(ESI): 532.4 (M+H)$^+$.

Example 196

Preparation of N-[2-[N,N-(bis)-2-methylpropyl)amino]thiazol-4-ylcarbonyl]-N'-[N-(4-pyridinylmethoxycarbonyl)-L-leucinyl]hydrazide Following the procedure of Example 186(a)–186(c), except substituting N,N-diisobutylamine for N-methylisobutylamine in step (a), the title compound was prepared as a yellow solid (60 mg, 39%). MS (ESI): 519.5 (M+H)$^+$.

Example 197

Preparation of N-(N-benzyloxycarbonyl-L-leucinyl)-N'-[2-N,N-(bis)-2-methylpropyl)amino]thiazol-4-ylcarbonyl]hydrazide Following the procedure of Example 186(a)–186(c), except substituting N,N-diisobutylamine for N-methylisobutylamine in step (a) and N-benzyloxycarbonyl-L-leucine for N-(4-pyridinylmethoxycarbonyl)-L-leucine in the final step, the title compound was prepared as a yellow solid (131 mg, 69%). MS (ESI): 518.4 (M+H)$^+$.

Example 198

Preparation of N-[2-(4-morpholino)thiazol-4-ylcarbonyl]-N'-[N-4-pyridinylmethoxycarbonyl)-L-leucinyl]hydrazide Following the procedure of Example 186(a)–186(c), except substituting morpholine for N-methylisobutylamine in step (a), the title compound was prepared as a white solid (45 mg, 31%). MS (ESI): 477.3 (M+H)$^+$.

Example 199

Preparation of N-[2-[2-4-pyridinylmethoxy)phenyl]thiazol-4-ylcarbonyl]-N'-[N-(4-pyridinylmethoxycarbonyl)-L-leucinyl]hydrazide a) 2-methoxymethoxybromobenzene To a stirring suspension of sodium hydride (1.2 g, 52.1 mmol, 60% dispersion in mineral oil) in DMF (75 mL) at 0° C. was added 2-bromophenol (6.0 g, 34.7 mmol) dropwise. After stirring for 20 min, bromomethyl methyl ether (4.3 g, 34.7 mmol) was added. After stirring for 16 h at room temperature, the mixture was poured into water (250 mL) and extracted with hexane. The organic layer was washed with brine, dried (MgSO$_4$), filtered and concentrated. The residue was purified by column chromatography (silica gel, hexane) to yield the title compound as a colorless oil (4.0 g, 53%). $^1$HNMR (400 MHz, CDCl$_3$) δ7.55 (d, 1H), 7.28 (t, 1H), 7.16 (d, 1H), 6.91 (t, 1H), 5.25 (s, 2H), 3.54 (s, 3H).

b) ethyl 2-(2-methoxymethoxyphenyl)thiazole-4-carboxylate

Following the procedure of Example 112(a)–112(b) and 112(d)–112(e), except substituting 2-methoxymethoxybromobenzene for 2-benzyloxybromobenzene in step (d), the title compound was prepared. MS(ESI): 294.3 (M+H)$^+$.

c) ethyl 2-(2-hydroxyphenyl)thiazole-4-carboxylate

To a stirring solution of the compound of Example 199(b) (0.839 g, 2.86 mmol) in ethanol (25 mL) was added 10 drops of concentrated hydrochloric acid. After stirring at reflux for 2 h the solution was concentrated then redissolved in ethyl acetate. The solution was washed successively with saturated sodium bicarbonate, and brine, dried (MgSO$_4$), filtered and concentrated to yield the title compound as a pale yellow solid (0.674 g, 95%). MS(ESI): 250.2 (M+H)$^+$.

d) ethyl 2-[2-(4-pyridylmethoxy)phenyl]thiazole-4-carboxylate

To a stirring solution of the compound of Example 199(c) (0.125 g, 0.502 mmol), 4-pyridylcarbinol (0.071 g, 0.653 mmol), and triphenylphosphine (0.171 g, 0.653 mmol) in THF (5 mL) at 0° C. was added diisopropyl azodicarboxylate (0.132 g, 0.653 mmol) dropwise. After stirring at room temperature for 16 h, the solution was concentrated and purified by column chromatography (silica gel, ethyl acetate/hexane) to yield the title compound as a white solid (0.100 g, 59%). MS(ESI): 341.3 (M+H)$^+$.

e) N-[2-[2-(4-pyridinylmethoxy)phenyl]thiazol-4-ylcarbonyl]-N'-[N-(4-pyridinylmethoxycarbonyl)-L-leucinyl]hydrazide Following the procedure of Example 112(f)–112(g), except substituting ethyl 2-[2-(4-pyridylmethoxy)phenyl]thiazole-4-carboxylate for ethyl 2-(2-benzyloxyphenyl)thiazole-4-carboxylate in step (f), the title compound was prepared as a white solid (146 mg, 83%). MS(ESI): 575.4 (M+H)$^+$.

Example 200

Preparation of N-[2-(2-naphthyl)thiazol-4-ylcarbonyl]-N'-[N-(4-pyridinylmethoxycarbonyl)-L-leucinyl]hydrazide Following the procedure of Example 112(a)–112(g), except substituting 2-naphthylboronic acid for 2-benzyloxyphenyl boronic acid in step (e), the title compound was prepared as a white solid (226 mg, 75%). MS (ESI): 518.4 (M+H)$^+$.

Example 201

Preparation of N-[2-[N,N-(bis)-2-methylpropyl)amino]thiazol-4-ylcarbonyl]-N'-[N-methyl-N-(4-pyridinylmethoxycarbonyl)-L-leucinyl]hydrazide Following the procedure of Example 186(a)–186(c), except substituting N,N-diisobutylamine for N-methylisobutylamine in step (a) and N-methyl-N-(4-pyridinylmethoxycarbonyl)-L-leucine for N-(4-pyridinylmethoxycarbonyl)-L-leucine in the final step, the title compound was prepared as a yellow solid (30 mg, 25%). MS (ESI): 533.3 (M+H)$^+$.

Example 202

Preparation of N-(N-benzyloxycarbonyl-L-leucinyl)-N'-[2-(4-morpholino)thiazol-4-ylcarbonyl]hydrazide Following the procedure of Example 186(a)–186(c), except substituting morpholine for N-methylisobutylamine in step (a) and N-benzyloxycarbonyl-L-leucine for N-(4-pyridinylmethoxycarbonyl)-L-leucine in the final step, the title compound was prepared as a white solid (115 mg, 67%). MS (ESI): 576.4 (M+H)$^+$.

Example 203

Preparation of N-[-(4-pyridinylmethoxycarbonyl)-L-leucinyl]-N'-[2-(4-thiomorpholino)thiazol-4-ylcarbonyl]hydrazide Following the procedure of Example 186(a)–186(c), except substituting thiomorpholine for N-methylisobutylamine in step (a), the title compound was prepared as a white solid (35 mg, 20%). MS (ESI): 493.4 (M+H)$^+$.

Example 204

Preparation of N-(N-benzyloxycarbonyl-L-leucinyl)-N'-[2-(4-thiomorpholino)thiazol-4-ylcarbonyl]hydrazide Following the procedure of Example 186(a)–186(c), except substituting thiomorpholine for N-methylisobutylamine in step (a) and N-benzyloxycarbonyl-L-leucine for N-(4-pyridinylmethoxycarbonyl)-L-leucine in the final step, the title compound was prepared as a white solid (20 mg, 20%). MS (ESI): 492.3 (M+H)$^+$.

Example 205

Preparation of N-[2-(2,3-ethylenedioxy-4-methoxyphenyl)thiazol-4-ylcarbonyl]-N'-[N-(4-pyridinylmethoxycarbonyl)-L-leucinyl]hydrazide Following the procedure of Example 112(a)–112(g), except substituting 2,3-ethylenedioxy-4-methoxybromobenzene for 2-benzyloxybromobenzene in step (d), the title compound was prepared as a white solid (31 mg, 26%). MS (ESI): 556.4 (M+H)$^+$.

Example 206

Preparation of N-[2-[N,N-(bis)-2-methylpropyl)amino]thiazol-4-ylcarbonyl]-N'-[N-methyl-N-(3-pyridinylmethoxycarbonyl)-L-leucinyl]hydrazide Following the procedure of Example 186(a)–186(c), except substituting N,N-diisobutylamine for N-methylisobutylamine in step (a) and N-methyl-N-(3-pyridinylmethoxycarbonyl)-L-leucine for N-(4-pyridinylmethoxycarbonyl)-L-leucine in the final step, the title compound was prepared as a yellow solid (30 mg, 30%). MS (ESI): 533.5 (M+H)$^+$.

Example 207

Preparation of N-[2-(N-cyclopropylmethyl-N-propylamino)thiazol-4-ylcarbonyl]-N'-[N-(4-pyridinylmethoxycarbonyl)-L-leucinyl]hydrazide Following the procedure of Example 186(a)–186(c), except substituting N-cyclopropylmethylpropylamine for N-methylisobutylamine in step (a), the title compound was prepared as a yellow solid (60 mg, 23%). MS (ESI): 503.3 (M+H)$^+$.

Example 208

Preparation of N-[N-(pyridinylmethoxycarbonyl)-L-leucinyl]-N'-[2-(8-quinolyl)thiazol-4-ylcarbonyl]hydrazide Following the procedure of Example 112(a)–112(g), except substituting 8-bromoquinoline for 2-benzyloxybromobenzene in step (d), the title compound was prepared as a white solid (134 mg, 56%). MS (ESI): 519.3 (M+H)$^+$.

Example 209

Preparation of N-[N-methyl-N-(4-pyrindinylmethoxycarbonyl)-L-leucinyl]-N'-[2-(8-quinolyl)thiazol-4-ylcarbonyl]hydrazide Following the procedure of Example 112(a)–112(g), except substituting 8-bromoquinoline for 2-benzyloxybromobenzene in step (d) and N-methyl-N-(4-pyridinylmethoxycarbonyl)-L-leucine for N-(4-pyridinylmethoxycarbonyl)-L-leucine in step (g), the title compound was prepared as a white solid (53 mg, 22%). MS (ESI): 533.3 (M+H)$^+$.

Example 210

Preparation of 1-N-(N-Cbz-leucinyl)-amino-3-N-(4-biphenyl-sulfonyl)-amino-propan-2-one a) 4-biphenyl sulfonyl chloride 4-Biphenyl sulfonic acid (2.4 g, 10 mmol) was heated to 100 C. with phosphorus pentachoride (2.1 g, 10 mmol) overnight. The reaction was cooled to RT, diluted with water, filtered and washed with water. The solid was then triturated with EtOAc-ether and the beige solid was used in the next reaction without further purification.

b) 1-N-(N-Cbz-leucinyl)-amino-3-N-(4-biphenyl-sulfonyl)-amino-propan-2-one

Following the procedure of Example 51(a), except substituting "4-biphenyl sulfonyl chloride" for "4-(3-Chloro-2-cyano-phenoxy)-phenyl sulfonyl chloride", the title compound was prepared: MS(ES) M-H$^+$=550.

Example 211

Preparation of 1-N-(N-Cbz-leucinyl)-amino-3-N-(3-biphenyl-sulfonyl)-amino-propan-2-one a) 3-biphenyl-sulfonyl chloride 3-Biphenyl bromide (9.3 g, 40 mmol) was dissolved in THF (40 ml) and a Grignard reagent was prepared in standard fashion with magnesium powder (1.2 g, 50 mmol). The reaction was cannulated into a solution of sulfuryl chloride (10.5 g, 6.4 ml, 80 mmol) in hexanes (25 ml) and was stirred at RT for 2h. The reaction was quenched with ice-water, extracted with ether, dried with magnesium sulfate, filtered, concentrated, and was used in the next reaction without further purification.

b) 1-N-(N-Cbz-leucinyl)-amino-3-N-(3-biphenyl-sulfonyl)-amino-propan-2-one

Following the procedure of Example 51(a), except substituting "3-biphenyl sulfonyl chloride" for "4-(3-Chloro-2-cyano-phenoxy)-phenyl sulfonyl chloride", the title compound was prepared: MS(ES) M–H$^+$=550.

Example 212

Preparation of 1-N-(N-Cbz-leucinyl)-amino-3-N-(2-benzyloxy-phenyl-sulfonyl)-amino-propan-2-one a) 2-benzyloxy-phenyl-sulfonyl chloride Following the procedure of Example 211(a), except substituting "2-benzyloxy-phenyl bromide" for "3-biphenyl bromide", the title compound was prepared and was used in the next step without further purification.

b) 1-N-(N-Cbz-leucinyl)-amino-3-N-(2-benzyloxy-phenyl-sulfonyl)-amino-propan-2-one Following the procedure of Example 51(a), except substituting "2-benzyloxy phenyl sulfonyl chloride" for "4-(3-Chloro-2-cyano-phenoxy)-phenyl sulfonyl chloride", the title compound was prepared: MS(ES) M+H$^+$=581, M+Na$^+$=604, 2M+Na$^+$=1185.

Example 213

Preparation of 1-N-(N-Cbz-leucinyl)-amino-3-N-(4-phenoxy-phenyl-sulfonyl)-amino-propan-2-one a) 4-phenoxy-phenyl-sulfonyl chloride Following the procedure of Example 211(a), except substituting "4-phenoxy phenyl bromide" for "3-biphenyl bromide", the title compound was prepared and was used in the next step without further purification.

b) 1-N-(N-Cbz-leucinyl)-amino3-N-(4-phenoxy-phenyl-sulfonyl)-amino-propan-2-one

Following the procedure of Example 51(a), except substituting "4-phenoxy-phenyl-sulfonyl chloride" for "4-(3-Chloro-2-cyano-phenoxy)-phenyl sulfonyl chloride", the title compound was prepared: MS(ES) M+H$^+$=568, M+Na$^+$=590.

Example 214

Preparation of 1-N-(N-Cbz-leucinyl)-amino-3-N-(2-dibenzofuran-sulfonyl)-amino-propan-2-one a) 4phenoxy-phenyl-sulfonyl chloride Following the procedure of Example 210 (a), except substituting "2-dibenzofuran-sulfonic acid" for "4-biphenyl-sulfonic acid", the title compound was prepared and was used in the next step without further purification.

b) 1-N-(N-Cbz-leucinyl)-amino-3-N-(2-dibenzofuran-sulfonyl)-amino-propan-2-one

Following the procedure of Example 51(a), except substituting "4-phenoxy phenyl sulfonyl chloride" for "4-(3-Chloro-2-cyano-phenoxy)-phenyl sulfonyl chloride", the title compound was prepared: MS(ES) M+H$^+$=566, M+Na$^+$=588.

Example 215

Preparation of 1-N-(N-Cbz-Ieucinyl)-amino-3-N-(3,4-dimethoxy-phenyl-sulfonyl)-amino-propan-2-one Following the procedure of Example 51, except substituting "3,4-dimethoxy-phenyl-sulfonyl chloride" for "4-(3-Chloro-2-cyano-phenoxy)-phenyl sulfonyl chloride", the title compound was prepared: MS(ES) M+H$^+$=536, M+NH$_4^+$=553.

Example 216

Preparation of 1-N-(N-Cbz-leucinyl)-amino-3-N-(2,5-dichlorothiophene-3-sulfonyl)-amino-propan-2-one Following the procedure of Example 51, except substituting "2,5-dichlorothiophene-3-sulfonyl chloride" for "4-(3-Chloro-2-cyano-phenoxy)-phenyl sulfonyl chloride", the title compound was prepared: MS(ES) M+NH$_4^+$=567, 2M+H$^+$=1101.

Example 217

Preparation of 1-N-(N-Cbz-leucinyl)-amino-3-N-(phenyl-sulfone-5-thiophene-2-sulfonyl)-amino-propan-2-one Following the procedure of Example 51, except substituting "phenyl sulfone-5-thiophene-2-sulfonyl chloride" for "4-(3-Chloro-2-cyano-phenoxy)-phenyl sulfonyl chloride", the title compound was prepared: MS(ES) M+H$^+$=622.

Example 218

Preparation of 1-N-(N-Cbz-leucinyl)-amino-3-N-(8-quinoline-sulfonyl)-amino-propan-2-one Following the procedure of Example 51, except substituting "8-quinoline-sulfonyl chloride" for "4-(3-Chloro-2-cyano-phenoxy)-phenyl sulfonyl chloride", the title compound was prepared: MS(ES) M+H$^+$=527.

Example 219

Preparation of 1-N-(N-Cbz-leucinyl)-amino-3-N-(2-pyridyl-sulfonyl)-amino-propan-2-one Following the procedure of Example 51, except substituting "2-pyridyl-sulfonyl chloride" (as described in *J. Org. Chem.* 1989, 54, 392) for "4(3-Chloro-2-cyano-phenoxy)-phenyl sulfonyl chloride", the title compound was prepared: MS(ES) M+H$^+$=477, M+Na$^+$=499.

Example 220

Preparation of 1-N-(N-Cbz-leucinyl)-amino-3-N-(2-pyridyl-sulfonyl)-amino-propan-2-one a) 1-N-(N-Cbz-leucinyl)-amino-3-N-(4-phenoxy-phenyl-sulfonyl)-amino-propan-2-ol 1,3-Diamino propan-2-ol (6.75 g, 75 mmol) was dissolved in DMF (100 mi) and Cbz-leucine (20 g, 75.5 mmol), HOBT-hydrate (11 g, 81.5 mmol), and EDCI (15.5 g, 81.2 mmol) were added. The reaction was stirred overnight at RT. A portion of the reaction mixture (30 ml) was concentrated in vacuo, then ether (50 ml) and MeOH (30 ml) were added. A 1N solution of hydrochloric acid in ether was added (1 M, 30 ml) and a white gum formed, which was washed several times with ether. MeOH-acetone were added and heated until the gum became a white solid. The white solid was dissolved in DMF (25 ml) and DIEA (5 ml), then 4-phenoxy phenyl sulfonyl chloride was added. The reaction was stirred for 2h, concentrated in vacuo, then chromatographed (silica gel, 1:1 EtOAc: hexanes) to provide the desired product as a white solid.

b) Leucinyl-amino-3-N-(4-phenoxy phenyl sulfonyl)-amino-propan-2-ol

1-N-(Cbz-leucinyl)-amino-3-N-(4-phenoxy-phenyl-sulfonyl)-amino-propan-2-ol (1.0 g, 1.8 mmol) was dissolved in EtOH (30 ml), then 10% Pd/C (0.22 g) was added followed by 6N hydrochloric acid (2.5 ml), and the reaction was stirred under a baloon of hydrogen gas for 4h at RT. The reaction mixture was filtered, concentrated, and azeotroped with toluene to provide a white glass which was used in the next reaction without further purification.

c) 1-N-(N-4-pyridyl acetyl-leucinyl)-amino-3-N-(4-phenoxy-phenyl-sulfonyl)-amino-propan-2-ol Leucinyl-amino-3-N-(4-phenoxy phenyl sulfonyl)-amino-propan-2-ol (0.36 g, 0.76 mmol) was dissolved in DMF (5 ml), then NMM (0.45 ml, 4 mmol) was added followed by 4-pyridyl acetic acid (0.13 g, 0.75 mmol) and HBTU (0.29 g, 0.76 mmol) and the reaction was stirred at RT overnight. The reaction mixture was concentrated in vacuo, then chromatographed (silica gel, 5% MeOH: methylene chloride) to provide the desired product as a white solid (90 mg, MS(ES): M+H$^+$=555.

d) 1-N-(N-4-pyridyl acetyl-leucinyl)-amino-3-N-(4-phenoxy-phenyl-sulfonyl)-amino-propan-2-one 1-N-(N-4-pyridyl-acetyl-leucinyl)-amino3-N-(4-phenoxy-phenyl-sulfonyl)-amino-propan-2-ol (45 mg, 0.08 mmol) was dissolved in acetone (5 ml), then 1N hydrochloric acid (2 ml) was added. The reaction was concentrated in vacuo, then redissolved in acetone. Jones reagent (1.5 M, several drops) was added and the reaction mixture was stirred for 6h at RT. Isopropanol (0.5 ml) was added and the reaction mixture was concentrated in vacuo. The reaction was diluted with pH 7 buffer and then was extracted with EtOAc, dried with magnesium sulfate, filtered, concentrated in vacuo, then chromatographed (silica gel, 5% MeOH-methylene chloride) to give the desired product as a white solid (27 mg, 50%): MS(ES): M+H$^+$=553.

Example 221

Preparation of 1-N-(N-2-pyridyl-sulfonyl-leucinyl)-amino-3-N-(4-phenoxy-phenyl-sulfonyl)-amino-propan-2-one Following the procedure of Example 220(a)–(d), except substituting "2-pyridyl-sulfonyl chloride" (as described in *J. Org. Chem.* 1989, 54, 392) for "4-pyridyl-acetic acid and HBTU", the title compound was prepared: MS(ES) M+H$^+$=475, M+Na$^+$=497, 2M+Na$^+$=1171.

Example 222

Preparation of 1-N-(N-morpholino-carbonyl-leucinyl)-amino-3-N-(4-phenoxy-phenyl-sulfonyl)-amino-propan-2-one Following the procedure of Example 220(a)–(d), except substituting "N-morpholino-carbonyl chloride" for "4-pyridyl acetic acid and HBTU", the title compound was prepared: MS(ES) M+H$^+$=547, M+Na$^+$=569, 2M+Na$^+$=1115.

Example 223

Preparation of 1-N-(N-4-pyridyl-carbonyl-leucinyl)-amino-3-N-(4-phenoxy-phenyl-sulfonyl)-amino-propan-2-one Following the procedure of Example 220(a)–(d), except substituting "4-pyridyl-carboxylic acid" for "4-pyridyl acetic acid", the title compound was prepared: MS(ES) M+H$^+$=539.

Example 224

Preparation of 1-N-(N-acetyl-leucinyl)-amino-3-N-(4-phenoxy-phenyl-sulfonyl)-amino-propan-2-one Following the procedure of Example 220(a)–(d), except substituting "acetyl chloride" for "4-pyridyl-acetic acid and HBTU", the title compound was prepared: MS(ES) M+H$^+$=476, M+Na$^+$=498, 2M+Na$^+$=973.

Example 225

Preparation of 1-N-(N-imidazole acetyl-leucinyl)-amino-3-N-(4-phenoxy-phenyl-sulfonyl)-amino-propan-2-one Following the procedure of Example 220(a)–(d), except substituting "imidazole acetic acid" for "4-pyridyl acetic acid", the title compound was prepared: MS(ES) M+H$^+$=542.

Example 226

Preparation of 1-N-(N-4-carboxymethyl benzoyl-leucinyl)-amino-3-N-(4-phenoxy-phenyl-sulfonyl)-amino-propan-2-one Following the procedure of Example 220(a)–(d), except substituting "4-carboxymethyl benzoic acid" for "4-pyridyl acetic acid", the title compound was prepared: MS(ES) M+H$^+$=596, M+Na$^+$=618, 2M+Na$^+$=1213.

Example 227

Preparation of 1-N-(N-(N,N-dimethyl glycinyl)-leucinyl)-amino-3-N-(4-phenoxy-phenyl-sulfonyl)-amino-propan-2-one Following the procedure of Example 220(a)–(d), except substituting "N,N-dimethyl glycine" for "4-pyridyl acetic acid", the title compound was prepared: MS(ES) M+H$^+$=519.

Example 228

Preparation of 1-N-(N-8-quinoline-sulfonamide-leucinyl)-amino-3-N-(4-phenoxy-phenyl-sulfonyl)-amino-propan-2-one Following the procedure of Example 220(a)–(d), except substituting "8-quinoline sulfonyl chloride" for "4pyridyl-acetic acid and HBTU", the title compound was prepared: MS(ES) M+H$^+$=625.

Example 229

Preparation of 1-N-(N-Cbz-leucinyl)-amino-3-N-(8-quinoline-carbonyl)-amino-propan-2-one 1,3-Diamino propan-2-ol (6.75 g, 75 mmol) was dissolved in DMF (100 ml) and Cbz-leucine (20 g, 75.5 mmol), HOBT-hydrate (11 g, 81.5 mmol), and EDCI (15.5 g, 81.2 mmol) was added. The reaction was stirred overnight at RT. A portion of the reaction mixture (30 ml) was concentrated in vacuo, then ether (50 ml) and MeOH (30 ml) were added. A 1N solution of hydrochloric acid in ether was added (1 M, 30 ml) and a white gum formed, which was washed several times with ether. MeOH-acetone were added and heated until the gum became a white solid. The white solid (0.44 g, 1.1 mmol) was dissolved in DMF (3 ml) and NMM (0.33 ml, 0.3 mmol), then 8-quinoline carboxylic acid (0.17 g, 1.0 mmol), and HBTU (0.38 g, 1.0 mmol) were added and the reaction was stirred at RT overnight. The reaction mixture was concentrated in vacuo, then chromatographed (silica gel, 7:2 EtOAc: hexanes). The solid was then dissolved in acetone (5 ml), then 1N hydrochloric acid (2 ml) was added. The reaction was concentrated in vacuo, then redissolved in acetone. Jones reagent (1.5 M, several drops) was added and the reaction mixture was stirred for 6h at RT. Isopropanol (0.5 ml) was added and the reaction mixture was concentrated in vacuo. The reaction was diluted with pH 7 buffer and then was extracted with EtOAc, dried with magnesium sulfate, filtered, concentrated in vacuo, then chromatographed (silica gel, 5% MeOH-methylene chloride) to give the desired product as a white solid (23 mg, 41%): MS(S): M+H$^+$=491.

Example 230

Preparation of 1-N-(N-Cbz-leucinyl)-amino-3-N-(6-quinoline-carbonyl)-amino-propan-2-one Following the procedure of Example 229, except substituting "6-quinoline-carboxylic acid" for "8-quinoline carboxylic acid", the title compound was prepared: MS(ES) M+H$^+$=491.

Example 231

Preparation of 1-N-(N-Cbz-leucinyl)-amino-3-N-(2-(4-biphenyl)-4-methyl-propanamide)-propan-2-one Following the procedure of Example 229, except substituting "2-isobutyl4-biphenyl acetic acid" for "8-quinoline carboxylic acid", the title compound was prepared: MS(ES) M+H$^+$=586, M+Na$^+$=608, 2M+Na$^+$=1193.

Example 232

Preparation of 1-N-(N-Cbz-leucinyl)-amino-3-N-(N-4-pyridyl-methyleneoxy carbonyl-leucinyl)-amino-propan-2-one Following the procedure of Example 229, except substituting "4-pyridyl methyleneoxy carbonyl leucine" for "8-quinoline-carboxylic acid", the title compound was prepared: MS(ES) M+H$^+$=584.

Example 233

Preparation of 1-N-(N-Cbz-leucinyl)-amino-3-N-(benzoyl)-amino-propan-2-one

Following the procedure of Example 229, except substituting "benzoyl chloride" for "8-quinoline carboxylic acid and HBTU", the title compound was prepared: MS(ES) M+H$^+$=440, M+Na$^+$=462, 2M+Na$^+$=901.

Example 234

Preparation of 1-N-(N-Cbz-leucinyl)-amino-3-N-(2.4-dimethyl-3-sulfonyl)-amino-propan-2-one Following the procedure of Example 51, except substituting "2,4-dimethyl-3-sulfonyl chloride" for "4-(3-Chloro-2-cyano-phenoxy)-phenyl sulfonyl chloride", the title compound was prepared: MS(ES) M+H$^+$=494.

Example 235

Preparation of 1-N-(N-Cbz-leucinyl)-amino-3-N-(1,3-dimethyl-5-chloro-pyrazole-4-sulfonyl)-amino-propan-2-one Following the procedure of Example 51, except substituting "1,3-dimethyl-5-chloro-pyrazole-4-sulfonyl chloride" for "4-(3-Chloro-2-cyano-phenoxy)-phenyl sulfonyl chloride", the title compound was prepared: MS(ES) M+H$^+$=494.

Example 236

Preparation of 1-N-(N-4-pyridyl-methyleneoxy carbonyl-leucinyl)-amino-3-N-(4-phenoxy-phenyl-sulfonyl)-amino-propan-2-one Following the procedure of Example 213(a), except substituting "4-pyridyl-methyleneoxy carbonyl-leucine" for "Cbz-leucine", the title compound was prepared: MS(ES) M+H$^+$=569.

Example 237

Preparation of 1-N-(N-3-pyridyl-methyleneoxy carbonyl-leucinyl)-amino-3-N-(4-phenoxy-phenyl-sulfonyl)-amino-propan-2-one Following the procedure of Example 213(a), except substituting "3-pyridyl-methyleneoxy carbonyl-leucine" for "Cbz-leucine", the title compound was prepared: MS(ES) M+H$^+$=569.

Example 238

Preparation of 1-N-(N-2-pyridyl-methyleneoxy-carbonyl-leucinyl)-amino-3-N-(4-phenoxy-phenyl-sulfonyl)-amino-propan-2-one Following the procedure of Example 213(a), except substituting "2-pyridyl-methyleneoxy carbonyl-leucine" for "Cbz-leucine", the title compound was prepared: MS(ES) M+H$^+$=569.

Example 239

Preparation of 1-N-(N-4-carboxy-benzoyl-leucinyl)-amino-3-N-(4-phenoxy-phenyl-sulfonyl)-amino-propan-2-one 1-N-(4-carboxy methyl-benzoyl-leucinyl)-amino-3-N-(4-phenoxy-phenyl-sulfonyl)-amino-propan-2-one (0.105 g, 0.176 mmol) was dissolved in MeOH (5 ml) and water (1 ml), then LiOH-hydrate (15 mg, 0.35 mmol) was added and the reaction was stirred at RT for 1h. The reaction was diluted with water, acidified with 6N hydrochloric acid (1 ml), then with EtOAc (2×10 ml). The combined organics were dried with magnesium sulfate, filtered, concentrated, chromatographed (silica gel, 50:50:1 EtOAc: hexanes: AcOH) to give the desired product as a white solid (35.6 mg, 35%): MS(ES) M+H$^+$=582, M+Na$^+$=604.

Example 240

Preparation of 1-N-(N-Me-N-Cbz-leucinyl)-amino-3-N-(4-phenoxy-phenyl-sulfonyl)-amino-propan-2-one Following the procedure of Example 213(a), except "N-Me-N-Cbz-leucine" for "Cbz-leucine", the title compound was prepared: MS(ES) M+H$^+$=582, M+Na$^+$=604, 2M+Na$^+$=1185.

Example 241

Preparation of 1-N-(4-phenoxy benzoyl)-amino-3-N-(4-phenoxy-phenyl-sulfonyl)-amino-propan-2-one Following the procedure of Example 213(a), except "4-phenoxy benzoic acid" for "Cbz-leucine", the title compound was prepared: MS(ES) M+H$^+$=517, M+Na$^+$=539, 2M+Na$^+$=1055.

Example 242

Preparation of 1-N-(3-phenoxy-benzoyl)-amino-3-N-(4-phenoxy-phenyl-sulfonyl)-amino-propan-2-one Following the procedure of Example 213(a), except "3-phenoxy benzoic acid" for "Cbz-leucine", the title compound was prepared: MS(ES) M+H$^+$=517, M+Na$^+$=539, 2M+Na$^+$=1055.

Example 243

Preparation of 1-N-(4-phenoxy benzol)-amino-3-N (4-phenoxy-phenyl-sulfonyl)-amino-propan-2-one Following the procedure of Example 213(a), except "4-phenoxy benzoic acid" for "Cbz-leucine", the title compound was prepared: MS(ES) M+H$^+$=517, M+Na$^+$=539, 2M+Na$^+$=1055, M–H$^+$=515.

Example 244

Preparation of 1-N-(4-biphenyl acetyl)-amino-3-N-(4-phenoxy-phenyl-sulfonyl)-amino-propan-2-one Following the procedure of Example 213(a), except "4-biphenyl acetic acid " for "Cbz-leucine", the title compound was prepared: MS(ES) M+H$^+$=515, M+Na$^+$=537, 2M+Na$^+$=1051.

Example 245

Preparation of 1-N-(2-benzyloxy benzoyl)-amino-3-N-(4-phenoxy-phenyl-sulfonyl)-amino-propan-2-one Following the procedure of Example 213(a), except "2-benzyloxy- benzoic acid" for "Cbz-leucine", the title compound was prepared: MS(ES) M+H$^+$=531, M+Na$^+$=553, 2M+Na$^+$=1083.

Example 246

Preparation of 1-N-(N-Cbz-leucinyl)-amino-3-N-(4-benzyloxy-benzoyl)-amino-propan-2-one Following the procedure of Example 229, except substituting "4-benzyloxy-benzoic acid" for "8-quinoline carboxylic acid", the title compound was prepared: MS(ES) M+H$^+$=546, M+Na$^+$=568, 2M+Na$^+$=1113.

Example 247

Preparation of 1-N-(2-(4-biphenyl)-4-methyl-pentamido)-3-N-(4-phenoxy-phenyl-sulfonyl)-amino-propan-2-one Following the procedure of Example 213(a), except 2-(4-biphenyl)-4--methyl-pentanoic acid" for "Cbz-leucine", the title compound was prepared: MS(ES) M+H$^+$=571, M+Na$^+$=593.

Example 248

Preparation of 1-N-(2-(3-biphenyl)-4-methyl-pentamido)-3-N-(4-phenoxy-phenyl-sulfonyl)-amino-propan-2-one a) 3-bromo-phenyl methyl acetate 3-Bromo phenyl acetic acid (2.15 g, 10 mmol) was dissolved in ether, then was treated with a solution of diazomethane until the yellow color persisted. The reaction was then quenched with AcOH, concentrated in vacuo and was used in the next reaction without further purification.

b) 3-biphenyl methyl acetate 3-bromo-phenyl methyl acetate (2.29 g, 10 mmol) was dissolved in toluene (30 ml). Then, phenyl boronic acid (1.46 g, 12 mmol) was added followed by aqueous sodium carbonate (2M, 4.24 ml, 40 mmol), then tetrakis (triphenylphosphine) palladium (0.35 g, 0.3 mmol) and was refluxed overnight. The reaction was cooled to RT, diluted with saturated ammonium chloride, then extracted with EtOAc (2×10 ml). The combined organics were dried with magnesium sulfate, filtered, concentrated, and chromatographed (silica gel, 5% EtOAc: hexanes) to provide the desired product as a white solid (1.93 g, 84%): MS(ES): M+H$^+$=263.

c) 3-biphenyl acetic acid

3-Biphenyl acetyl methyl ester was dissolved in MeOH (40 ml) and water (6 ml), then LiOH-hydrate (0.7 g, 16.8 mmol) was added, and the reaction was stirred at RT for 2h. The reaction was diluted with water, acidified with 6N hydrochloric acid (1 ml), then with EtOAc (2×10 ml). The combined organics were dried with magnesium sulfate, filtered, and concentrated to give the desired product as a white solid (1.66 g, 93%): 1H NMR: d: 7.6-7.25 (m, 9H), 3.7 (s, 2H)

d) 3-(4-biphenyl)-4methyl-pent-4-enoic acid nBuLi (3.26 ml, 1.6 M in hexanes) was added dropwise to a solution of diisopropyl amine (0.74 ml, 5.3 mmol) in THF (6 ml) at 0 C. The reaction was stirred for 15 minutes, then was cooled to –78 C. 3-Biphenyl acetic acid (0.5 g, 2.35 mmol) wasa dissolved in TBF (2 ml) and was added dropwise to the LDA solution. The reaction was warmed to 0 C., stirred 40 minutes, then cooled to –78 C. Isobutenyl bromide (0.475 g, 3.52 mmol) was added and the reaction was stirred for 1h. Water (2 ml) was added and the THF was removed in vacuo. The reaction was diluted with water, acidified with 6N hydrochloric acid (1 ml), then with EtOAc (2×10 ml). The combined organics were dried with magnesium sulfate, filtered, concentrated, chromatographed (silica gel, 5% MeOH: methylene chloride) to give the desired product as a white solid (1.66 g, 93%): 1H NMR: d: 7.6-7.3 (m, 9H), 4.75 (d, 2H), 3.87 (t, 1H), 2.87 (dd, 1H), 2.50 (dd, 1H), 1.70 (s, 3H).

e) 3-(4-biphenyl)-4methyl-pentanoic acid 3-(4-Biphenyl)-4-methyl-pent-4-enoic acid (0.5 g, 1.87 mmol) was dissolved in EtOAc (25 ml). Then, 10% Pd/C (60 mg) was added and the reaction was stirred for 2.5 h under a balloon of hydrogen gas. The reaction was filtered, concentrated in vacuo, then was redissolved in 1:5 EtOAc: EtOH (15 ml). Then, 10% Pd/C (80 mg) was added and the reaction was stirred under a balloon of hydrogen gas overnight. The reaction was filtered, concentrated in vacuo, and chromatographed (silica gel, 5% MeOH: methylene chloride) to give the desired product as a white solid (1.66 g, 93%): 1H NMR: d: 7.6-7.3 (m, 9H), 3.7 (t, 1H), 2.07-1.95 (m, 1H), 1.8-1.7 (m, 1H), 1.6-1.45 (m, 1H).

f) 1-N-(2-(3-biphenyl)-4-methyl-pentamido)-3-N-(4-phenoxy-phenyl-sulfonyl)-amino-propan-2-one Following the procedure of Example 213(a), except 3-(4-biphenyl)-4-methyl-pentanoic acid" for "Cbz-leucine", the title compound was prepared: MS(ES) M+H$^+$=571, M+Na$^+$=593.

Example 249

Preparation of 1-N-(3-biphenyl acetyl)-amino-3-N-(4-phenoxy-phenyl-sulfonyl)-amine-propan-2-one Following the procedure of Example 213(a), except "3-biphenyl acetic acid" for "Cbz-leucine", the title compound was prepared: MS(ES) M+H$^+$=515, M+Na$^+$=537, 2M+Na$^+$=1051.

Example 250

Preparation of 1-N-(N-4-pyridyl acetyl-leucinyl)-amino-3-N-(2-benzyloxy-phenyl-sulfonyl)-amino-propan-2-one a) 1-N-(N-Boc-leucinyl)-amino-3-N-(2-benzyloxy phenyl-sulfonyl)-amino-propan-2-ol 1,3-Diamino-propan-2-ol (3.375 g, 37.5 mmol) was dissolved in DMF (60 ml). Then HOBT-hydrate was added (5.5 g, 40.7 mmol), followed by Boc-L-leucine (9.34 g, 37.5 mmol) and EDCI (7.77 g, 40.7 mmol). The reaction was stirred for 4h, then diluted with DMF to make a stock solution of a total volume of 100 ml (0.375 mmol/ml). The stock solution (18 ml, 6.75 mmol) was treated with NMM (0.89 ml, 7.28 mmol), then 2-benzyloxy phenyl sulfonyl chloride (1.9 g, 6.72 mmol). The reaction was stirred an additional 2h, then was diluted with water, extracted with EtOAc, dried with magnesium sulfate, filtered, concentrated, and chromatographed (silica gel, 20% EtOAc: hexanes): MS(ES) M+H$^+$=550.

b) 1-N-(leucinyl)-amino-3-N-(2-benzyloxy-phenyl-sulfonyl)-amino-propan-2-ol

1-N-(Boc-leucinyl)-amino-3-N-(2-benzyloxy phenyl sulfonyl)-amino-propan-2-ol (0.7 g, 1.3 mmol) was dissolved in 1:1 TFA: DCM (50 ml) and was stirred at RT for 2h, concentrated in vacuo and was used in the following reaction without further purification: MS(ES) M+H$^+$=450.

c) 1-N-(N-4-pyridyl acetyl-leucinyl)-amino-3-N-2-benzyloxy-phenyl-sulfonyl)-amino-propan-2-one Following the procedure of Example 220(b)–(c), except substituting "1-N-leucinyl-amino-3-N-(2-benzyloxy phenyl sulfonyl)-amino-propan-2-ol" for "N-leucinyl-amino-3-N-(4-phenoxy phenyl sulfonyl)-amino-propan-2-ol", the title compound was prepared: MS(ES) M+H$^+$=567.

Example 251

Preparation of 1-N-(N-4-pyridyl carbonyl-leucinyl)-amino-3-N-(2-benzyloxy-phenyl-sulfonyl)-amino-propan-2-one Following the procedure of Example 250(a)–(c), except substituting "4-pyridyl carboxylic acid" for "4-pyridyl acetic acid", the title compound was prepared: MS(ES) M+H$^+$=553.

Example 252

Preparation of 1-N-(N-4-imidazole acetic-leucinyl)-amino-3-N-(2-benzyloxy-phenyl-sulfonyl)-amino-propan-2-one Following the procedure of Example 250(a)–(c), except substituting "4-imidazole acid" for "4-pyridyl-acetic acid" the title compound was prepared: MS(ES) M+H$^+$=556.

Example 253

Preparation of 1-N-(N-(N,N-dimethyl glycyl)-leucinyl)-amino-3-N-(2-benzyloxy-phenyl-sulfonly)-amino-propan-2-one Following the procedure of Example 250(a)–(c), except substituting "N,N-dimethyl glycine" for "4-pyridyl-acetic acid", the title compound was prepared: MS(ES) M+H$^+$=533.

Example 254

Preparation of 1-N-(N-(N-methyl prolyl-leucinyl)-amino-3-N-(2-benzyloxy-phenyl-sulfonyl)-amino-propan-2-one Following the procedure of Example 250(a)–(c), except substituting "N-methyl proline" for "4-pyridyl acetic acid", the title compound was prepared: MS(ES) M+H$^+$=559.

Example 255

Preparation of 1-N-(N-(N-methyl piperidine-4-carbonyl)-leucinyl)-amino-3-N-(2-benzyloxy-phenyl-sulfonyl)-amino-propan-2-one Following the procedure of Example 250(a)–(c), except substituting "N-methyl-piperidine-4-carboxylic acid" for "4-pyridyl acetic acid", the title compound was prepared: MS(ES) M+H$^+$=573.

Example 256

Preparation of 1-N-(N-(N-methyl piperidine-4-carbonyl)-leucinyl)-amino-3-N-(2-dibenzofuran-sulfonyl)-amino-propan-2-one Following the procedure of Example 250(a)–(c), except substituting "N-methyl-piperidine-4-carboxylic acid" for "4-pyridyl acetic acid" and "2-dibenzofuran sulfonyl chloride" for "2-benzyloxy phenyl sulphonyl chloride" the title compound was prepared: MS(ES) M+H$^+$=557.

Example 257

Preparation of 1-N-(N-(N-methyl prolyl)-leucinyl)-amino-3-N-(2-dibenzofuran-sulfonyl)-amino-propan-2-one Following the procedure of Example 250(a)–(c), except substituting "N-methyl proline" for "4-pyridyl acetic acid" and "2-dibenzofuran sulfonyl chloride" for "2-benzyloxy phenyl sulphonyl chloride" the title compound was prepared: MS(ES) M+H$^+$=543.

Example 258

Preparation of 1-N-(N-(N,N-dimethyl glycyl)-leucinyl)-amino-3-N-(-(2-dibenzofuran-sulfonyl)-amino-propan-2-one Following the procedure of Example 250(a)–(c), except substituting N,N-dimethyl glycine" for "4-pyridyl acetic acid" and "2-dibenzofuran-sulfonyl chloride" for "2-benzyloxy phenyl sulphonyl chloride" the title compound was prepared: MS(ES) M+H$^+$=517.

Example 259

Preparation of 1-N-(N-4-imidazole acetic-leucinyl)-amino-3-N-(2-dibenzofuran-sulfonyl)-amino-propan-2-one Following the procedure of Example 250(a)–(c), except substituting "4-imidazole acetic acid" for "4-pyridyl acetic acid" and "2-dibenzofuran sulfonyl chloride" for "2-benzyloxy phenyl sulphonyl chloride" the title compound was prepared: MS(ES) M +H$^+$=526.

Example 260

Preparation of 1-N-(N-4-pyridyl carbonyl-leucinyl)-amino-3-N-(2-dibenzofuran-sulfonyl)-amino-propan-2-one Following the procedure of Example 250(a)–(c), except substituting "4-pyridyl carboxylic acid" for "4-pyridyl ace-

Example 261

Preparation of 1-N-(N-4-pyridyl acetyl-leucinyl)-amino-3-N2-dibenzofuran-sulfonyl)-amino-propan-2-one Following the procedure of Example 250(a)–(c), except substituting "2-dibenzofuran sulfonyl chloride" for "2-benzyloxy phenyl sulphonyl chloride" the title compound was prepared: MS(ES) M+H$^+$=551.

Example 262

Preparation of 1-N-(N-4-imidazole-acrylyl-leucinyl)-amino-3-N-(2-dibenzofuran-sulfonyl)-amino-propan-2-one Following the procedure of Example 250(a)–(c), except substituting "4-imidazole-acrylic acid" for "4-pyridyl acetic acid" and "2-dibenzofuran sulfonyl chloride" for "2-benzyloxy phenyl sulphonyl chloride" the title compound was prepared: MS(ES) M+H$^+$=552.

Example 263

Preparation of 1-N-(N-pyrazole-carbonyl-leucinyl)-amino-3-N-(2-dibenzofuran-sulfonyl)-amino-propan-2-one Following the procedure of Example 250(a)–(c), except substituting "pyrazole carboxylic acid" for "4-pyridyl acetic acid" and "2-dibenzofuran sulfonyl chloride" for "2-benzyloxy phenyl sulphonyl chloride" the title compound was prepared: MS(ES) M+H$^+$=538.

Example 264

Preparation of 1-N-(N-benzoyl-leucinyl)-amino-3-N-(8-quinoline-sulfonyl)-amino-propan-2-one Following the procedure of Example 250(a)–(c), except substituting "benzoic acid" for "4-pyridyl acetic acid" and "8-quinoline sulfonic acid" for "2-benzyloxy phenyl sulphonyl chloride" the title compound was prepared: MS(ES) M+H$^+$=497.

Example 265

Preparation of 1-N-(N-2,5-difluoro-benzoyl-leucinyl)-amino-3-N-(8-quinoline-sulfonyl)-amino-propan-2-one Following the procedure of Example 250(a)–(c), except substituting "2,5-difluoro-benzoic acid" for "4-pyridyl acetic acid" and "8-quinoline sulfonic acid" for "2-benzyloxy phenyl sulphonyl chloride" the title compound was prepared: MS(ES) M+H$^+$=535.

Example 266

Preparation of 1-N-(N-2,5-difluoro-phenyl acetyl-leucinyl)-amino-3-N-(8-quinoline-sulfonyl)-amino-propan-2-one Following the procedure of Example 250(a)–(c), except substituting "2,5-difluoro-phenyl acetic acid" for "4-pyridyl acetic acid" and "8-quinoline sulfonic acid" for "2-benzyloxy phenyl sulphonyl chloride" the title compound was prepared: MS(ES) M+H$^+$=547.

Example 267

Preparation of 1-N-(N-phenyl acetyl-leucinyl)-amino-3-N-(8-quinoline-sulfonyl)-amino-propan-2-one Following the procedure of Example 250(a)–(c), except substituting "phenyl acetic acid" for "4-pyridyl acetic acid" and "8-quinoline sulfonic acid" for "2-benzyloxy phenyl sulphonyl chloride" the title compound was prepared: MS(ES) M+H$^+$=511.

Example 268

Preparation of 1-N-(N-4-pyridyl acetyl-leucinyl)-amino-3-N-(8-quinoline-sulfonyl)-amino-propan-2-one Following the procedure of Example 250(a)–(c), except substituting "4-pyridyl acetic acid" for "4-pyridyl acetic acid" and "8-quinoline sulfonic acid" for "2-benzyloxy phenyl sulphonyl chloride" the title compound was prepared: MS(ES) M+H$^+$=512.

Example 269

Preparation of 1-N-(N-4-pyridyl carbonyl-leucinyl)-amino-3-N-(8-quinoline-sulfonyl)-amino-propan-2-one Following the procedure of Example 250(a)–(c), except substituting "4-pyridyl carboxylic acid" for "4-pyridyl acetic acid" and "8-quinoline sulfonic acid" for "2-benzyloxy phenyl sulphonyl chloride" the title compound was prepared: MS(ES) M+H$^+$=498.

Example 270

Preparation of 1-N-(N-4-imidazole acetyl-leucinyl)-amino-3-N-(8-quinoline-sulfonyl)-amino-propan-2-one Following the procedure of Example 250(a)–(c), except substituting "4-imidazole acetyl acid" for "4-pyridyl acetic acid" and "8-quinoline sulfonic acid" for "2-benzyloxy phenyl sulphonyl chloride" the title compound was prepared: MS(ES) M+H$^+$=501.

Example 271

Preparation of 1-N-(N-3-phenyl propionyl-leucinyl)-amino-3-N-(8-quinoline-sulfonyl)-amino-propan-2-one Following the procedure of Example 250(a)–(c), except substituting "hydrocinnamic acid" for "4-pyridyl acetic acid" and "8-quinoline sulfonic acid" for "2-benzyloxy phenyl sulphonyl chloride" the title compound was prepared: MS(ES) M+H$^+$=525.

Example 272

Preparation of bis-N,N'-(pyridyl methyleneoxy carbonyl-leucinyl)-1,3-diamino-propan-2-one Following the procedure of Example 37, except substituting "4-pyridyl-methyleneoxy-carbonyl-leucinyl" for "Cbz-leucine", the title compound was prepared: MS(ES) M+H$^+$=585.

Example 273

Preparation of bis-N,N'-(N-3-pyridyl methyleneoxy-carbonyl-leucinyl)-1,3-diamino-propan-2-one Following the procedure of Example 37, except substituting "3-pyridyl-methyleneoxy-carbonyl-leucinyl" for "Cbz-leucine", the title compound was prepared: MS(ES) M+H$^+$=585.

Example 274

Preparation of bis-N,N'-(N-2-pyridyl methyleneoxy carbonyl-leucinyl)-1,3-diamino-propan-2-one Following the procedure of Example 37, except substituting "2-pyridyl-methyleneoxy-carbonyl-leucinyl" for "Cbz-leucine", the title compound was prepared: MS(ES) M+H$^+$=585.

Example 275

Preparation of 1-N-(N-Cbz-leucinyl)-amino-3-N-(2-benzyloxy-benzoyl)-amino-propan-2-one Following the procedure of Example 229, except 2-benzyloxy-benzoic acid" for "8-quinoline-carboxylic acid", the title compound was prepared: MS(ES) M+H$^+$=546.

Example 276

Preparation of 1-N-(N-Cbz-leucinyl)-amino-3-N-(3-benzyloxy-benzoyl)-amino-propan-2-one Following the procedure of Example 229, except "3-benzyloxy benzoic acid" for "8-quinoline carboxylic acid", the title compound was prepared: MS(ES) M+H$^+$=546.

Example 277

Preparation of 1-N-(N-Cbz-leucinyl)-amino-3-N-(4-biphenyl-acetyl)-amino-propan-2-one Following the procedure of Example 229, except "4-biphenyl acetic acid" for "8-quinoline carboxylic acid", the title compound was prepared: MS(ES) M+H$^+$=530.

Example 278

Preparation of 1-N-(N-Cbz-leucinyl)-amino-3-N-(2-carboxymethyl-thiophene-3-sulfonyl)-amino-propan-2-one Following the procedure of Example 51, except substituting "2-carboxymethyl thiophene-3-sulfonyl" for "4-(3-Chloro-2-cyano-phenoxy)-phenyl sulfonyl chloride", the title compound was prepared: MS(ES) M−H$^+$=540.

Example 279

Preparation of 1-N-(N-Cbz-leucinyl)-amino3-N-methyl-N-(N-Cbz-leucinyl)-amino-propan-2-one a) N-(Cbz-leucinyl)-amino-propene N-Cbz-leucine (3.0 g, 11.3 mmol) was dissolved in DMF (50 ml), then NMM (1.3 g, 12.4 mmol) was added, followed by allyl amine (0.65 g, 0.85 mmol), and HBTU (4.3 g, 11.3 mmol) and the reaction was stirred overnight at RT. The reaction was diluted with water, extracted with EtOAc, dried with magnesium sulfate, filtered, concentrated, and chromatographed (silica gel, 40% EtOAc: hexanes): MS(ES) M+H$^+$=305.

b) N-(Cbz-leucinyl)-amino-propene oxide

N-(Cbz-leucinyl)-amino-propene (2.95 g, 9.7 mmol) was dissolved in methylene chloride (100 ml), then mCPBA (5.0 g, 29.1 mmol) was added and the reaction was stirred overnight. The reaction was diluted with saturated aqueous sodium bicarbonate, extracted with EtOAc, dried with magnesium sulfate, filtered, concentrated, and chromatographed (silica gel, 50% EtOAc: hexanes).

c) 1-N-(Cbz-leucinyl)-amino-3-N-methyl-amino-propan-2-ol

N-(Cbz-leucinyl)-amino-propene oxide (400 mg, 1.25 mmol) was dissolved in isopropanol (5 ml), then aqueous methyl amine (2 ml) was added and the reaction was heated to 70 C. in a sealed bomb for 2h. The reaction mixture was concentrated in vacuo and was used in the next reaction without further purification.

d) 1-N-(N-Cbz-leucinyl)-amino-3-N-methyl-N-(N-Cbz-leucinyl)-amino-propan-2-one

Following the procedure of Example 229(a), except substituting "1-N-(Cbz-leucinyl)-amino-3-N-methyl-amino-propan-2-ol" for "8-quinoline carboxylic acid", the title compound was prepared: MS(ES) M+H$^+$=597.

Example 280

Preparation of 1-N-(N-Cbz-leucinyl)-amino-3-N-methyl-N-(N-4-pyridyl-methyloxy-carbonyl-leucinyl)-amino-propan-2-one Following the procedure of Example 279(a)–(d), except substituting "4-pyridyl-methyleneoxy-carbonyl leucine" for "Cbz-leucine" in (d), the title compound was prepared: MS(ES) M+H$^+$=598.

Example 281

Preparation of 1-N-(N-Cbz-leucinyl)-amino-3-N-methyl-N-(2-dibenzofuran-sulfonyl)-amino-propan-2-one Following the procedure of Example 279(a)–(d), except substituting "2-dibenzofuran sulfonyl chloride" for "Cbz-leucine and HBTU" in (d), the title compound was prepared: MS(ES) M+H$^+$=580, M+Na$^+$=602.

Example 282

Preparation of 1-N- methyl-1-N-(N-Cbz-leucinyl)-amino-3-N-(2-dibenzofuran-sulfonyl)-amino-propan-2-one Following the procedure of Example 279(a)–(d), except substituting "2-dibenzofuran sulfonyl chloride" for "Cbz-leucine and HBTU" in (a), the title compound was prepared: MS(ES) M+H$^+$=580

Example 283

Preparation of 1-N-methyl-1 N-(N-Cbz-leucinyl)-amino-3- N-(2-dibenzofuran-sulfonyl)-amino-propan-2-one Following the procedure of Example 279(a)–(d), except substituting "2-dibenzofuran sulfonyl chloride" for "N-Cbz-leucine" in step (a) and "4-pyridyl methyleneoxy carbonyl-leucine" for "Cbz-leucine" in step (d), the title compound was prepared: MS(ES) M+H$^+$=580.

Example 284

Preparation of 1-N-(2-dibenzofuran sulfonyl)-N-methyl)-amino-3N-(N-4-pyridyl-methyleneoxy carbonyl-leucinyl)-amino-propan-2-one Following the procedure of Example 279(a)–(d), except substituting "4-pyridyl methyl amine" for "allyl amine" and "2-dibenzofuran sulfonyl chloride" for "N-Cbz-leucine" in step (a) and "N-pyridyl methyleneoxy carbonyl-leucinyl" for "N-Cbz-leucine and HBTU" in step (d), the title compound was prepared: MS(ES) M+H$^+$=581.

Example 285

Preparation of 1-N-(N-Cbz-leucinyl)-amino-3-N-(4-pyridyl-methylene)-3N-(N-Cbz-leucinyl)-amino-propan-2-one Following the procedure of Example 279(a)–(d), except substituting "4-pyridyl methyl amine" for "methyl amine", the title compound was prepared: MS(ES) M+H$^+$=674.

Example 286

Preparation of 1-N-(Cbz-leucinyl)-amino-3-N-(4-pyridyl-methylene)-3N-(2-dibenzofuran sulfonyl)-amino-propan-2-one Following the procedure of Example 284(a)–(d), except substituting "2-dibenzofuran sulfonyl chloride "Cbz-leucine and HBTU" in step (d), the title compound was prepared: MS(ES) M+H$^+$=657.

Example 287

Preparation of 1-N-(Cbz-leucinyl)-amino-3-N-(4-pyridyl-methylene)-3N-(2-dibenzofuran sulfonyl)-amino-propan-2-one Following the procedure of Example 284(a)–(d), except substituting "2-dibenzofuran sulfonyl chloride "Cbz-leucine and HBTU" in step (d), the title compound was prepared: MS(ES) M+H$^+$=657.

Example 288

Preparation of 1-N-(4-biphenyl acetyl)-amino-3-N-(4-pyridyl-methylene)-3N-(N-Cbz-leucinyl)-amino-propan-2-one Following the procedure of Example 279(a)–(d), except substituting "4-biphenyl acetic acid" for "Cbz-leucine" in step (a), "4-pyridyl methyl amine" for "methyl amine", the title compound was prepared: MS(ES) M+H$^+$=621.

Example 289

Preparation of 1-N-(4-phenoxy-benzoyl)-amino-3-N-(4-pyridyl-methylene)-3N-(N-Cbz-leucinyl)-amino-propan-2-one Following the procedure of Example 279(a)–(d), except substituting "4-phenoxy benzoic acid" for "Cbz-leucine" in step (a), "4-pyridyl methyl amine" for "methyl amine", the title compound was prepared: MS(ES) M+H$^+$=623.

Example 290

Preparation of 1-N-(2-dibenzofuran-sulfonyl)-amino-3-N-(4-pyridyl-methylene)-3N-(N-Cbz-leucinyl)-amino-propan-2-one Following the procedure of Example 279(a)–(d), except substituting "2-dibenzofuran sulfonyl chloride" for "Cbz-leucine and HBTU" in step (a), "4-pyridyl methyl amine" for "methyl amine", the title compound was prepared: MS(ES) M+H$^+$=657.

Example 291

Preparation of 1-N-(N-3-pyridyl-methyleneoxy-carbonyl-leucinyl)-amino-3-N-methyl-N-(2-dibenzofuran-sulfonyl)-amino-propan-2-one Following the procedure of Example 279(a)–(d), except substituting "N-methyl-N-allyl amine" for "allyl amine" in (a), and "3-pyridyl-methyleneoxy-carbonyl-leucine" for "Cbz-leucine" in step (d), the title compound was prepared: MS(ES) M+H$^+$=581.

The above specification and Examples fully disclose how to make and use the compounds of the present invention. However, the present invention is not limited to the particular embodiments described hereinabove, but includes all modifications thereof within the scope of the following claims. The various references to journals, patents and other publications which are cited herein comprise the state of the art and are incorporated herein by reference as though fully set forth.

We claim:

1. A compound of Formula VII wherein:

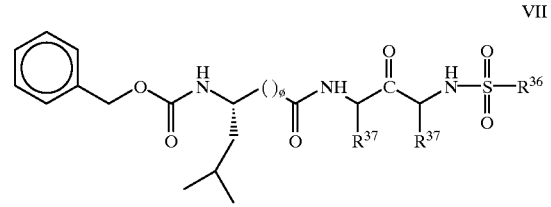

wherein:
  $R^{34}$ is —H or $C_{1-6}$alkyl;
  $R^{36}$ is aryl, heteroaryl, pyridyl, or isoquinolinyl;
  $R^{37}$ is $C_{1-6}$alkyl, —CH$_2$Ph, or —CH$_2$CH$_2$CO$_2$R$^{34}$. O is 0, 1 or 2 or a pharmaceutically acceptable salt, hydrate or solvate thereof.

2. A compound according to claim 1 wherein $R^{36}$ is selected from the group consisting of:

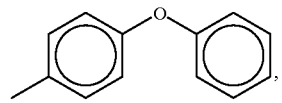

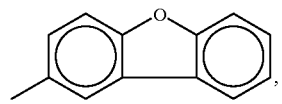

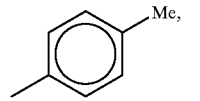

and

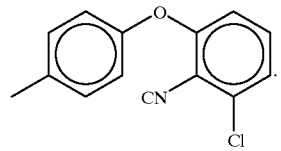

3. A compound according to claim 1 wherein $R^{37}$ of said compound is Me.

4. A compound according to claim 2 selected from the group consisting of:

1-(Cbz-leucinyl)-amino-3-(4(3-chloro-2-cyano-phenoxy) phenyl sulfonamido)-propan-2-one;

1-(Cbz-leucinyl)-amino-3-(tosyl-amino)-propan-2-one;

1-(Cbz-leucinyl)-amino-3-((4-phenoxy-phenyl)-sulfonamido)propan-2-one;

1-(Cbz-leucinyl)-amino-3-(2-dibenzofuransulfonamido)-propan-2-one;

1-(Cbz-homo-leucinyl)-amino-3-(2-dibenzofuransulfonamido)propan-2-one; and 1-(Cbz-leucinyl)-amino-3-(2-dibenzofuransulfonamido)-(S)-butan-2-one.

5. A compound according to claim 4 known as 1-(Cbz-leucinyl)-amino-3-((4-phenoxy-phenyl)-sulfonamido)-propan-2-one.

6. A compound according to claim 4 known as 1-(Cbz-leucinyl)-amino-3-(2-dibenzofuransulfonamido)-(S)-butan-2-one.

7. A compound according to claim 4 known as 1-(Cbz-leucinyl)-amino-3-(2-dibenzofuransulfonamido)-propan-2-one.

8. A pharmaceutical composition comprising a compound according to claim 1 and a pharmaceutically acceptable carrier, diluent or excipient.

9. A method of inhibiting a cysteine protease comprising administering to a patient in need thereof an effective amount of a compound according to claim 1.

10. A method according to claim 9 wherein said cysteine protease is cathepsin K.

11. A method of treating a disease characterized by bone loss comprising inhibiting said bone loss by administering to a patient in need thereof an effective amount of a compound according to claim 1.

12. A method according to claim 11 wherein said disease is osteoporosis.

13. A method according to claim 11 wherein said disease is periodontitis.

14. A method according to claim 11 wherein said disease is gingivitis.

15. A method of treating a disease characterized by excessive cartilage or matrix degradation comprising inhibiting said excessive cartilage or matrix degradation by administering to a patient in need thereof an effective amount of a compound according to claim 1.

16. A method according to claim 15 wherein said disease is osteoarthritis.

17. A method according to claim 15 wherein said disease is rheumatoid arthritis.

* * * * *